(12) United States Patent
Patel

(10) Patent No.: US 11,071,795 B2
(45) Date of Patent: Jul. 27, 2021

(54) INDICATING DEVICES BASED ON ETCHING OF METALS

(71) Applicant: JP Laboratories, Middlesex, NJ (US)

(72) Inventor: Gordhanbhai N Patel, Somerset, NJ (US)

(73) Assignee: JP Laboratories Inc., Middlesex, NJ (US)

( * ) Notice: Subject to any disclaimer, the term of this patent is extended or adjusted under 35 U.S.C. 154(b) by 334 days.

(21) Appl. No.: 15/602,035

(22) Filed: May 22, 2017

(65) Prior Publication Data

US 2018/0024011 A1  Jan. 25, 2018

Related U.S. Application Data

(63) Continuation of application No. 13/692,939, filed on Dec. 3, 2012, now abandoned, which is a continuation
(Continued)

(51) Int. Cl.
*A61L 2/07* (2006.01)
*G01N 33/02* (2006.01)
(Continued)

(52) U.S. Cl.
CPC .............. *A61L 2/07* (2013.01); *A61L 2/206* (2013.01); *A61L 2/28* (2013.01); *C09D 11/037* (2013.01);
(Continued)

(58) Field of Classification Search
CPC ... A61L 2/07; A61L 2/206; A61L 2/28; A61L 2202/14; C09D 11/037; C09D 11/322;
(Continued)

(56) References Cited

U.S. PATENT DOCUMENTS 3,084,658 A    3/1963 Schell
4,233,195 A †  11/1980 Mills
(Continued)

FOREIGN PATENT DOCUMENTS

EP    2102615    12/2011
JP    S61176879   8/1986
(Continued)

OTHER PUBLICATIONS

Inder P Batra et al, "Chemisorption of oxygen on aluminum surfaces", Journal of electron spectroscopy and Related Phenomena, vol. 33, No. 3 pp. 175-241.
(Continued)

*Primary Examiner* — Lore R Jarrett
(74) *Attorney, Agent, or Firm* — Joseph T. Guy; Patent Filing Specialist Inc.

(57) ABSTRACT

Compositions, devices and processes related to etching of a very thin layer or fine particles of a metal are disclosed for monitoring a variety of parameters, such as time, temperature, time-temperature, thawing, freezing, microwave, humidity, ionizing radiation, sterilization and chemicals. These devices have capabilities of producing a long and sharp induction period of an irreversible visual change. The devices are composed of an indicator comprising a very thin layer of a metal and an activator, e.g., a reactant, such as water, water vapor, an acid, a base, oxidizing agent or their precursors, which is capable of reacting with the said indicator. Ink formulations composed of a metal powder and a proper activator can be used for monitoring several sterilization processes, such as sterilization with steam. When water is used as an activator, a thin layer of metals, such as that of aluminum can be used as steam sterilization or humidity indicator.

46 Claims, 47 Drawing Sheets

Related U.S. Application Data of application No. 12/478,232, filed on Jun. 4, 2009, now Pat. No. 8,343,437.

(60) Provisional application No. 61/130,928, filed on Jun. 4, 2008, provisional application No. 61/132,799, filed on Jun. 23, 2008, provisional application No. 61/081,763, filed on Jul. 18, 2008, provisional application No. 61/095,058, filed on Sep. 8, 2008, provisional application No. 61/122,547, filed on Dec. 15, 2008, provisional application No. 61/162,539, filed on Mar. 23, 2009, provisional application No. 61/215,939, filed on May 12, 2009.

(51) Int. Cl.

| | | |
|---|---|---|
| *G01N 31/22* | (2006.01) | |
| *G01K 3/04* | (2006.01) | |
| *A61L 2/20* | (2006.01) | |
| *A61L 2/28* | (2006.01) | |
| *C09D 11/037* | (2014.01) | |
| *C09D 11/322* | (2014.01) | |
| *C12Q 1/22* | (2006.01) | |
| *G01N 33/52* | (2006.01) | |

(52) U.S. Cl.
CPC ............ *C09D 11/322* (2013.01); *C12Q 1/22* (2013.01); *G01K 3/04* (2013.01); *G01N 31/229* (2013.01); *G01N 33/02* (2013.01); *G01N 33/52* (2013.01); *A61L 2202/14* (2013.01); *Y10T 156/10* (2015.01); *Y10T 436/206664* (2015.01)

(58) Field of Classification Search
CPC .......... C12Q 1/22; G01N 33/52; G01N 33/02; G01N 31/229; G01K 3/04; Y10T 436/206664; Y10T 156/10
See application file for complete search history.

(56) References Cited

U.S. PATENT DOCUMENTS

| | | | |
|---|---|---|---|
| 4,298,569 A † | 11/1981 | Read | |
| 4,576,795 A * | 3/1986 | Bruso | A61L 2/28 |
| | | | 422/416 |
| 4,646,674 A | 3/1987 | Preziosi | |
| 4,909,179 A | 3/1990 | McBride | |
| 5,053,339 A † | 10/1991 | Patel | |
| 5,160,600 A | 11/1992 | Patel | |
| 5,254,473 A * | 10/1993 | Patel | G01N 31/229 |
| | | | 116/216 |
| 5,470,430 A | 11/1995 | Lewis | |
| 5,606,633 A | 2/1997 | Groger | |
| 5,667,303 A † | 9/1997 | Arens | |
| 5,846,310 A * | 12/1998 | Noguchi | A61K 8/28 |
| | | | 106/482 |
| 5,916,816 A † | 6/1999 | Read | |
| 6,318,760 B1 | 6/2001 | Shadle | |
| 6,270,122 B1 † | 8/2001 | Shadle | |
| 6,452,873 B1 | 9/2002 | Holt | |
| 6,488,890 B1 † | 12/2002 | Kirckof | |
| 6,801,477 B2 | 10/2004 | Braunberger | |
| 6,896,296 B2 | 5/2005 | Shadle | |
| 7,102,526 B2 † | 9/2006 | Zweig | |
| 7,141,214 B2 † | 11/2006 | Puntambekar | |
| 7,280,441 B2 | 11/2007 | MacDonald | |
| 7,290,925 B1 | 11/2007 | Skjervold | |
| 7,430,982 B2 | 10/2008 | Koivukunnas | |
| 8,267,576 B2 | 9/2012 | Haarer | |
| 8,343,437 B2 † | 1/2013 | Patel | |
| 2004/0051299 A1 | 3/2004 | Shadle | |
| 2007/0210173 A1 | 9/2007 | Nagel | |
| 2008/0023647 A1 | 1/2008 | Patel | |
| 2008/0116361 A1 | 5/2008 | Sanders | |

FOREIGN PATENT DOCUMENTS

| | | | |
|---|---|---|---|
| WO | 01/25472 A1 † | 4/2001 | |
| WO | 2004077001 | 9/2004 | |
| WO | 2006/048412 A1 † | 5/2006 | |
| WO | 2006048412 | 5/2006 | |
| WO | 2007/089799 A2 † | 8/2007 | |
| WO | 2008083926 | 6/2008 | |
| WO | 2008/083926 A1 † | 7/2008 | |
| WO | 2009149243 | 12/2009 | |

OTHER PUBLICATIONS

Wefers; Misra, "Oxides and Hydroxides of Aluminum", Alcoa Technical Paper No. 19, (1987).
IPR2017-00538, USPTO.
International search report PCT/US2009/046228 dated Dec. 10, 2009.
Supplementary search report EP2288879 dated Jul. 17, 2015.
Fatah et al., "Guide for the Selection of Chemical and Biological Decontamination Equipment for Emergency First Responders" NIJ Guide 103-00, vol. 1, National Institute of Justice, Office of Science and Technology, Washington, DC, 2001.†
Bruze M, et al. "Chemical skin burns," In: "Irritant dermatitis," Chew A, et al. (eds) Springer, Berlin, pp. 53-61 (2006).†
Sitzmann et al "Photoinitiators: Their Mechanisms, Use, and Applications" in "Handbook of Coatings Additives, Second Edition," Florio and Miller, eds., Marcel Dekker, Inc., New York, NY, pp. 61, 79-80 (2004).†
Dumas et al. Growth of Thin Alumina Film Onaluminium at Room Temperature : Akinetic and Spectroscopic Study Bysurface Plasmon Excitation, Journal de Physique Colloques, 44 (C10, supplement No. 12), pp. C10-205-C10-208 (1983).†
Wefers and Misra, "Oxides and Hydroxides of Aluminum", Alcoa Technical Paper No. 19, Revised (1987).†
Batra, "Chemisoprtion of oxygen on aluminum surfaces," Journal of Electron Spectroscopy and Related Phenomena, 33:175-241 (1984).†
IPR2017-00538 "Judgment and Final Decision, Granting Request for Adverse Judgment After Institution of Trial, 35 U.S.C. 318(a); 37 C.F.R. 42.73(b)" Nov. 3, 2017.†
IPR2017-00538 "Decision, Institution of Inter Partes Review, 37 C.F.R. 42.108" Jul. 12, 2017.†

\* cited by examiner
† cited by third party (c)

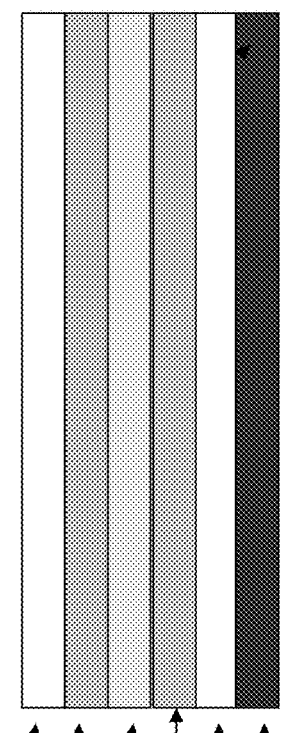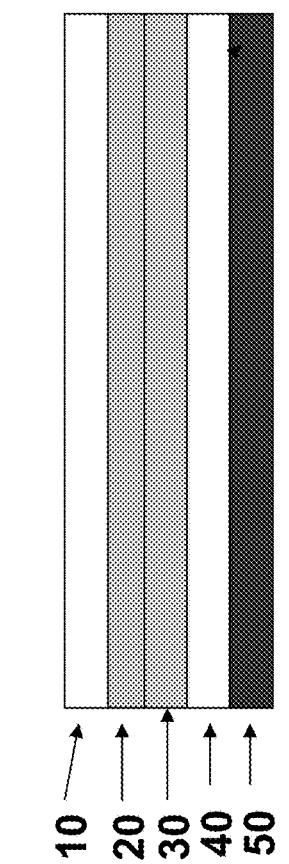
Fig.8

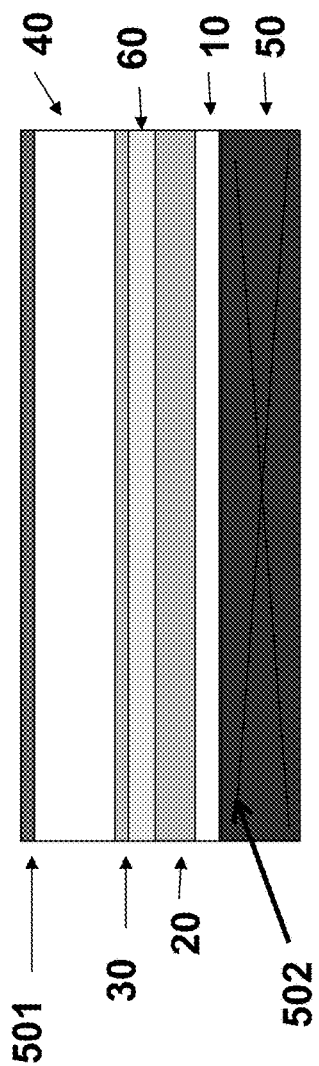
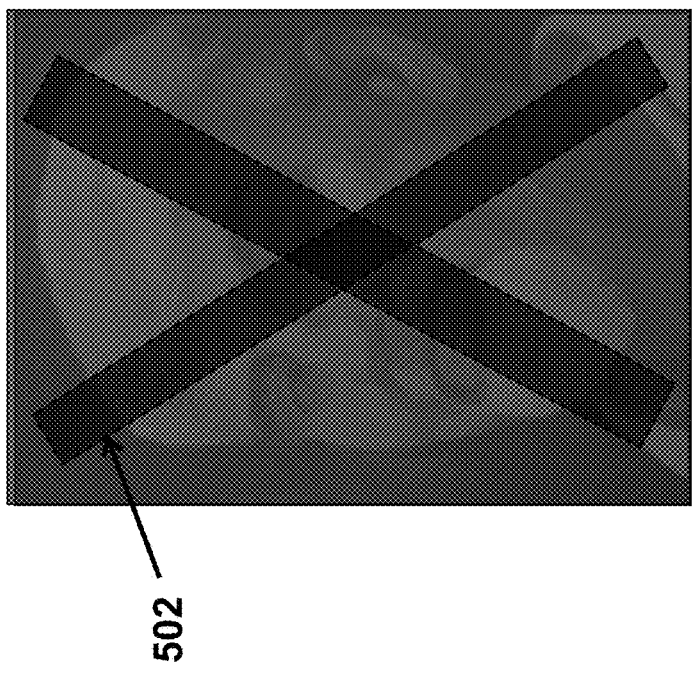
Fig. 11

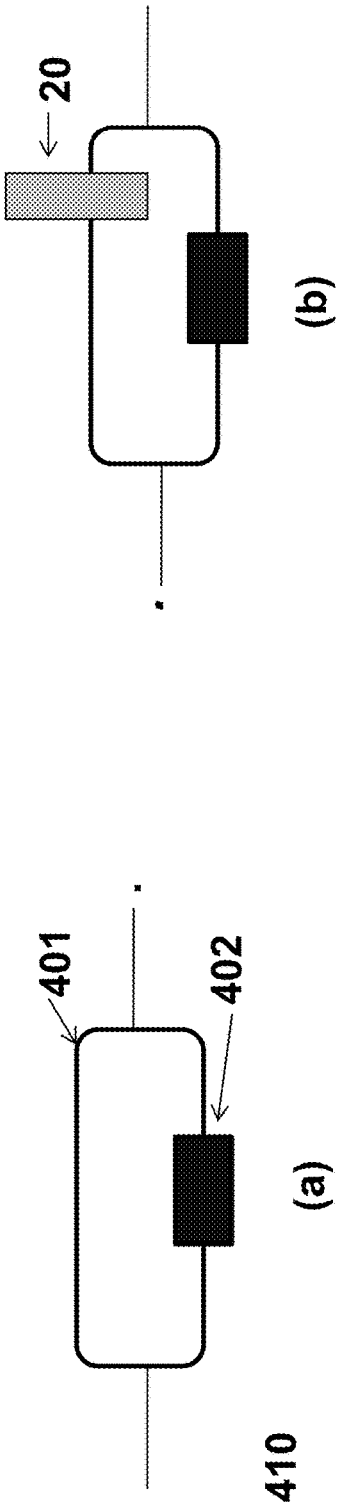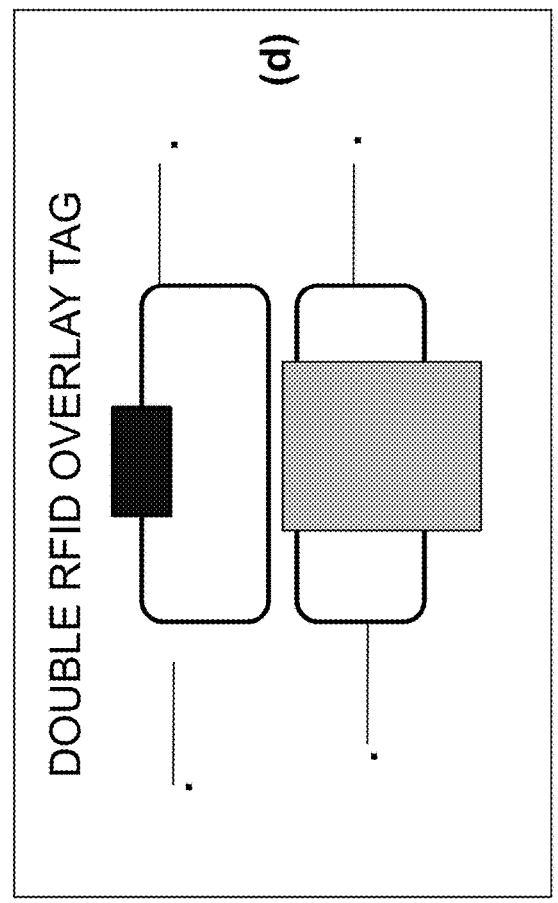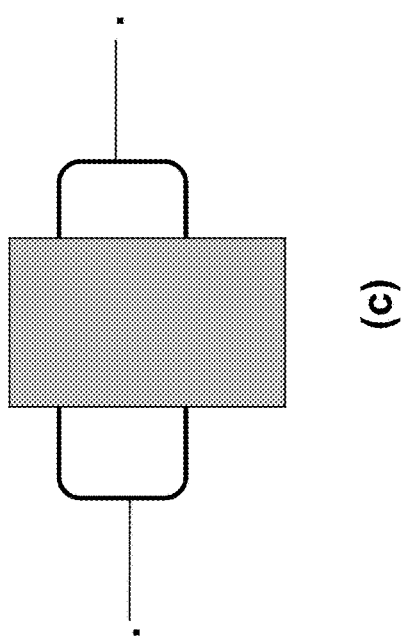
Fig. 24

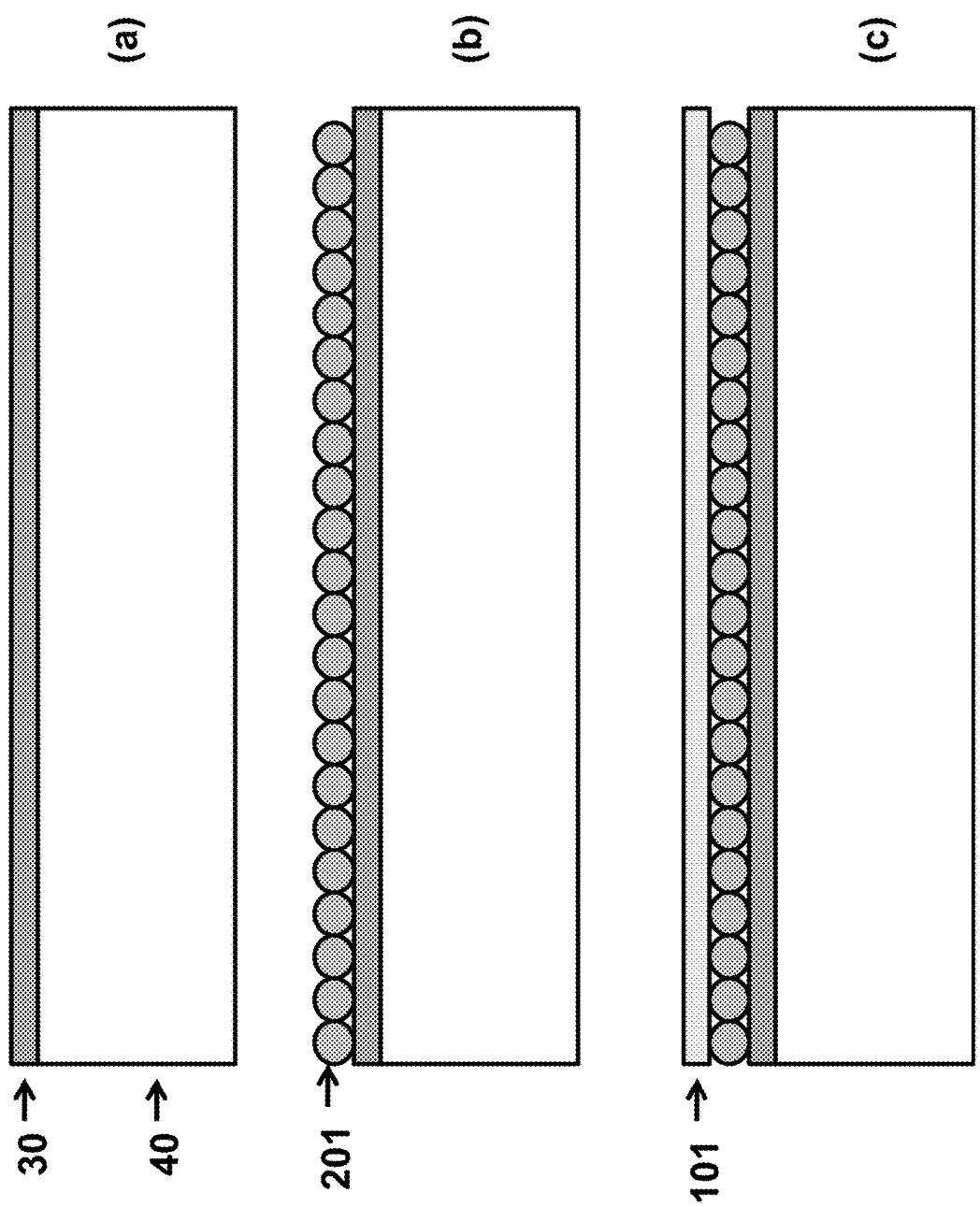

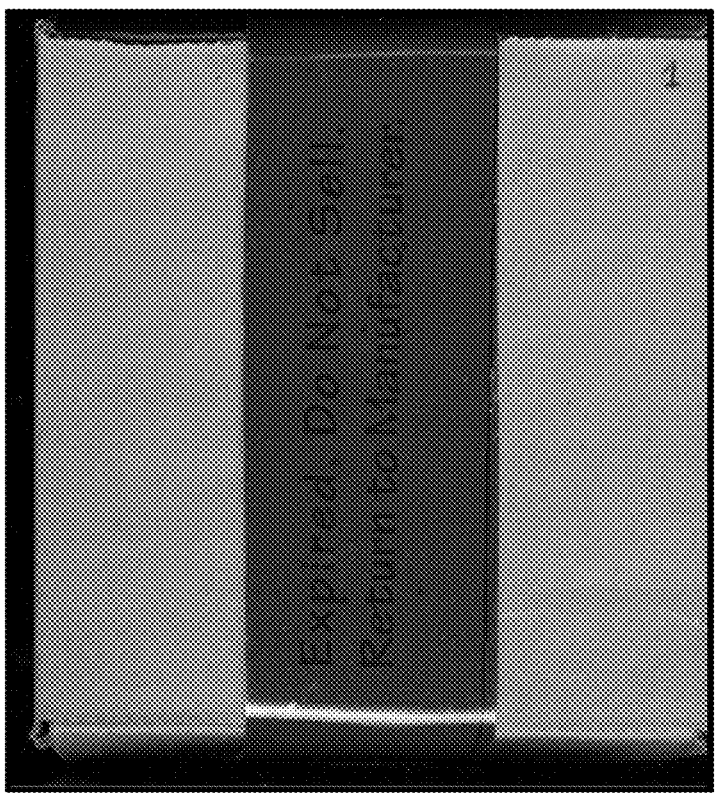
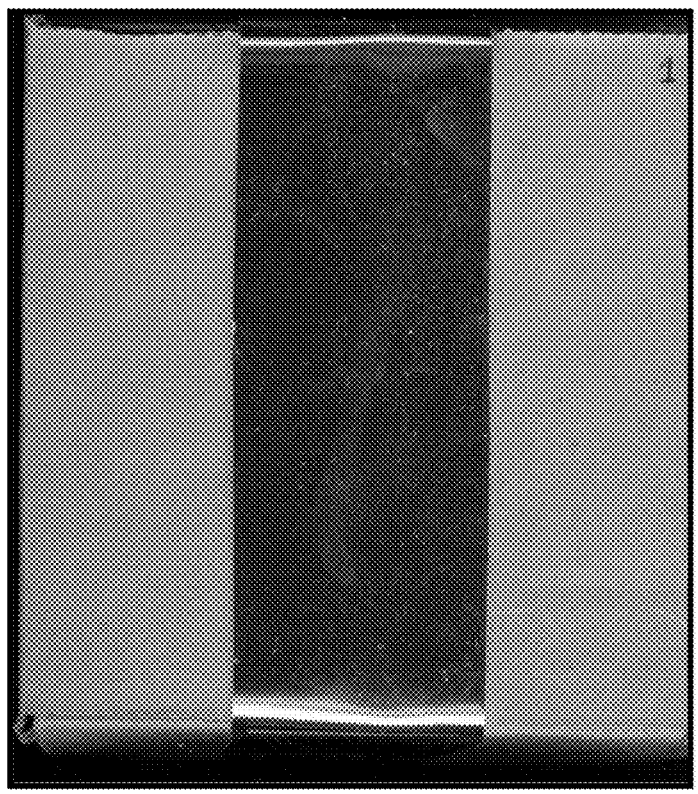
Fig. 35

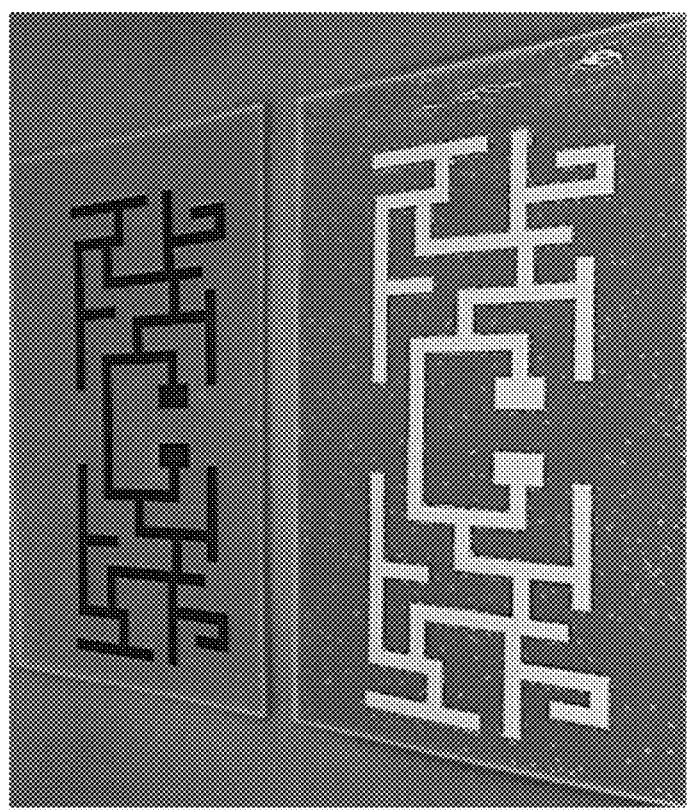
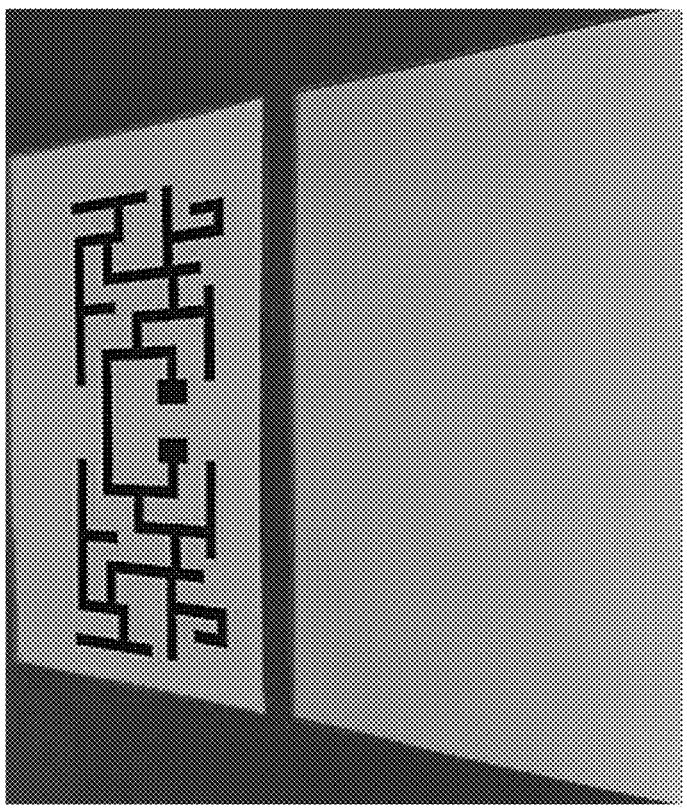
Fig. 38

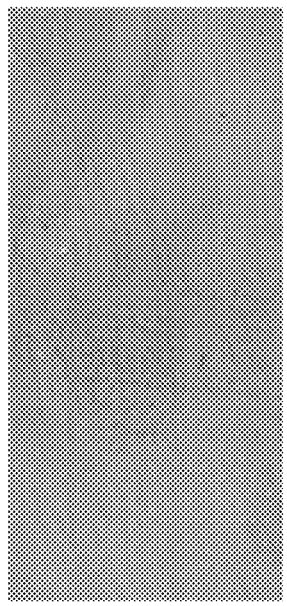
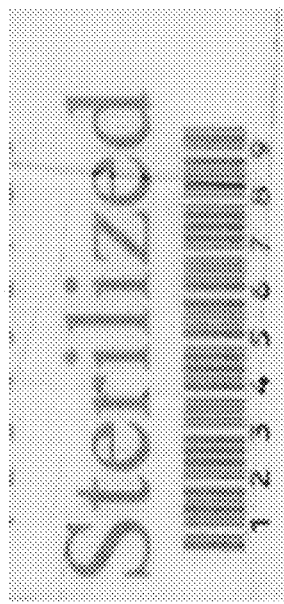
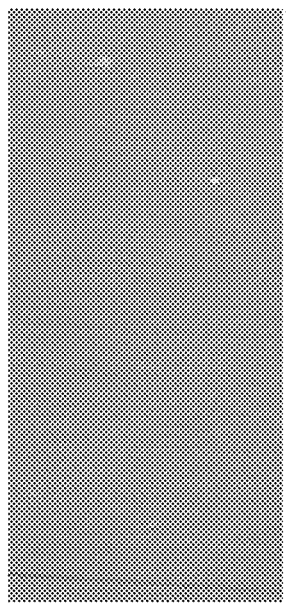
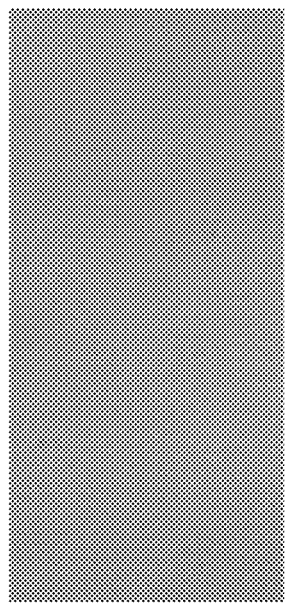
Fig. 40

INDICATING DEVICES BASED ON
ETCHING OF METALS

CROSS-REFERENCE TO RELATED
APPLICATIONS

This application is a continuation of U.S. application Ser. No. 13/692,939, filed Dec. 3, 2012, which is a continuation of U.S. application Ser. No. 12/478,232, filed Jun. 4, 2009 which claims priority to U.S. Provisional Patent Applications Nos. 61/130,928; filed Jun. 4, 2008; 61/132,799, filed Jun. 23, 2008; 61/081,763, filed Jul. 18, 2008; 61/095,058, filed Sep. 8, 2008; 61/122,547, filed Dec. 15, 2008; 61/162,539, filed Mar. 23, 2009; and 61/245,982, filed May 12, 2009, which are incorporated herein by reference in their entireties.

FIELD OF THE INVENTION

The present invention relates to a system and processes for monitoring time, time-temperature, humidity, defrost, radiation, chemical and biological agents and sterilization based on etching of a thin layer or fine particles of a metal. The invention also relates to formation of patterns, printing plates, electronic circuits and RFID devices.

BACKGROUND OF THE INVENTION

Brief Description of Prior Art

Perishable products have measurable shelf-lives, which are usually expressed within specified limits as the time left for available end use. The term "perishable(s)" or "perishable product(s)" is meant herein to include perishable foods, such as fresh, refrigerated, and frozen, vegetables, fruits, meats, fish, poultry, dairy products, bakery products, juices, pre-cooked foods, soft and alcoholic beverages, and also including nonfood items having shelf lives ranging from a few hours to several years including pharmaceuticals, vaccines, sera, blood, blood plasma, cosmetics, reactive chemical compounds, bio-chemicals, bio-products, batteries, X-ray film and photographic films which have a measurable shelf life.

Whenever a clock or timer is impractical or too expensive to use, color changing time indicators or indicating devices in forms of labels, stickers or badges are used. Indicators for monitoring the passage of a relative amount of time are referred herein to as time indicator (TI) or time indicating device including but not limited to visual validation of time, safety sticker, self-timing retail sticker, biological industrial process monitoring, self-expiring stickers to prevent re-use, employee ID and security ID labels, visitors badges, self-expiring parking tags, package and shipping labels, wrist bands, time indicating tickets for trains, buses, sport events, theaters etc, self-expiring passes for tours, emergency rooms, hospitals, museums, and other locations, event passes, security labels for screened luggage, purses, bags at airports to show the aircraft control people that the particular items were inspected, unmanned but video controlled entrances for visitors where the self-expiring visitor label issued electronically. It also includes limited use items for consumers where once opened or in use should be used within certain period, including but not limited to drinks, food items, health, personal and family care products. TI can also be used for monitoring shelf life of perishables.

Time-temperature indicator(s) (TTI) devices provide a way of indicating a cumulative exposure to time and temperature. A TTI device may be capable of indicating whether a commodity has been exposed to a temperature greater than a predetermined temperature for a period of time or to an integral value of time and temperature. For example, a TTI device might indicate exposure to an excessive temperature for an excessive period of time or both. A large number of time-temperature indicating devices and time indicating devices for monitoring thermal degradation of perishables and self-expiring labels, tickets and badges have been reported in patent literature. Many of these devices are based on diffusion of a chemical from one matrix to the other, sometimes through a permeable layer, to introduce a color change in the indicator layer. The other TTIs are based on chemical reactions, such as the solid state polymerization of diacetylenes, change in pH and change in photochromism and thermochromism.

A large number of devices have been reported in the patent literature for monitoring time and integral value of time and temperature.

Patel, in U.S. Pat. No. 5,053,339 discloses a color changing device for monitoring the time-temperature storage history, i.e. shelf life of perishable products. The device is composed of (1) an activator tape, containing an activator composition and matrix on a substrate, (2) an indicator tape, containing an indicating composition, matrix and (3) an optional permeable layer. The permeable layer is often referred to as a barrier layer in the prior art. The device is activated by applying the activator tape over the indicator tape. This and similar devices in general are often referred herein to as two-tape devices, two-tape TTI and TI. The term "binder", "medium", "ink", "paint", "vehicle", "coating' and "matrix" are also used interchangeably herein. Based on this technology, Bowater PLC, London, UK was the first to introduce two-tape TTI/TI products, one in the form of stickers and the other in the form of foldable bands during 1991 and 1993 (ReacTT™ Brochure of Bower PLC, London, UK, 1992) in the market.

Haas and his co-inventors in a series of U.S. Pat. Nos. 4,903,254; 5,053,339; 5,446,705; 5,602,804; 5,633,835; 5,699,326; 5,715,215; 5,719,828; 5,785,354; 5,822,280; 5,862,101; 5,873,606; 5,930,206; 6,446,865, 6,452,873; 6,752,430; 7,139,226; and 7,263,037 have disclosed time monitoring devices and related processes. All these patents are hereby incorporated by reference into the specification of this application. These devices are also based on diffusion of an activator (which also includes a dye) through a medium. The indicator has a matrix, e.g., an ink which has a binder.

The following patents are some other representative examples of TI and TTI devices: U.S. Pat. Nos. 2,896,568; 3,018,611; 3,046,786; 3,078,182; 3,311,084; 3,520,124; 3,921,318; 3,954,011; 3,962,920; 3,999,946; 4,154,107; 4,195,058; 4,212,153; 4,382,063; 4,404,922; 4,432,630; 4,432,656; 4,448,548; 4,480,749; 4,542,982; 4,573,711; 4,629,330; 4,643,122; 4,643,588; 4,646,066; 4,737,463; 4,779,120; 4,812,053; 4,846,095; 4,846,502; 4,917,503; 5,053,339; 5,058,088; 5,120,137; 5,293,648; 5,317,980; 5,364,132; 5,378,430; 5,446,705; 5,602,804; 5,633,836; 5,667,303; 5,699,326; 5,709,472; 5,715,215; 5,719,828; 5,785,354; 5,822,280; 5,862,101; 5,873,606; 5,930,206; 5,957,458; 5,974,003; 5,997,927; 6,042,264; 6,103,351; 6,214,623; 6,254,969; 6,514,462; 6,524,000; 6,536,370; 6,614,728; 6,752,430; 6,822,931; 6,916,116; 7,156,597; 7,157,048; 7,209,042; 7,280,441; 7,290,925 and 7,294,379. All these patents are hereby incorporated by reference into the specification of this patent application.

None of these and any other two-tape indicating devices reported in the literature are based a metal as an indicator and etching of a metal.

Pre-cooked, ready-to-eat frozen foods are widely used today. The pre-cooked frozen food is heated either in a conventional oven (for example, heated with natural gas or electricity) or more conveniently in a microwave oven. A microwave oven does not heat the food uniformly. Some portions of food may not be done while the other portions may be over heated. Hence, there is a need for an indicating device that changes color when steam is emitted by the food.

Microwave interactive materials generally provide, for example, enhanced surface heating, microwave shielding, enhanced microwave transmission, and energy distribution functions in packaging. Susceptors are employed in the preparation of food products in microwave ovens to convert some of the microwave energy to heat in order to assist in cooking the food by conduction, convection and/or radiant heating as well as microwave radiation. Numerous microwave energy susceptors are described in the prior art. Exemplary susceptors are disclosed in U.S. Pat. Nos. 6,501,059; 5,530,231; 5,220,143; 5,038,009; 4,914,266; 4,908,246; 4,883,936; 4,641,005 and 4,267,420 the disclosures of which are incorporated herein by reference. A number of approaches have also emerged on patterning of conventional metal microwave-absorbing layers by selective demetallization to control the amount of heating in predetermined regions of the susceptor. A number of techniques have been utilized to provide the desired patterning. Exemplary techniques are described in U.S. Pat. Nos. 5,614,259; 5,300,746; 5,254,821; 5,185,506; 4,959,120; 4,927,991; 4,685,997; 4,610,755 and 4,552,614, the disclosures of which are incorporated herein by reference.

There is no report on use of microwave energy susceptors as an aid for microwave doneness indicating devices.

There are a variety of defrost indicating devices reported in the literature, including those in the following patents: U.S. Pat. Nos. 3,233,459; 3,702,077; 3,786,777; 4,038,936; 4,114,443; 4,120,818; 4,144,834; 4,163,427; 4,280,361; 4,735,745; 4,892,677; 5,267,794; 5,685,641 and 5,695,284. This type of indicating devices undergo a color change when the product temperature undesirably exceeded about 0° C. These devices have not proven entirely satisfactory due either to deficiencies in their visual perceptual character or in the danger of their use, in their sensitivity to thawing conditions or in their complexity of manufacture or use. The shortcomings of such devices are that they often fail in practice.

The quality of certain frozen perishables, such as ice creams, frozen foods, blood products and certain pharmaceuticals deteriorate rapidly if they are brought above the freezing temperature (usually zero degree centigrade). Hence, there is a strong need for defrost or thaw indicating devices. A number of thaw indicating devices have been reported in the literature. None of the thaw indicating device has been successful in the market mainly because they change color too rapidly. When one goes grocery shopping, one picks up a frozen food package, places it in the cart, checks out, places it in the car/trunk and goes home to put it in a freezer. The perishable does not lose its quality during this normal handling or just because the surface of the container or a small portion of the food inside was above the freezing temperature for a short while. Hence, there is a need for thaw indicating devices with a delayed effect for the color change. For monitoring frozen state and shelf life or quality of frozen perishable, one needs "thaw-time-temperature (TTT) indicating devices". There is a need for indicating devices for monitoring thawing as well as effect of integral value of time and temperature above the freezing temperature.

Many products of commerce are temperature sensitive and may spoil, deteriorate or lose quality if they suffer even a brief exposure to a temperature near or below freezing. Some flowers, salad greens, vegetables and herbs, wilt, shrink and become dark colored, useless and/or unappealing when exposed to freezing or near-freezing temperatures. Such changes are well known and are largely caused by ice crystals destroying the integrity of the botanical cells. Other freeze sensitive products include pharmaceuticals, sera, vaccines, fresh produce, flowers, latexes, paints, emulsions, such as milk, fruit juices, and yogurt. Hence, there is a need for a freeze indicating device.

U.S. Pat. No. 3,934,069 discloses a method of encapsulation of solution of a salt/dye and an organic carboxylic acid in an organic water-immiscible solvent. U.S. Pat. No. 3,888,631 discloses a temperature indicating device for monitoring deep frozen products, comprising paper-like fibrous material containing a binder and two water soluble colorless reagents. U.S. Pat. No. 4,163,427 discloses a freeze-thaw indicating device apparatus comprising a plurality of frangible microcapsules. U.S. Pat. No. 5,910,314 discloses a process for the preparation of a microcapsule composition.

However, there is no report on a freeze indicating device based on release of an activator/etchant upon freezing and etching of a thin metal layer or fine particles of a metal.

A wide variety of medical supplies and other items are sterilized with materials and techniques, such as steam, dry heat, ethylene oxide, plasma, peracetic acid, formaldehyde and high-energy radiation. Kitchenware, such as dishes, cutlery, and utensils used at home and restaurants are also sterilized in dishwashers with hot water and hot air usually around 90° C. It is essential to assure that these items are sterilized or meet required specifications. A number of sterilization indicating devices, dosimeters and monitors are proposed in the literature. They include biological and chemical indicating devices. The color changing chemical indicating devices are inexpensive and are widely used.

A wide variety of foods especially canned foods, pharmaceuticals, hospital and medical supplies are sterilized. These and other products, such as linens are sterilized to kill living organisms to an acceptable level. Direct testing for sterility is destructive and expensive and hence indirect testing methods, such as color changing indicating devices are used.

Pressurized steam is used in hospitals to sterilize reusable medical equipment and supplies, such as gowns and linens. To differentiate between a tray containing sterilized goods and one containing non-sterile goods, which may not have been processed, an indicating device is used. The process of sterilization causes the device to change color. Often the original color is light, and the color after processing is dark. The change in color is caused by a chemical reaction in the ink. The indicating device may be in the form of a strip, card, or tape. By observation of the color of the sterilization indicating device, one can determine whether or not the package has been passed through the sterilization cycle.

There are international standards, such as the International Organization for Standardization (ISO) and the European Standards (EN) that deal with sterilization testing including steam sterilization. International standards for the air removal tests for pre-vacuum steam sterilizers comprise a chemical indicating device in a test pack are found in the ISO and EN series. These packs incorporate the Bowie-Dick test and have similar performance standards as seen in AAMI (American Association of Medical Instrumentation), but use different testing procedures.

Many steam sterilization indicating devices are reported in the literature and some of them are used for monitoring sterilization. A few of them use heavy and toxic metal compounds, such as those of lead or bismuth. For example, U.S. Pat. No. 3,523,011 describes an indicating device material consisting of calcium sulfide and lead carbonate. A number of patents are issued based on color changing sterilization indicating devices (e.g., those for steam, dry heat, ethylene oxide, plasma, peracetic acid, formaldehyde and high-energy radiation) using inorganic and organic compounds, including a variety of dyes and pigments.

They include the following U.S. patents:

U.S. Pat. Nos. 2,798,885; 2,826,073; 3,098,751; 3,360,337; 3,360,338; 3,360,339; 3,386,807; 3,471,422; 3,568,627; 3,852,034; 3,862,824; 3,932,134; 3,981,683; 4,094,642; 4,121,714; 4,138,216; 4,195,055; 4,407,960; 4,410,493; 4,436,819; 4,486,387; 4,514,361; 4,576,795; 4,579,715; 4,596,696; 4,692,307; 4,678,640; 5,064,576; 5,087,659; 5,158,363; 5,200,147; 5,223,401; 5,252,484; 5,258,065; 5,451,372; 5,788,925; 5,801,010; 5,866,356; 5,916,816; 5,990,199; 6,063,631; 6,485,978; 6,589,479; 6,659,036; 6,800,124; 6,884,394; 7,141,214 and 7,189,355.

All these patents are hereby incorporated by reference into the specification of this patent application.

The prior art discloses use of polyvalent compounds of metals but none of them disclose use of a zero valent metal or an alloy (i.e., a metal as an indicator).

Despite the widespread use and low cost of such indicating devices, there are several disadvantages associated with them. Firstly, the ink has a tendency to transfer to and stain articles with which it comes into contact in the autoclave. Secondly, the sensitivity of the ink diminishes with time, especially when stored in humid conditions, such that the initial and final colors may be compromised. There are numerous other color changing systems capable of detecting steam sterilization, containing metal salts, organic acids, oxidizing agents or other compounds. Many of these are still toxic, have limited color changes and/or are expensive. There is a need for sterilization indicating devices which do not have these drawbacks.

Patel, in PCT application number #WO 01/10471 A1, has disclosed ink formulations and devices for monitoring sterilization with ethylene oxide. The device is made by coating a mixture of (a) a polymeric binder, (b) an ethylene oxide reactive salt, such as sodium thiocyanate and tetraethylammonium bromide and (c) a pH sensitive dye, such as bromothymol blue and bromocresol purple. When contacted with ethylene oxide, the device undergoes at least one color change due to production of a base, such as sodium hydroxide. However, these devices and formulations are color changing.

Patel, in PCT application #WO 00/61200, has disclosed formulations and devices for monitoring sterilization with plasma. The devices are made by coating a mixture of at least one (a) polymeric binder, (b) plasma activator and (c) plasma indicator. The devices undergo a color change when treated with plasma, especially that of hydrogen peroxide. For example, a coating of phenol red and tetraethylammonium bromide in a binder, such as a polyacrylate undergoes a color change from yellow-to-blue when exposed to hydrogen peroxide and its plasma due to halogenation of the dye. However, these devices and formulations are color changing.

Micro-encapsulation is a process in which tiny particles or liquid droplets are surrounded by a layer or coating to give small capsules. Microcapsules herein include many other similar systems, such as micelles, emulsion, dispersion, liposomes and similar phase separated systems. The material inside the microcapsule is referred to as the core, internal phase, or fill, whereas the wall is sometimes called a shell, coating, or membrane. Most microcapsules have diameters between a fraction of micrometer and a few millimeters. Processes of microencapsulation are well known and disclosed in U.S. Pat. Nos. 2,730,456; 2,800,457; 2,986,477; 3,516,941; 4,001,140; 4,081,376; 4,089,802; 4,100,103; 4,105,823; 4,197,346;4,428,982; 4,444,699; 4,547,429; 4,552,811; 4,622,267; 6,084,010 and 6,592,990.

In thermally responsive printing systems, such as direct thermal printing, basic chromogenic material, acidic color developer material and a sensitizer are contained in a coating on a substrate which, when heated to a suitable temperature, melts or softens to permit said materials to react, thereby producing a colored mark. These solid materials are incorporated into a coating along with pigments, binders, and additives. This coating is then applied to the surface of paper or other support system, such as a plastic film using various types of coating application systems and dried. Images are formed on the coated surface by application of heat to melt and interact the three color producing materials.

The materials and process for thermal printing are disclosed in U.S. Pat. Nos. 3,539,375; 3,674,535; 3,746,675; 4,151,748; 4,181,771; 4,246,318; 4,370,370; 4,388,362; 4,424,245; 4,444,819; 4,470,057; 4,507,669; 4,551,738; 4,682,194; 4,722,921; 4,742,043; 4,783,439 and 4,942,150

The development of thermal print heads (linear arrays of individually-addressable resistors) has led to the development of a wide variety of thermally-sensitive media. Heat is used to convert a colorless coating on a single sheet into a colored image, in a process known as "direct thermal" imaging. Direct thermal imaging systems use several different chemical mechanisms to produce a change in color. Some employ compounds that are intrinsically unstable and which decompose to form a visible color when heated. Such color changes may involve a unimolecular chemical reaction. Thermal paper also contains thermal reactive dyes, such as azo or leuco dyes used with a developer. Leuco dyes are colorless or light colored basic substances which become colored when oxidized by acidic substances (developers). The dye and developer are preferably solid at ambient temperature and have a melting point below the operating temperature of a thermal print head of a thermal imaging apparatus. The materials and processes for thermal printing are disclosed in U.S. Pat. Nos. 3,488,705; 3,539,375; 3,745,009; 3,832,212; 4,243,052; 4,380,629; 4,401,717; 4,415,633. 4,602,263; 4,720,449; 5,350,870 and 4,636,819

A waveguide is a structure which guides waves, such as that of light through a dielectric medium usually an optical fiber. A number of monitoring devices based on optical wave guide have been reported in the literature. It is known that it is possible to alter the transmission properties of an optical waveguide by causing certain chemical reactions to occur in the cladding layer, a layer over the optical fiber. Metallized optical fibers are also reported. However, there is no report on monitoring devices based on etching of metallized optical fiber.

The electronic industry needs enhanced performance from products, such as wiring boards at a lower cost. Printed wiring board circuitry can reside on a rigid fiberglass reinforced plastic or on flexible films to which are adhered a metal layer used to form conductive circuit connections. The boards can contain interconnecting circuitry on one layer, two layers, or multiple layers. Boards with three or more layers can be manufactured using multiple two layer boards laminated together forming a multi-layer construction, or can be built up from a two layer board by sequentially adding dielectric layers and circuits.

Electronic article surveillance (EAS) is a technological method for preventing shoplifting from retail stores or unauthorized removal of books from libraries. Special tags are fixed to merchandise or books. These tags are removed or deactivated by the clerks when the items are properly bought or checked out. At the exits of the store, a detection system sounds an alarm or otherwise alerts the staff when it senses active tags. Radio frequency EAS tags are essentially an LC tank circuit that has a resonance peak anywhere from 1.75 MHz to 9.5 MHz. An LC circuit is a variety of resonant circuit or tuned circuit and consists of an inductor and a capacitor. When connected together, an electric current can alternate between them at the circuit's resonant frequency. Deactivation of the tag is achieved by detuning the circuit by partially destroying the capacitor. This is done by submitting the tag to a strong electromagnetic field at the resonant frequency which will induce voltages exceeding the capacitor's breakdown voltage, which is artificially reduced by puncturing the tag.

The permanent EAS tags are made of a non-linear element (a diode) coupled to one microwave and one electrostatic antenna. At the exit, one antenna emits a low-frequency (about 100 kHz) field, and another one emits a microwave field. The tag acts as a mixer re-emitting a combination of signals from both fields. This modulated signal triggers the alarm. These tags are permanent and somewhat costly. They are mostly used in clothing stores.

Metallized polymer sheeting is now commonly employed as a substitute for decorative chrome parts, especially in the automotive industry. Typically, such metallized polymer sheeting includes a layer of metal disposed between two polymer sheets.

Typically metallized polymer sheeting is created by etching the metal layer with a base, e.g., sodium hydroxide or an acid, e.g., nitric acid solution. These are multistep, somewhat hazardous and polluting processes. Therefore, a need exists for a metallized composite made by least hazardous and simple means.

Thin metal foils (e.g., between 10 to 1,000 microns) are widely used for a variety of applications. Metal foils are used and/or have been suggested as a substrate for many of the above described devices. When a metal foil is used as a substrate it is thick, usually more than 10 micron thick. Etching, including selective etching of metals with a liquid etchant is well known and is widely used in industry for creating many products. Etching is typically done by dipping a metal part in an etchant, such as an acid or a base solution. Etching and dissolution, as defined herein. also includes reactions such as corrosion, rusting, oxidation and/or conversion to other compounds of metals, semimetals, semiconductors and alloys.

Metallized plastics and plastic films are also widely used for a large number of applications including both functional and decorative purposes as they have conductive and reflective surfaces. Metallized plastic films are also used as substrates for many devices including those described herein. Fine particles (e.g., from nano sized or larger) of metals, such as that of aluminum and bronzes (alloys of copper, tin, aluminum and zinc) are widely used to make silver, gold and other color inks and paints (including conductive inks, paints and paste). However, there is no report on creation of indicating devices, such as indicators for monitoring time, time-temperature, sterilization, humidity, microwave doneness, defrost and other devices, such as patterning, EAS, electronic devices, printed electronics, printed electrodes and imaging based on etching of a very thin layer of metals or fine particles of metals with an etchant/activator.

A variety of indicating devices based on use of metal compounds are reported but there is no report on use of a very thin layer of a metal or fine particles of a metal as indicators described herein. Similarly, metallized plastic films are proposed (e.g., U.S. Pat. No. 7,430,982) as substrates for indicators but not as indicators.

Etching of metals, e.g., with acids and bases is well known. Indicators for monitoring end of etching also have been proposed (e.g., U.S. Pat. No. 7,361,286). However, there is no report on use of the indicating devices based on etching of metals.

Dissolution/destruction/reaction of fine powder of metals, such as aluminum, copper, zinc and their alloys with water, acids, oxidizing agents and bases is well known. Matter of fact fine power of aluminum and its alloys are recommended to generate hydrogen as a fuel by reacting with water. Etching/dissolution of metals including aluminum is well known and practiced widely in industry. However, there is no report on use of metals, either as a fine powder or coated on a substrate, as indicating devices, such as time, time-temperature and sterilization indicating devices and devices, such as RFID and electronic article surveillance (EAS).

Fine powder of many metals, e.g., that of aluminum, is considered flammable. The dust can form explosive mixture with air, especially when damp. The dry powder is stable. It is known that bulk aluminum powder or dust in contact with water may heat spontaneously. Moist, finely divided aluminum powder may ignite in air, with formation of flammable hydrogen gas. The hazard increases as the aluminum particle size decreases. Damp bulk dust may heat spontaneously and form flammable hydrogen gas. Aluminum powders are used in paints, pigments, protective coatings, printing inks, rocket fuel, explosives, abrasives and ceramics; production of inorganic and organic aluminum chemicals and as catalysts.

However, there is no report on use of an ultra thin layer (e.g., 100 Angstroms) of flammable metals, such as aluminum, zinc and their alloys as humidity or steam sterilization indicating devices.

None of the indicating devices reported in the literature are based on etching or destruction of the indicator layer which is ultra thin/small, opaque and in form of coating stickers or labels. There is a need for indicating devices where the indicator layer is completely destroyed and hence cannot be tampered, reversed or re-used. There is also a need for indicating devices in form sealing tape which can be used for sealing boxes, e.g., that of perishables. Some of the above devices, such as those based on polymerization of diacetylenes (marketed by Temptime Corporation, Morris Plains, N.J.) require protection against UV/sunlight. There is also a need for highly environmentally stable indicating devices so they don't provide false signals. The two-tape indicating devices reported in the prior art provide very little induction period unless a permeable/barrier layer is used. Even with the use of a permeable layer, the induction period is short and not sharp. Hence, there is a need for indicating devices having a long and sharp induction period so a better "go-no go" type devices can be developed. There are also needs for many desired and required features, such as making indicating devices tamper resistant, tamper evident, a variety of expiration/doneness colors, messages for self-reading, and images by simple and easy means. The term "expiration" or "doneness" used herein is for indicators, colors, messages and images, layers and/or alike and processes associated with them which appear or indicate expiration or doneness of indicating devices.

Most of the time, consumers want to know whether a product is good, bad, acceptable, not acceptable, valid, not valid etc. Some people don't know or understand partially good and the remaining bad. As far as consumer acceptability is concerned, it is acceptable or not acceptable, there is little in-between. They prefer self reading indicating devices rather than color changing devices which are subject to interpretation. Consumers generally want to know whether the food is good or not good, fresh or not fresh, usable or not usable etc. Doctors, pharmacists and hospitals generally want to know whether pharmaceuticals are potent or not potent, effective or not effective, usable or not usable etc and the medical supplies are sterilized or not sterilized. Security personnel generally want to know whether the visitor/employee is valid or not valid and should be allowed or not allowed. Hence, there is a need for go/no-go types of self reading indicating devices rather than confusing gradually color changing type with color reference charts.

The term metallic is used for a material which is a metal, metal like or having one or more properties of a metal that can be used as an indicator for one or more devices of the system of the present inventions. Such materials and properties include one or more of the followings: which can be etched or destroyed with an activator, which can react with water, oxygen, acids, bases and salts, where the activator reacts with the said material on its surface (top-to-bottom, if flat or outside-to-inside/center, if it is in a particle form) i.e., undergoes a heterogeneous reaction, whose reaction with activators has a definite end, which is non-porous/impermeable to almost all chemicals, which has no (or does not need a) binder or can be coated on a substrate without a binder, which is self binding, which has an ability to bond with a substrate without a need for a binder, which is significantly opaque, which is reflective, which is opaque and reflective, which is electrical conductive or semi-conductive, which has extremely high optical density to thickness ratio (e.g., optical density of ~1 at thickness of ~100 Angstroms), undergoes a change in opacity by it dissolution, undergoes a change in opacity from substantially opaque to completely transparent or semi-transparent/translucent if the thickness less than 1,000 Angstroms, an abrupt change in optical density at the end of the reaction, whose atoms are bonded by metallic bonds, has a naturally formed oxide layer or has an ability to form an oxide layer and/or where a change in opacity has an induction period. The term "metallized" is used for a substrate having a metallic coating. The terms, "metal", "metal like", "metallic" and having properties of metal are used interchangeably herein for indicator materials of the devices.

The term "metallic" may also include many semimetals and some semi-conductive materials which are self binding, opaque, undergo heterogeneous reaction with an activator.

The two most desired properties of the metallic indicator (an indicator of the current invention) for the system are opaqueness and non-diffusive/heterogeneous reaction with an activator or an agent for the devices based on visual change. Metal, semi-metals and often some semi-conductors have these two properties.

Indicating devices of the present inventions, such as that for time (TI), time-temperature (TTI), thaw, freeze, humidity, ionizing radiation, temperature, microwave, sterilization (SI) (including that with steam, ethylene oxide, plasma, formaldehyde, dry heat, hydrogen peroxide and peracetic acid), chemicals, biological and chemical agents, microwave and all other devices (e.g., printed circuit board, RFID and EAS), including those defined above and herein, individually or collectively are often referred herein to as indicating device(s) or simply as a device or system. An indicating device or indicating system also includes other formulations, devices and processes disclosed herein. We have also used the word integrator, integrating device, sensor, detector and monitor and monitoring devices interchangeably with indicating device and indicating system.

The term indicator is also used for any indicia including dyes, pigments, barcodes, images, messages and alike.

The term "color change" used herein includes change in optical density including change in fluorescence, translucency, opacity and transparency and under certain circumstances conductivity.

The terms, "chemical(s)", "chemical agent(s)", "biological agent(s)", "chemical and biological agent(s)", and simply "agent(s)" are used interchangeably herein for materials like water/steam, acids, bases which either react directly (i.e., activators) with metallic indicator or like biochemicals or chemicals such as ethylene oxide and hydrogen peroxide which when react with a precursor for an activator produce an activator which then reacts with a metallic indicator. The metallic indicating devices are also used for monitoring these agents and/or processes, such as sterilization. An agent, such as water/steam, an acid or a base can also be an activator and vice versa.

The information provided in this section of "Background of the invention" is hereby incorporated by reference into the specification of the present invention.

Each patent described and cited above is incorporated herein in specification of this application by reference to the extent each provides guidance regarding formulations, materials, processes and devices that can be used to make formulations, materials, processes and devices disclosed herein.

BRIEF DESCRIPTION AND OBJECTS OF THE INVENTION

The main objective of this invention is to provide a system of indicating and non-indicating devices for monitoring materials and processes such as time, temperature, time-temperature, thaw, freeze, humidity, ionizing radiation, microwave, sterilization (including steam, ethylene oxide, plasma, formaldehyde, dry heat, hydrogen peroxide and peracetic acid), chemicals, biological and chemical agents, and electronic devices, such as RFID, EAS, printed electronics, printed electrodes and alike based on significant etching of a thin layer and/or fine particles of metallic materials such as a metal, semimetal, semiconductor or an alloy.

Another main objective of this invention/system is to provide devices based on significant change in opacity of a layer or destruction of a substantially non-permeable layer.

Another main objective of this invention is to provide electronic devices or support for electronic devices, such as printed circuit boards, antenna, RFID, printed electronics, printed electrodes and EAS by etching a thin layer or fine particles of a metallic material and a patterned layer.

Another main objective of this invention is to provide said devices for quantitative measurements of materials including chemicals and chemical or biological agents based on etching of metal or metallized optical wave guide Another main objective of the invention is to provide an indicating formulation, such as inks and paints comprising particles of a metallic material as an indicator and an activator which reacts with the metallic material.

Another main objective of this invention is to provide said indicating devices composed of an activator tape and an indicator tape.

Another main objective of this invention is to provide said indicating devices composed of a layer of a metallic material as an indicator.

Another main objective of this invention is to provide said indicating devices composed of a layer of aluminum, copper, zinc, tin or their alloys as an indicator.

Another main objective of this invention is to provide said indicating devices in form of a tape.

Another main objective of this invention is to provide said indicating devices in form of a tape for sealing boxes to indicate status or quality of the products inside them.

Another main objective of this invention is to apply the said tape and seal a box containing items to be processed or monitored.

Another main objective of this invention is to provide a process for monitoring the said indicating sealing or packing tape or label.

Another main objective of this invention is to provide a device having a substrate, a substantially thin metallic layer such as that of a metal, a layer of activator over the metal layer which substantially changes the nature of the metallic layer.

Another main objective of this invention is to provide a device having a substrate having thereon a layer composed of fine particles of a metal and a material such as an activator which substantially changes the nature of the metal particles.

Another main objective of this invention is to provide self expiring indicating devices having a metal as an indicator for intelligent packaging and supply chain management.

Yet other main objectives of this invention/system are to provide a device including said indicating devices:

- having a long and relatively sharp induction period.
- having a thin and highly opaque indicator layer.
- having a light reflective indicator layer.
- having a indicator layer which gets destroyed
- having an indicator layer which is electrically conductive.
- composed of an indicator layer which has no matrix.
- composed of an indicator layer which has no matrix and is very thin and/or highly opaque.
- composed of an indicator layer which is a metallic.
- composed of an indicator layer which is a metal or its alloy.
- composed of an indicator layer which is a semimetal or semiconductor.
- composed of an indicator layer made from aluminum, copper, zinc, tin or their alloys.
- having a substantially opaque indicator layer which becomes substantially transparent when contacted with an activator.
- having a substantially opaque indicator layer which becomes substantially transparent when contacted with an activator which is an acid, base or salt.
- having a layer of activator or precursor for activator.
- having a layer of activator or precursor for activator which is substantially transparent.
- having an activator layer for introducing a noticeable change in the indicator layer.
- having an activator which is a food or food additive.
- having an activator which makes the indicator either non-conductive, non-reflective, transparent or vice versa.
- having an indicator layer which has an uneven or embossed surface.
- having an opaque indicator layer which becomes substantially transparent when contacted with an activator which is a food additive.
- having a thin indicator layer composed of aluminum which becomes substantially transparent when contacted with an activator or precursor for an activator which is phosphoric acid, phosphorous acid, phosphorous pentoxide, sodium acetate, sodium thiocyanate, tetraethylammonium bromide, sodium bromide, sodium carbonate, sodium nitrate, ammonium bromide or sodium bicarbonate.
- having an indicator tape composed of a substrate having a thin and highly opaque indicator layer on one surface and a message or message providing layer on either surface of the substrate.
- having an indicator tape composed of a substrate having a thin and highly opaque indicator layer on one surface, having a message or message providing layer on the exposed surface of the said metal and a message or message providing layer on either surface of the substrate.
- having an indicator tape composed of a substrate having thin and highly opaque indicator layers on both the surfaces of the substrate.
- having an indicator tape composed of a substrate having a thin and highly opaque indicator layer on one surface and a message indicating layer on either surface of the substrate, wherein the said message indicating layer is composed of different colors, messages and/or images.
- having an activator tape composed of a substrate having an activator layer on one surface and a message indicating layer on the other surface.
- having an activator tape composed of a substrate having an activator layer on one surface and an message indicating layer on the other surface, wherein the said message indicating layer is composed of different colors, messages and/or images.
- having a layer permeable or barrier to activator.
- having a permeable or barrier layer on the indicator layer.
- having a permeable or barrier layer on the activator layer.
- having a permeable or barrier layer between the activator and indicator layers.
- having a permeable or barrier layer and a message indicating layer.
- having a permeable or barrier layer and a message indicating layer which is composed of different colors, messages and/or images.
- having a permeable or barrier layer which protects the indicator.
- having a permeable or barrier layer which is naturally formed.
- having a permeable or barrier layer which is an oxide and/or hydroxide.
- having a permeable or barrier layer made by treating the metal surface with a reactant.
- having the said permeable or barrier layer which is either continuous or discontinuous.
- having permeable or barrier layers which are naturally formed and made by treating the metal surface with a reactant or by coating.
- having a barrier layer which destructible.

having a barrier layer which destructible by an activator or an agent.

having an indicating tape device composed of a substrate having a thin and highly opaque indicator layer additionally having a permeable or barrier layer on one surface and a message indicating layer on the other surface.

having a barrier or permeable layer which reacts with an activator.

having a barrier or permeable layer which can be destroyed or dissolved by an activator.

having a barrier or permeable layer which is substantially transparent.

having a permeable or barrier layer which is polymeric.

composed of activator and indicator tapes wherein the said indicator tape is composed of a thin and highly opaque indicator layer and a permeable or barrier layer between the tapes.

having at least one tamper indicator and/or tamper indicator layer.

having a layer which is an indicator and tamper indicating.

composed of activator and indicator tapes wherein the said indicator tape is composed of a thin and highly opaque indicator layer and the said activator tape is composed of an activator and also has a tamper indicator layer.

composed of activator and indicator tapes wherein the said indicator tape is composed of a thin and highly opaque indicator layer and a permeable or barrier layer and also has a tamper indicator layer.

having at least one bonding layer to bond the layers of the said devices.

wherein the said bonding layer is pressure sensitive adhesive.

wherein the said bonding layer is not a pressure sensitive adhesive.

having at least one binder for indicator or activator.

having at least one release layer.

having an activation indicator.

having an activation indicator layer.

composed of activator and indicator tapes wherein the said indicator tape is composed of a thin and highly opaque indicator layer and a permeable layer and also has an activation layer which indicates the activation of the device.

having a wedged shaped permeable layer.

having a wedge shaped indicator layer.

having a wedge shaped activator layer.

having a wedge shaped precursor layer.

having a wedged shaped permeable layer on the indicator layer.

having a wedged shaped permeable layer on the activator layer.

having a wedged shaped permeable layer between the indicator and activator layers.

having multiple of wedge shaped layers.

composed of activator and indicator tapes wherein the said indicator tape is composed of a thin and highly opaque indicator layer and a wedge shaped permeable layer between the tapes.

composed of activator and indicator tapes wherein the said indicator tape is composed of a thin and highly opaque indicator layer and a wedge shaped permeable layer between the tapes and a message indicating layer which may be composed of different colors, messages and/or images.

having a message layer having a top message layer.

having a bottom message layer.

having a message layer in-between any two layers of the said device.

having a top and bottom message indicating layers.

having a top and bottom message indicating layers which provide different messages.

having a top and bottom message indicating layers which provide one new message.

having a mask or barrier layer.

having a mask or barrier layer in form of a message.

having a mask or barrier layer on the indicator layer.

in form of a band.

in form of a band made from the compositions, layers and tapes and having features mentioned herein.

one of the layer is in form a image, pattern, barcode or message.

comprising: one coded indicia for identifying an object or container; a second coded indicia for identifying a condition, quality and alike of its content; with either one of them printed on either surface of indicator, activator, permeable or barrier layer or a substrate and means for changing the appearance of the indicia.

Yet another objective of this invention is to provide an activator formulation comprising a binder and an activator for the said metallic indicator.

Yet another objective of this invention is to provide an activator formulation comprising a binder, an activator or precursor for the said metallic indicator and a solvent.

Yet another objective of this invention is to provide a method of applying the said activator formulation of the said metallic layer.

Yet other main objectives of this invention are to provide the said devices having one or more of the above features.

Yet another objective of the present invention is to provide an indicating device which indicates good, usable, processed, expired, non-usable, not processed and alike status.

Yet other main objectives of the present invention are to activate or assemble the indicating devices herein.

Provided are indicating devices/systems and processes based on change in light scattering, opacity and/or reflectivity of an indicator or indicating layer.

Provided are indicating devices/systems and processes having antimicrobial materials as indicators or activators.

Provided are indicating devices/systems and processes providing more than one message.

Provided is a wear, rub, scuff, grind or erode indicating device wherein the wearing layer is an opaque layer.

Provided is a wear, rub, scuff, grind or erode indicating devices wherein the wearing layer is an opaque layer and a message is printed underneath.

Provided is a wear, rub, scuff, grind or erode indicating device wherein the wearing layer is a metal layer and a message is printed underneath.

Provided is a wear indicating device where an opaque wedge shaped layer is removed by wear or wear is indicated with a message printed underneath appears gradually indicating degree of usage.

Provided is a control release device wherein a thin layer of metal is used to encapsulate, cover or protect a substance to be released by dissolution of the said metal.

Provided are fine particles of metals, such as aluminum, copper, zinc, tin and their alloys as an indicator.

Provided are inks, coating formulations and dried coating of fine particles of metals, such as aluminum, copper, zinc and their alloys as an indicator.

Yet other main objectives of the present invention/indicating system are to provide processes of/for:

- making the formulations, compositions, layers, tapes and devices disclosed herein.
- applying the activator tape over indicator tape with or without some of the layers and compositions disclosed herein.
- applying the said devices disclosed herein on to an object.
- applying the said indicating devices disclosed herein on a box.
- applying the said devices disclosed herein on a human or animal.
- applying the said devices disclosed herein to an object requiring monitoring of time.
- applying the said devices disclosed herein to an object requiring monitoring of time and temperature.
- applying the said devices disclosed herein to a human, clothing or perishables.
- monitoring transparency change, appearance or disappearance of messages or images of the said devices herein.
- reading the said devices herein.
- reading the said devices herein with a machine.

Yet another main objective of the present invention is to monitor expiration and stages in between of the said devices herein and perishables they are applied on.

Yet another objective of the present invention is to provide said devices herein which have essential no liquid.

Yet another objective of the present invention is to provide said devices herein which are low cost.

Yet another objective of the present invention is to provide said devices herein which are self reading.

Yet another objective of the present invention is to provide said devices herein which are self expiring.

The other objectives of this invention/system are to provide:

- an indicating device for notification of an item or process that needs to be done after the passage of a pre-determined time.
- a warning label or sign on which the message appears or disappears after a pre-determined time.
- a game wherein answers or solutions to questions, a message, image or problems become visible or disappears after a pre-determined time.
- a badge, label or sticker which provides a relatively clear indication of expiration of a pre-determined time.
- an indicating device wherein the time required for a noticeable change including change in opacity can be varied by easy or simple means.
- an indicating device which can provide the user with a clear indication of the increments of time.
- an indicating device that rapidly changes color after a specific time interval.
- an indicating device which can provide information upon the passage.
- an indicating device which provides a clear indication of expiration and remains visible for long periods of time.
- a warning label or sign which warns about the passage of time by appearance or disappearance of the warning.
- an identification badge, label or sticker that may be replaced without replacing the fastening means.
- a shelf life indicating device wherein the device changes color or words appears or disappears after specified intervals of time corresponding to the shelf life of the product.
- a time indicating device for indicating the passage of long periods of time, including months and even years.
- a time indicating band that cannot be transferred between persons without breaking, cutting or otherwise tampering with the band.
- a time indicating band which fits wrist and other objects.
- a band or tape which self-expires after the passage of a time interval.
- a product age indicating device wherein the device is applied to products prior to transportation, and the indicating device changes with time to show the relative age of the product.
- a label for use with perishable products including pharmaceutical products which self-expires upon reaching the end of the useful life of the product.
- a self-expiring security tape for use in customs and checked baggage facilities wherein the security tape self-expires after set intervals to prevent reissue thereof
- self expiring sensors
- a self-expiring parking permit which enables a parking attendant to determine from a relatively long distance whether the parking permit has expired.
- self-expiring transportation tickets, passes and transfers, including admission tickets for parks, theater and other events which expire upon the passing of set intervals, including one day tickets, one week tickets, one month tickets and tickets of other time intervals.
- a price tag which, after a time interval, changes to indicate a reduced price.
- a parking time indicating device which is disposable and is relatively inexpensive.
- a self-changing retail sticker wherein a sticker is applied to purchased goods at the point of purchase and the sticker self-expires to prevent the purchaser from reusing the sticker at another time.
- a self-expiring parking permit which enables a parking attendant to determine from a relatively long distance whether the parking permit has expired.
- an advertising or promotional product wherein latent information becomes visible after a specified interval of time.
- an indicating device which indicates that service is required after the passage of an interval of time, for use in such applications as changing oil, changing lubricants, changing water, etc.
- an indicating device which, after the passage of an interval of time, indicates that a product should be replaced, e.g., an air filter, a water filter, batteries, etc.
- an identification badge which can be assembled at the location of use, such as at a convention center, a trade show or a meeting room.
- an identification badge wherein the possibility of duplication, tampering with, or counterfeiting is minimized.
- an indicating device which is a ticket which self-voids after the passage of a time interval.
- an indicating device which is a self-voiding bar code.
- a time indicating device which is not easily counterfeited.
- a warning label or sign which the warning message self-expires or disappears after a specified interval of time.
- a tamper indicating packaging tape which indicates that a package has been tampered with.

Yet another objective of the present invention is to provide indicating devices herein in form a band.

Provided is an indicating device which is foldable.

Provided is a method of making name badges.

Provided are indicating devices having a thin metallic layer, e.g., that of a metal for monitoring doneness of food.

Provided is a self-heating package doneness indicating device composed of at least one substrate having at least one metallic indicator and at least one activator.

Provided is a self-heating package doneness indicating device composed of at least one substrate having a metallic indicator and an activator which react with the said metallic indicator.

Provided is a self-heating package doneness indicating device composed of at least one substrate having a metallic layer as an indicator and an activator which melts and react with the said metallic layer at a predetermined temperature.

Provided is a microwave energy interactive indicating device.

Provided is a microwave doneness indicating device composed of at least one substrate having at least one metallic indicator and at least one activator.

Provided is a microwave doneness indicating device composed of at least one substrate having a metallic indicator and an activator which reacts with the said metallic layer.

Provided is a microwave doneness indicating device composed of at least one substrate having a metallic as an indicator and an activator which melts and react with the said metallic layer at a predetermined temperature.

Provided is a microwave energy interactive indicating device comprising a microwave energy interactive material supported on a polymeric layer, an activator layer superposed with the microwave energy interactive layer and a metallic indicator layer.

Provided is a microwave doneness indicating device composed of a layer of polymeric fibrous material, a layer of thermoplastic polymer layer having microwave susceptive layer, an activator layer on a microwave energy susceptive layer and a metallic indicator layer.

Provided is an above described microwave doneness indicating devices and bonded into an integral structure by application of heat and/or pressure.

Provided is a microwave energy interactive indicating device composed of a paper or board substrate, a layer of a polymer, a metal or other microwave interactive susceptor material on a polymer layer, an activator layer either in an overall layer or preselected pattern and their plurality.

Provided is a microwave susceptor indicating device which includes a layer of thermoplastic polymer material having a microwave susceptive material, a layer of patterned activator in contact with and capable of etching microwave susceptive material, a polymeric fibrous material layer on the activator layer and bonded into an integral structure by application of heat and pressure.

Provided is microwave energy interactive indicating device composed of a metallic layer which is less than 20 Angstroms.

Provided are indicating device applied on self-heating meal package and doneness of microwaveable foods.

Provided are above devices and process where metallic layer is a metal or an alloy.

Provided are above devices and process where metallic layer is aluminum, tin, copper, zinc and their alloys.

Provided is a microwave energy interactive indicating device composed of a low melting metal or an alloy.

Provided is a temperature indicating device composed of at least one substrate having at least one metallic indicator and at least one activator.

Provided is a temperature indicating device composed of at least one substrate having a metal as indicator and an activator which react with the said metal.

Provided is a temperature indicating device composed of at least one substrate having a metal as an indicator and an activator which melts and react with the said metal at a predetermined temperature or temperature range.

It is an object of the present invention to provide a temperature followed by time-temperature indicating devices having a metallic layer.

It is an object of the present invention to provide an indicating device having a metallic layer for monitoring a pre-determined temperature which also monitors time-temperature once the said temperature is reached.

It is an object of the present invention to provide below ambient temperature and time-temperature indicating devices having a metallic layer.

It is an object of the present invention to provide above ambient temperature-and-time-temperature indicating devices having a metallic layer.

It is an object of the present invention to provide freeze and time-temperature indicating devices having a metallic layer.

It is an object of the present invention to provide a temperature and time-temperature indicating devices wherein a metal is used as an indicator.

It is an object of the present invention to provide a temperature and time-temperature indicating devices wherein a metal is used as an indicator and a solid activator which melts at or around 0° C.

It is an object of the present invention to provide an indicating device for a pre-determined temperature which also monitors time-temperature once the said temperature is reached wherein a metal is used as an indicator.

It is an object of the present invention to provide below ambient temperature and time-temperature indicating devices wherein a metal is used as an indicator.

It is an object of the present invention to provide freeze and time-temperature indicating devices wherein a metal is used as an indicator.

It is another object of the present invention to provide a device which irreversibly indicates a temperature excursion below a threshold temperature wherein a metallized plastic film is used as an indicator.

Provided is a temperature indicating device, including freezing comprising: (a) a metallized substrate; (b) a layer of an activator on the said metallized substrate which upon cooling to a pre-determined low temperature, releases an activator.

Provided is a process of monitoring a temperature including steps of freezing of an object comprising the above said device.

It is an object of the present invention to provide a temperature and time-temperature indicating device wherein a metal is used as an indicator and a layer for controlled release of an activator.

It is an object of the present invention to provide a temperature and time-temperature indicating device wherein a metal is used as an indicator and a layer for controlled release of an activator is provided by rupturing of microcapsules.

It is an object of the present invention to provide a temperature and time-temperature indicating device wherein a metal is used as an indicator and a layer for controlled release of an activator is provided by dissolution or melting of microcapsules.

Yet other main objective of this invention is to provide indicating device in form of a long tape.

Yet other main objective of this invention is to provide indicating device in form of a long tape having an adhesive.

Yet other main objectives of this invention are to provide an indicating device:
  in form of a long adhesive tape for application on a box or carton of perishables or time and/or temperature sensitive objects.
  used as a sealing tape.
  in form of a sealing tape for monitoring shelf lives of perishables.
  used as a sealing tape having all features of time, temperature, time-temperature, thawing, freezing, microwave, humidity, ionizing radiation and sterilization and/or other indicating devices disclosed herein.

Provided is an indicating device sealing tape comprised of an activator tape and an indicator tape to form an indicating device tape.

Provided is an indicating tape device made by applying an indicator sealing tape on an activator tape.

Provided is an indicating tape device further having an adhesive layer to apply on an object.

Provided is an indicating device which is activated by heating, pressure, radiation and water.

Provided is an indicating tape device applied on a packaging tape.

Provided is an indicating tape device applied under a packaging tape.

Provided is a process of applying an indicating tape device on an object.

Provided is a process of applying an indicating tape device on a box containing perishables.

Provided is a process of applying an indicating tape device on a box containing items which are sensitive to time, temperature, time-temperature, humidity and/or steam.

Provided is a process of applying an indicating tape device to seal a box or a package.

Provided is a process of applying an indicating tape device on a box containing items to be processed or monitored.

Provided are above said indicating tape devices having a metallic layer.

Provided is a flow chart of making decision at different stages of activated indicating device.

Provided are one or more processes of making an indicating device (with or without a metallic layer), applying on a box containing units of a product to be processed or process to be monitored, indicator undergoing a noticeable change, quality of the units being accessed after the process, decision made to accept, use, reject or return, indicator tape being removed or cut, product being accepted or rejected.

Provided are hand held and powered indicating dispensing systems which hold indicator and activator tapes, activates them, dispense the activated device and apply on an object.

Provided is a tape dispenser to dispense an activated device and apply on an object including a perishable or container of a perishable.

Provided is a tape dispenser to dispense an activated device and apply on a box.

Provided is a tape dispenser to dispense an activated device sealing a box containing more than one unit of an item including perishables.

Provided is a label dispenser to dispense an activated label device and apply on a box.

Yet other main objectives of the present invention are to provide:
  a sterilization indicating device composed of a thin metallic layer.
  a sterilization indicating device composed of a thin layer of a metal or an alloy.
  a sterilization indicating device composed of a thin layer of aluminum, copper, zinc, tin or their alloys.
  a sterilization indicating device composed of a 10-10,000 Angstroms layer of aluminum, tin, copper, zinc or their alloys.
  a sterilization indicating device composed of a thin metallic layer on a plastic substrate.
  a sterilization indicating device composed of a 10-10,000 Angstroms layer of aluminum, copper, zinc or their alloys on a plastic substrate.
  a sterilization indicating device composed of a thin metallic layer on a plastic substrate and additionally having at least one permeable or barrier layer.
  a sterilization indicating device composed of a thin layer of a metal or an alloy on a plastic substrate and additionally having at least one permeable or barrier layer on the said metal.
  a sterilization indicating device composed of a thin metallic layer on a plastic substrate and additionally having at least one permeable or barrier layer in form of a wedge.
  a sterilization indicating device composed of a thin layer of aluminum, copper, zinc or their alloys on a plastic substrate and additionally having at least one permeable or barrier layer on the said metal.
  a sterilization indicating device composed of a 10-10,000 Angstroms layer of aluminum, copper, zinc or their alloys on a plastic substrate and additionally having at least one permeable or barrier layer on the said metal.
  a sterilization indicating device composed of a thin layer of a metal or an alloy on a plastic substrate and additionally having a layer containing an activator.
  a sterilization indicating device composed of a thin layer of a metal or an alloy on a plastic substrate and additionally having a layer containing an activator composed of an acid, a base, a salt or chelating agent.
  a sterilization indicating formulation composed of particles of a metal or a metal alloy as an indicator and an activator which reacts with the metal or the metal alloy.
  a sterilization indicating formulation composed of particles of aluminum, copper, tin, zinc or their alloys as an indicator and an activator which reacts with the said metals.
  a said sterilization indicating formulations coated on a substrate to make a sterilization indicating device.
  a said sterilization indicating formulations coated on container including a pouch containing an object to be sterilized.
  a said sterilization indicating device having properties or features of TI and TTI disclosed herein.
  a process of monitoring sterilization with the said sterilization indicating devices.
  a method of steam sterilization of an article comprising a steam sterilization indicating composition comprising a thin metallic layer.
  a method of steam sterilization of an article comprising a steam sterilization indicating composition comprising a thin metallic layer of a metal or an alloy on a substrate.

a method of monitoring steam sterilization of an article comprising a steam sterilization indicating composition comprising a thin layer of a metal or an alloy on a substrate and capable of reacting with steam.

a method of monitoring steam sterilization of an article comprising a steam sterilization indicating composition comprising a thin layer of a metal or an alloy on a substrate and capable of reacting with steam and being destroyed.

a method of monitoring steam sterilization of an article comprising a steam sterilization indicating composition comprising a thin layer of metal on a substrate and capable of reacting with steam but not with dry heat.

a sterilization indicating composition containing a metallic indicator and binder further comprising a binder which is polymeric.

a sterilization indicating composition further comprising a surfactant, a defoamer, a filler, a metallic indicator, a plasticizer, a flow aid, a binder, an activator and/or a solvent.

a steam sterilization indicating composition preparable by combining components comprising a metal or an alloy, a binder and an activator.

a steam sterilization indicating device comprising a substrate having coated thereon at least a portion of one major surface thereof the metallic steam sterilization indicating formulation.

a sterilization indicating device adapted for insertion into a sterilization chamber of a pre-vacuum steam sterilizer for indicating the presence of unacceptable levels of non-condensable gas comprising a metallic indicator.

sterilization indicating devices composed of a metallic indicator and water, water vapor, steam, humidity, moisture, ethylene oxide, hydrogen peroxide, peracetic acid, formaldehyde, ozone plasma, ionizing radiation and dry heat as agents for the processes.

said sterilization indicating devices wherein said activator is created from its precursor.

said sterilization indicating devices having a catalyst to accelerate the reaction.

Provided are said (metallic) indicating devices applied on an item or a box containing items to be sterilized.

Provided are said (metallic) indicating devices applied on an item or a container containing a biological waste.

Provided are said (metallic) indicating devices applied on an item or a box containing items to be sterilized with steam, dry heat, ethylene oxide, plasma, peracetic acid, formaldehyde, ozone and high-energy radiation.

Yet other main objectives of the present invention are to provide:

an ink, paint, plastisol or coating formulation composed of fine particles of a metallic indicator, a binder a vehicle and an activator or its precursor.

a coating composed of fine particles of a metallic indicator, a binder and an activator or its precursor.

a coating composed of fine particles of a metal, a binder and an activator.

a coating composed of fine particles of a aluminum, copper, zinc, tin or their alloys, a binder and an activator.

an ink or paint formulation and its dried coating on a substrate composed of fine particles of aluminum, a binder, a vehicle and an activator or a precursor which is acidic, basic, or oxidant having capability reacting with aluminum, copper, zinc and their alloys, their oxides or a dried coating of it on a substrate.

a process of treating the above coatings with hot water, water vapor, humidity, moisture or high temperature steam.

a process of treating the above coatings with hot water, water vapor, humidity, moisture or high temperature steam and determining the treatment by change in opacity of the said coating.

It is an object of the present invention to provide a relatively small, inexpensive and disposable test pack composed of the said indicating device for use in pre-vacuum steam sterilizers to determine whether the sterilizer is functioning in accordance with proper standards by simulating air evacuation and steam penetration conditions of the conventional pack described in the Bowie and Dick protocol so as to define an appropriate challenge for a residual air test in a pre-vacuum sterilizer.

It is another object to provide the above and related objects of the present invention to obtain a device adapted for insertion into a sterilization chamber for indicating the presence of unacceptable levels of non-condensable gas.

Provided are metallic encapsulated indicating devices which can be activated when desired and composed of at least one metallic indicator, such as a thin layer of metal or fine particles of a metal and at least one activator, in which at least one of the components is encapsulated, protected or separated with a barrier layer to prevent one reacting with the another.

Provided are metallic encapsulated devices having at least one additional protective, reactive, permeable, barrier or activating layer.

Provided are activated metallic encapsulated devices for monitoring time, time-temperature, thaw, freeze, humidity, ionizing radiation, temperature, microwave, sterilization (including steam, ethylene oxide, plasma, formaldehyde, dry heat, hydrogen peroxide and peracetic acid), chemical, biological and chemical agents and/or electronic devices, such as RFID, EAS and alike based on controlled etching of the said indicator with the said activator.

Provided are metallic encapsulated devices having a thin metal layer and a layer of microcapsules of an activator or is precursor on to the metal layer, both being on the same side of a substrate.

Provided are processes of activation of metallic encapsulated devices destroying the integrity of the said barrier layer.

Provided are processes of activation of metallic encapsulated devices by pressure, heat, light, laser, moisture, humidity, steam, water and chemicals.

Provided are metallic encapsulated devices applied on an object.

Provided are optical waveguide sensors and processes for monitoring changes in chemical or physical parameters, using a metallized optical fiber, with and without a coating of an activator or its precursor.

Provided are optical waveguide sensors for monitoring time, temperature, freezing, defrost, time-temperature, radiation, sterilization, a chemical, an agent, pressure, stress and alike using a metallized optical fiber with and without a coating of an activator or its precursor.

Provided are agent indicating/monitoring devices composed of a metallic indicator and a precursor for an activator for monitoring exposure to a chemical or biological agent.

Provided are said agent monitoring devices applied on an object for monitoring exposure to a toxic chemical agent including a war chemical, such as muster and nerve agents, biological agents, such as a virus (e.g., anthrax) and bacteria (e.g., small pox), a hazardous chemical, such as chlorine, chlorine dioxide, ozone, hydrogen peroxide, hydrogen sulfide, carbon monoxide, nitrogen dioxide, ammonia, and hydrazine and humidity/moisture and oxygen.

Provided are agent indicating monitoring devices composed of a metallic indicator for monitoring concentration of an agent.

Provided is a device for the manufacture of printed circuit boards comprising: a substrate coated there on a metal layer, a resist or barrier layer in form of a pattern of printed circuit and an activator layer.

It is an object of the invention to create an electronic circuit device composed of a substrate having a thin metal layer and a layer of patterned activator having capability of etching the said metal layer or having a patterned barrier layer between the metal and activator layers.

It is an object of the invention to create a multilayer device composed of alternating layers of a substrate having a thin metal layer and a patterned layer of activator or a pattern barrier layer between the metal and activator layers.

It is an object of the invention to create a multilayer device composed of alternating layers of a substrate having a thin metal layer and a patterned layer of activator having capability of etching the said metal layer or a pattern barrier layer between the metal and activator layers, wherein said activator melts and etch at an elevated temperature.

Provided is a device for the manufacture of printed circuit boards comprising: a substrate coated their on a metal layer, an activator layer or a barrier layer in form of a pattern of a printed circuit and an insulating layer.

Provided is a method for making a printed circuit board comprising: providing a substrate coated their on a metal layer, applying an activator layer in form of a pattern of a printed circuit.

Provided is a method for making a printed circuit board comprising: providing a substrate coated their on a metal layer, applying a resist or a barrier in form of a pattern of printed circuit and an activator layer.

Provided is a method for making a printed circuit board comprising: providing a substrate coated their on a metal layer, applying an activator layer in form of a pattern of a printed circuit and an insulating layer.

Provided is an EAS device composed of: a dielectric layer having a thin metal layer on both the sides, an activator layer on the metal layers and a means of creating circuit patterns.

Provided is an EAS device composed of: a dielectric layer having a thin metal layer on both the sides, an activator layer on the metal layers and a means of creating circuit patterns and protecting the device dielectric layers.

Provided is a method of making an EAS device comprising: depositing a metal layer on each side of a dielectric substrate, applying patterned barrier layer of the circuit and applying an activator layer on each side of the metal layers.

Provided is a method of making an EAS device comprising: depositing a metal layer on each side of a dielectric substrate, applying patterned activator layer on each side of the metal layers to create circuit patterns.

Provided is a method of making an EAS device comprising: depositing a metal layer on each side of a dielectric substrate, applying patterned activator layer on each side of the metal layers and etching the metal layers to create circuit patterns.

Provided is a method of making an EAS device comprising: creating conductive circuit patterns on both the sides of a dielectric layer having a metal layer on each side and by etching with an activator tape.

Provided also is an EAS device composed of circuit patterns on dielectric substrates and their utility in radio frequency electronic article surveillance tag circuits.

Yet other main objectives of the present invention are to provide:

an activator tape capable of reacting with a conducting surface.

a process of applying an activator tape on an electronic device.

a process of applying an activator tape on a conducting path of an electronic device.

a process of applying an activator tape on a conducting path or a layer of an electronic circuit.

an activator tape capable of reacting with a conducting path or a layer of an electronic circuit.

an activator tape when applied is capable of reacting and substantially destroying or reducing the conductivity of the conducting path or a layer of an electronic circuit.

an activator tape capable of reacting with a conducting layer and creating conducting lines.

an activator or an activator tape upon reacting with a conducting path capable of making the device substantially ineffective or responding in a different way.

a process of applying an activator tape on an inlay of a RFID device.

a process of applying an activator tape on an antenna or a conducting path of a RFID device.

an activator tape when applied is capable of reacting with an antenna or a conducting path of a RFID device substantially reducing or destroying the conductivity of the path.

an activator tape when applied is capable of reacting with an antenna or a conducting path of a RFID device substantially reducing or destroying the conductivity and making the device non-readable.

an activator tape when applied on a metal layer is capable of creating an antenna from a conductive layer.

an RFID device having two RFID inlays, one having an activator tape which is capable of destroying its conductive paths.

a process of creating a RFID device by applying an activator tape on a conductive surface having a patterned barrier layer.

a process of reading a RFID device before and after activation or de-activation.

a process of reading a RFID device after creating an antenna.

a process of applying activated RFID device on an object said RFID devices used as time, temperature, time-temperature, thawing, freezing, microwave, humidity, ionizing radiation and sterilization and/or other indicating devices disclosed herein including monitoring of an agent.

Provided is a metallized patterning composite comprising: a polymer layer having a thin metal layer, a discontinuous layer of activator in form of a pattern to create a design and a protective polymer layer.

Provided is a metallized patterning composite comprising: a polymer layer having a thin metal layer, a patterned barrier layer and a layer of activator and a protective polymer layer.

Provided is a patterning metallized composite comprising: a polymer layer having a thin metal layer, a discontinuous layer of activator in form of a pattern to create a design, a protective polymer layer and a bonding layer to bond the composite to a substrate either polymer layer.

Provided is the said metallized pattern composite wherein said layers are laminated together.

Provided is the said metallized pattern composite wherein said bonding layer is composed of a pressure sensitive, heat activated adhesive or radiation cured adhesive.

It is another object to provide a toy, gimmick, message, gift card, greeting card etc made from the indicating device.

Further provided are binders, emulsions, latexes and solutions of polymers for the said devices which are self crosslinking or can be crosslinked with an additive.

Further provided are emulsions, latexes and binders for the said devices which are unaffected by sterilants including humidity and steam.

Further provided are pH neutral or near neutral polymeric solutions, latexes, and dispersions as binders for the said devices.

Further provided are polyurethane and carboxylated polyacrylics/polyacrylates as binders for the said devices.

Further provided is a mixture of at least one indicating dye or pigment for the said devices.

Further provided is a mixture of color indicators of different nature or non-indicating pigments or dyes for the said devices.

Provided is a substrate or similar layer for the above said devices composed of polyethylene, polypropylene, a polymeric ionomer, polyvinyl fluoride, polyvinylidene chloride, acrylonitrile butadiene styrene, polyvinylidene fluoride, thermoplastic olefin, thermoplastic polyurethane, polyvinyl chloride, polyethylvinyl acetates, polyesters or polyamides.

Provided is an adhesive or similar layer for the above said devices composed of a pressure sensitive or heat activated adhesive composed of acrylic pressure-sensitive adhesives, silicone pressure-sensitive adhesives, thermally activated adhesive, polyester and isocyanate adhesive, polychloroprene and isocyanate adhesive, polyurethane and isocyanate adhesive, polyurethane and aziridine adhesive.

Provided is a metal or similar layer for the above said devices composed of zinc, tin, gallium, aluminum, magnesium, cadmium, copper, nickel, cobalt, iron, stainless steel, gold, platinum, chromium, palladium, rhodium and their alloys.

Further provided are said indicating device wherein at least one layer is larger than the rest of the device.

Further provided is an apparatus and processes for reading the said indicating device comprising a bar code reader, spectrophotometer, optical densitometer or a linear charge coupled device (CCD) capable of detecting the said changes.

Further provided are precursors for the said activators.

Further provided are precursors for the said activators for said indicating device.

Further provided are precursors for production of acids, bases and salts.

Further provided are precursors for the said activator for time, temperature, time-temperature, thaw, freeze, humidity, ionizing radiation, microwave, sterilization (including steam, ethylene oxide, plasma, formaldehyde, dry heat, hydrogen peroxide and peracetic acid), chemicals, biological and chemical agents, and electronic devices, such as RFID, EAS, printed electronics, printed electrodes and alike.

Also provided are processes and means of production of activators from said precursors.

It is an object of this invention to provide for an indicating system that overcomes the deficiencies of the prior art by providing a more relatively sharp induction period of the indicating event.

It is also an object of the invention that the system provides for an easily readable indication of the indicated event or objective.

It is another object of the invention to provide an indicating system that can signal either a specific occurrence or the progress of an ongoing occurrence.

It is yet another object of the invention to provide for a system that can provide a message, warning, further instructions, expiration times.

It is another object of the invention to provide for an indicating system that is self-expiring or self-voiding.

This invention relates to an indicating system that can be used in a variety of indicating devices.

BRIEF DESCRIPTION OF THE FIGURES

The foregoing and other objects, features and advantages will be apparent from the following description of the preferred embodiments of the invention as illustrated in the accompanying drawings, examples and preferred embodiment. The invention is more fully described below in conjunction with the figures wherein:

FIG. 8 shows a schematic presentation of some selected basic layers of an indicating device with (b) and without (a) a permeable layer.

FIG. 11 shows a schematic presentation of a self expiring visitor's badge (time indicator) having a colored opaque activator substrate with dark X printed on it and an optional permeable layer; (a) cross sectional view of the badge, (b) visitor's photo viewed from top when issued and (c) the photo viewed from the top after the expiration.

FIG. 24 shows a schematic presentation of RFID inlays without an activator tape (a) and an activator tape applied at different locations on the antenna (b) and (c). A RFID device with two RFID inlays, one having an activator tape is shown in (d).

FIG. 35 shows an example of box sealed with an indicating sealing tape upon activation (a) and upon expiration (b).

FIG. 38 shows an example of creation of an antenna for a RFID and similar electronic devices.

FIG. 40 shows an example of a steam sterilization indicating device made from a aluminum powder and an activator treated with different sterilization conditions.

BRIEF DESCRIPTION OF THE INVENTION AND PREFERRED EMBODIMENTS

Figure 1:
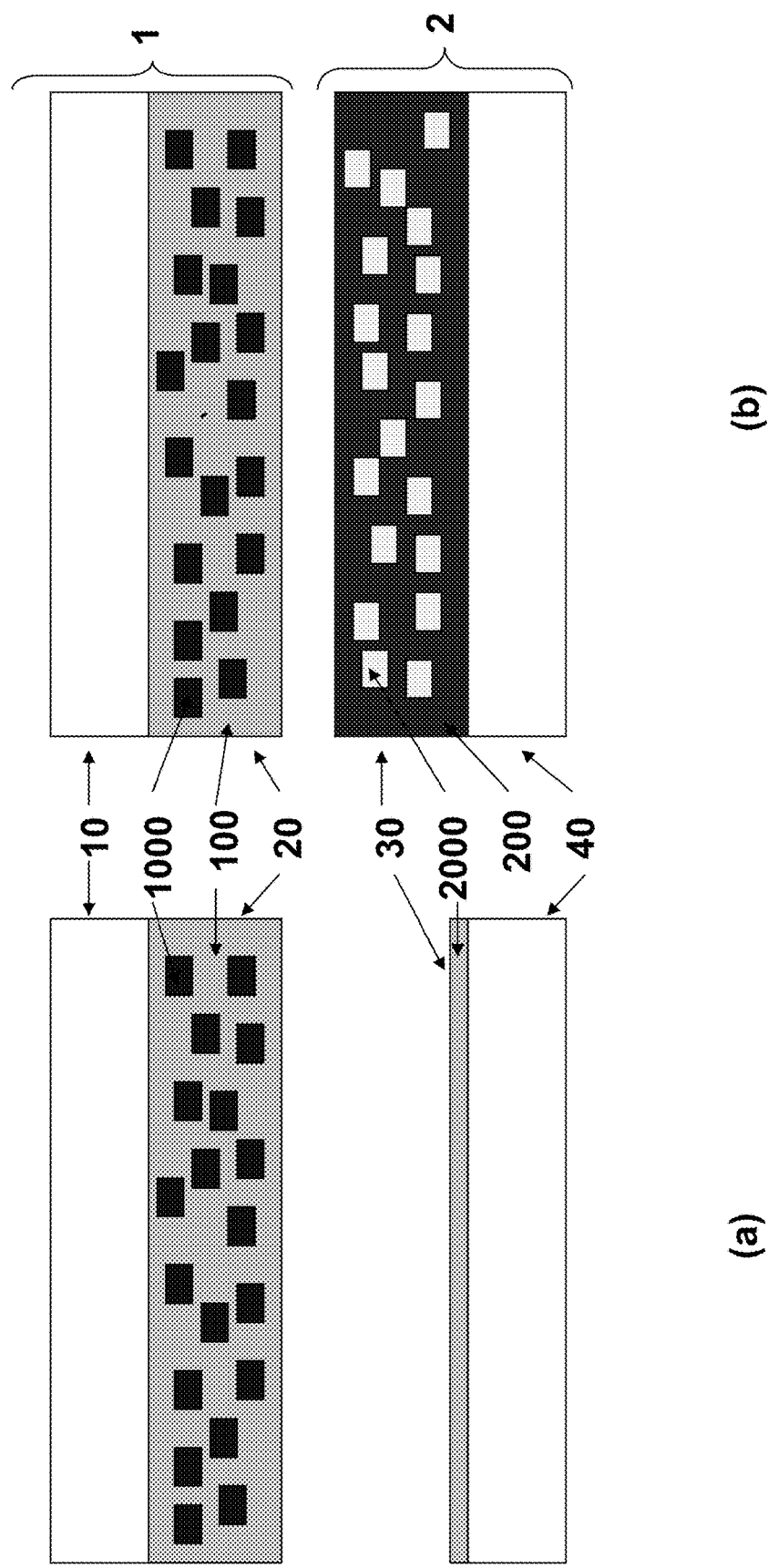
FIG. 1 shows schematic cross sectional views of a basic current (a) and prior art (b) indicating devices. Cross sectional view of the activator 20 and the metal layer 30.2 with its naturally formed oxide layer 30.1 on substrate 40 is shown in FIG. 1(c). The ultra thin oxide layer is not shown in the rest of the Figures.
Figure 1:
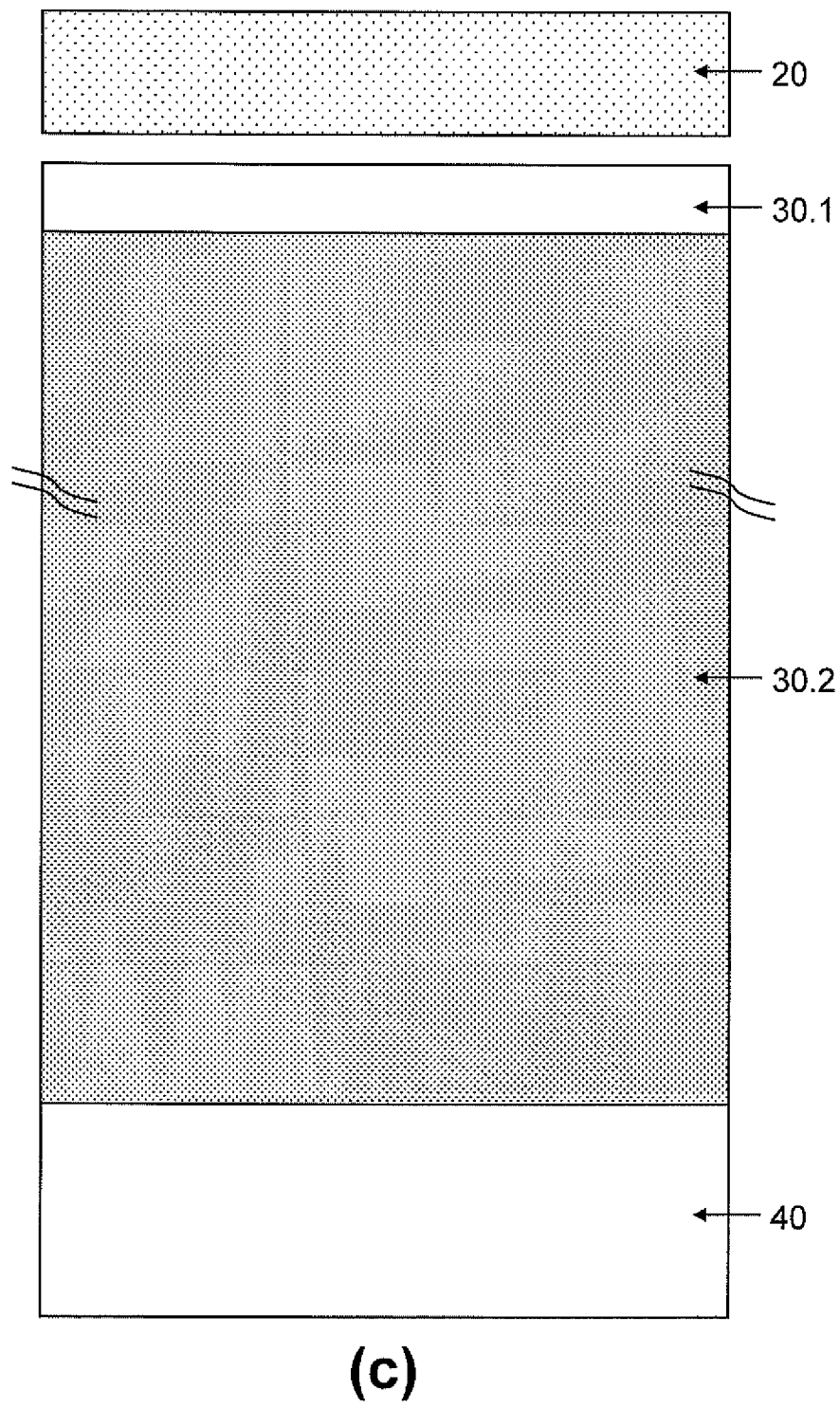

This invention relates to an indicating system that can be used in a variety of indicating devices.

The indicating system of the invention is comprised of a metallic indicator layer and an activator layer, wherein the metallic layer is a metal, a metal alloy, a semi-metallic material or a semi-conducting material. The activator is comprised of an agent that is capable of irreversibly changing the indicator layer by etching, or destroying the layer or by changing the properties of the layer.

The indicator layer of the invention comprises a material that is conductive or becomes conductive, reflective, highly opaque, self binding and/or impermeable and which becomes invisible, transparent, semi-transparent, non-conductive or is destroyed when contacted/reacted with an activator of the invention.

Preferred indicator materials of the invention include a metal, such as alkali metals, alkaline earth metals, transition metals, post transition metals, lanthanide and actinides metals and their alloys or more preferably low melting metals, bronzes and alloys.

Preferred metals include aluminum, tin, zinc, copper, manganese, magnesium, nickel, cobalt, iron, sodium, potassium, lithium, calcium, gallium, cesium, germanium, indium and their alloys. Most preferred is aluminum, copper, zinc or tin and their alloys.

Preferred metals and metal alloys of the invention include those that are more sensitive to water and also to acids, bases, chemical or biological agents and salts. An alloy of more than one metal, such as that of aluminum-magnesium-copper can also be used. Alloys of aluminum are described in many books, e.g., "Aluminum and aluminum alloys", Joseph R. Davis, J. R. Davis & Associates, ASM International, Materials Park, Ohio, 1993 and many of them could be used to make the indicator.

A variety of aluminum bronzes of differing compositions, found to have industrial uses, with most ranging from 5% to 11% aluminum by weight, the remaining mass being copper or other alloying agents, such as iron, nickel and silicon are also useful in the invention. Aluminum and other bronzes, such as copper-zinc can also be used as indicators.

The activator of the invention comprises any composition that can react with the indicator to cause an irreversible change in the chemical composition of the indicator. More particularly, activators of the invention comprise acids, bases, salts, chemical or biological agents, —chelates, water and oxygen that readily attack metals and their alloys. Also contemplated within the invention are precursors of the activators, that is, compositions that can be acted on by additional components of the indicating system to form the activators of the invention.

In a preferred embodiment are inorganic acids, such as phosphoric acid, phosphorous acid, hydrochloric acid, nitric acid, sulfuric acid, sulfonic acid, carboxylic acid, their precursors or a mixture thereof.

In another preferred embodiment are a hydroxide, alkoxide or aryloxide of a metal or a cation of nitrogen. In another embodiment of the invention the activator is a combination of a salt of a weak acid and a strong base, a strong acid and a weak base, a strong acid and a strong base, or a weak acid and a weak base.

In another embodiment are a halide, oxide, nitrate, nitrite, phosphate, phosphate, phosphonate, sulfate, bisulfate, silicate, sulfite, sulfide, bisulfide, sulfonate, cyanate, cyanide, thiocyanate, acetylacetonate, carboxylate, percarboxylate, carbonate or bicarbonate anion of a mono, di and trivalent cation of a metal or polyatomic anion of nitrogen, sulfur and phosphorous or mixture thereof, for example ammonium bromide, ammonium thiocyanate, calcium chloride, copper chloride, copper ammonia complex, lithium acetylacetonate, lithium chloride, lithium formate, phosphorous, phosphorous pentoxide, potassium acetate, potassium benzoate, potassium bromide, potassium chloride, potassium ferrocyanide, potassium ferricyanide, potassium formate, sodium acetate, sodium bicarbonate, sodium bromide, sodium carbonate, sodium cyanate, sodium diethyldithiocarbamate, sodium iodide, sodium metasilicate, sodium nitrate, sodium sulfite, sodium tetrafluoroborate, sodium tetraborate, sodium thiocyanate, sodium thiosulfate, tetraethylammonium bromide, zinc chloride or a mixture thereof.

Additional preferred activators include a chelate or complex of a metal cation, such as that of a transition metal cation, or an amine or ammonia complex of copper chloride or nickel chloride.

A preferred embodiment of the invention relates to an indicating system comprising a) a metallic indicator layer; and b) an activator or a precursor of the activator in close contact with or in proximity of the indicator layer. Examples of this embodiment include devices wherein the activator is oxygen, water in the form of ambient humidity or steam, vapor of an agent, or microwave radiation, wherein the activator reacts directly with metal layer without being placed directly in contact with the metal layer by way of a tape or other applicator. More particularly, a thin metal layer, such as a metallized plastic film, can be used for monitoring chemicals such as water and toxic chemicals wherein the water and toxic chemicals act as activators for the metal on the plastic film. This is an example of the indicating system of the invention wherein the activator is an activator layer without a binder. Claim 1 calls for an indicating system wherein the activator or precursor layer does not react with the indicator until it is exposed to an agent or a process to be monitored.

In a particular embodiment, the agent is steam, ethylene oxide, formaldehyde, ozone, peracetic acid, hydrogen peroxide, a chemical agent or a biological agent. Another embodiment of the invention relates to an indicating system comprising; a) a metallic indicator layer; and b) an activator or a precursor of the activator on the said metallic indicator layer. Examples of this embodiment include a device wherein a dry coat is deposited on metal layer for sterilization, wherein the dry coat does not react with the indicator until it is exposed to an agent, for example steam, ethylene oxide, hydrogen peroxide and the like. The indicator layer may be deposited on a substrate such as a plastic film.

In another embodiment the indicator layer is deposited on a substrate, wherein the substrate is a plastic film having a continuous metal layer thickness of less than about 10,000 Angstroms. The indicator layer typically is a continuous metal layer having a thickness of less than about 1,000 Angstroms or a particulate layer having a thickness of less than about 10 microns.

Another embodiment of the invention relates to an indicating system which comprises a) a metallic indicator layer; and b) an activator or a precursor capable of producing an activator; c) a binder for the activator and d) an optional binder which binds the activator and indicator layers. In this embodiment it is preferred that the indicator be affixed to a substrate wherein the substrate is for example a plastic film with an optional pressure sensitive adhesive layer.

Another embodiment of the invention relates to an indicating system which comprises a) an indicator tape and b) an activator tape, wherein the indicator tape comprises a substrate to which is affixed at least one metallic layer and the activator tape comprises an activator or a precursor capable of producing an activator which is dissolved or dispersed in at least one matrix layer.

Yet another embodiment of the invention relates to an indicating system which comprises a composite an indicator tape and an activator tape, bonded together with at least one bonding layer wherein the indicator tape comprises a substrate which is affixed to at least one metallic layer; the activator tape or a tape containing a precursor capable of producing activator is comprised of a substrate which is affixed to at least one matrix layer containing an activator.

Another embodiment of the invention relates to an indicating system which can monitor a material or a process.

More preferred is the indicating system wherein the material is a chemical, a chemical agent or a biological agent or its concentration and the process is time, temperature, time-temperature, freeze, thaw, humidity, doneness of food, microwave, pressure, radiation and sterilization including, for example, sterilization with steam, ethylene oxide, peroxide, plasmas of peroxide, formaldehyde, dry heat and ionizing radiation.

In another embodiment of the invention the indicating system is used to indicate the status of a perishable wherein the perishable is a food item, such as fresh, refrigerated, or frozen, vegetables, fruits, meats, fish, poultry, dairy products, bakery products, juices, pre-cooked foods, soft and alcoholic beverages, or a nonfood item such as a pharmaceutical, vaccine, biological sample such as sera, blood, or blood plasma, cosmetics, reactive chemical compound, biochemical product, battery, x-ray film or photographic film.

In another embodiment of the invention the indicating system is used as, for example, in, for or on a safety sticker, self-timing retail sticker, biological industrial process monitor, self-expiring sticker to prevent re-use, security ID label, visitors badge, self-expiring parking tag, package and shipping label, wrist band, time indicating ticket for trains, buses, spot events, theaters etc, self-expiring pass for tours, emergency rooms, hospitals, museums, and other locations, race track pass, security label for screened luggage, purse, bag at airports to indicate that such items have been inspected, and at unmanned but video controlled entrances for visitors where a self-expiring visitor label is issued electronically. In addition, the indicating system can be used to indicate limited time consumer use for items that have been opened or in use and should be used within certain period, including but not limited to drinks, food items, health, personal and family care products. Also included are "gimmick" type applications such as in toys, gimmick, messages, patterns, designs, gift cards, and greeting cards In another embodiment of the invention, the indicating system is used for or applied on medical products, food, biological waste, or to monitor the sterilization of such items.

In another embodiment, the tape can also have an adhesive layer to attach the indicating system to the item to be monitored.

In another embodiment of the invention, the indicating system of the invention can be used as an RFID or printed circuit board. More particularly the invention relates to a device comprising a substrate having a thin metal layer, a patterned layer of a barrier material and an activator layer. When the device is activated, certain areas on the indicator layer are protected by the barrier material, allowing the remaining metal layer to create at least one conductive path for an electronic device or a metallic pattern. The electronic device can additionally have an electronic chip or component. Further, in a more particular embodiment, in an electronic device composed of an RFID inlay or a conductive path connected to an electronic chip, the activator layer can destroy a conductive path of the indicator, thus destroying the electronic device. Also contemplated is an EAS device composed of: a dielectric layer having a thin metal layer and an activator layer on both the sides.

The indicating system of the invention can also have at least one message which appears as a word or symbol on at least on one side of the indicator layer. The message can be in color. A message can be on both sides of the indicator layer. In certain instances the system can contain at least two messages which do not start to become observable at the same time. An example is an indicator of the status or quality of an item when the indicating system is applied on or before the treatment of the item and a second message alone or in combination with the first indicating status or quality of the item after its treatment, such as, where the first message indicates un-doneness, freshness, usability, acceptability of the item and the second message alone or in combination with the first indicates doneness, spoilage, not usability and unacceptability of the item after a treatment or where the first message indicates non-sterile, non-usability, not-acceptability of the item and the second message alone or in combination with the first indicates doneness, sterile, usability and acceptability of the item after a treatment.

In another embodiment of the invention the indicator layer is comprised of indicating ink, paint, gel, plastisol and the like. The metallic indicator is in the form of particles and can have a solvent vehicle or not. More particularly, an embodiment comprises indicating ink, paint, gel, plastisol and alike composition comprising; a) said indicator in form of particles b) said activator and c) a binder applied on a substrate (dried coating, i.e., no solvent). Another embodiment comprises an indicating device that can monitor (1) a material which is a chemical, biochemical, chemical agent or biological agent, its concentration or (2) a process which is time, temperature, time-temperature, freeze, thaw, humidity, pressure, radiation and sterilization including sterilization with steam, ethylene oxide, peroxide, plasmas of peroxide, formaldehyde and ionizing radiation.

In another embodiment of the indicating system, the activator layer comprises a precursor for the activator, such as an acid, base or salt. An example of a precursor is phosphorous pentoxide, which produces phosphoric acid when it reacts with water, and the like.

Another embodiment of the invention comprises a precursor for said precursor, such as phosphorous since white or yellow phosphorous reacts with oxygen to produce a precursor, phosphorous pentoxide, which further reacts with water to produce activator, phosphoric acid.

Additional precursors of an activator comprise monomeric or polymeric halo, halonium, sulfonium or phosphonium compounds.

Another embodiment of the invention relates to the process of using the indicating system of the invention on an object containing items to be processed or monitored.

Another embodiment of the indicating system of the invention comprises a system wherein an additional one or more layers are added to the system, wherein the layers are selected from a binder layer, a permeable to activator layer, a wedge shaped permeable to activator layer, a barrier to activator layer, reactive, destroyable or degradable barrier layer, an expiration indicating layer, a tamper indicating layer, an activation indicating layer, a message or image creating layer or a separating layer, a removable layer, a naturally formed oxide layer, a disappearing layer, an activatable layer, a microencapsulated layer, thermally printable, and the like, as are known in the art Yet another embodiment of the invention comprises an indicating sealing tape, comprising a two tape dispenser for the indicator sealing tape and the activator sealing tape, wherein the two tapes are dispensed simultaneously when applying the sealing tape on a container.

Printing on the indicating system of the invention, more especially on a substrate of the system, can be thermal printing, more particularly, direct thermal printing.

It is contemplated that any layer of the indicating system can contain a message or writing on either side of each layer.

Another embodiment is an indicating system wherein the time required for a change in the indicator layer or activation energy of the system is varied or adjusted by changing one or more of the parameters selected from the group of: thickness of the activator layer, thickness of the indicator layer, thickness of the permeable layer, concentration of the activator, concentration of the precursor, concentration of an additive in the activator, concentration of an additive in the permeable layer, nature of a solvent, surfactant and a catalyst, nature of the activator layer, nature of the indicator layer, nature of the permeable layer, nature of the additive and nature of a reaction accelerator and retarder.

Another embodiment of the invention is a high accuracy optical waveguide monitor, an electronic circuit or an EAS.

Also contemplated within the invention is an indicating system which is in the form of a safety sticker, self-timing retail sticker, biological industrial process monitor, self-expiring sticker to prevent re-use, security ID label, visitors badge, self-expiring parking tag, package and shipping label, wrist band, time indicating ticket for trains, buses, spot events, theaters, self-expiring pass for tours, emergency rooms, hospitals, museums, and other locations, race track pass, security label for screened luggage, purse, bag at airports to indicate that such items have been inspected, and at unmanned but video controlled entrances for visitors where a self-expiring visitor label is issued electronically.

In another embodiment, the indicating system is in the form of a toy, gimmick, message, pattern, design, gift card, or greeting card.

In another embodiment the indicating system is a part of an RFID, EAS or printed circuit board.

Another embodiment of the invention is a process to monitor the status of medical products, food, or biological waste which comprises placing the indicating system on the packaging of such medical products, food, or biological waste.

Yet another embodiment of the invention relates to process to monitor the presence or absence of a toxic chemical, an agent or water which comprises placing the indicating system in the area to be monitored and obtaining the information from the indicating system.

Another embodiment is a process to monitor a perishable item by placing the indicating system on or near the perishable item wherein the perishable item is a food item, or a nonfood item. More particularly one can monitor the limited time consumer use for items that have been on or the item to be monitored, wherein the item is selected from the group of drinks, food items, health, personal and family care products.

The invention also relates to a process of making the indicating systems of the invention. In one embodiment, the indicating tape of the invention can be made by laminating an activator tape on a metallic indicator tape. In another embodiment a layer of activator is coated on a metallic indicator with and without a permeable layer. In another embodiment, additional layers can be added to the indicating system.

Yet another embodiment of the invention relates to the detection and quantitative measurement or monitoring of chemical, biochemical or biological agents which is based on etching of metal or metallized optical wave guide. Chemical agents include a lethal agent, a blister causing agent, a blood affecting agent, a nerve agent, a pulmonary agent, an incapacitating agent or a riot control agent, such, for example, cyanogen chloride, hydrogen cyanide, ethyl-dichloroarsine, methyldichloroarsine, phenyldichloroarsine, Lewisite, 1,5-dichloro-3-thiapentane, 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether, bis(2-chloroethyl) ethylamine, bis(2-chloroethyl) methylamine, tris(2-chloroethyl)amine, tabun, cerin sarin, soman, cyclosarin, GV, VE, VG, VM, VR, VX chlorine, chloropicrin, phosgene, diphosphene, agent 15 (BZ), EA 3167, kolokol-1, pepper spray, CS gas, CN gas, CR gas and the like. Chemicals include toxic industrial chemicals such as, for example, acetone cyanohydrin, acrolein, acrylonitrile, allyl alcohol, allyl amine, allyl chlorocarbonate, allyl isothiocyanate, ammonia, arsenic trichloride, arsine, boron tribromide, boron trichloride, boron trifluoride, bromine, bromine chloride, bromine pentafluoride, bromine trifluoride, carbon disulfide, carbon monoxide, carbonyl fluoride, carbonyl sulfide, chlorine, chlorine pentafluoride, chlorine trifluoride, chloroacetaldehyde, chloroacetone, chloroacetonitrile, chloroacetyl chloride, chlorosulfonic acid, crotonaldehyde, cyanogen, 1,2-dimethyl hydrazine, diborane, diketene, dimethyl sulfate, diphenylmethane-4'-diisocyanate, ethyl chloroformate, ethyl chlorothioformate, ethyl phosphonothioicdichloride, ethyl phosphonous dichloride, ethylene dibromide, ethylene imine, ethylene oxide, fluorine, formaldehyde, hexachlorocyclopentadiene, hydrogen bromide, hydrogen chloride, hydrogen cyanide, hydrogen fluoride, hydrogen iodide, hydrogen selenide, hydrogen sulfide, iron pentacarbonyl, isobutyl chloroformate, isopropyl chloroformate, isopropyl isocyanate, methanesulfonyl chloride, methyl bromide, methyl chloroformate, methyl chlorosilane, methyl hydrazine, methyl isocyanate, methyl mercaptan, n-butyl chloroformate, n-butyl isocyanate, nitric acid, fuming, nitric oxide, nitrogen dioxide, n-propyl chloroformate, parathion, perchloromethyl mercaptan, phosgene, phosphine, phosphorus oxychloride, phosphorus pentafluoride, phosphorus trichloride, sec-butyl chloroformate, selenium hexafluoride, silicon tetrafluoride, stibine, sulfur dioxide, sulfur trioxide, sulfuric acid, sulfuryl chloride, sulfuryl fluoride, tellurium hexafluoride, tert-butyl isocyanate, tert-octyl mercaptan, tetraethyl lead, tetraethyl pyrophosphate, tetramethyl lead, titanium tetrachloride, toluene 2,4-diisocyanate, toluene 2,6-diisocyanate, trichloroacetyl chloride, trifluoroacetyl chloride, tungsten hexafluoride and the like.

In another embodiment is a device to monitor radon and alpha particles.

In another embodiment, the indicating system the indicator layer is on a substrate, optionally on both sides of the substrate.

In another embodiment, the indicating system is an indicating device for different classes of sterilization.

Yet another embodiment of the invention is a process to determine the concentration of an agent by either monitoring the time required for the dissolution or partial dissolution of the indicator layer or by monitoring the change in conductivity, or opacity of the indicator layer.

The indicating system of the present invention can best be more fully described by reference to the figures. For simplicity and clarity of illustration, figures are not necessarily drawn to scale. For example, the dimensions of some of the elements may be disproportionally over exaggerated (e.g., to show a thin metal layer) relative to each other for clarity. Though the metallic indicator and its layer 30 of the indicating system in the FIGS and examples herein could be any material having suitable metallic properties, we have exemplified them with a metal, especially aluminum or its layer and often referred simply as an indicator and/or indicator layer. Furthermore, where considered appropriate, reference numerals have been repeated amongst the figures to indicate corresponding elements.

FIG. 1 shows cross sectional views of a basic current (a) and prior art (b) devices. Most of the metals have naturally formed, protective, passivating oxide layer as shown schematically in FIG. 1(c). The thickness of the naturally formed oxide layer depends of metal, its purity and any treatment. For clarity of the FIGS naturally formed oxide layer on the metal layer is not shown in the rest of the FIGS. Both the prior art and the current devices have (1) an activator tape 1 comprising a substrate 10 having thereon an activator layer 20 composed of an activator matrix 100 containing an activator 1,000 and (2) an indicator tape 2 comprising an indicator or indicator layer 30 on a substrate 40. However, the current device (device of this invention) differs significantly and fundamentally in the nature, composition and design of the indicator tape 2 and indicator layer 30. The indicator layer 30 in the prior art (which is non-metallic) requires and is composed of a matrix 200 such as a binder/resin/ink/paint or pressure sensitive adhesive containing an indicator 2000. The indicator layer of the current device does not have a matrix. The indicator 30 of the current invention, e.g., a metal is film forming. An indicator layer not requiring a matrix/binder is novel for an indicating device and is a preferred embodiment of this invention. The indicator layer of the current device does not require a matrix. It is applied directly on the indicator substrate as a layer/film without a matrix and it still bonds and undergoes a color change or change in transparency/opacity. The indicator layer acts as a matrix, an indicator and its layer. The indicator of the current invention has an ability to bond itself and bonds with its substrate. An example of the indicator of the current device is a metal, such as aluminum. Aluminum can be coated directly on a plastic film by vacuum deposition (e.g., evaporation or sputtering) and can undergo a color change and change in opacity, e.g., from silvery white/opaque, mirror like finish to essentially transparent, colorless, an invisible salt when reacted with selected activators, such as acids, bases and salts. The metallic luster/sheens are also often called colors herein and change in opacity is also often called color change. Use of a metal or its alloy as an indicator is novel for an indicating device and is a preferred embodiment of this invention.

Additionally, the metals have a naturally formed oxide layer which acts as a permeable or barrier layer for the activator as shown in FIG. 1(c). In the prior art devices the permeable/barrier layer needs to be applied. We have observed that this naturally formed oxide layer plays an important role as a destroyable barrier or permeable layer in the indicating devices, especially in increasing the time required for the reaction to complete. We also believe that the oxide layer is impermeable to most of the activators and agents and hence most likely gets destroyed, i.e., undergoes a heterogeneous reaction with them. This type of impermeable barriers or their layers, transparent, opaque, colored or otherwise, naturally formed or intentionally applied or created, can introduce an induction period. This naturally formed barrier layer which can be destroyed by a heterogeneous reaction is novel for an indicating device and is a preferred embodiment of this invention. As this naturally formed oxide type layer is typically much thinner than the metal layer, for clarity of the drawings it is not shown in the rest of the figures.

A thin layer of a metal or its alloy, with or without its metal oxide layer and with or without a layer of precursor, for example, as shown schematically in FIG. 1(c) is an indicating device by itself. Metals and their alloys are known to react with a large number of materials/chemicals/agents. When exposed to such chemicals, a thin layer of metal can either react directly with such chemical or with an activator produced by the reaction of a chemical with the precursor layer.

There are many other nonmetallic materials, such as polymeric dyes and polydiacetylenes which are self colored materials and a layer of a sublimed dye can also be used instead of a metal because they may not need a binder. Polymeric dyes and polydiacetylenes are polymeric and a very thin layer of a dye, e.g., obtained by procedures, such as sublimation, will also be very thin, less than 1 micron. A thin metallic indicator layer which is opaque, without binder/matrix, self bonding and/or self coloring is novel for an indicating device and is a preferred embodiment of this invention.

Figure 2:
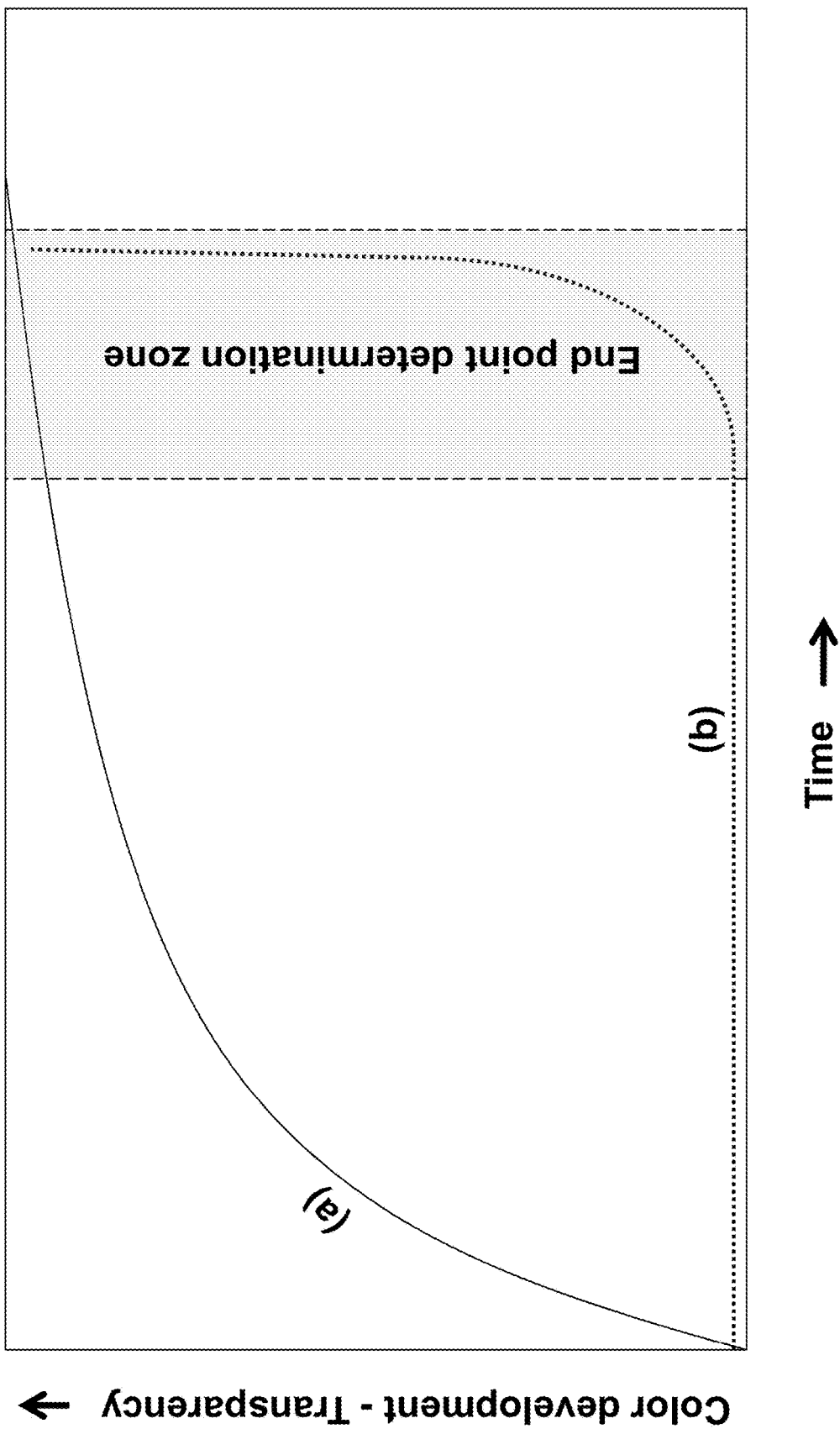
FIG. 2 shows a schematic presentation of color development versus time after the activation of a prior art (a) and current indicating (b) devices.

FIG. 2 shows expected plots of color development (reaction rate, intensity of color development, color change or change in transparency) versus time after the activation of the prior art and current devices. Typically, the color development of the prior art devices is asymptotic [plot (a) in FIG. 2], a gradual color development/change (which will be rapid in the beginning and gradually slowing down) without any induction period because the activator gradually diffuses/migrates or reacted through the indicator matrix. As can be seen from FIG. 2, the reaction of a metal layer with an activator/chemical is completely opposite in nature [plot (b) in FIG. 2] to the prior art. This essentially opposite nature of the color/transparency change is novel for an indicating device and is a preferred embodiment of this invention. The term migrate/migration and diffuse/diffusion are used interchangeably herein. In the prior art devices the reaction occurs within a matrix, e.g., in the indicator matrix. The current indicator layer has no matrix and is non-permeable. An indicator layer being non-permeable is novel for an indicating device and is a preferred embodiment of this invention. Additionally it has an oxide layer. Hence the reaction occurs essentially on its surface. Thus the reaction is heterogeneous. This heterogeneous reaction occurring at the surface of the indicator layer without the activator diffusing through the indicator layer and resultant induction period of the device is novel for an indicating device and is a preferred embodiment of this invention. The induction period can also be due to slow diffusion of activator through the oxide layer and/or destruction of the oxide layer. Compared to the prior art, where the indicator/dye can and does diffuse through the activator matrix, the indicator/metal of the current invention does not diffuse through the activator matrix. This non-diffusion or non-migration of activator through a matrix is novel for an indicating device and is a preferred embodiment of this invention. The current device shows very little color development or change in transparency for a certain time (i.e., induction period) and then rapidly changes color, becomes colorless/transparent when most of the metal layer is consumed. It takes certain time for the activator to destroy the indicator and an oxide layer on it. The etching reaction/dissolution/destruction of an indicator layer and its oxide layer at a steady rate is also novel for an indicating device and is a preferred embodiment of this invention. As metals are the most opaque materials, the color/opacity remains essentially the same till an ultra thin layer of the metal is left unreacted. Once the final thin layer is destroyed the indicator layer becomes transparent. The resultant induction period of the color/opacity change is novel for an indicating device and is a preferred embodiment of this invention. The color change for the prior art devices in the end point determination zone is very little (e.g., less than 5%). The change in transparency for the current invention is typically more than 80% in the end point determination zone. This significant color/transparency in the end point determination zone is novel for an indicating device and is a preferred embodiment of this invention. This rapid and significant color/transparency in the end point determination zone makes the current device significantly more accurate than the prior art devices.

An indicating device with a long induction period, similar to that shown in plot (b) of FIG. 2 can also be obtained with many of the prior art devices if the device has a barrier layer or can be added which is non-permeable to an activator or an agent and undergoes an etching type heterogeneous/surface reaction with the activator or the agent, i.e., its integrity as a barrier layer is destroyed. This type of destructible layers and method of producing a long and/or sharp induction period by the layer with an activator/agent by a surface/heterogeneous reaction are novel for an indicating device and is a preferred embodiment of this invention. The destructible barrier layer can be organic, inorganic or polymeric. Preferred destructible barrier layer is that of an inorganic material such as a metal oxide.

The color change in prior art is usually subject to interpretation while the change from opaque to transparent is not.

Figure 3:
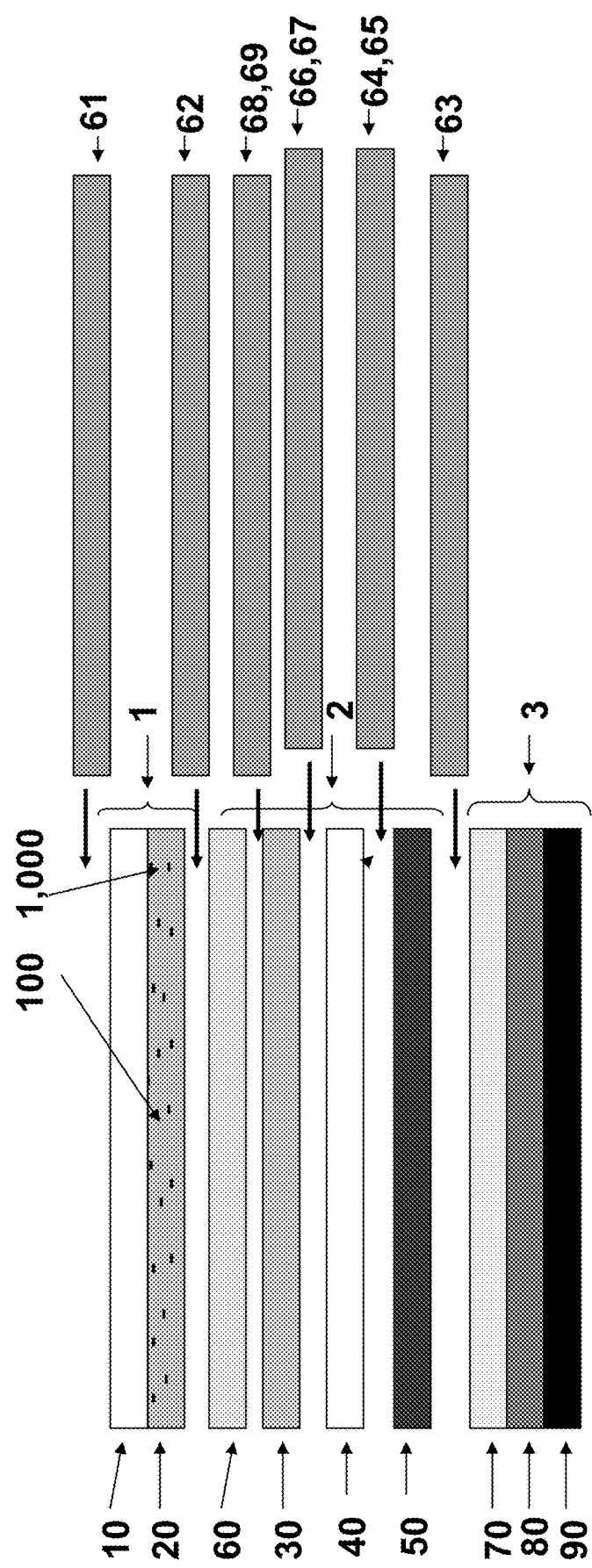
FIG. 3 shows a schematic presentation of some basic and optional layers of the device. The naturally formed oxide layer on the metal layer is not shown.
Figure 15:
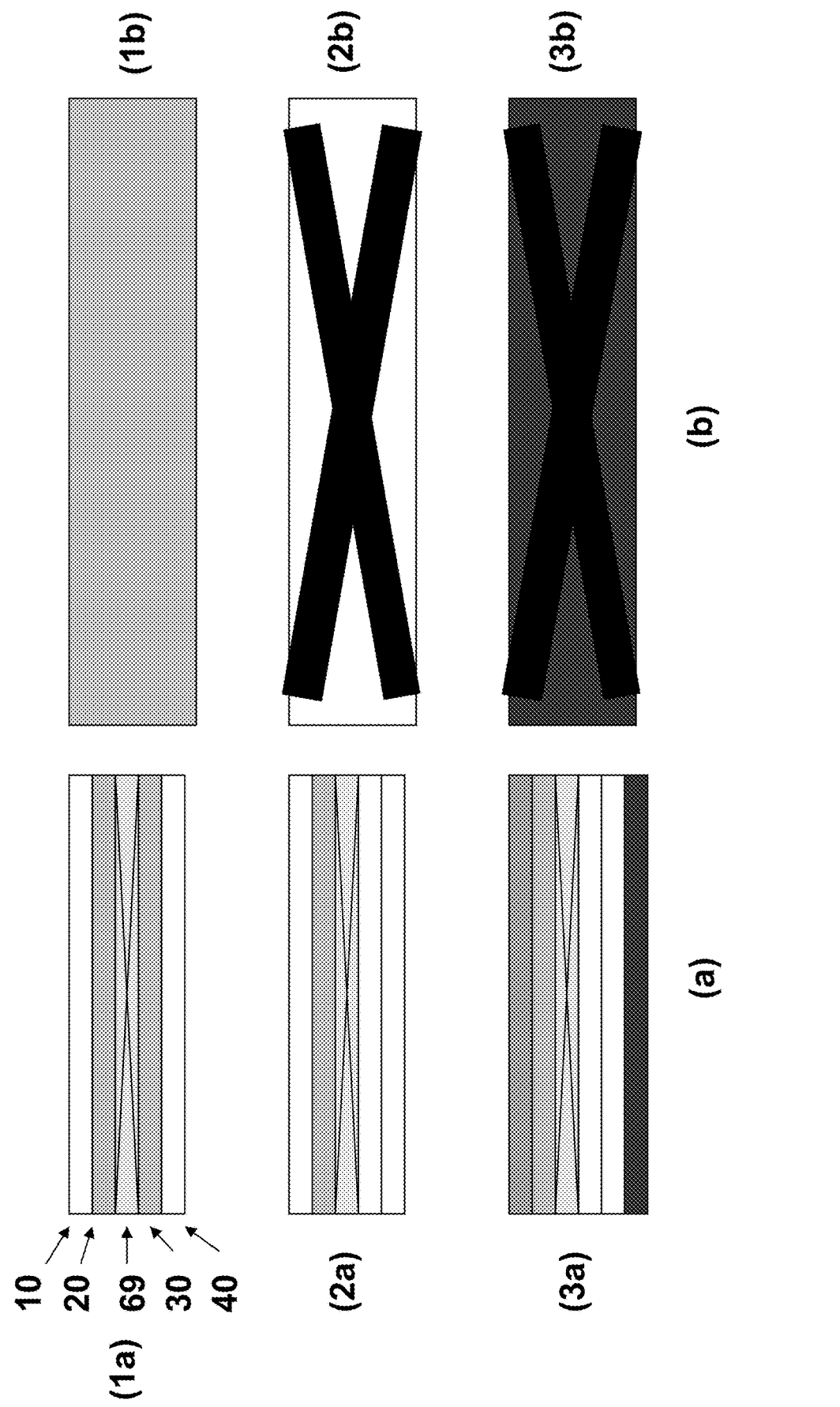
FIG. 15 shows a schematic cross sectional (a) and top (b) views of an indicating device having a X-shaped barrier layer (an etching mask) on the indicator layer, (1) when activated, (2) expired and (3) expired device having a colored expiration indicator layer.
Figure 23:
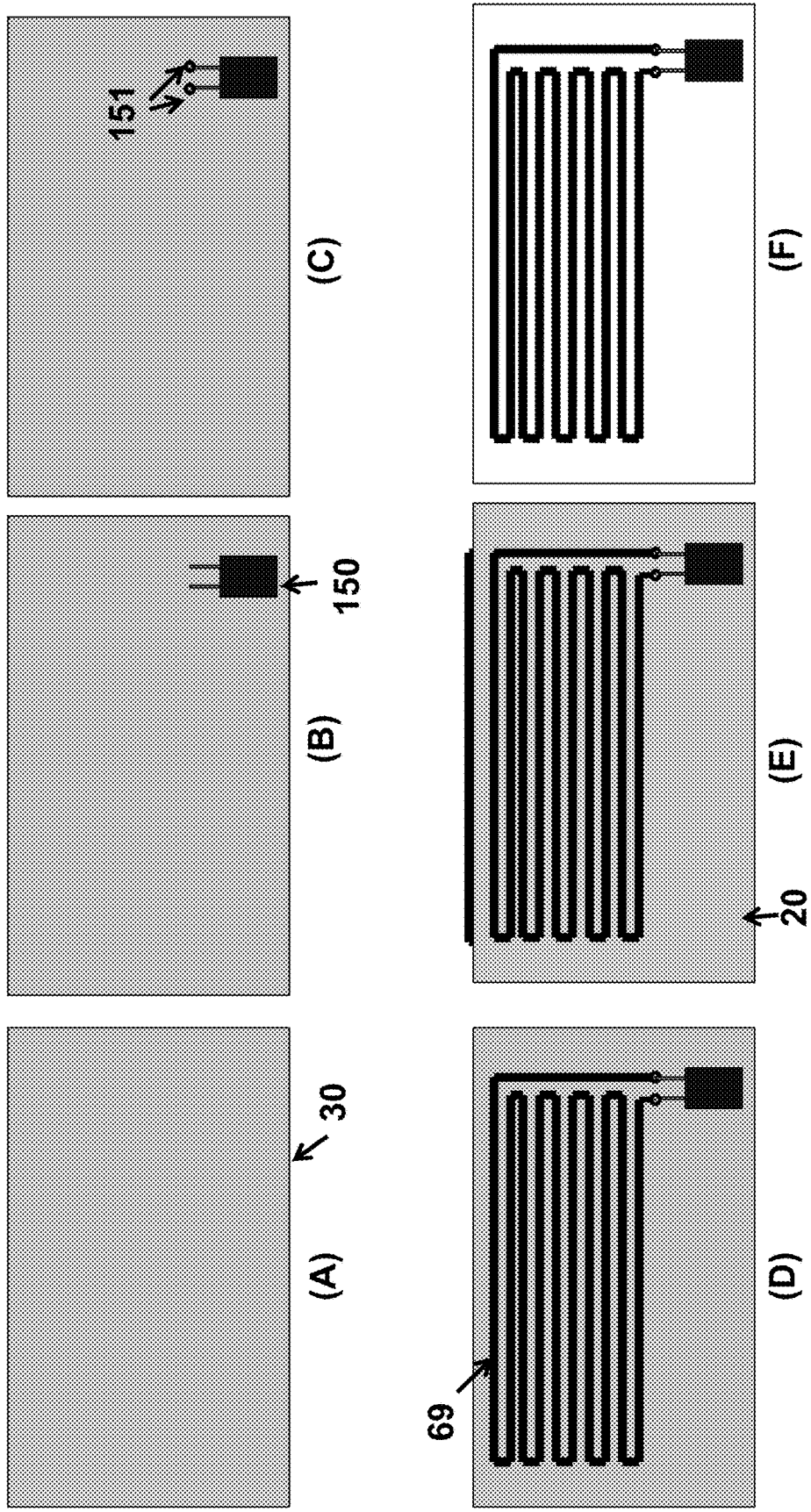
FIG. 23 shows a schematic top view of a method of making a RFID indicating device.

A schematic presentation of some basic and optional layers of the current device is shown in FIG. 3. There could also be many additional layers as desired. These layers can have any color, shape, thickness, size and nature as desired. The position of these and other optional layers relative to one another can often be changed and can often be interchanged. Most of these layers could be whole, partial or discontinuous. Some of these layers could be in form of a pattern, message or image. The basic device is composed of (1) an activator tape 1 having substrate 10 having thereon an activator layer 20 composed of an activator matrix 100 and activator 1,000, (2) an indicator tape 2 having substrate 40 having thereon an indicator layer 30 and an expiration indicating layer 50 and optionally a permeable layer 60 and (3) storage tape 3 composed of a pressure sensitive adhesive (PSA) layer 70, a release layer 80 and a release liner 90. The expiration indicating layer 50 is highly desirable but not essential. The expiration indicating layer is a layer which becomes visible when the indicator layer becomes transparent. The expiration layer 50 can also be between the indicator substrate 40 and the indicator layer 30. The permeable layer 60 can be used to increase an induction period of the reaction/transparency change, vary time required for the transparency change and vary the activation energy. The indicator layer has the naturally formed oxide layer (not shown) which is also a naturally formed permeable/barrier layer. In order to store and apply devices disclosed herein on an object, the indicator substrate 40 or the expiration indicating layer 50 can have the storage tape 3. The PSA layer 70 can be applied directly on the indicator substrate 40 and the release layer 80 can be applied on the activator substrate 10 or vice versa. The device is activated by applying the activator tape 1 on the indicator tape 2. The device is applied on to an object by removing the release liner 90 and the release layer 80. The device could have many additional optional layers, e.g., optional—top color or message layer 61, optional—activation indictor layer 62, optional—tamper indicator layer 63 and etching/reaction mask 69 (not shown in FIG. 3 but shown in FIGS. 15, 23 and 38) if desired/required. These optional layers, such as top message layer, activation layer, tamper indicating layer and reaction preventing mask layers are novel for an indicating device and are preferred embodiments of this invention. The optional layers 60-69 provide additional colors, desired effects, messages, images and indications. The layers of the activators and indicator tapes and the optional layers 60-69 may require one or two layers of an adhesive/binder such as a PSA to bond them with the adjacent layers. The nature and transparency of these different layers of the device will depend upon the application of the device. For example, the activator and/or indicator substrates for most of the applications will be a transparent and/or clear plastic film. However, for certain applications, for example, as shown in FIGS. 10, 11, 34 and 35, they can be opaque, semi transparent, colored or having a message or image. One of the optional layers can be a tamper indicating layer, which could also be anywhere at an appropriate location in the device. There are many other optional layers which can be added in the device, for example, one can add a precursor layer 68 and an etch mask layer 69 (as shown in FIGS. 15, 23 and 38) for selective etching of the indicator layer. It is also possible to have more than one of the same layer in a device, e.g., two metal/indicator layers, and/or two activator layers. These layers may have their own binder. These optional layers may be composed of a microencapsulated material, such as an activator.

There are many other layers and many other ways these layers can be added/arranged above and below the indicator layer. One such example is a precursor layer 68 on or above the indicator layer 30. Many precursors when react with another precursor, activator or agent can produce another activator which will dissolve the metal. For example, a precursor layer of ammonium nitrate, sodium nitrate or sodium nitrite on the indicator layer will not affect the indicator. When activated with a weak acid, such as phosphoric acid, the nitrates can produce nitric acid and nitrite can produce a relatively stronger acid such as nitrous or nitric acid which can react with the indicator much faster than phosphoric acid. It will otherwise be difficult and/or hazardous to use strong acids and bases as activators. Thus, one can generate activators in situ and on demand.

The term dissolve is used herein to describe processes, such as etching and reactions of a metal to substantially destroy its metallic properties.

Depending upon the need, application and situation, a matrix of a layer, e.g., that of an activator layer can be an adhesive or a non-adhesive and can even be directly applied on the indicator or other layers. For example, to make a two-tape TTI, one can use an adhesive, such as a pressure sensitive adhesive. However, for certain other applications, such as a steam sterilization indicating device, the activator matrix could be a non-adhesive matrix/resin containing an activator or a precursor for an activator and can be applied directly on the indicator layer. These non-adhesive matrices can hold an activator or precursor for an activator which become effective under proper conditions, e.g., when certain temperature and humidity levels are reached.

Depending upon the need, application and situation, an activator can be replaced with its precursor. For example, for sterilization with ethylene oxide and hydrogen peroxide, one can use precursors, such as sodium thiocyanate and tetrabutylammonium bromide respectively. Sodium thiocyanate when reacts with ethylene oxide produces sodium hydroxide which can react/dissolve the metal layer. Similarly, tetrabutylammonium bromide can react with oxidizing agents, such as hydrogen peroxide or its plasma to produce an acid, such as hydrobromous acid which can also dissolve the metal.

All devices shown herein may have an opaque, e.g., white layer in the back of the devices, so all messages and images can be seen.

In order to store a tape having a PSA as the top layer may have a release layer and/or release liner (which is not shown in many FIGS), so it can wound on itself and stored until used.

Figure 4:
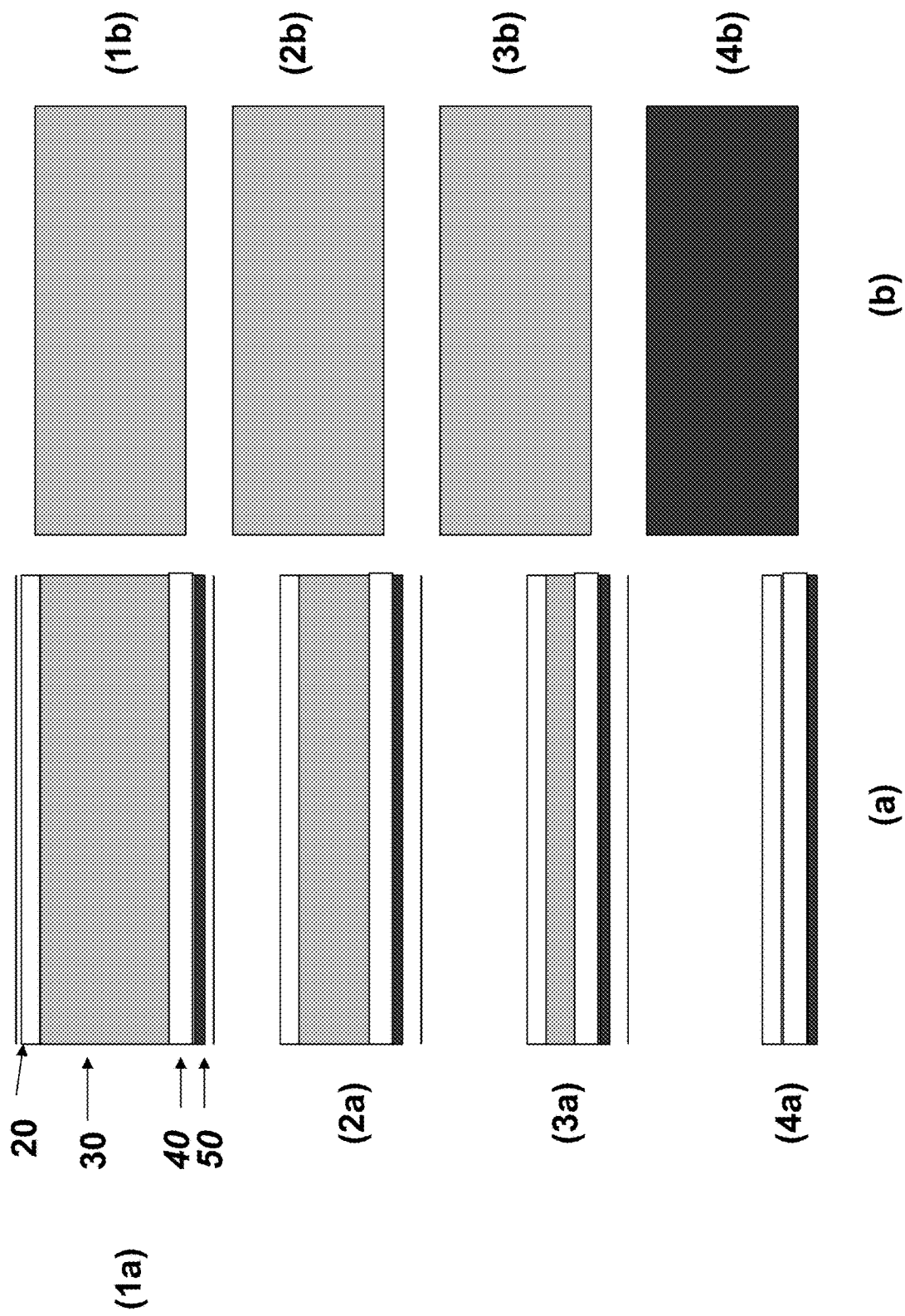
FIG. 4 shows a schematic cross sectional (a) and top (b) views of an indicating device at different stages after activation. Dissolution of the oxide layer of the metal is not shown.

FIG. 4 shows a partial cross sectional (a) and top (b) views of the device at different stages, e.g., 0, 1/3, 2/3 and full/expiration time after its activation. When the device is activated by applying an activator tape on to the indicator tape, the device shows the silvery white (when a thin layer of aluminum is used as an indicator), reflective surface of the indicator layer 30 (as shown in disproportionally exploded view in FIG. 4). The activator will start reacting/etching (often called dissolving herein, even though the metal is not truly dissolved) the oxide layer and then the metal layer. Even though the reaction is proceeding, the color of the aluminum layer does not change very much [as shown schematically in the top three sets of drawings, 0, 1/3 and 2/3 reaction in FIG. 4(b)], until a very thin layer is left unreacted. When all aluminum is etched away, one can see the color of the expiration indicating layer 50 [the bottom two drawings in FIGS. 4(a) and 4(b)]. Thus, the device provides an induction period even though the reaction does not appear to have an induction period. Even though the indicator layer does not undergo any color change, the device shows a color change from silvery white/opaque to the color of the expiration indicating layer, e.g., red or any other color, and it is a novelty for an indicating device and is a preferred embodiment of this invention. There are other possibilities for the induction period to occur, e.g., requirement of sufficient quantity or concentration for the activator for the etching reaction to proceed. Thus, it is possible to obtain essentially any expiration color by selecting the desired color for the expiration indicating layer 50 e.g., green, red, blue and yellow.

Expiration indicating layer 50 can be a colored plastic film or a colored coating on the substrate 40 and can be on the either side of the substrate. For time indicating device, different color badges can be used for different days of a conference, group or occasion.

Figure 5:
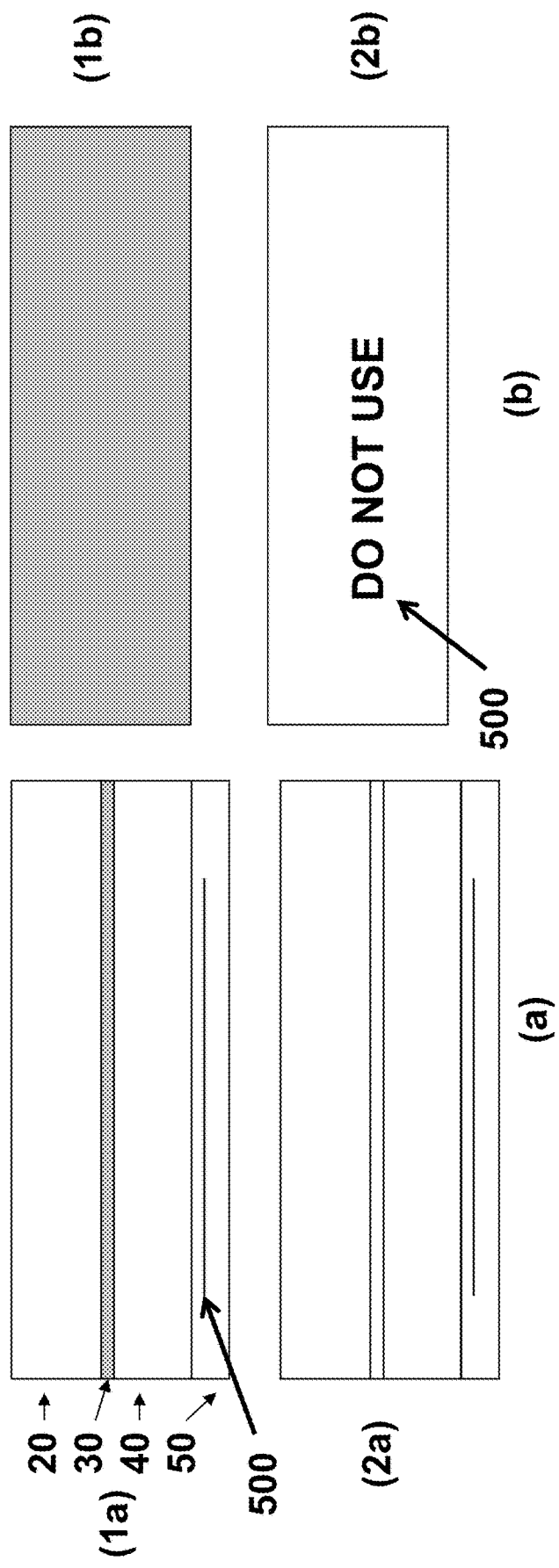
FIG. 5 shows a schematic cross sectional (a) and top (b) views of an indicating device with expiration indicator layer having a message before (1) and after (2) the expiration.
Figure 6:
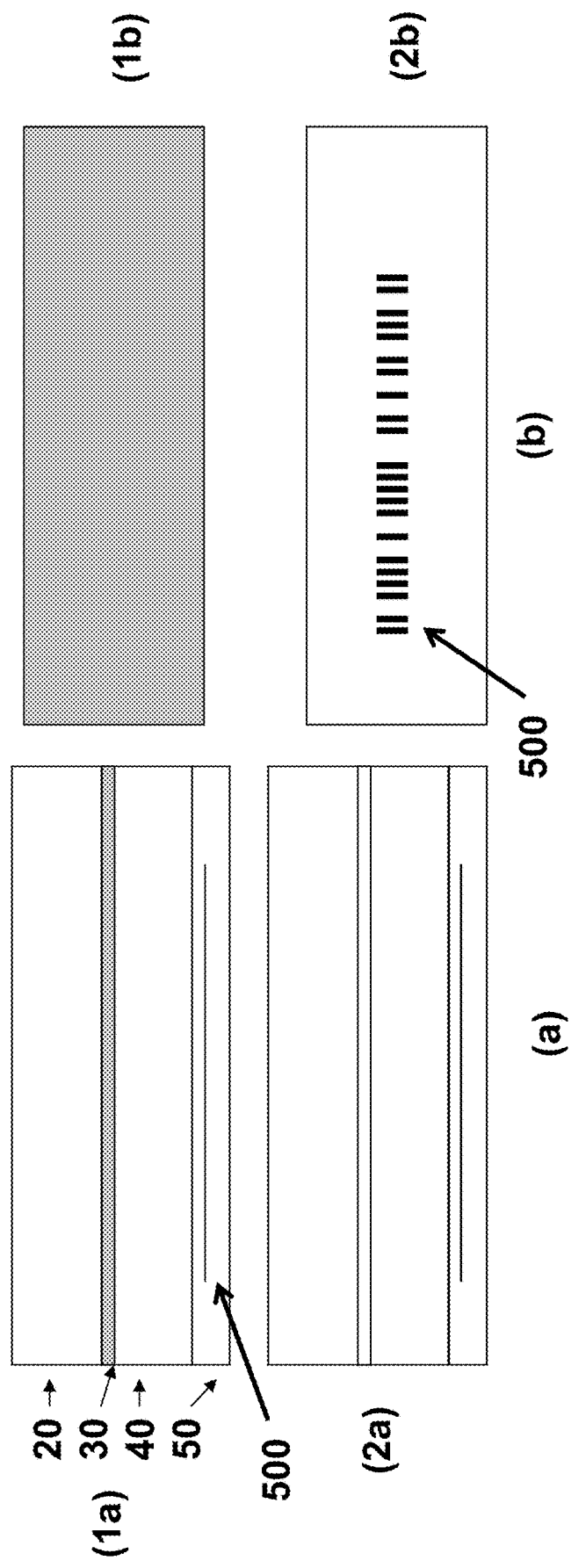
FIG. 6 shows a schematic cross sectional (a) and top (b) views of an indicating device with expiration indicator layer having a barcode before (1) and after (2) the expiration.

The expiration indicating layer 50 can also be printed with any desired shape, pattern, number, message or image 500 as shown in FIG. 5. Instead of selecting a colored expiration indicating layer, one may print any shape, pattern, number, photo, image or message 500 or a barcode, e.g., as shown in FIG. 6 so an optical scanner, CCD camera or a reader/detector can read and indicate rejection of the expired product. The barcode could have any format including a two dimensional barcode. The message could be any e.g., "DO NOT USE", "EXPIRED", "HAZARD" etc. Thus, this device provides a simple and easy way to obtain essentially unlimited final/expiration colors, shapes, pattern, photos, images, messages and alike. This process of getting essentially unlimited and any color or message upon expiration of the device is novel for an indicating device and is a preferred embodiment of this invention.

Figure 7:
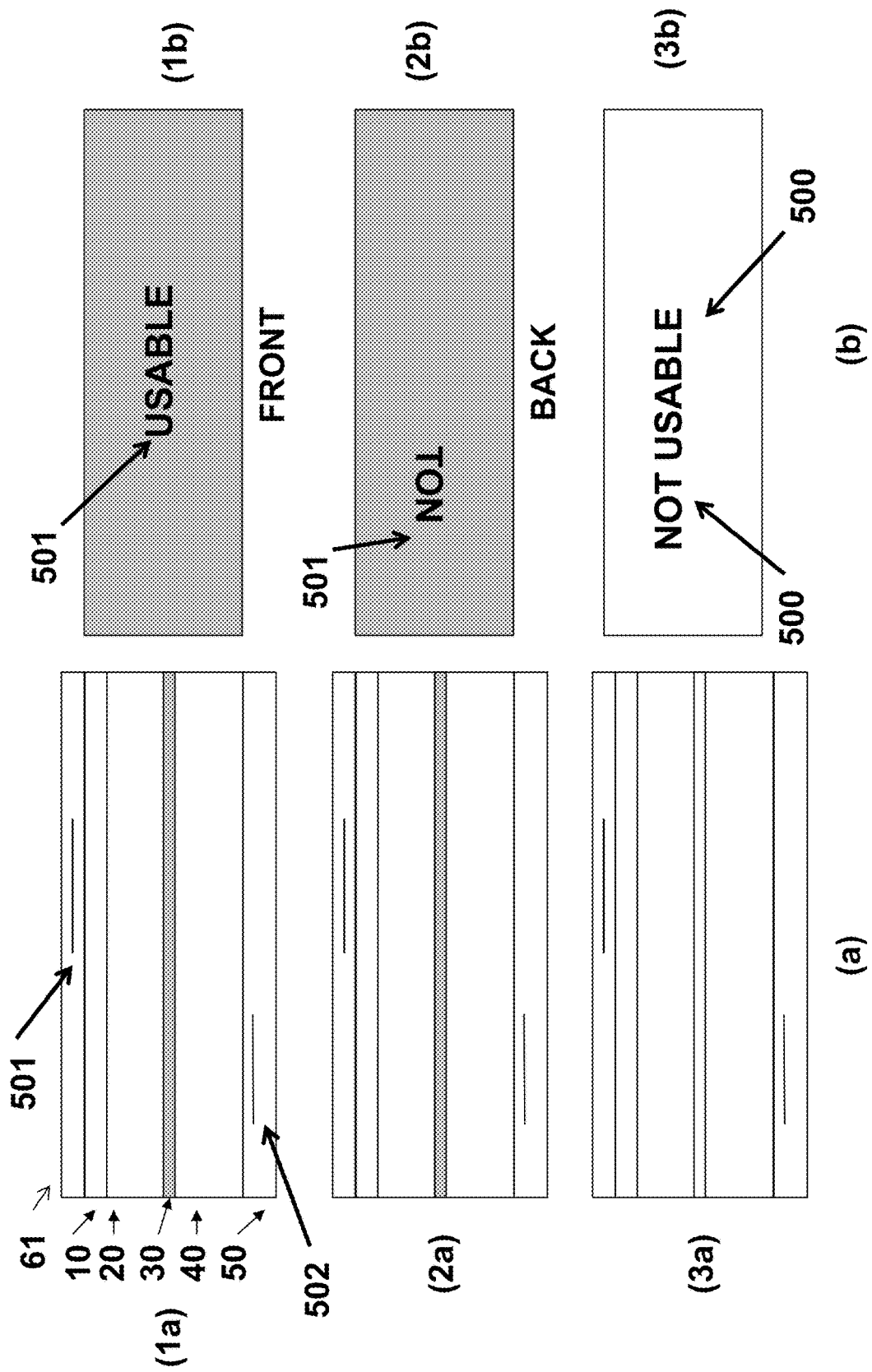
FIG. 7 shows a schematic cross sectional (a) and top (b) views of an indicating device with a message printed over the activator layer and another message printed on the expiration indicator layer to create a new message.

FIG. 7 shows schematic cross sectional (a) and top (b) views of the device with a message 501 printed on, under or inside a layer 61 or on a surface of the activator substrate 10 as a top message and another message 502 on, under or inside the expiration layer 50 or on the indicator substrate 40. In this case, both the messages 501 and 502 when combined make a new and final message when the device expires. A part of the final message, e.g., "USABLE" is printed on the surface of activator substrate which can be seen when viewed from the top of the device as shown in FIG. 7(1b). The message indicates the perishable is usable. The remaining part of the message, e.g., "NOT" is printed on the back surface of indicator substrate as shown in FIG. 7(2b). This layer/message ("NOT" in mirror image) is not visible when viewed from the top because the indicator layer is opaque. When the device expires, the indicator layer becomes transparent and the message "NOT" becomes visible and when viewed from the top it appears as "NOT USABLE" as shown in FIG. 7(3b). Thus the combined message "NOT USABLE" indicates that the perishable is not usable. Thus, using this type of devices, there is no need to print instructions for the user. These devices are self-reading/indicating/instructing. The combining two messages, one of them appearing or become visible at a later stage of the device and creating a new message is novel for an indicating device and is a preferred embodiment of this invention.

Similarly, a large number of messages and images can be combined to make final message/image, for example, "NOT GOOD" "NOT COSUMABLE", "DON'T USE" and "NOT OK" or symbols and images to convey similar messages.

Many systems undergo a color change, often gradual and hence require a color reference chart. By using the selective etching methods described herein, it is also possible to create messages, such as "STERILIZED" by printing with a barrier ink/binder of essentially of the same color but unaffected by the etchant. The message will not be easily noticeable. When the device is treated, e.g., a sterilization process, such as dry heat or steam, the metal coating will undergo a transparency change, leaving the message easily noticeable.

Certain symbols, such as a check mark (√) means OK (e.g., when fresh) and X can be used to indicate acceptability and unacceptability.

Similarly devices can be created with a part of a bar code or a bar code on the activator substrate and the remaining of the bar code or another bar code on the back of indicator substrate. In this case, both the messages when combined can make a new final number/barcode or both barcodes readable when the device expires. The first barcode message could be the price and the second barcode message could be interpreted as expired, reject or don't sell. These barcodes could be of different sizes/thickness and also of different formats. Instead of the barcode, it could be any code, pattern, message or image.

Similarly, one can make a message disappear by selecting the color of the message and expiration layer the same.

Similarly, one can also make a portion of the final message disappear if printed on a layer above the indicator layer which disappears when contacted with an activator and the device expires.

In the above examples, the message is in words and barcode. However, the message could be any, e.g., patterns and images. By combining words, barcodes, patterns and images, it is possible to create essentially unlimited combinations of messages.

The indicating devices of the present inventions don't require a color reference charts/bars because the easily noticeable mirror like, opaque indicator disappears and a color or any message printed underneath becomes visible. However, if desired, color reference chart can be added/printed because the current device shows color changes from silvery/white mirror like finish→dull gray→light gray-→clear/colorless (or color of the expiration indicating, e.g., red). Hence, in order to match currently commercially available devices, one can print color reference charts and instruction to read/interpret the devices. These types of devices can offer best of both the self reading and color matching.

FIG. 8 shows a schematic presentation of some of basic preferred layers of the device with (b) and without (a) a permeable layer. Though the basic device without the permeable layer will provide an induction period, one can increase the induction period and the time required for the transparency change by selecting a proper permeable layer 60 which can be applied/coated on the indicator layer 30.

Figure 9:
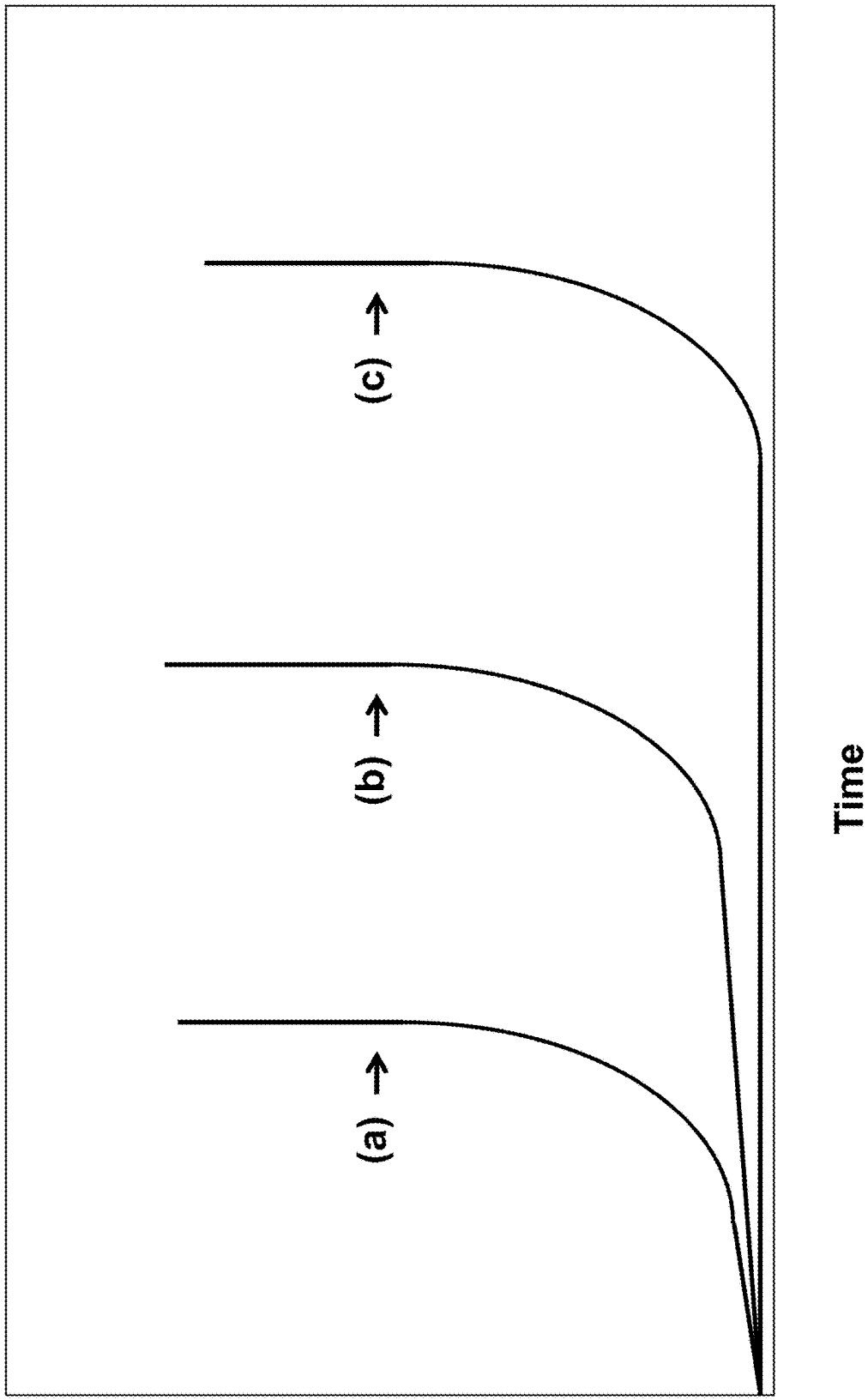
FIG. 9 shows a schematic presentation of color development or change in transparency versus time after the activation of the device without a permeable layer (a) and with more (b) and less (c) permeable layers.

FIG. 9 shows expected plots of color development (color change or change in transparency) versus time after the activation of the device with and without a permeable layer. The length of induction period will depend on many parameters, including the nature, permeability and thickness of the permeable layer. As shown in FIG. 9, a device having a more permeable and/or thinner permeable layer will provide shorter induction period compared to that having thicker and/or less permeable layer. We have observed that by selecting proper conditions, such as thickness of aluminum and permeable layers, the induction period can be increased to over 90% or higher. We have also observed that a thicker layer of aluminum makes the transparency change and the boundary in the case of the moving boundary devices of FIG. 10 much sharper.

Because the time required for the indicator layer to disappear is short, the indicating device having a less permeable layer (i.e., slow diffusion of the activator) will provide a longer and sharper induction period and vice versa. Thus, this type of devices can provide a better "go-no go" indicating device, which is especially required for many of the indicating devices mentioned herein, e.g., time indicators (TI), such as visitors' passes.

Figure 10:
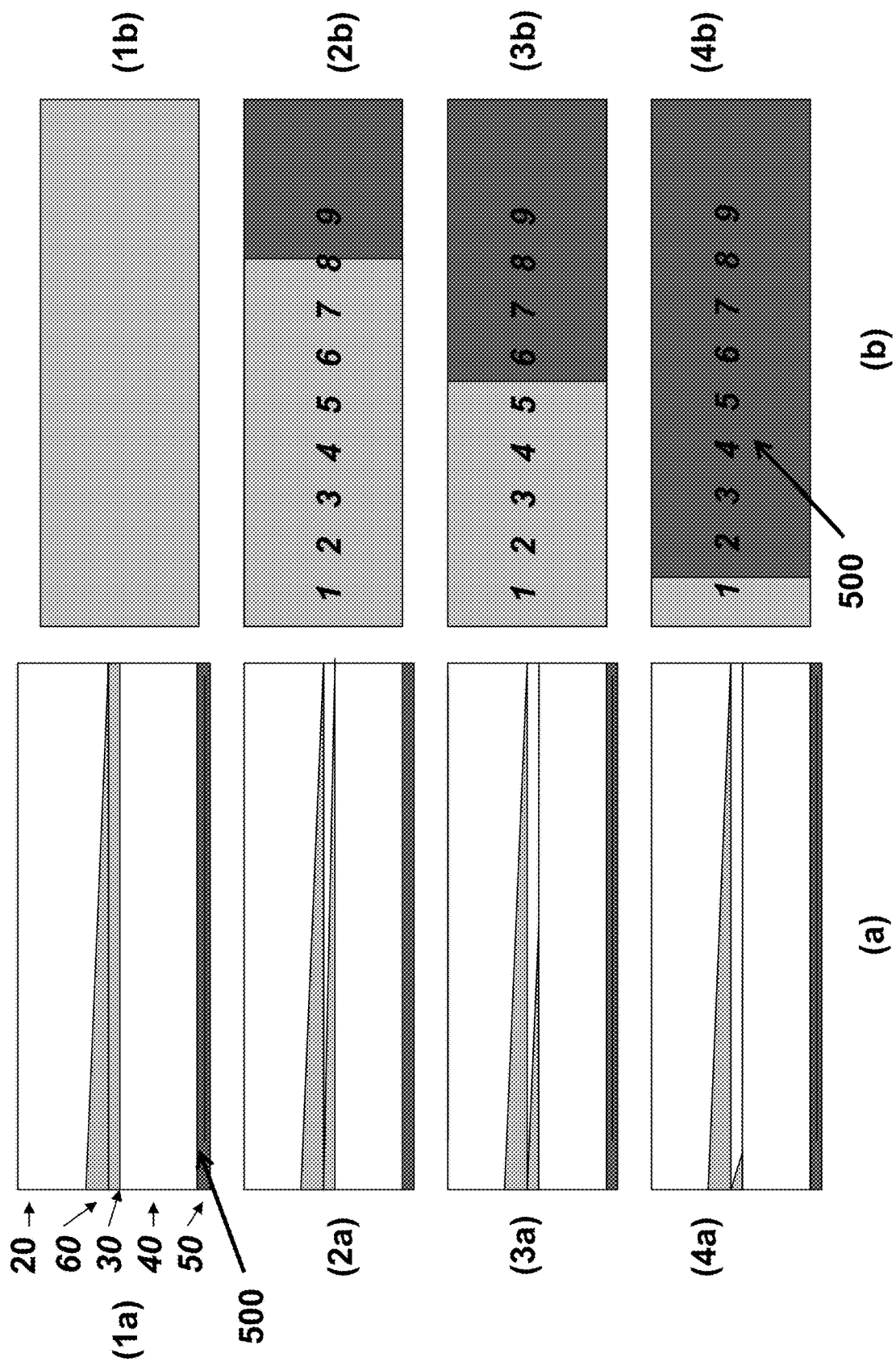
FIG. 10 shows a schematic cross sectional (a) and top (b) views of an indicating device having a wedge shaped permeable layer having numbers printed on a colored expiration indication layer, at different stages after the activation of the device.

FIG. 10 shows schematic cross sectional (a) and top (b) views of the device having a wedge shaped permeable layer at different stages after the activation of the device. If the permeable layer is of uniform thickness, it will show the transparency change within a narrow period. However, if the permeable layer is in form a wedge, as shown in FIG. 10, the transparency change will be continuous from thin end to the thick end of the permeable layer and hence one can see a boundary created between the unreacted metal layer and the color of the expiration indicating layer. The mechanism for creation of the moving boundary by the wedge shaped permeable/barrier layer is explained in U.S. Pat. No. 5,045,283 and is incorporated herein as reference. If the expiration indicating layer is printed with numbers, the numbers will start appearing from the thin to the thick end of the permeable layer. This type of boundary will be sharper compared to the diffusion based prior art devices (e.g., two-tape moving boundary device of U.S. Pat. No. 5,045,283). The permeable layer material could be any organic or inorganic material, however, a polymeric material, preferably substantially amorphous is preferred. In the current case, a sharper moving boundary device can also be created by using a wedge shaped indicator layer because the reaction occurs on the surface of the device and has no matrix.

Similarly, one can use a step wedge rather than continuous wedge. The step wedge will provide a sequential, stepwise appearance of the number or any message.

The material for the wedge shaped layer could be a destructible barrier layer as well.

Figure 36:
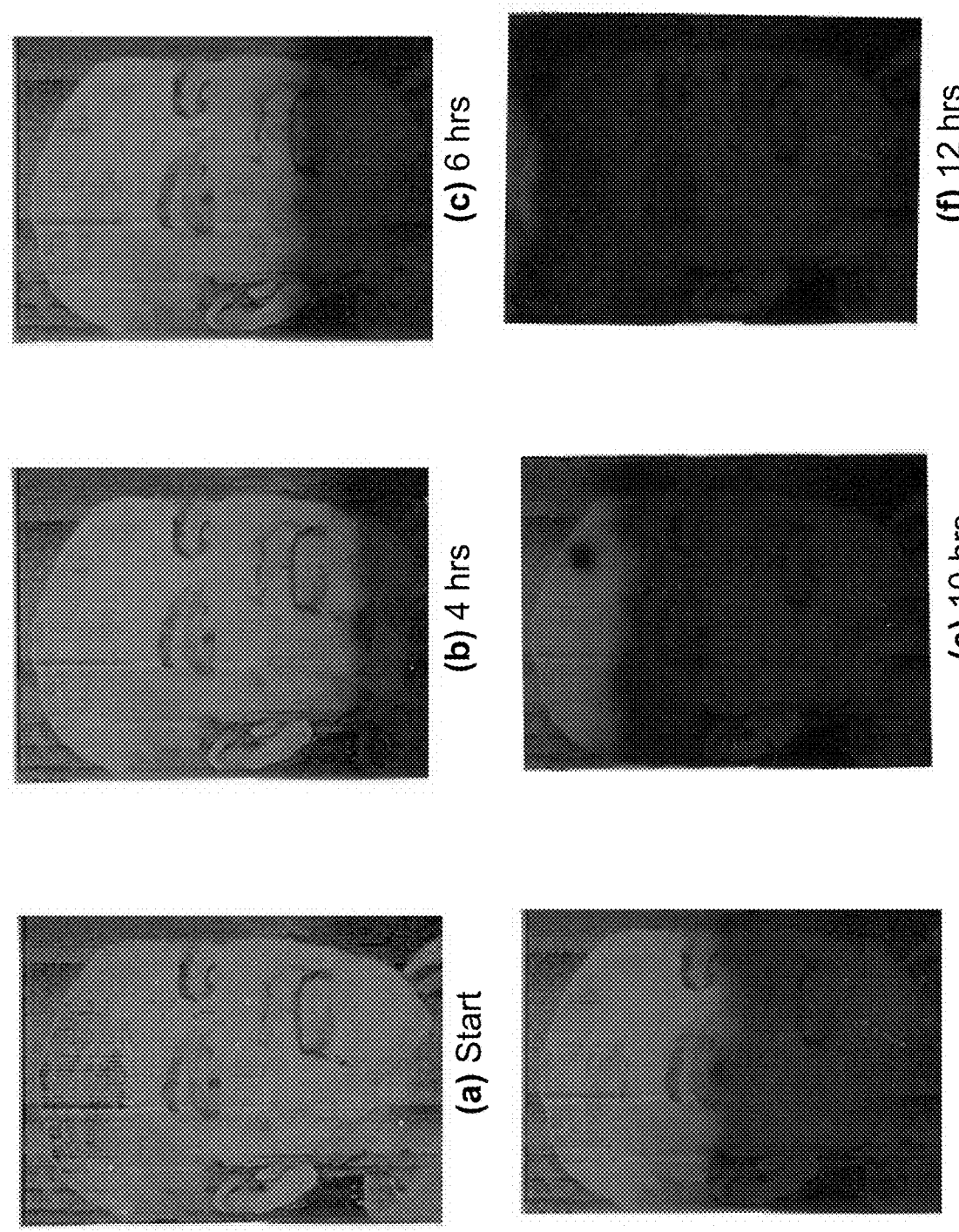
FIG. 36 shows an example of a visitor's badge having a wedge shaped permeable layer between the indicator and activator layers at different stages after activation.

It is also possible to make an indicating device where photos, messages, images etc appear, disappear, blurred, darkened or lightened by printing them below and above the different layers of the device of FIG. 3. An example to make visitors' badges is shown in FIG. 11 and results are shown in FIG. 36. A photo of a visitor 501 can be printed (e.g., by a printing method/equipment, such as laser, inkjet, dye-sublimation etc) on a clear indicator substrate 40 having an indicator layer 30 (e.g., a metallized polyester film) and optionally a permeable layer 60 on the indicator layer 30 as shown in FIG. 11(a). This assembly (indicator tape) is applied on to the activator tape having an opaque activator substrate 10 and activator layer 20 composed of an activator matrix containing an activator (e.g., phosphoric acid) to make the visitor's badge. Upon activation of the device, the photo 501 will appear as shown in FIG. 11(b) when viewed from the top of the badge and nothing will be visible from the back because the opaque substrate 10 of the activator tape and the indicator layer are opaque. Upon expiration of the badge, the indicator layer will disappear/become transparent and the photo will appear red colored/blurred and another message as shown in FIG. 11(c) due to the colored background of the substrate 10. If the activator substrate is transparent, one can see the photo from both the sides. If the activator substrate is printed with any other message 502 (e.g., X in this case), the photo will be darkened with red background and "X" will appear as shown in FIG. 11(c). We made several devices with only "X", only red background, "X" with red background, words such as "EXPIRED", "NOT VALID" and "VALID" on the top and "NOT" in the back. The time required for the transparency change in all of the above devices can be varied by varying the thickness, nature of the permeable layer and/or other variables listed herein.

Figure 12:
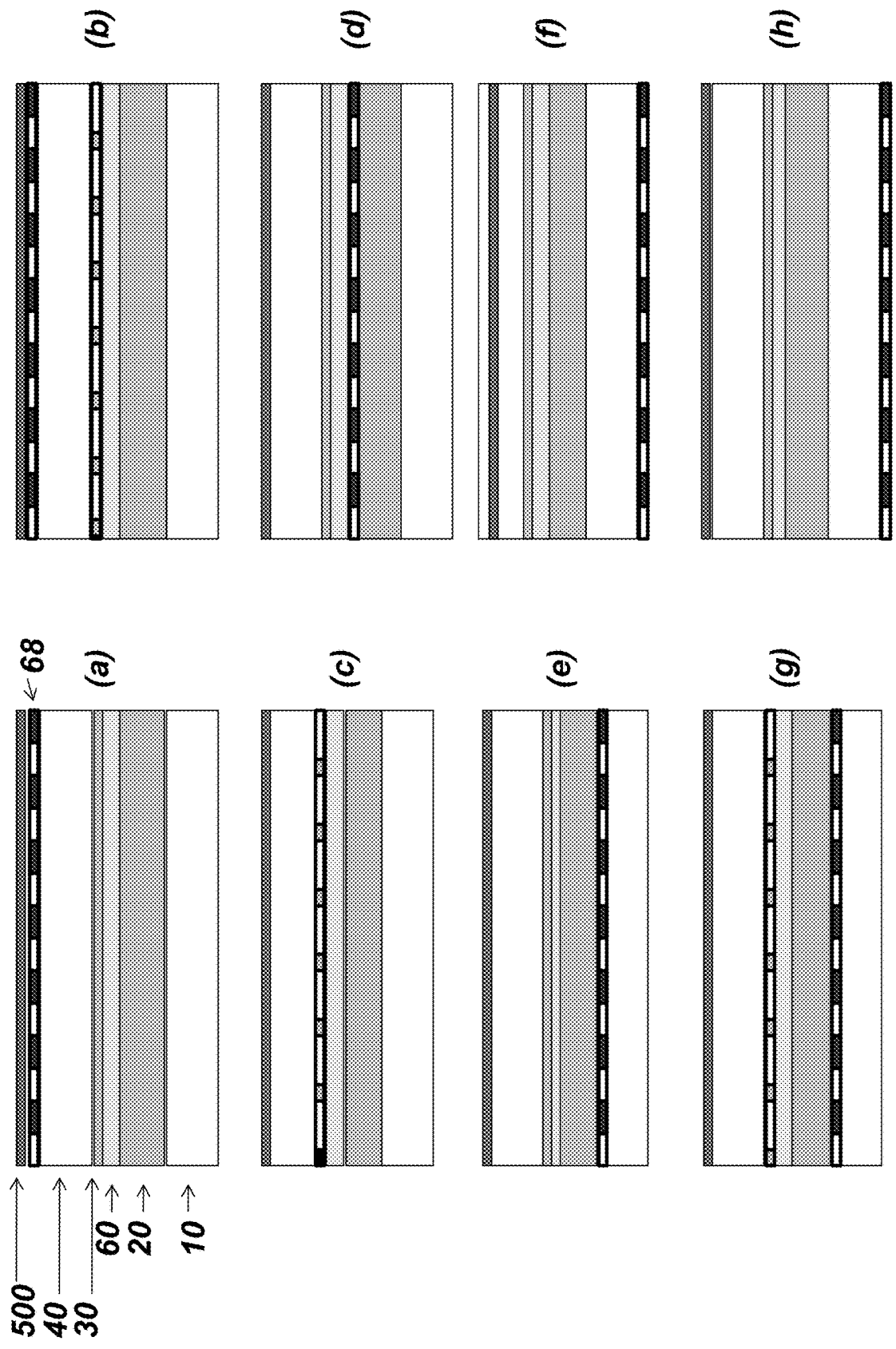
FIG. 12 shows a schematic cross sectional views of indicating device having some different discontinuous layers at selected different locations of the device.

FIG. 12 shows schematic cross sectional views of indicating device having some different layers (discontinuous in this case) at different locations and their combinations. The discontinuous or continuous layer could be essentially in any form, shape and size including an image, logo, sign, lines and grid of any color or message. If the device is a TI, e.g., a visitor's badge, the indicating device may have a photo 500 printed on the top. The discontinuous layer 68 could be under the photo or on the indicator substrate as shown in FIGS. 12(a) and 12(b). The indicator layer itself could be discontinuous as shown in FIGS. 12(b) and 12(c). The discontinuous layer could be printed on the barrier layer as shown in FIG. 12(d) and on the activator substrate as shown in FIGS. 12(e)-12(h). Many combinations of these discontinuous layers are possible. The device could have more than two discontinuous layers. FIG. 12 also shows that the location/position of a layer can be interchanged.

The permeable layer of devices of FIGS. 11 and 12 is of uniform thickness. If the permeable layer of the device is wedge shaped, the photo will gradually change color. A demonstration of this moving boundary concept is shown in FIG. 36. This type of devices will warn the user and security personnel about the remaining time. The images, messages and photos can be made of any visibility/opacity by selecting proper layers, colors and their opacity. A photo or message can also be printed on the indicator layer.

Above devices show a full coverage of the photo. One can also cover the photo partially and/or in any direction. Similarly, one can make any message appear on the photo, e.g., "CANCELED", "EXPIRED" etc.

There are many variations of the devices. All one needs to do is vary the nature, shape, size, format, color and position of different layers. For example, one can make a pre-printed ID and similar items, or portions thereof, slowly blurred or darkened if the indicator layer becomes opaque or changes color from colorless or any color-A to any color-B. Yet another way to cancel/expire a pre-printed ID and similar items is to cover the existing images with the activated two-tape device. In this type of devices, the indicating device is made by applying the activator tape (having an activator layer on a clear substrate on to the indicator tape (having a wedge shaped permeable layer, an opaque indicator, and a PSA layer, on a clear substrate. The activated indicating device is then applied on to an image or photo for a partial coverage. The activated tape will gradually become clear from the thin end of the tape to the thick and the photo underneath will become gradually visible with time. The coverage of the ID or similar devices with the activated indicating device could be in direction. This type of activated indicating device tape could have a feature of tamper indicator as described in our provisional patent application No. 61/127,565 dated May 14, 2008 and is incorporated herein as a reference.

This sudden and/or steady appearance, disappearance, blurring, crossing out, coloring. etc, of an image, message, pattern and alike including the moving boundary are novel for an indicating device and is a preferred embodiment of this invention.

The indicator layer in the above devices could have varied opacity and colors. The above described indicating device can have a tamper indicating layer, e.g., the adhesive layer 70 could have selected pattern of a silicone coating. If the indicating device is tampered, e.g., pulled, it will be evident. Thus, this invention can convert pre-printed ID and similar objects/documents, into time dependant, self-expiring and also tamper indicating if required.

These types of indicating devices, such as visitors' badges may have a fastener attached to the device or a holder to hold the device.

There is yet another way to create a moving boundary effect and devices associated with it by making the indicator and or activator layer wedge shaped, i.e., thicker at one end and thinner at the other. We made several moving boundary devices with wedge shaped activator layer.

Figure 13:
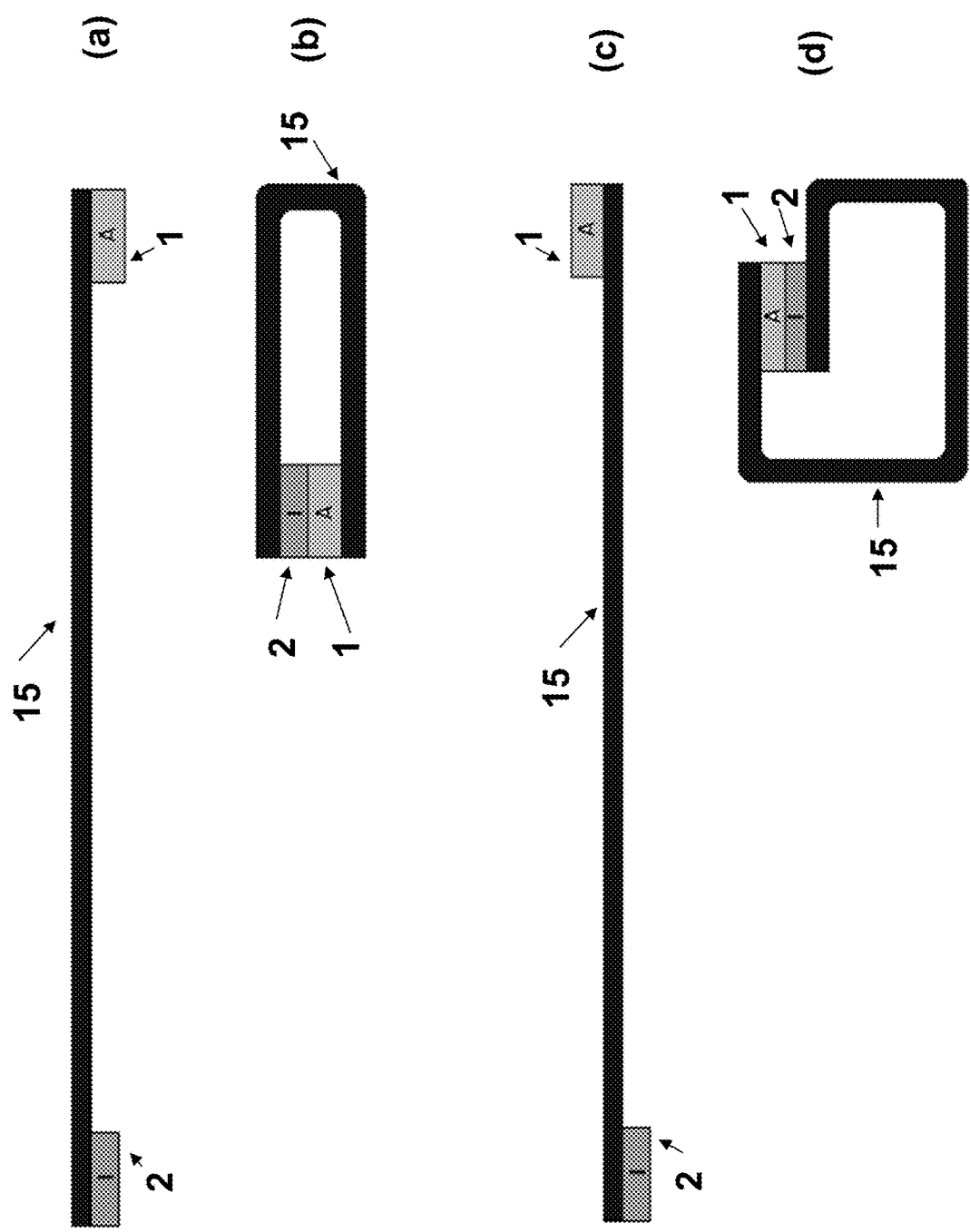
FIG. 13 shows a schematic cross sectional presentations of two of many possible modifications of a band or foldable indicating device having activator and indicator tapes at the ends of a substrate.

FIG. 13 shows two of the many band or foldable modifications of the current device. The activator and indicator tapes can be attached or directly coated/applied at different locations and sides on a substrate which is in form a strip or open band. For example, FIG. 13 shows the activator tape "A" and indicator tape "I" being on the same side/surface of the band/substrate 15. The band 15 is folded around an object (not shown), such as a perishable package or human wrist and the device is activated by applying the activator tape on to the indicator tape as shown in FIG. 13(b). Another example is shown in FIG. 13(c), where the activator tape 1 and indicator tape 2 are on the opposite sides/surfaces of the band 15. The band 15 is folded around an object, such as a human wrist and the device is activated by applying the activator tape on to the indicator tape as shown in FIG. 13(d). In order to see the color change of the resultant indicating device, at least one of the substrates has to be transparent or the activator and/or indicator tape should be attached at the end of band.

Figure 14:
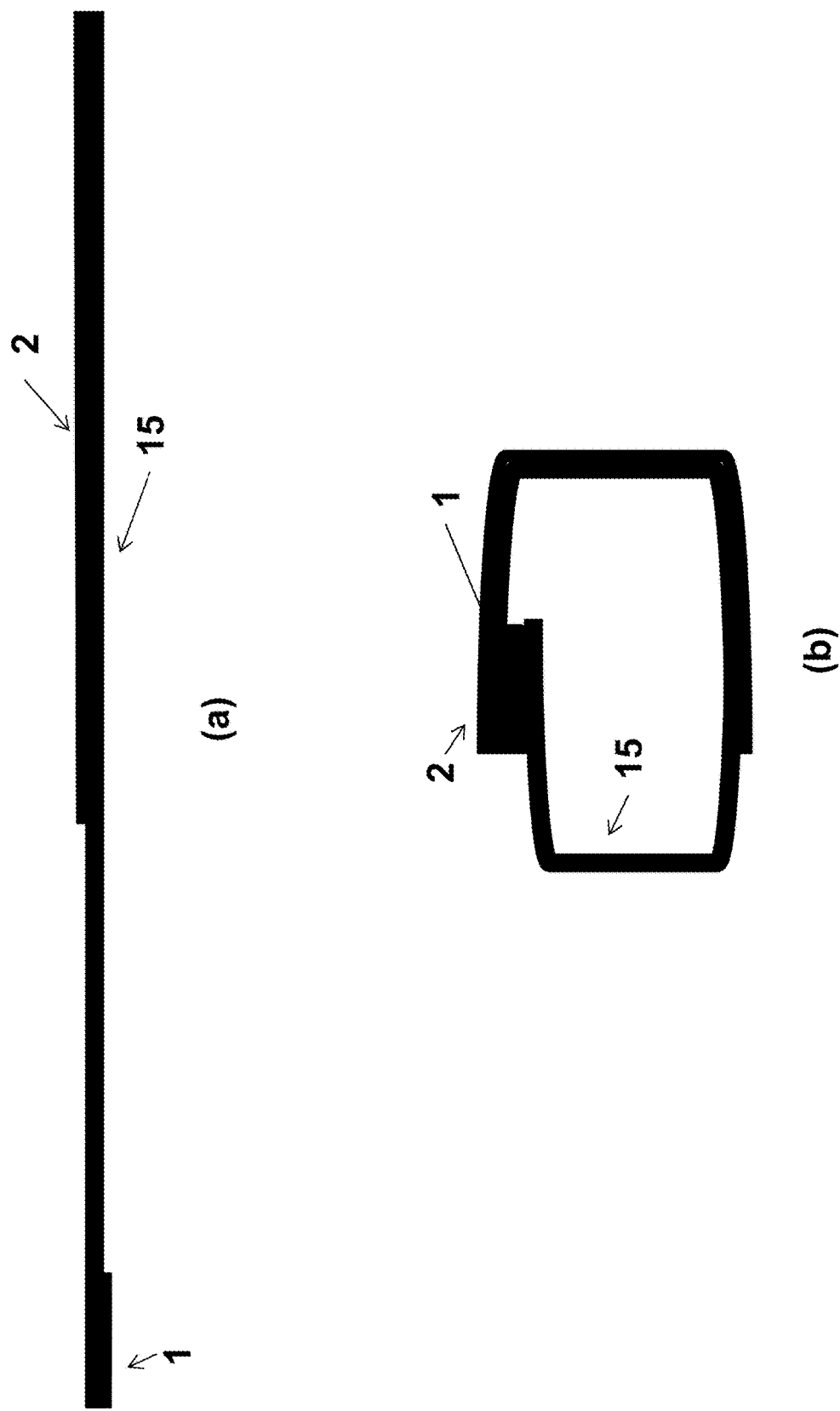
FIG. 14 shows a schematic cross sectional presentations of another modification of a band or foldable indicating device having a major portion of the substrate covered with an indicator layer before (a) and after folding/activation (b).

FIG. 14 shows schematic cross sectional presentation of yet another modification of a band or foldable indicating device having a major portion of the substrate covered with an indicator layer, e.g., metallized plastic film before (a) and after folding/activation (b). This type of device can be easily prepared, e.g., preferably by coating indicator layer on a portion of one half of one side and activator layer on a portion of the other half of the other side. The band is made by folding and applying the activator layer over the indicator layer. This type of reflective bands can be easily noticed from a distance and can also be easily differentiated when expired.

In the devices of FIGS. 13 and 14 only a portion/end of the band is used to apply the tapes. If the band is made from a piece of a metallized plastic film, one would not need an indicator tape for the indicating device because the metal layer will act as an indicator. One can make the device by applying an activator matrix having an activator on the other side/surface of the band. This is one of the simpler ways to make a band indicating device.

This type of band indicating device made from a metallized plastic film offers another advantage. When the metallized layer is dissolved by the activator, the band will automatically delaminate or will be weakened, making it automatically non-usable. The band could have a half portion metallized with aluminum layer and the remaining half with activator/matrix. When activated, the band will cover the object, e.g., wrist and can be visible/noticed from a distance because of the shiny nature of the aluminum layer. This type of indicating device could also have a tamper indicator as well. A tamper indicating band can be made by using the activator tape having selective coating of release barrier layer. The release barrier layer is a material made from a non-stick coating, such as silicone which also substantially prevents migration of the activator. An indicating device having this type of release barrier layer will make the indicating device tamper indicating.

A band can also be created by jointing activator and activator tapes at the ends. They can be joined by many sealing methods, such as with an adhesive or by ultrasonic welding.

All other features, such as different colors, messages, barcodes, images etc disclosed herein can also be incorporated in the band indicating device.

The indicator layer (aluminum) of the current device gets destroyed at the end of the reaction. As a result the bonding between indicator substrate and permeable layer (if used) or the adhesive of the activator layer gets destroyed and hence the indicating device loses its integrity. This may be an advantage for certain applications where one wants to know the expiration by de-lamination, e.g., visitor's badges or band. However, for the other applications, the de-lamination or weakening of the integrity of the device may not be acceptable. Hence, in order to keep the indicating device attached to an object, the device needs an outer layer having an adhesive e.g., PSA which is larger than the rest of the device. There are many ways the indicating device can be made to remain its integrity even after the expiration. For example, an indicating device having the activator tape being larger than the indicator tape or an indicating device having an extra tape having an adhesive layer (a PSA layer on a substrate). Yet another way is to use a partially metallized indicator layer, e.g., tiny dots or lines of metallized layer rather than continuous metallized layer. The portion which is not metallized will remain bonded even when the device expires. A much simpler way is to keep to prevent de-lamination and maintain the integrity of the device is to coat a polymer layer above and/or below the metal layer which becomes stronger PSA when connected with the activator. Acids and bases can be used as tackifier. For example, we have found that phosphoric acid is a tackifier for polyvinylether, such as polyvinylethylether. If one applies a thin layer of a polyvinylether on or under the metal layer, the de-lamination will not occur because when phosphoric acid contacts polyvinylether layer, it will make polyvinylether a strong PSA, thereby preventing the de-lamination. Yet another way to prevent de-lamination is to use a PSA for the activator layer which is very strong PSA and the activator is a tackifier or a PSA which reacts with metal salts resulted from dissolution of aluminum layer.

Additionally we have observed that the de-lamination of an activator in a PSA is not a major problem because the metal layer is so thin (~100 Angstroms) that its dissolution makes very little difference in bonding of the layers. Formation of metal salts may be helping in retaining the bonding.

A tamper indicating device can also be made by using the substrates made from a destructible/breakable plastic, such as polystyrene, polyvinyl chloride (PVC) and cellulose acetate. These and other tamper indicating materials and processes described in our provisional patent application No. 61/127,565 filed on May 14, 2008 can be used to make the indicating device tamper indicating.

There are many different ways the indicating device can be made by varying the nature and location of different layers of FIG. 3 or by adding extra layers as needed. One of such ways is to have a mask layer, reaction preventing layer or etching mask over the indicator layer. The words mask, mask layer, barrier layer reaction preventing layer or etching mask are used interchangeably herein. An etching mask is a barrier layer made from a material which significantly prevents diffusion of the activator and protects the indicator layer from being attacked. The total area of the etching mask should be smaller than that of the indicator layer.

FIG. 15 shows schematic cross sectional (a) and top (b) views of the device having an X-shaped etching mask 69 on the indicator layer 30 (1) when activated, (2) expired and (3) expire device having red colored expiration indicating layer 40. When the device is activated, the etching mask 69 will prevent diffusion of the activator, which is an etchant for the aluminum layer in this case. The etching mask could be made preferably from a clear polymeric material. When the indicating device having an etched masked printed in form of "X" is activated, the impression of the mask will not be visible and the device will appear as shown in FIG. 15(1b). Upon expiration of the device, the area(s) not protected by the mask/barrier will be etched away and become clear. As the activator/etchant will not diffuse through the mask/barrier, the area under it will remain un-etched/un-reacted and hence a pattern [e.g., X in FIG. 15(2b)] will appear. If the device has a colored expiration indicating layer, it will appear as shown in FIG. 15(3b). Instead of printing X, one can print any message, e.g., words, barcodes, patterns and images. By combining words, barcodes, patterns and images, it is possible to create essential any combination of messages with the etching mask. The etching mask, a reaction preventing layer is a kind of highly impermeable and non-destructive layer which is a barrier for activator.

Using an etching mask, permeable and no permeable layer, it is possible to vary the time required for the transparency change from extremely long to very short.

An etch mask 69 can be used in a fashion similar to the permeable layer 60 and hence devices created by the permeable layer can also be created by the etch mask having properties similar to that of permeable layer. The properties of the devices created the etch mask and permeable layer will be essentially identical. It is also possible to monitor time lapsed after the expiration of the device. The etchant/activator can diffuse under the mask and start etching the indicator layer.

Perishable manufacturers and other users of indicating devices are often not willing to use small TTI and other indicating labels on individual units of perishables or other items for many reasons, such as (1) special equipment and enormous quantity of properly sized TTI stickers are required to apply at proper locations on the container, (2) loss of individual TTI labels, tampering and liability are concerns, (3) cost of TTI labels and their application is high, (4) consumers are not educated/trained to interpret TTIs, (5) returned and rejected product are also concerns and (6) acceptable "Go-No go" type TTI were not available.

However, perishable manufacturers likely to use a TTI on carton/box of perishables as they want to make sure that the perishables are not thermally abused or stored for unacceptably long period before they were put on store shelves. Additionally, the current TTI are too small to be noticed on large boxes. Boxes are typically sealed with a pressure sensitive sealing tape. Boxes also have big labels to identify the product and manufacturer. If the sealing tape or label themselves are TTIs, perishable manufactures/distributors are highly likely to use sealing tape TTIs on each box because (1) no special equipment and large quantity of properly sized TTI stickers are required, (2) no worry about loss of individual TTI labels and tampering by consumer, (3) cost of this type of sealing tape TTI labels will be very low per unit, (4) consumers need not to be educated/trained, (5) the TTI devices disclosed here will be acceptable as they are self reading or have dramatic changes and (6) application of labels and sealing tape don't require any additional manpower. The sealing tape and label TTI serve essentially the same purpose but at a lower cost without unnecessary concerns.

The current technology offers an opportunity to make sealing tape and label TTI. Activator and indicator tapes dispensed from a double-tape/two-tape dispenser and applied on a perishable box will seals the box and will also monitor shelf life. The person opening the box will easily notice whether the perishable inside the box is of good quality or shelf life expired.

The current TTI tape does not need any special equipment for sealing boxes. Use of TTI tape would not increase the cost to a level that perishable manufacturers/distributors will not use. They would like to know that their product is of good quality before it goes on the selves. It is also easy to train the employees loading perishables on the shelves rather than the consumers. There is no real training required as the current TTI is either highly noticeable or self reading.

Tape dispensers are known in the art. Typically, a tape dispenser is comprised of a system capable of retaining and dispensing a single roll of tape. The current two-tape dispenser is a dispenser for holding two rolls (activator and indicator rolls), mechanism for their lamination/activation and cutting laminated/activated tape of desired length. A powered and automatic label applicator system for applying prior art two-tape labels/stickers of the activator and indicator labels was developed by Avery Dennison for dispensing individual TTI labels. However, this system peels the labels of indicator and activator tapes, aligns them and applies on a container. The current dispenser does not require peeling of labels as there are no labels and many other features of small labels.

Figure 16:
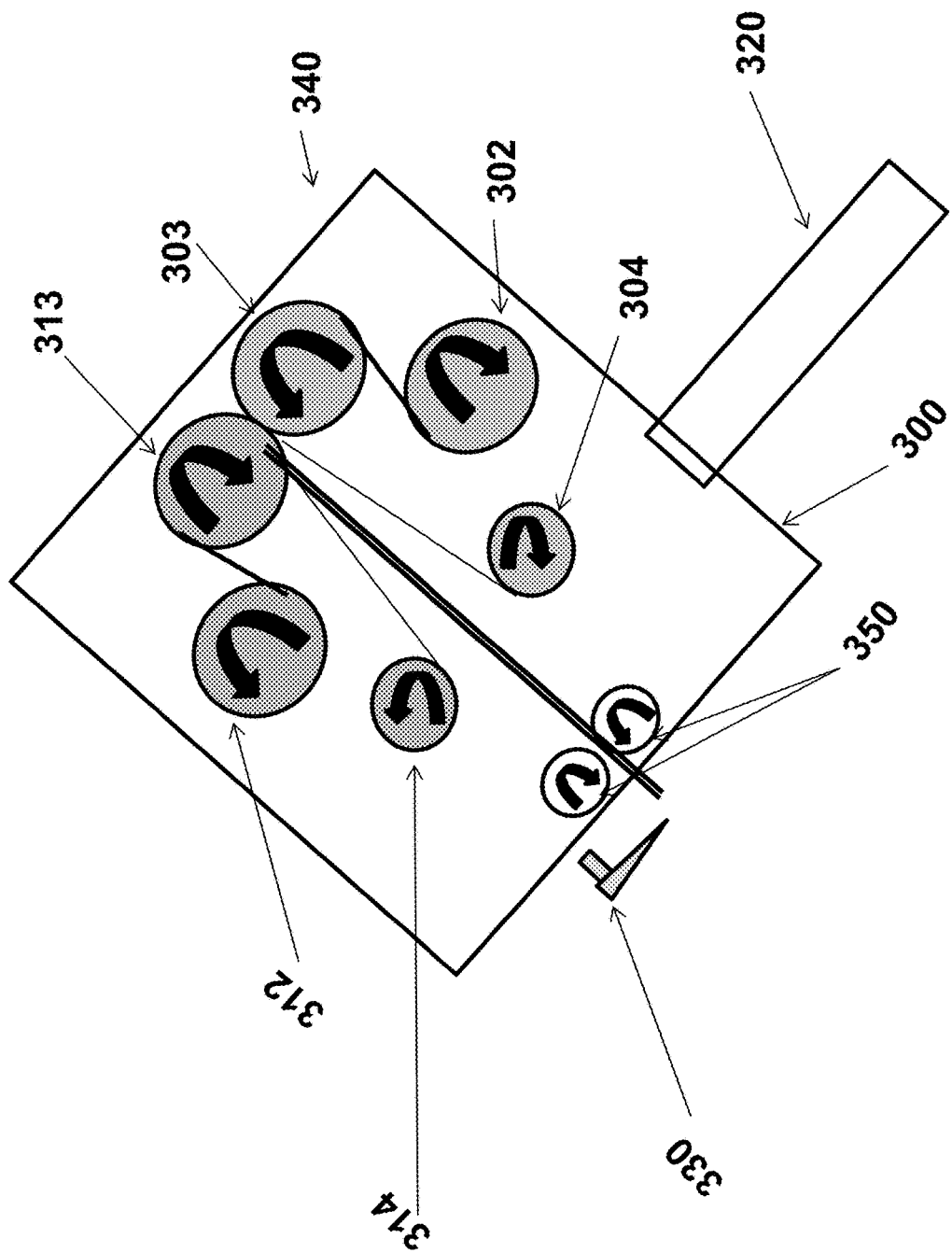
FIG. 16 shows a schematic cross sectional presentation of some parts of a two-tape dispenser for dispensing activated tape.

FIG. 16 shows is a schematic cross sectional presentation of a basic double tape dispenser for dispensing activated tape having some basic features. The dispenser, 300 is composed of a housing system (frame structures) 340 with a door with hinges (not shown) to open to load the rolls, close it and a pistol grip 320 type handle or base to fix the dispenser to a production line. The dispenser also includes axles and tension controls (not shown) to hold indicator and activator rolls/tapes 302 and 312 respectively, spools 304 and 314 to uptake release layers (if used), lamination rollers 303 and 313, guide rollers 350, knife/cutter 330 to cut the tapes and alike at proper locations in the housing. The dispenser could be powered, especially to tape boxes on line. The powered dispenser could have motors, sensors, e.g., optical sensor and a computer (CPU) for proper dispensing of the tape and operation of the dispenser.

A small version of the hand held dispenser can be used by small users, such as at homes, restaurants, food caterers and alike.

With respect to the above disclosed sealing tape dispenser, it is to be understood by one skilled in the art that one can vary the dimensions, materials, functions, operations, assembly and use of the dispenser.

Figure 17:
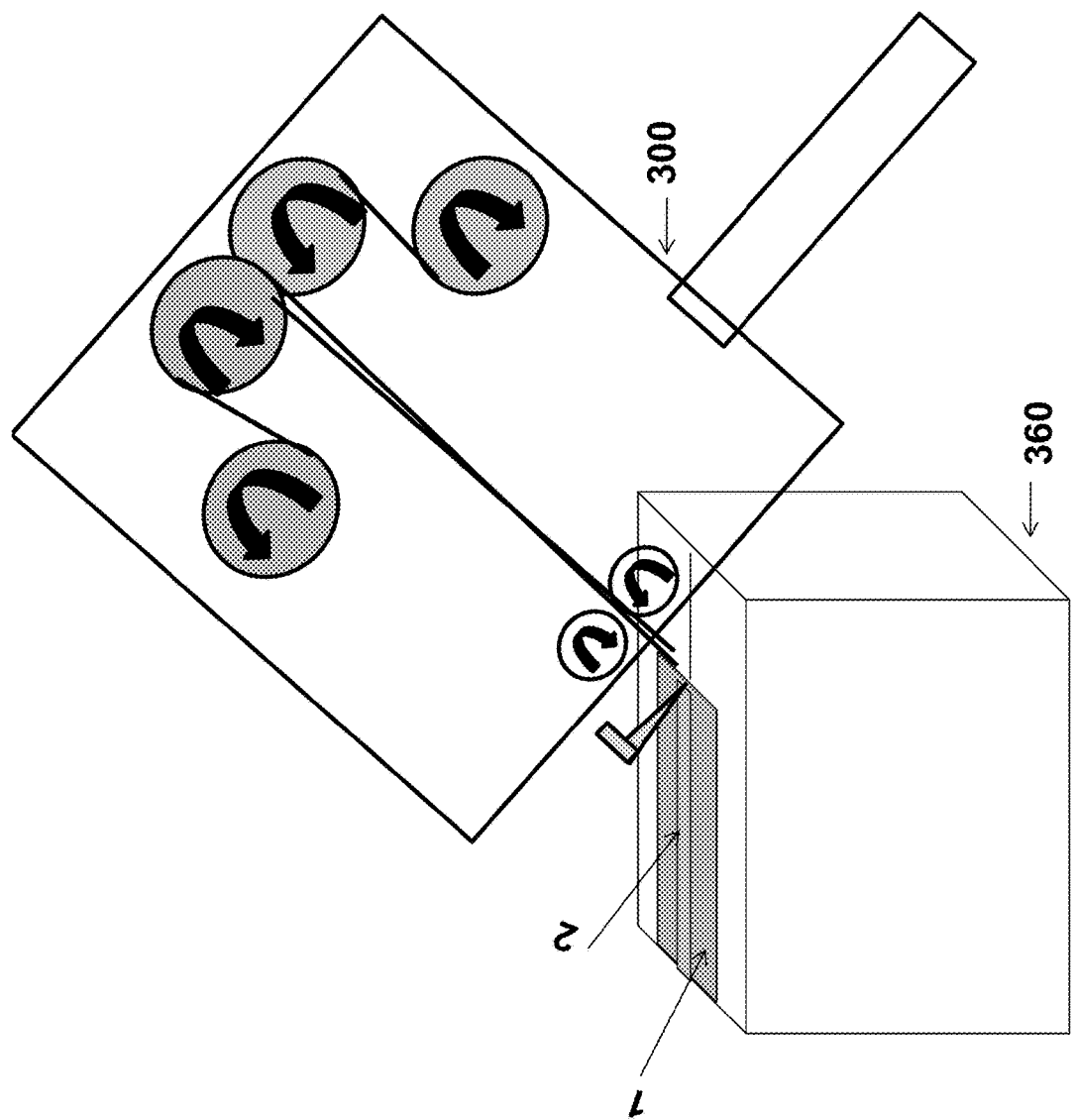
FIG. 17 shows a schematic presentation of sealing of a box, e.g., containing perishables, with activated indicating tape device from a tape dispenser.

FIG. 17 shows a schematic presentation of sealing of a box 360 e.g., containing perishables, with activated indicating device from a tape dispenser.

In order to seal a perishable box 360 the user pulls the lead of the laminated/activated sealing tape and applies to an object, such as a box as shown in FIG. 17 and pulls the dispenser or move the box and cut the desired length.

Figure 18:
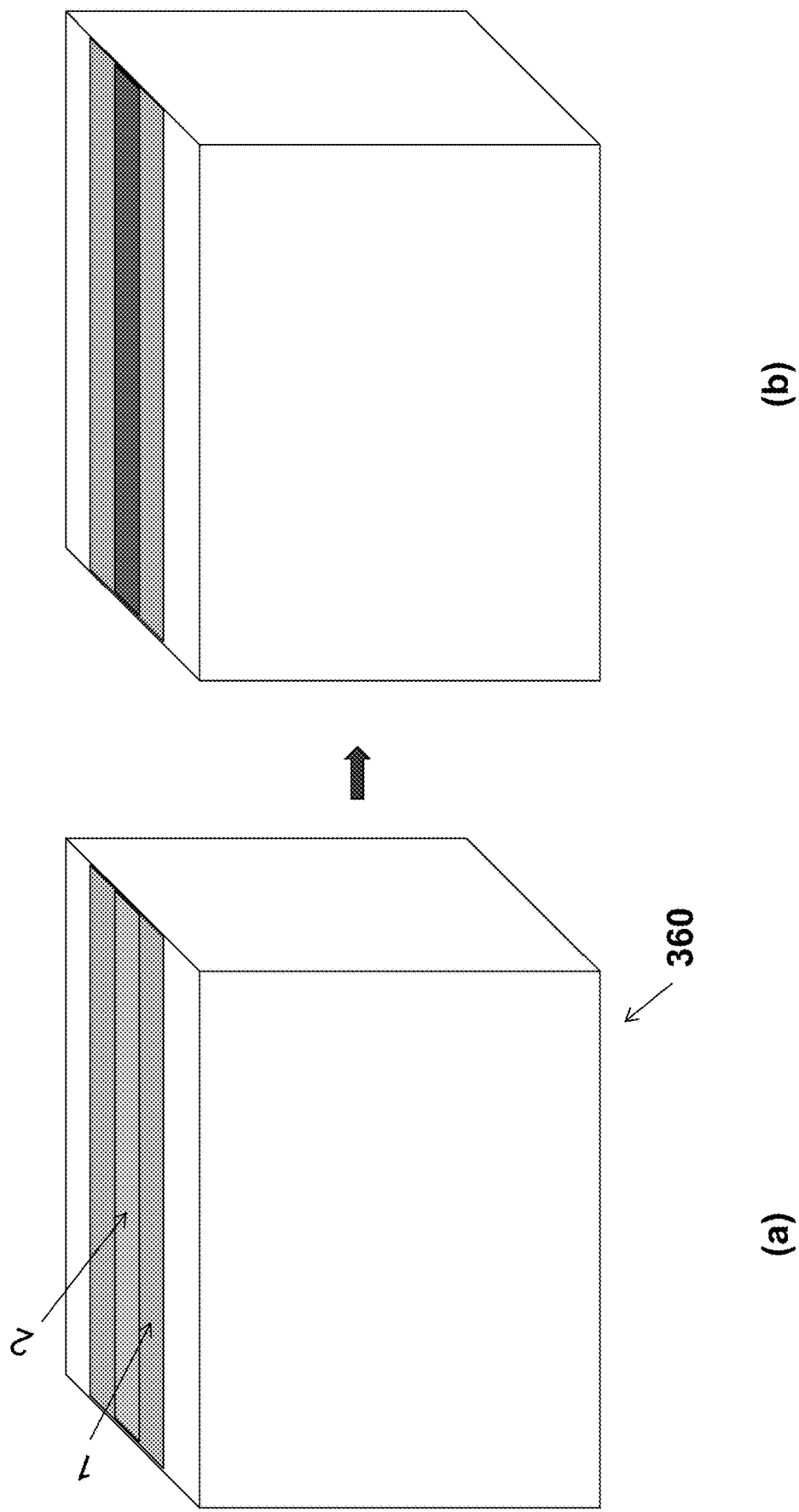
FIG. 18 shows a schematic presentation of a box sealed with an activated indicating device, (a) having an activator tape over a narrow indicator tape and upon expiration of the indicating tape device (b).

FIG. 18 shows a schematic presentation of a box sealed with an activated indicating device (a) having an activator tape 1 over an indicator tape 2 and upon expiration of the indicating device (b). It is not necessary to have an adhesive on the indicator tape. Indicator could be smaller than the activator tape.

A box can also be sealed with an activated indicating device having an indicator tape over an activator tape.

The activator and indicator tapes don't have to be of the same size. One tape could be smaller or wider than the other. Preferred is the one tape being narrower than the other. The objective is to seal the box with an activated TTI. Depending upon the design of the indicator and activator tapes and loading in the dispenser, one can make activator tape over indicator tape or vice versa. When the shelf life of the perishables expires, the indicator tape will become transparent and message and color underneath will become visible.

A box can be sealed with an indicator tape in form a large label and activated with an activator tape.

The sealing tapes and labels could have the many of those features of other indicating device described earlier in this application, for example, other basic and optional layers to get moving boundary, barcodes, numbers, patterns, colors, images and messages.

The smaller tape may or may not have an adhesive depending upon the tapes and box to be sealed. One or both tapes could be tamper indicating.

The activated sealing tape could be applied only on the top closers/flaps or whole box and even crossing the previously applied activated sealing tape.

One can apply one tape (e.g., activator tape) with one dispenser and the other (indicator tape) with other dispenser. There can be two stations, one for applications of indicator tape and the other for the activator tape.

The current system allows perishable manufacturers, warehouse managers and store keepers properly rotate the boxes of perishables thereby minimizing the wastage of foods.

If a bag of a perishable is made from metallized plastic film, the device can be made just by applying an activator sealing tape.

Instead of using the sealing TTI tape for sealing boxes, the sealing tape could also be in form labels and applied on boxes as well. It is also possible to apply preprinted indicator tape as labels on the boxes and activate the labels by applying an activator tape when filled with perishables.

One can also create almost all of the above devices and processes also if the activator layer is substantially not mobile or migrating, e.g., a layer of polyacids (polyacrylic acid) or polyamine (e.g., polyethyleneimine) and a thin indicator layer (e.g., a pH dye) having ability to migrate and react with the non-mobile activator layer.

The sealing tape indicating device, like other devices can be pre-activated and stored cold till need to be applied. This can eliminate the need for a two-tape dispenser. Single dispenser can then be used.

Figure 19:
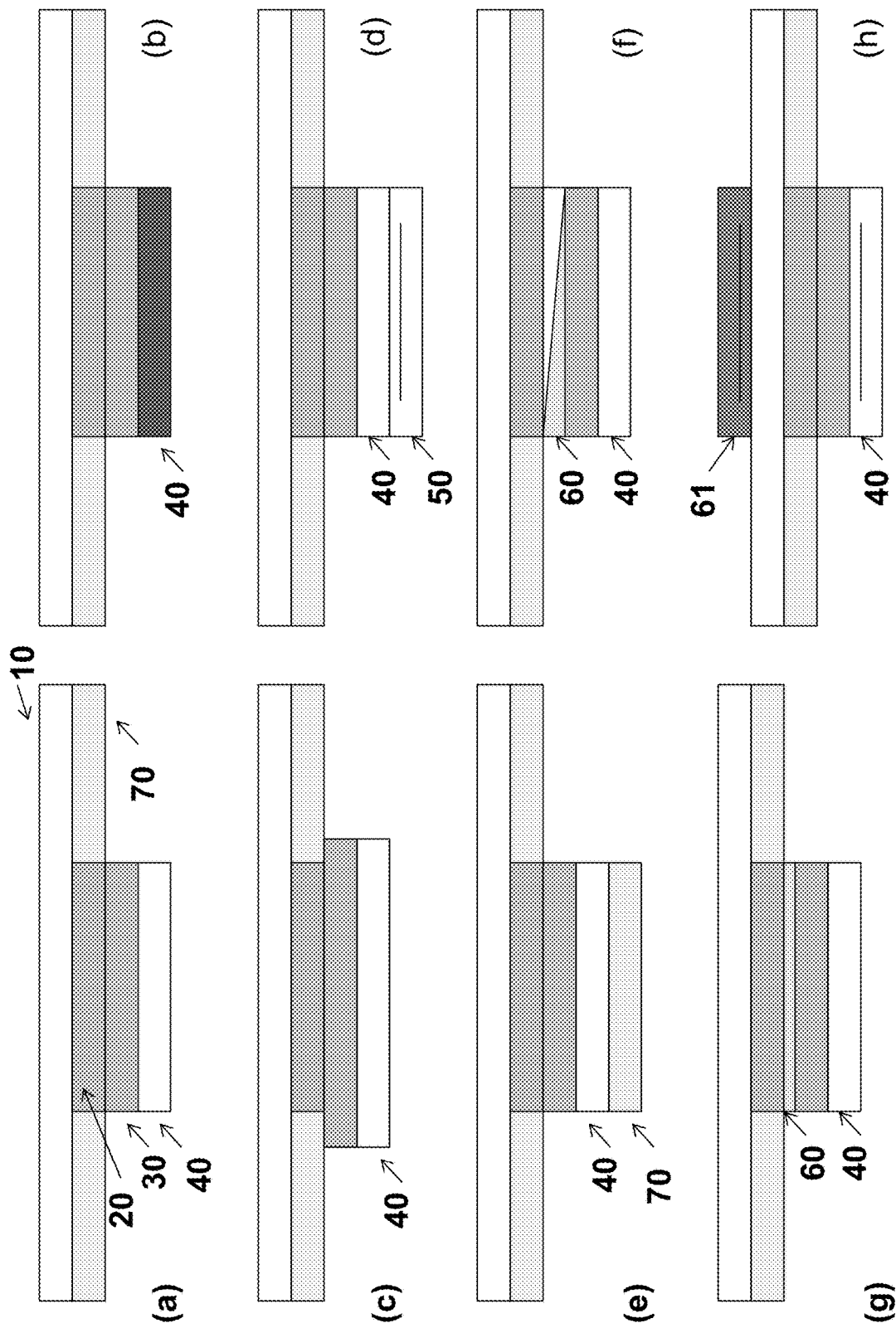
FIG. 19 shows a schematic cross sectional views of an indicating/sealing tapes having some desirable features of TTI for different purposes on a substrate having activator layer and conventional PSA layer on the same side.
Figure 20:
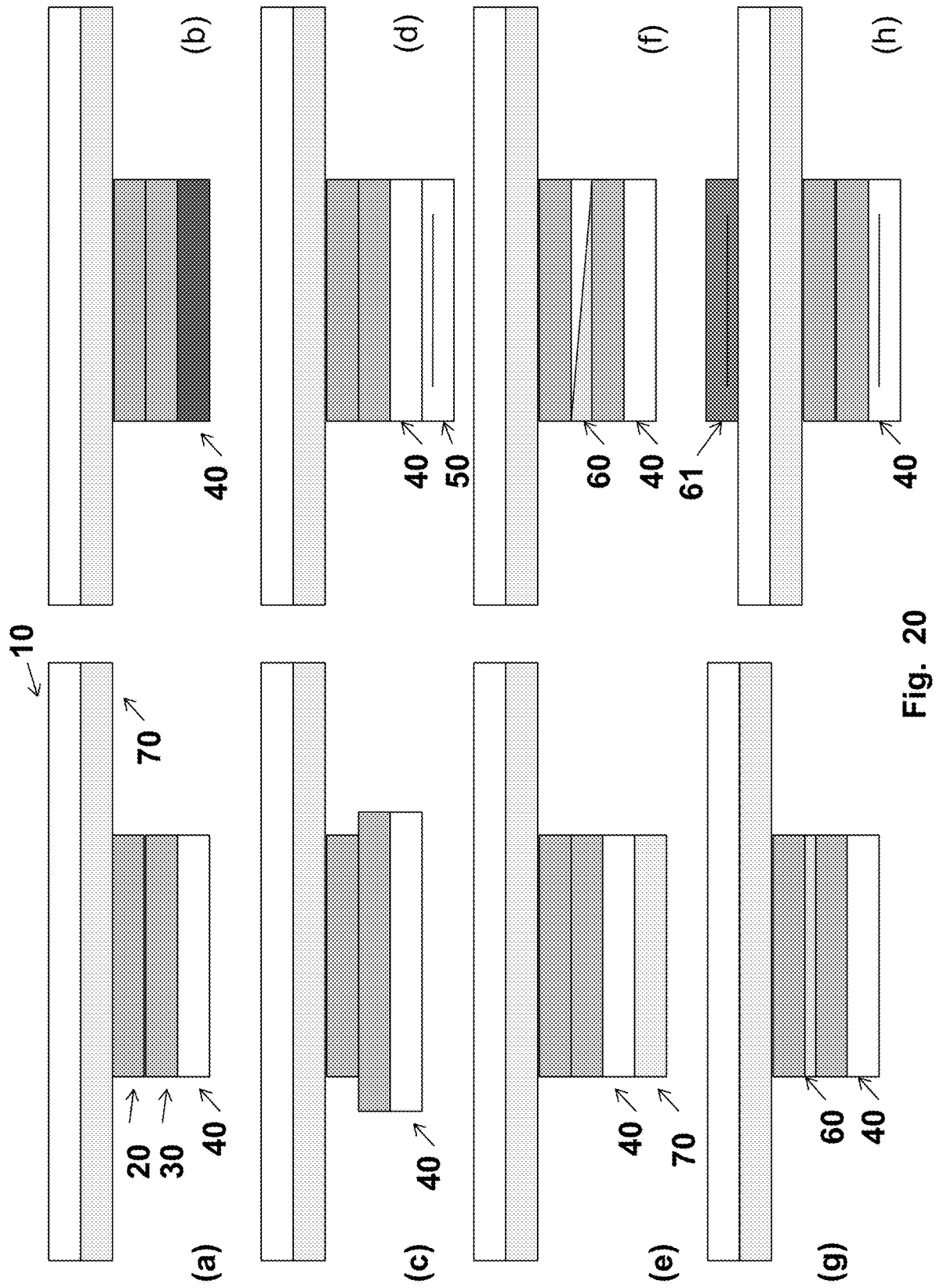
FIG. 20 shows a schematic cross sectional views of an indicating/sealing tapes having some desirable features of TTI for different purposes on a conventional sealing tape.
Figure 21:
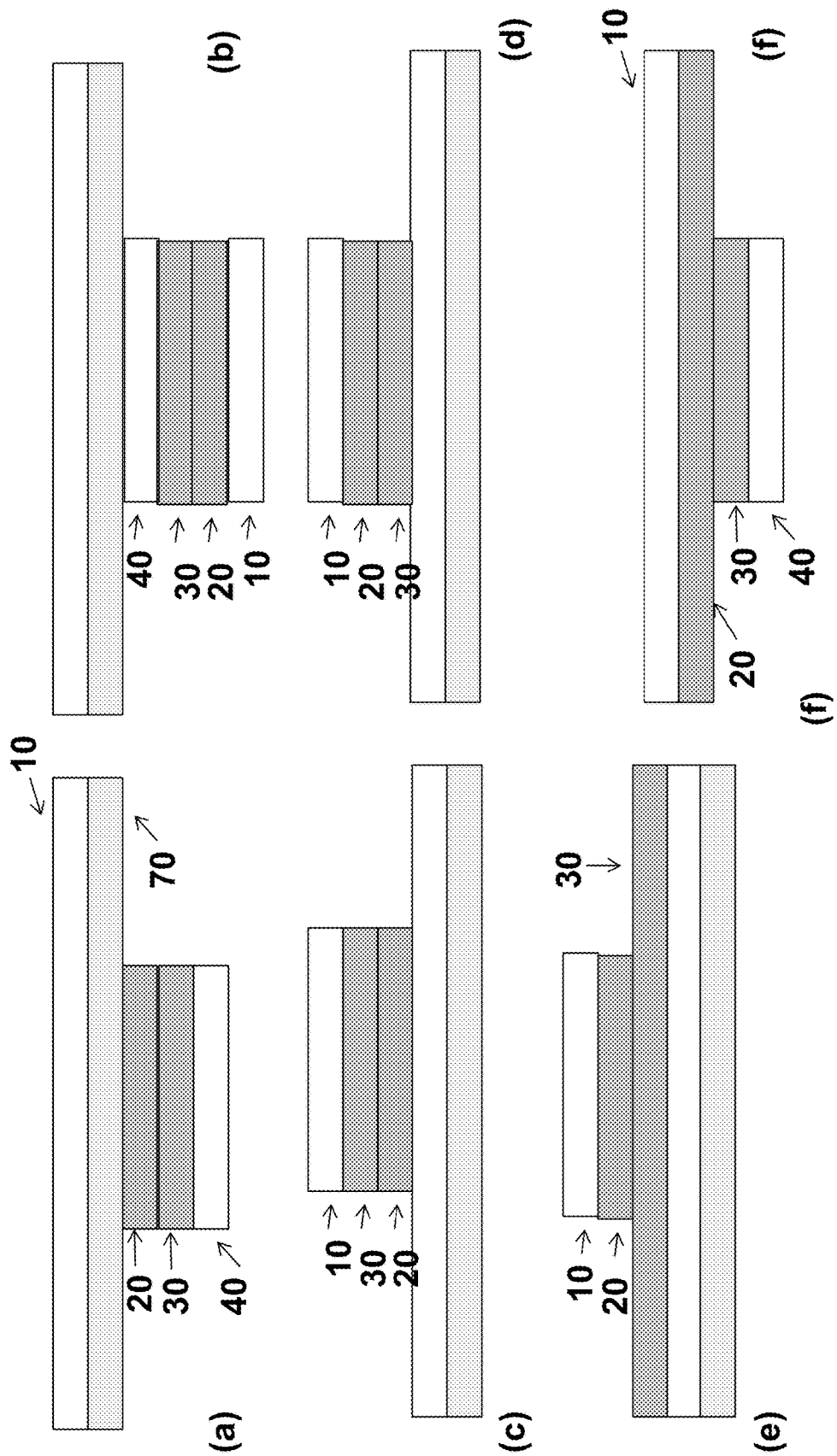
FIG. 21 shows a schematic cross sectional views of sealing tapes having some most desirable features of TTI on a conventional sealing tape.
Figure 22:
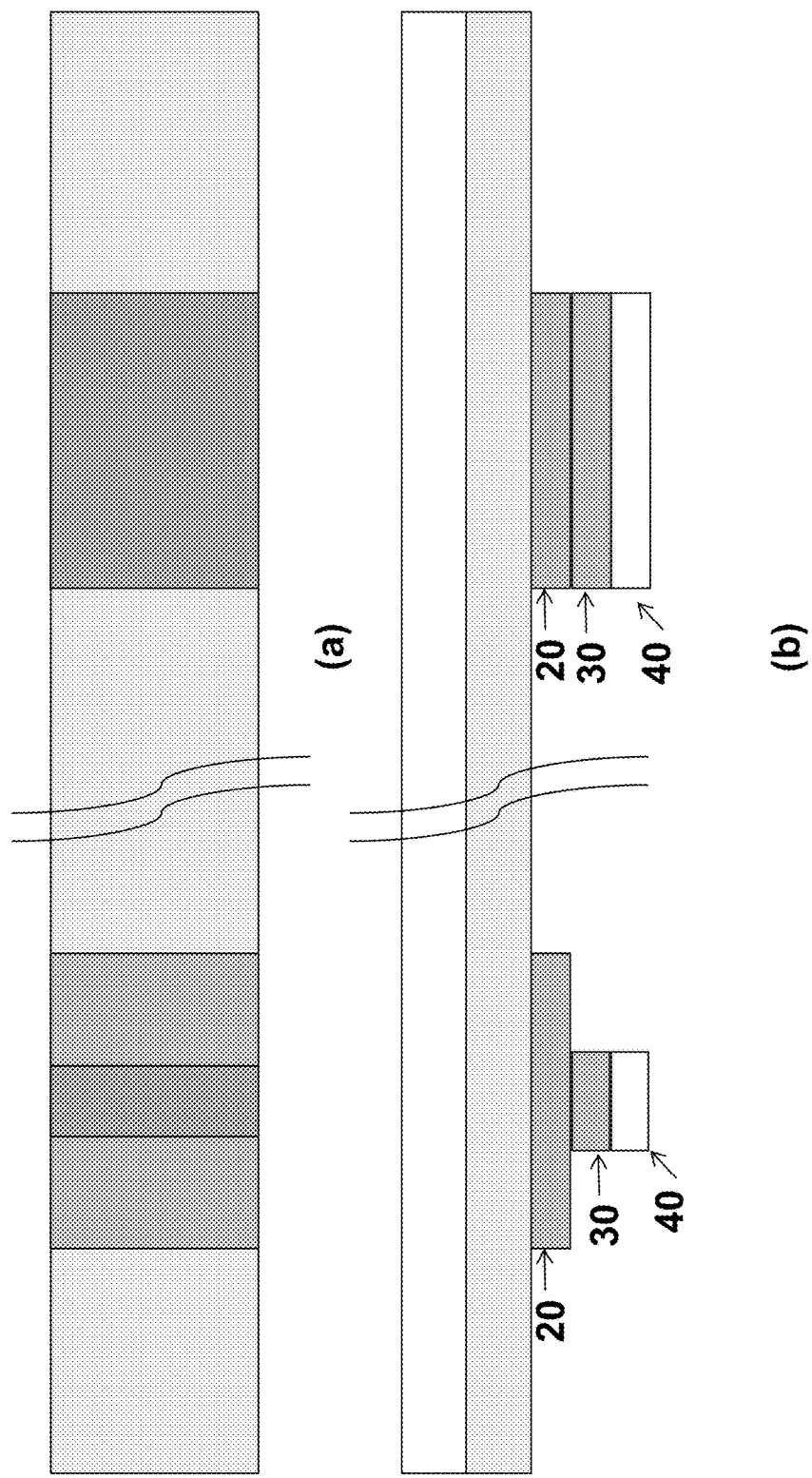
FIG. 22 shows a schematic cross sectional (a) top and (b) cross sectional views of a sealing tape having a couple of features of TTI on a conventional sealing tape in discontinuous fashion.

There many different ways sealing tape indicating device can be made. Sealing tape indicating device can have all the desired features of the TI and TTI. FIGS. 19-22 show some cross sectional views of the different ways the sealing tape and many of the other indicating device disclosed herein can be made. FIG. 19 shows schematic cross sectional views of indicating devices having some desirable features of TTI for different purposes on a substrate 10 having activator layer 20 and conventional PSA 70 on the same side. FIGS. 19-22 also show different locations, shapes, color, messages of different layers such as indicator layer 30, indicator substrate 40, expiration layer 50, permeable layer 60, PSA layer 70 for adhering to an object and a message layer 61. Similarly, FIG. 20 shows schematic cross sectional views of sealing indicating devices having some desirable features of TTI for different purposes on a conventional sealing tape. Though there are many ways to make sealing tape indicating device, there are some more economical ways as shown in FIG. 21. FIG. 21 shows some schematic cross sectional views of sealing tapes having some most desirable features of TTI on a substrate, 10 having conventional adhesive layer 70 and activator adhesive layer 20. It is not necessary to have the whole continuous sealing tape as TTI tape. FIG. 22 shows a schematic cross sectional view of a sealing tape having a couple features of TTI applied on a conventional sealing tape.

One can also make sterilization indicating devices, e.g., for ethylene oxide and hydrogen peroxide by using precursor for the activator. For example, when sodium thiocyanate is used as a precursor, it can produce activator like sodium hydroxide upon exposure to ethylene oxide. Sodium hydroxide thus produced will etch the indicator, thin aluminum layer or its fine particles. Similarly, if a precursor, such as tetrabutylammonium bromide is used, it can produce an acid, such as hydrobromous acid when exposed to hydrogen peroxide or its plasma. The acid will etch thin layer of aluminum or its fine particles. Hydrogen peroxide itself can etch the aluminum layer.

Using a strong resist/barrier layer which significantly prevents diffusion of the etchant/activator and by printing some circuits, not only one creates a message but one can create an electronic circuits, EAS and RFID devices. Top views of different steps of creating such devices, e.g., a RDID are shown schematically in FIG. 23. Electronic components, such as a microchip 150 can be attached/soldered 151 at proper locations on an indicator/metal layer 30 as shown in FIGS. 23(*a*)-23(*c*). Electronic components can be connected to the circuit or antenna with a conductive paint or by soldering. The microchip 151 will be inactive (a kind of sort circuited) and hence can't be read. A barrier/mask material in shape of an antenna 69 can then be printed on the metal layer as shown in FIG. 23(*d*). An activator tape is then applied on to the whole metal layer as shown in FIG. 23(*e*). The activator will etch the metal layer leaving un-etched area under the mask in form of an antenna and the connecting the chip to the antenna as shown in FIG. 23(*f*). Creation of an antenna or circuit by this method is shown in FIG. 38.

There are many different ways to create an RFID-indicating device and other similar devices, such as antennae for RFID, printed circuit boards, EAS (electronic article surveillance) devices and patterning in general. For example, one can use antenna pattern activator tape or print such pattern with an activator. Thus, one can create an antenna and circuit for a RFID and similar devices for monitoring the time, time-temperature, sterilization and alike. It is likely that under-etching may occur. In order to prevent under-etching, one may use an activator neutralizer layer (e.g., that containing a weak tertiary amine for phosphoric acid) under the metal layer. If the area is large enough one can visually see the expired device as well can be read with an RFID reader. An RFID device could also be in or on any of the indicating devices, such as time, time-temperature, freeze, thaw, sterilization indicating devices mentioned herein.

FIG. 24 shows a RFID inlays 410 composed of an electronic chip 402 and an antenna 401 without (a) and with (b) and (c) an activator tape 20 applied at different locations on the antenna 401. Only central part of the antenna is shown. A RFID device with two RFID inlays, one with and the other without an activator tape is shown in FIG. 24(d). The activator tape having sufficient quantity of an activator will etch the portion of the antenna under it. Depending upon the location of the activator tape on antenna, the ability of the inlay/chip to receive and transmit the RF signal will be reduced.

Figure 25:
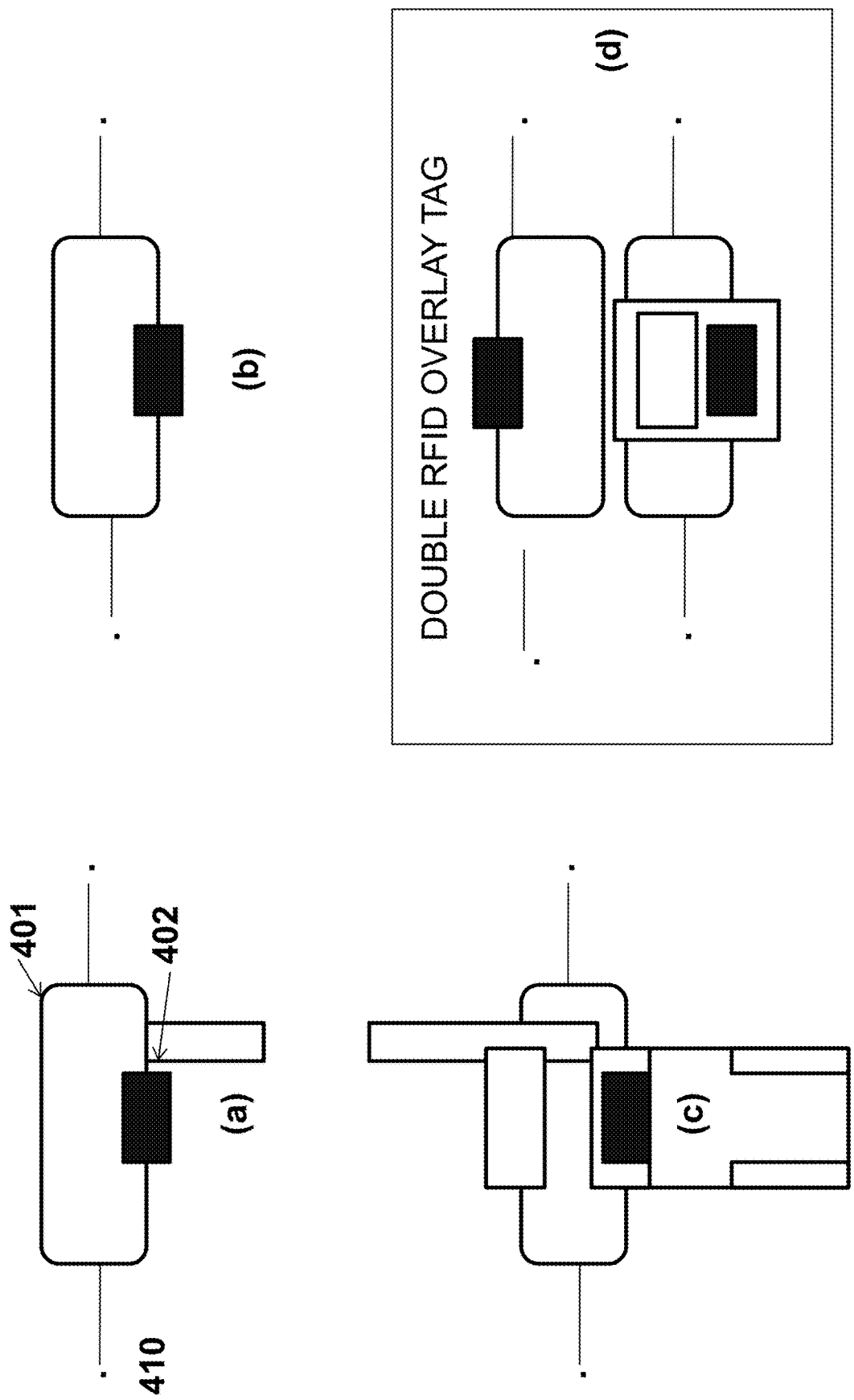
FIG. 25 shows a schematic presentation of RFID inlays of FIG. 24 after etching portions of antenna by the activator tape.

FIG. 25 shows RFID inlays of FIG. 24 after etching portions of the antenna by the activator tape. If the activator tape is applied near or on the RFID chip as shown in FIG. 24(c), one of the most preferred location for application of the activator tape, RFID chip can be completely disconnected from the antenna as shown in FIG. 25(c) and make it essentially inactive, ineffective and non-readable. In this case the antenna is an indicator. Thus, when an activator tape which has ability to etch away the antenna is applied on the antenna, the inlay becomes an indicating device, such as a TTI. If properly designed and applied, one can make the RFID device inactive when the shelf life of the content inside a box expires.

Figure 26:
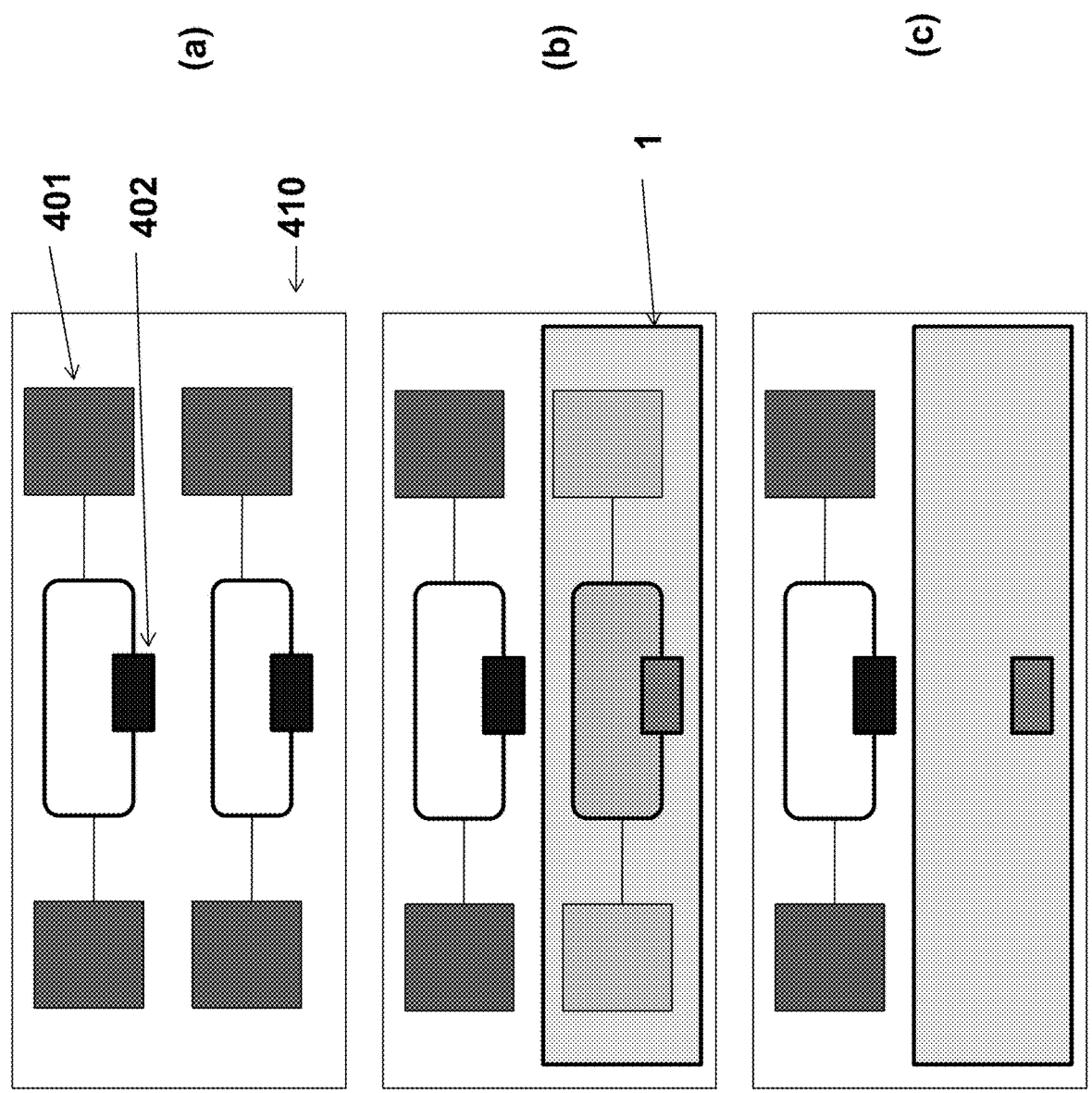
FIG. 26 shows a schematic cross sectional views of (a) a double RFID indicating device, (b) with an activator tape applied on one RFID inlay and (c) after making the inlay non-readable upon etching of the antenna.

FIG. 26 shows schematic top views of a double inlay RFID-indicating device 410 (a) with an activator tape 1 applied on one RFID inlay (b) and after the inlay made non-readable (de-activated or disconnected) (c) upon etching of the antenna by the activator tape 1. This device 410 has two RFID inlays, each having its own antenna 401 and an electronic chip 402. The device is activated by applying the activator tape 1 only on one inlay as shown in FIG. 26(b). The inlay with activator tape will become inactive and non-readable when the antenna or a portion of it is etched away.

Unprotected and those coated with an activator layer RFID inlays can also be used for many other devices disclosed herein including monitoring sterilization, e.g., steam sterilization. Steam and hot water have ability to dissolve aluminum. If the antenna is made from an aluminum alloy which is more sensitive to water, the RFID can be made inactive faster. In order to use a double RFID for monitoring sterilization, one of the antennae need to be protected with a protective layer, such as a mask which will protect from water.

The RFID devices can be activated prior or after applied on an object.

It is also possible to make the indicating devices, such as TI, TTI and SI by using very fine particles of a metal, such as aluminum and its alloys. In this case a mixture of metal particles and an activator in an ink formulation can be coated on a substrate. The indicating device thus made could have a protective layer or permeable layer and all other features of TTI and indicating device described herein. This type of indicating device will require more aggressive and/or higher concentration of the activator to be used for TI or TTI and high temperature TTI or dry heat indicating device. This type of indicating devices are more suitable for dry heat or steam sterilization indicating device.

Figure 27:
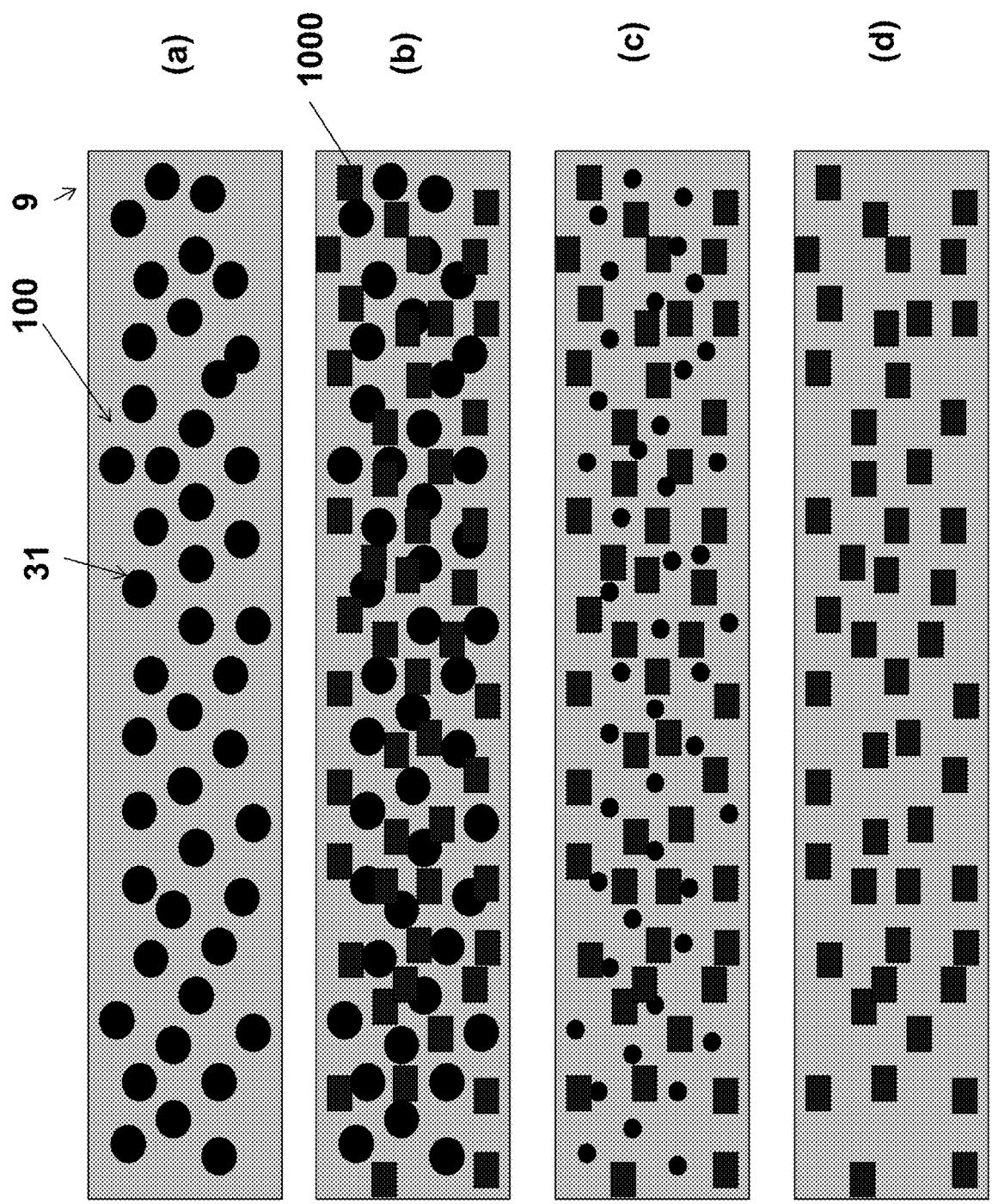
FIG. 27 shows a schematic cross sectional views of (a) an ink coating with metal particles, (b) metal particles and an activator, (c) partial reaction of activator on metal particles and (d) complete destruction of the metal particles.

FIG. 27 shows schematic cross sectional views of (a) an ink coating 9 with metal particles 31 and a binder 100(b) metal particles and an activator 1000(c) partial reaction of activator on metal particles and (d) complete destruction of the metal particles. It is not necessary to dissolve the metal particles completely. For a given metal, finer particles will get dissolved faster. Metal particles could be of any shape and have naturally formed (e.g., oxide) layer and/or an applied protective coating.

The devices based on FIG. 27 can also contain an indicator for the metal cation. Upon reaction of a metal with an activator, a metal cation/salt will be produced. The metal cation thus produced can react with an indicator providing an intermediate color and the final color of the indicator. When an activator, e.g., phosphoric acid reacts with a metal, such as aluminum, it will produce a metal salt, e.g., aluminum phosphate. An indicator which reacts with aluminum cation (e.g., $Al^{+3}$) can be added to monitor or detect the reaction.

Particles having an ultrathin coating of metal, e.g., a thin layer of copper on iron particles which can be obtained for example by dipping iron particles in copper solution can also be used and some preferred for the transparency change for the indicating devices, such as sterilization (e.g., steam, ethylene oxide, plasma etc). These metal coated particles will undergo transparency change similar to metallized plastic film, e.g., copper coated particles of can undergo a red to the color of the substrate particle on which copper was coated. Thin coating can be obtained by many other different ways.

Figure 28:
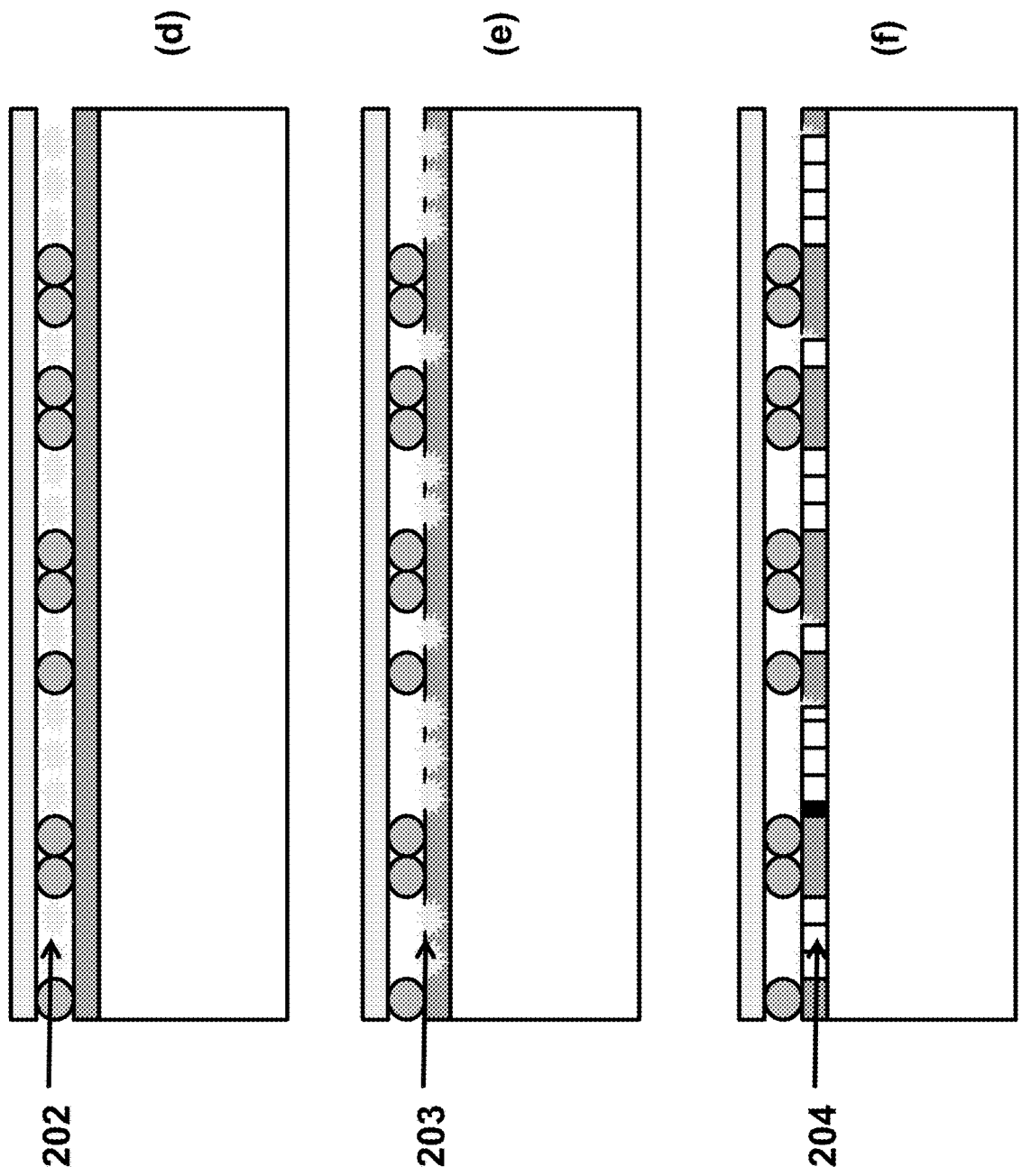
FIG. 28 shows a schematic presentation of a method of making (a-c) a thermally activatable indicating device having a layer of thermally activatable microencapsulated activator on a metal layer and different stages (d-f) of the device after activation.

In order to make the indicating devices activatable on demand, one can use microencapsulated activator and/or indicator. FIG. 28 shows a schematic cross sectional presentation of a method [FIGS. 28(a)-28(c)] of making a thermally activatable indicating device having a layer of thermally activatable microencapsulated activator on a metal layer and different stages [FIG. 28(d)-28(f)] of the device after activation. The device can be created by applying a layer of microencapsulated activator 201 (e.g., phosphoric acid or its solution) which can be ruptured e.g., by application of heat or pressure on a metal layer 30 on a substrate 40 [as shown in FIGS. 28(a) and 28(b)]. The device can have other layers, such as an adhesive layer with a release linear on the back (not shown). A protective coat 101 can be applied on the microcapsules as shown in FIG. 28(c). Using a thermal printer, one can print a message or image (or write with a blunt object/pen) as shown in FIG. 28(d). The microcapsules will rupture 202 and release the activator/phosphoric acid. An image will appear. The device can be applied on to an object or person by removing the release liner from the back. The released activator/phosphoric acid will etch 203 the metal layer as shown in FIG. 28(e). When the metal is completely etched 204 the printed message and/or color printed underneath will appear as shown in FIG. 28(f). Many variations of this and many similar devices disclosed herein are possible, e.g., by varying the nature of the layers, applying additional layers and by changing locations of the layers.

Figure 29:
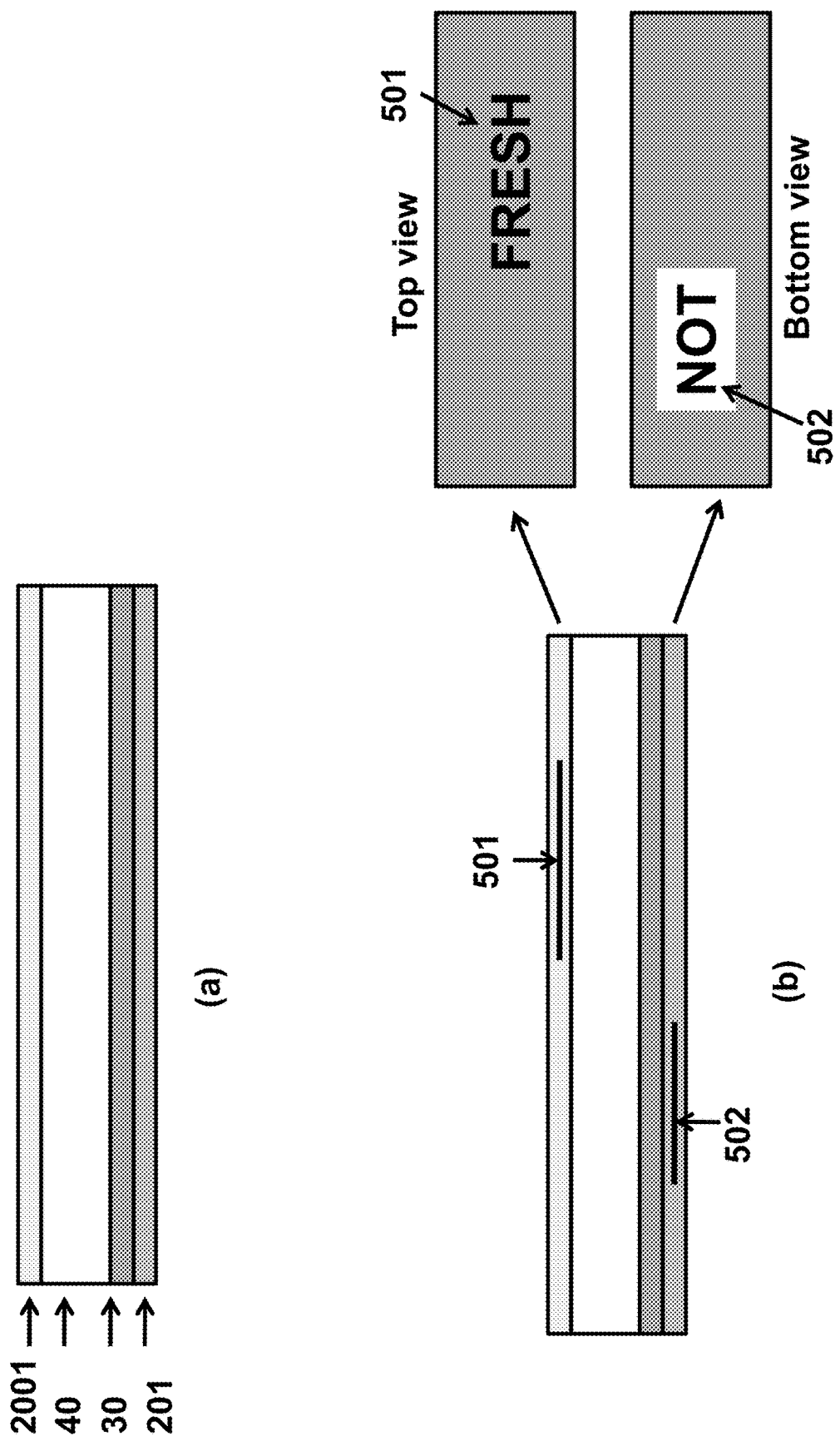
FIG. 29 shows a schematic presentation of a thermally activatable indicating device (a) having a layer of thermally activatable microencapsulated activator on a metal layer on one side and conventional thermally printable layer on the other side and appearance after activation (b) and upon expiration (c-d).
Figure 29:
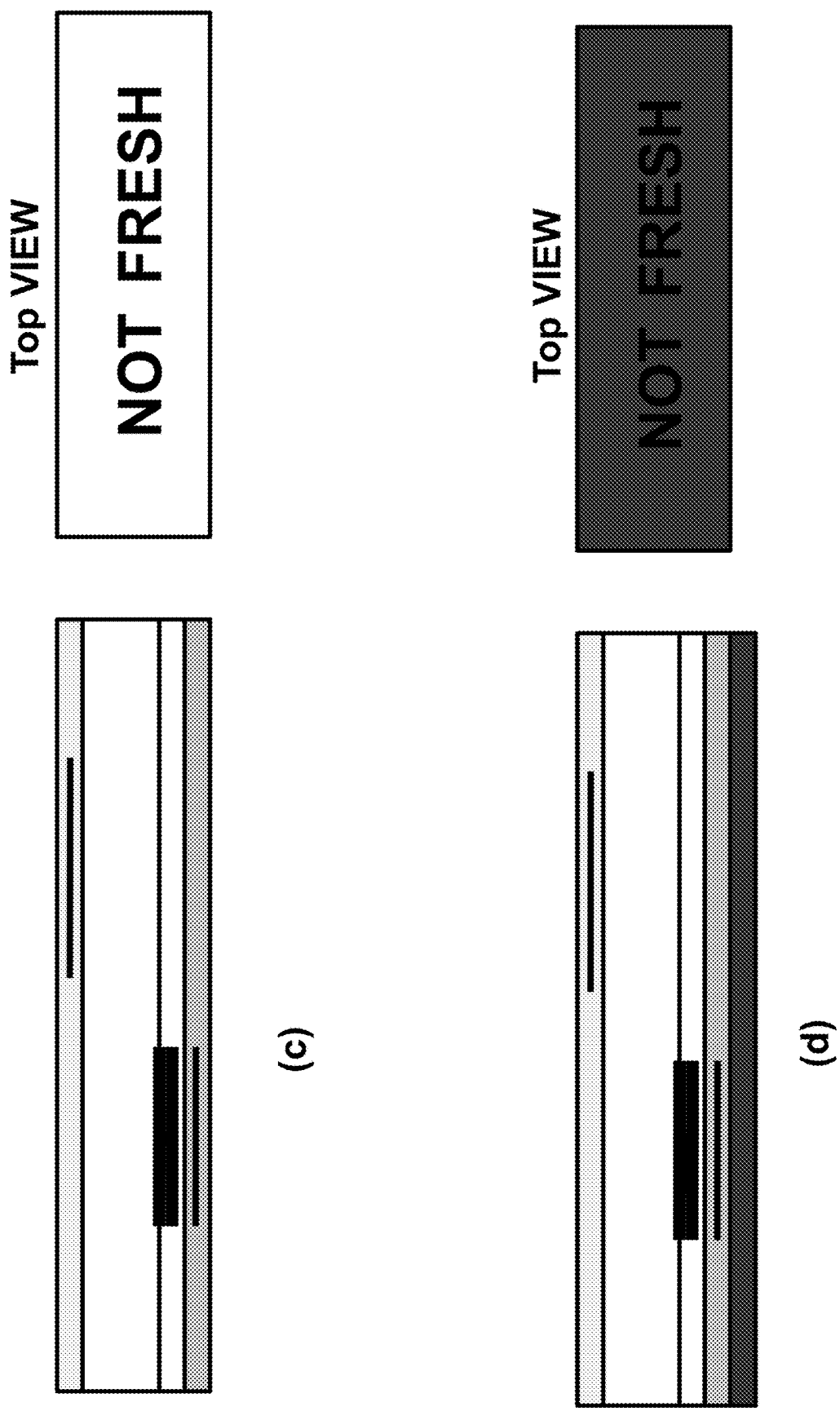

FIG. 29 shows a schematic presentation of an online thermally activatable indicating device as shown in FIG. 29(a) having a layer of thermally activatable microencapsulated activator 201 on a metal layer 30 on one side and conventional thermally printable layer 2001 on the other side of a substrate 40 and appearance after activation [FIG. 29(b)] and upon expiration [FIGS. 29(c) and (d)]. The device of FIG. 29(a) can be made by applying a thermally activatable layer 2001 on the plastic side of a metallized plastic film and by applying microencapsulated activator layer 201 on the metal layer 30. Desired messages can be printed on both the sides of the device [FIG. 29(b)]. When viewed from the top only one message 501 (e.g., FRESH) can be seen. Upon activation, the activator will etch the metal layer. Upon expiration, the message 502 printed on the metal (e.g., NOT) can be seen from the top and one can see the full message (NOT FRESH) as shown schematically in [FIG. 29(c). A proper color layer can be applied on the back if a color is also desired upon expiration [FIG. 29(d)].

Figure 30:
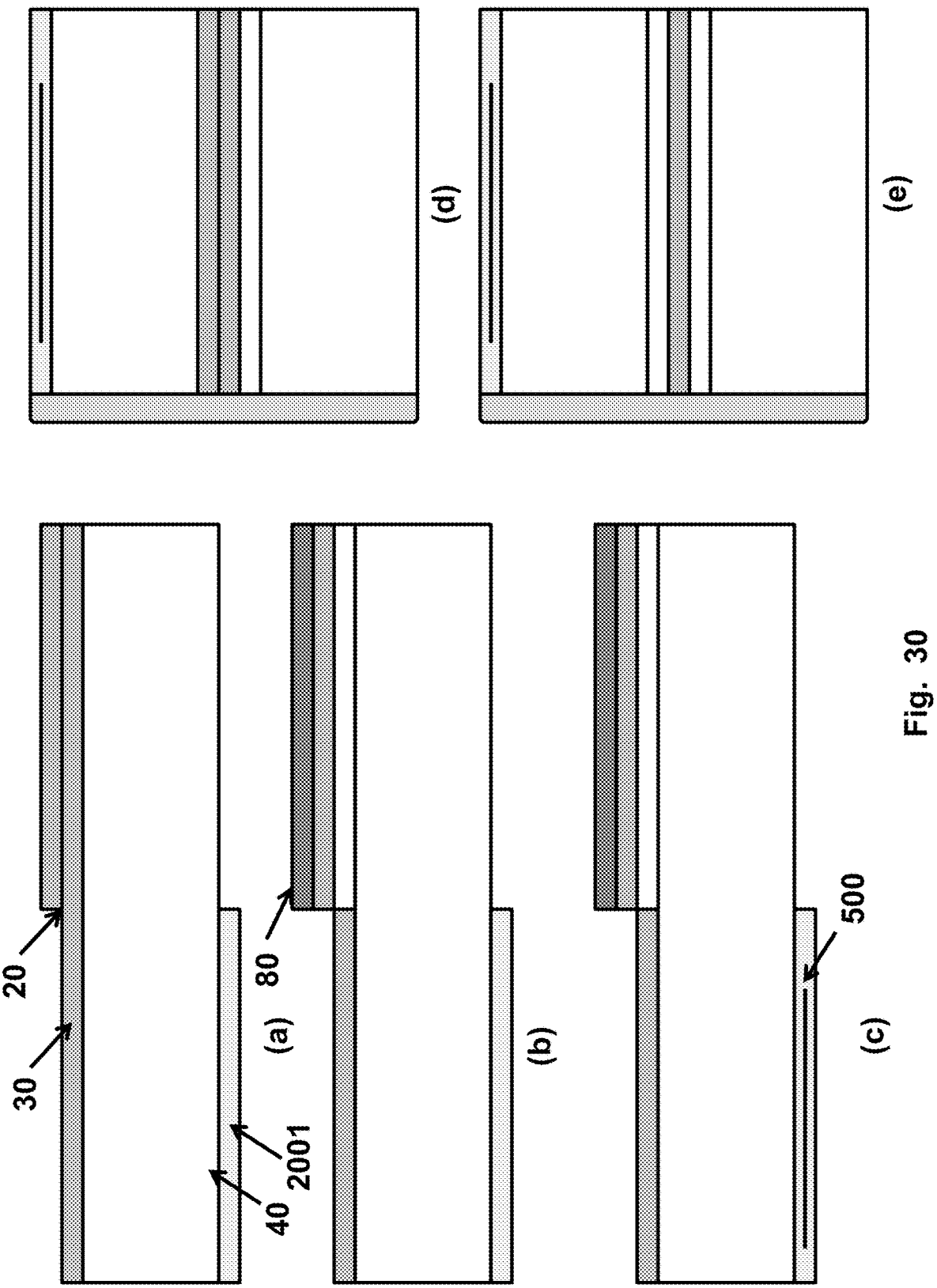
FIG. 30 shows a cross sectional schematic presentation of a method of making a direct thermal printable indicating device made by folding.

There are many different ways to make thermally activatable indicating devices. For example, a time indicating device as visitor's badge can be created by a method shown schematically in FIG. 30. The device can be made by applying a pressure sensitive adhesive containing an activator 20 (e.g., phosphoric acid) on one half of the metal layer 30 and thermally activatable layer 2001 on a substrate 40 [FIG. 30(a)]. A release liner 80 is applied on the activator layer 20 [FIG. 30(b)]. Activator 20 will dissolve the metal layer 30 underneath and make activator portion of the metallized plastic film clear [FIG. 30(b)]. A message 500 (e.g., expired or a photo of a visitor depending upon the application) can be printed on the back of the substrate 40 having a thermally activatable layer 2001 [FIG. 30(c)]. The release liner 80 from the activator layer is removed and the device is folded in the middle [FIG. 30(d)]. The message 500 will be on the top of the activated device. When the device expires (metal layer will get dissolved), a color and/or a printed message, e.g., red color, "X", "Not Valid" etc can appear under the message/photo [FIG. 30(e)].

Figure 31:
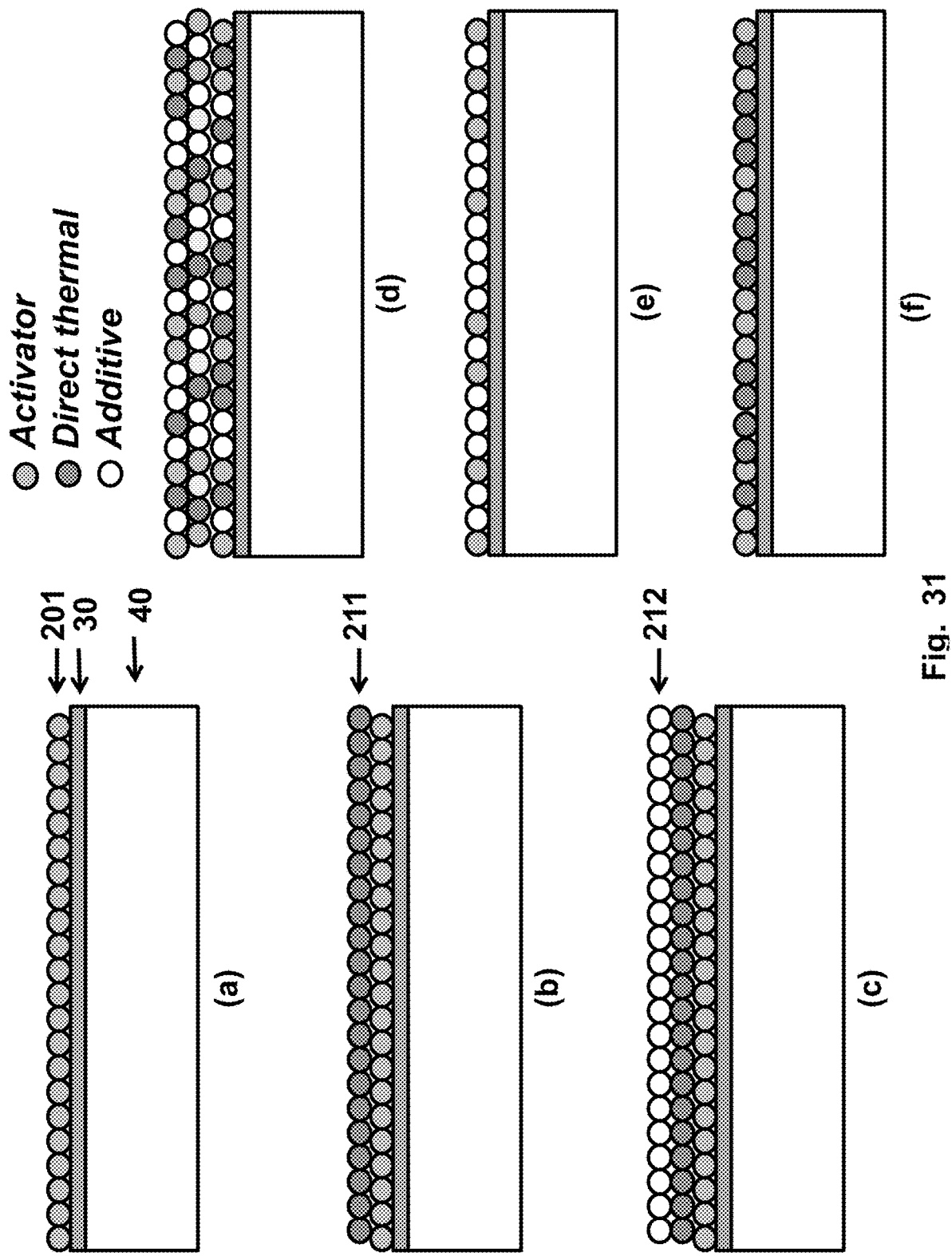
FIG. 31 shows a cross sectional schematic presentation of some of the different ways a microencapsulated activator, an indicator and an additive can be applied on an indicator layer.

FIG. 31 shows a cross sectional schematic presentation of some examples of the different ways microencapsulated activator, indicator and an additive can be applied on an indicator layer. The metal layer may have only one layer of microencapsulated activator 201 [FIG. 31(a)], a layer of microencapsulated activator and direct thermal printable materials 211 [FIG. 31(b)], a layer of microencapsulated activator, direct thermal printable materials and an additive 212 [FIG. 31(c)], a layer of mixture of microencapsulated activator, direct thermal printable materials and an additive [FIG. 31(d)], a layer of mixture of microencapsulated activator and an additive [FIG. 31(e)] and a layer of mixture of microencapsulated activator and direct thermal printable materials [FIG. 31(f)]. When metal particles are used as an activator, there is no need for a metal layer 30. In such case, these layers can have metal particles on substrate 40 or mixed with the other encapsulated materials.

Figure 32:
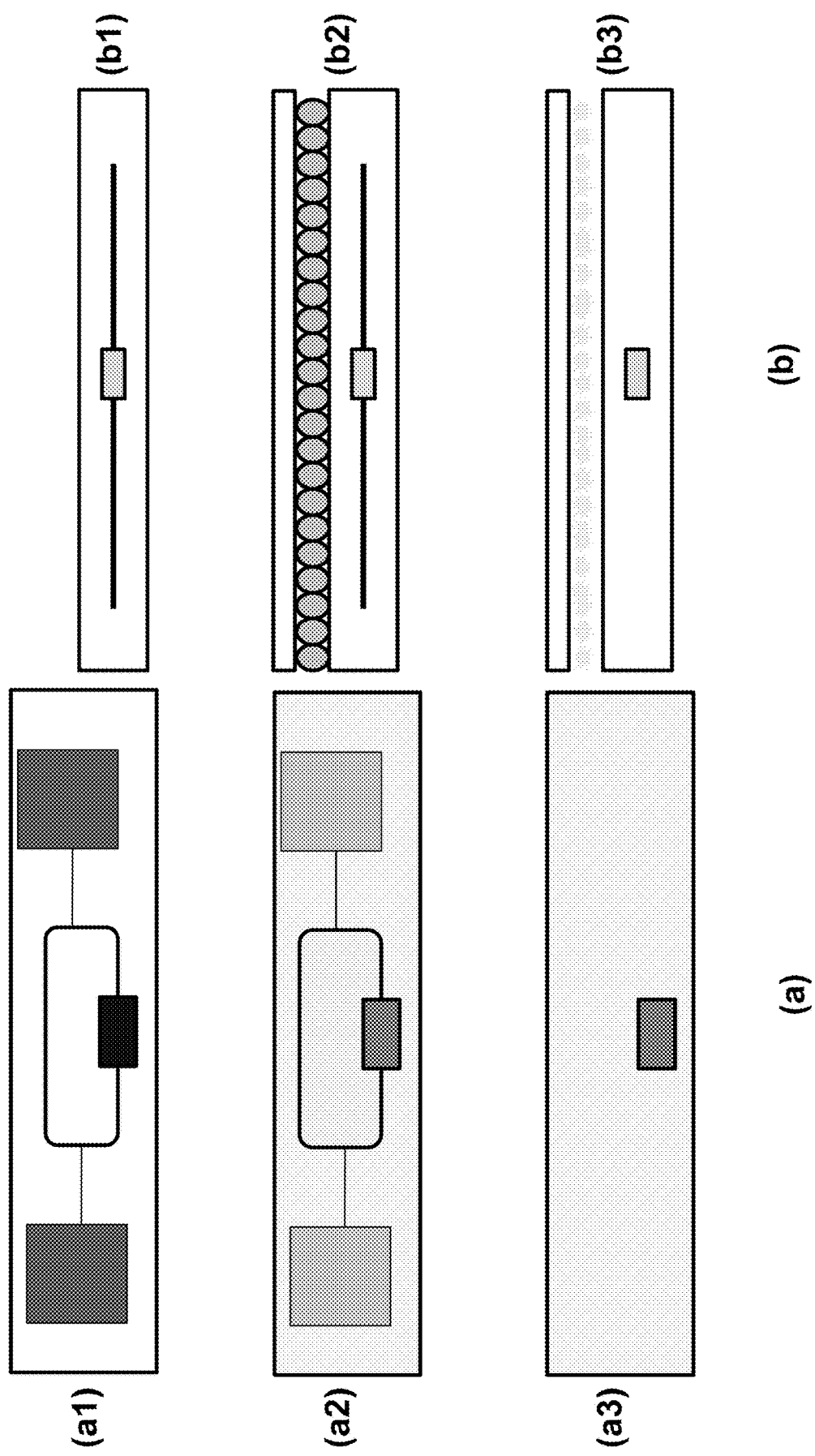
FIG. 32 shows a schematic top (a) and cross sectional (b) views of a RFID inlay (a1 and b1) having a layer of microencapsulated activator tape applied on the RFID inlay (a2 and b2) and upon expiration (a3 and b3).

There are a number of other ways an indicating device can be made using a microencapsulated layer. An example of use of a microencapsulated layer, e.g., an activator tape (a substrate having a coating of microencapsulated activator) to make an indicating device is shown in FIG. 32. An activator can be applied on a RFID inlay as shown in FIGS. 32(a1) and 32(b1). The device can be activated by rupturing the microcapsules, FIGS. 32(a2) and 32(b2). Released activator will etch the antenna and make the readable RFID, non-readable, FIGS. 32(a3) and 32(b3). Similarly many other indicating devices can also be made.

Figure 33:
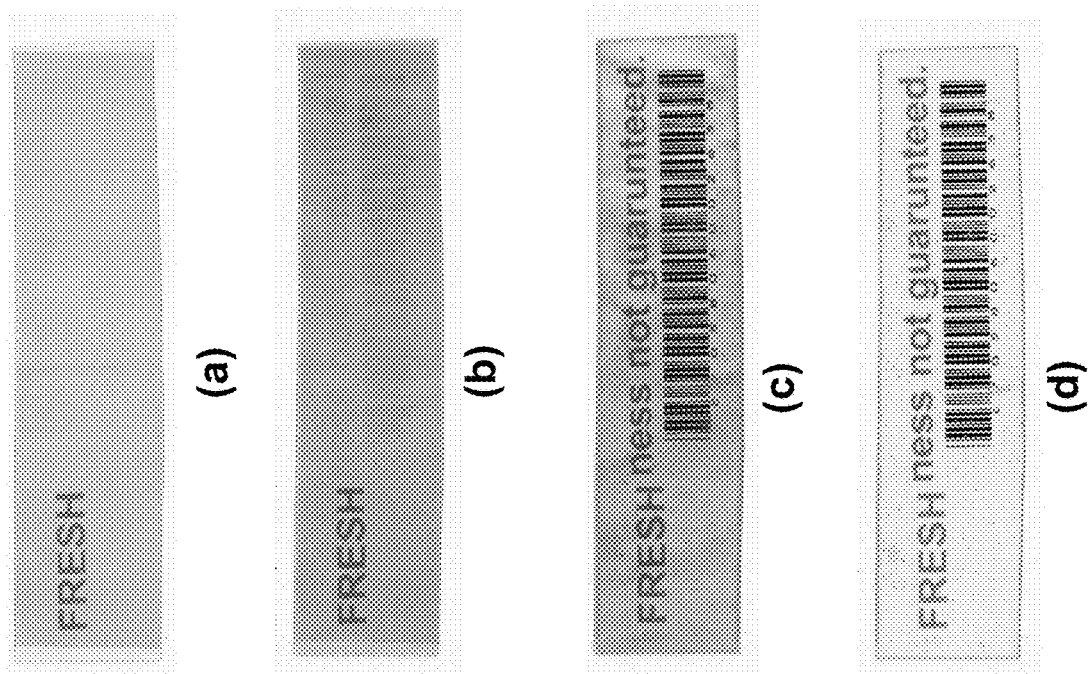
FIG. 33 shows an example of a TTI device showing two messages during and after the induction period.

FIG. 33 shows a TTI device showing a message "FRESH" during the induction period and "ness not guaranteed" and a barcode appearing after the induction period (see Example 7 for detail for this indicating device).

Figure 34:
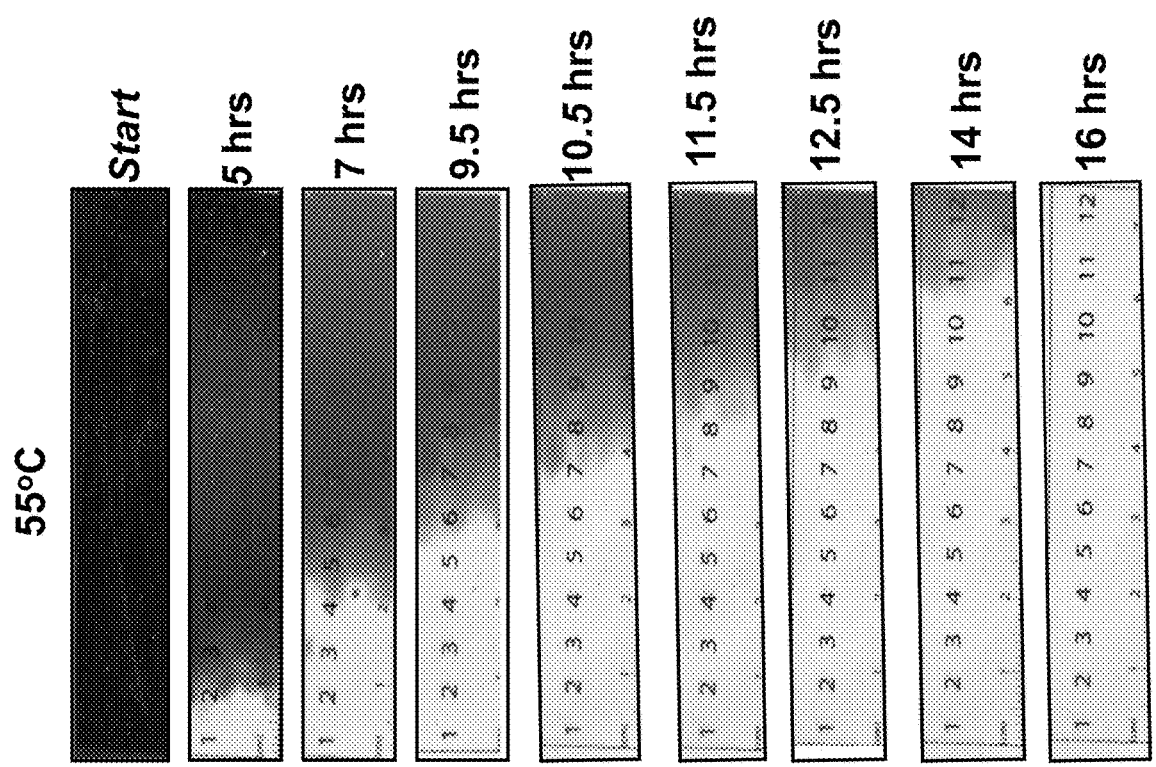
FIG. 34 shows an example of a moving boundary indicating device having a wedge shaped permeable barrier.

FIG. 34 shows a moving boundary indicating device having a wedge shaped permeable barrier annealed for different periods of time at 55° C. (see Example 8 for detail for this indicating device).

FIG. 35 shows a box sealed with an indicating sealing tape upon activation (a) and upon expiration (b) (see Example 10 for detail for this indicating device).

FIG. 36 shows a visitor's badge having a wedge shaped permeable layer between the indicator and activator layers annealed for different periods of time at 55° C. (see Example 11 for detail for this indicating device).

Figure 37:
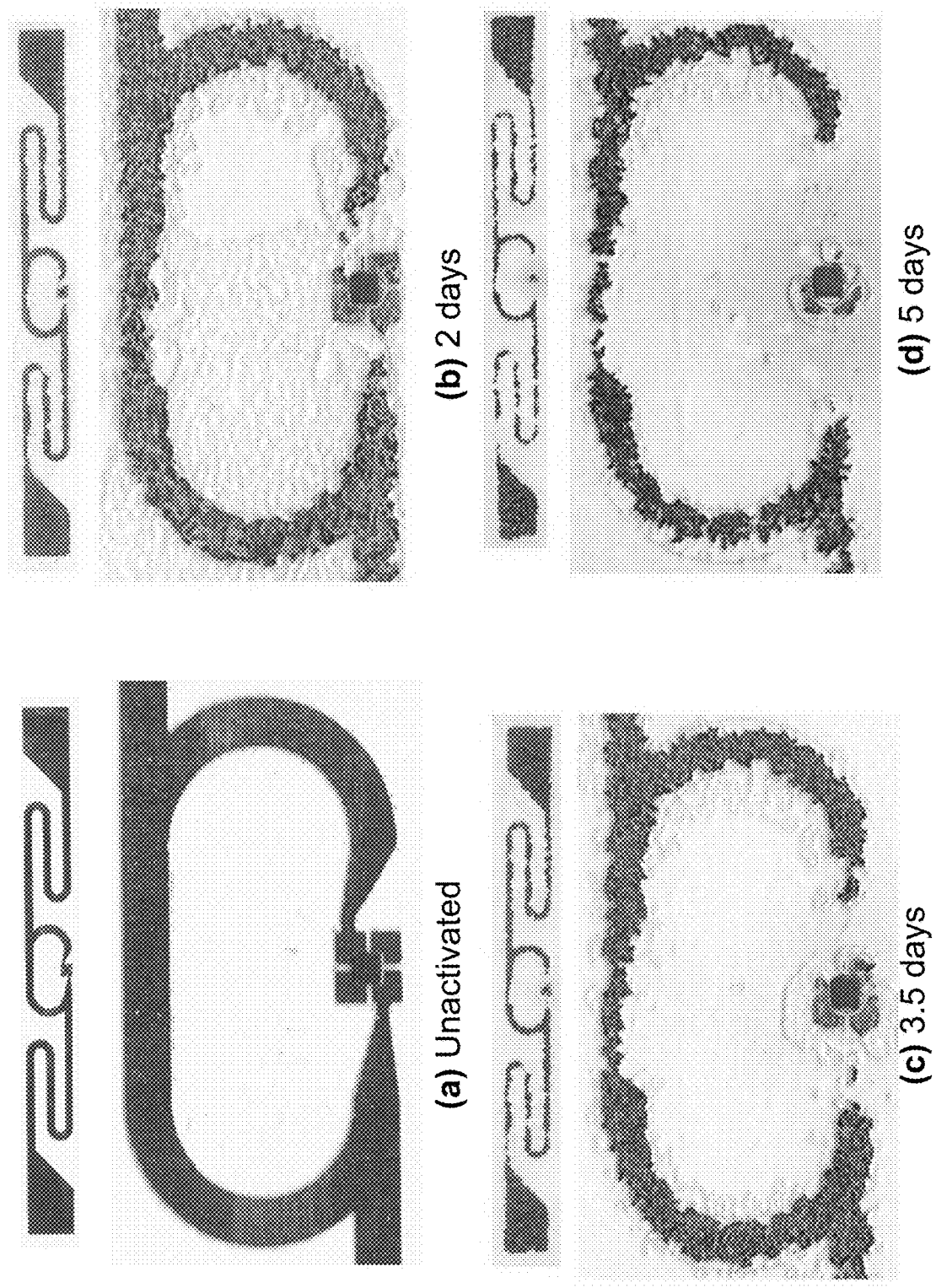
FIG. 37 shows an example of a RFID-indicating device at different stages after the activation with an activator tape.

FIG. 37 shows an activated RFID-indicating device inlay annealed for different periods of time at 25° C. (see Example 15 for detail for this indicating device).

FIG. 38 shows two pieces (bottom piece is upside down) of metallized polyester film printed with an antenna on indicator (a) and after storing at room temperature for 3 days (b) (see Example 16-B for detail for this indicating device).

Figure 39:
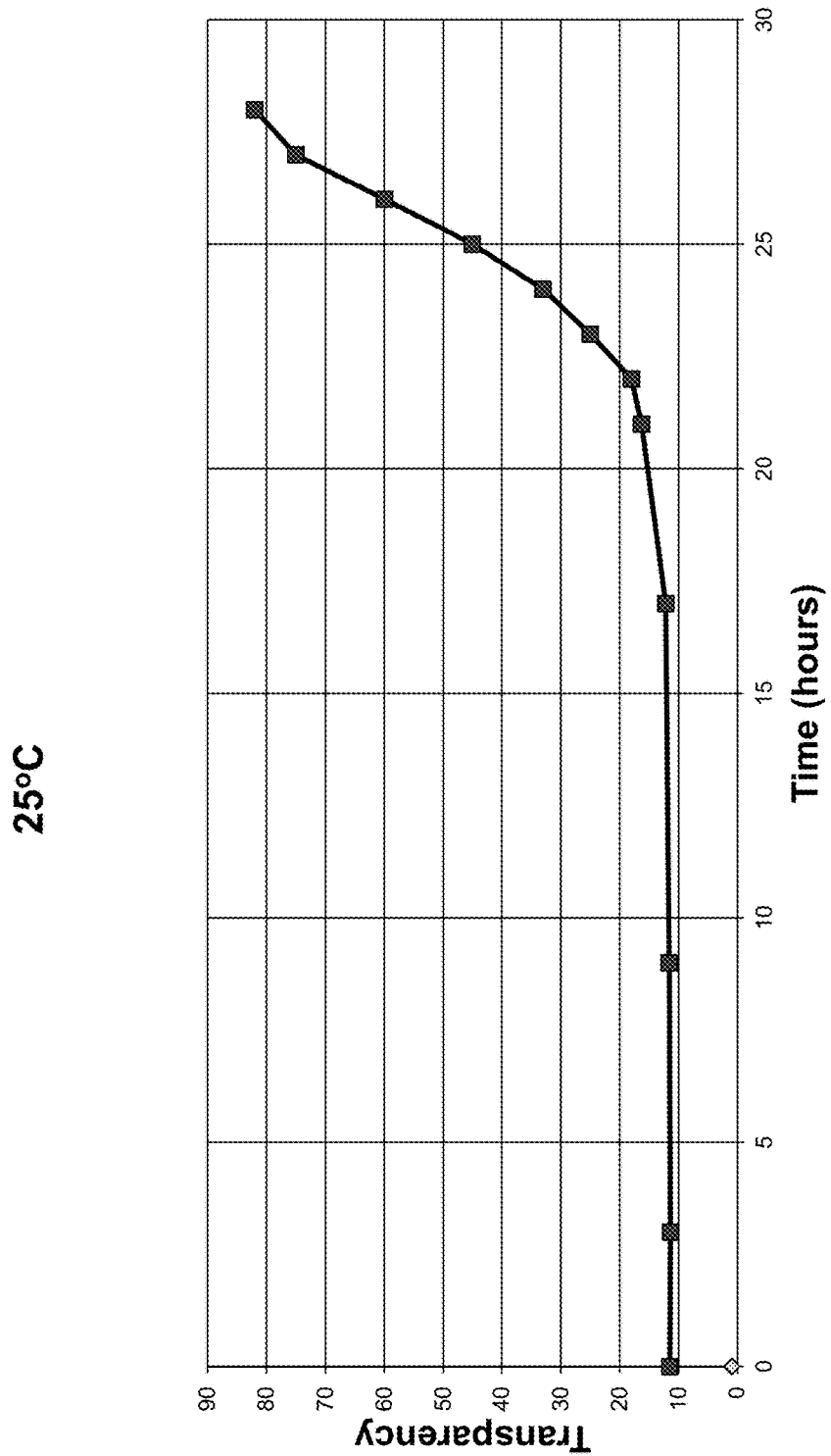
FIG. 39 shows a plot of percent transparency of an indicating device versus time.

FIG. 39 shows a plot of percent transparency of an indicating device with time at 25° C. As can be seen from the FIG. the device has a long induction period (see Example 17 for detail for this indicating device).

FIG. 40 shows a steam sterilization indicating device made from an aluminum (powder) ink and varied concentration of sodium acetate treated under different conditions (see Example 26 for detail for this indicating device). An aluminum ink formulation containing varied amount of sodium acetate were coated on a clear polyester film and dried. Strips of the coating were treated with different conditions. As can be seen from FIG. 40, the device changes color (becomes transparent) only when proper sterilization conditions are met and does not change under other conditions.

Figure 41:
FIG. 41 shows an example of a moving boundary steam sterilization indicating device treated with steam for different periods of time at 120° C.

FIG. 41 shows an example of a moving boundary steam sterilization indicating device treated with steam for different time at 120° C. (see Example 27 for detail for this indicating device). The rate of movement of the boundary can be controlled by many parameters such as the nature and thickness of the permeable wedge layer and activator. A polyurethane layer is more permeable than a polyacrylic layer.

Figure 42:
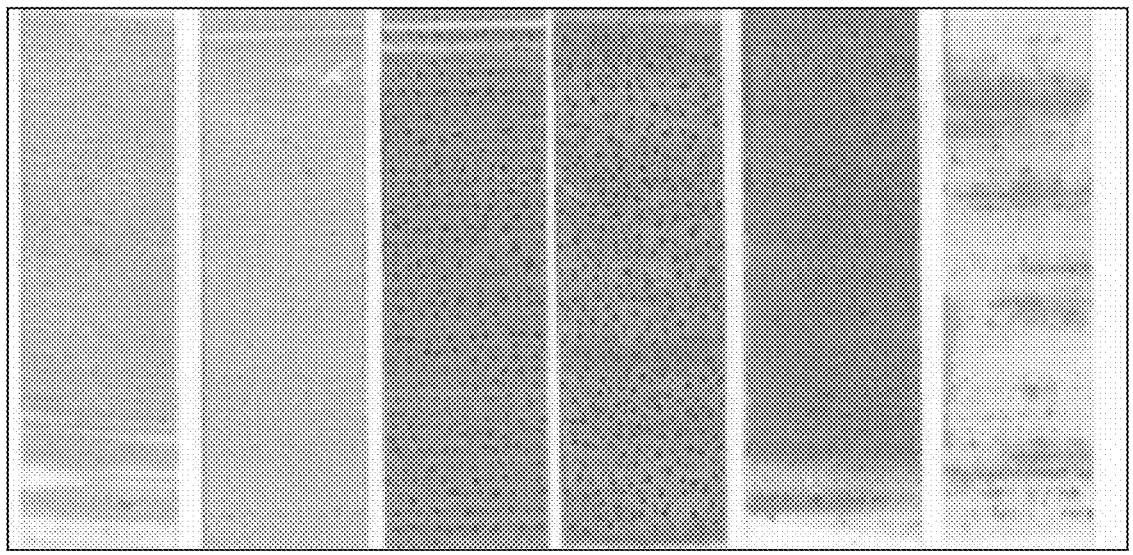
FIG. 42 shows an example of a hydrogen peroxide sterilization indicating device made from a aluminum powder and a precursor treated with different sterilization conditions.

FIG. 42 shows a hydrogen peroxide sterilization indicating device made from aluminum ink and tetrabutylammonium bromide under different treatment conditions (see Example 28 for detail for this indicating device). The device is very selective to hydrogen peroxide. The devices can be used for monitoring sterilization with hydrogen peroxide plasma. Tetrabutyl ammonium bromide and other bromides, such as potassium bromide, most likely produce hydrobromous acid which etch the metal particles and hence selective to hydrogen bromide.

Figure 43:
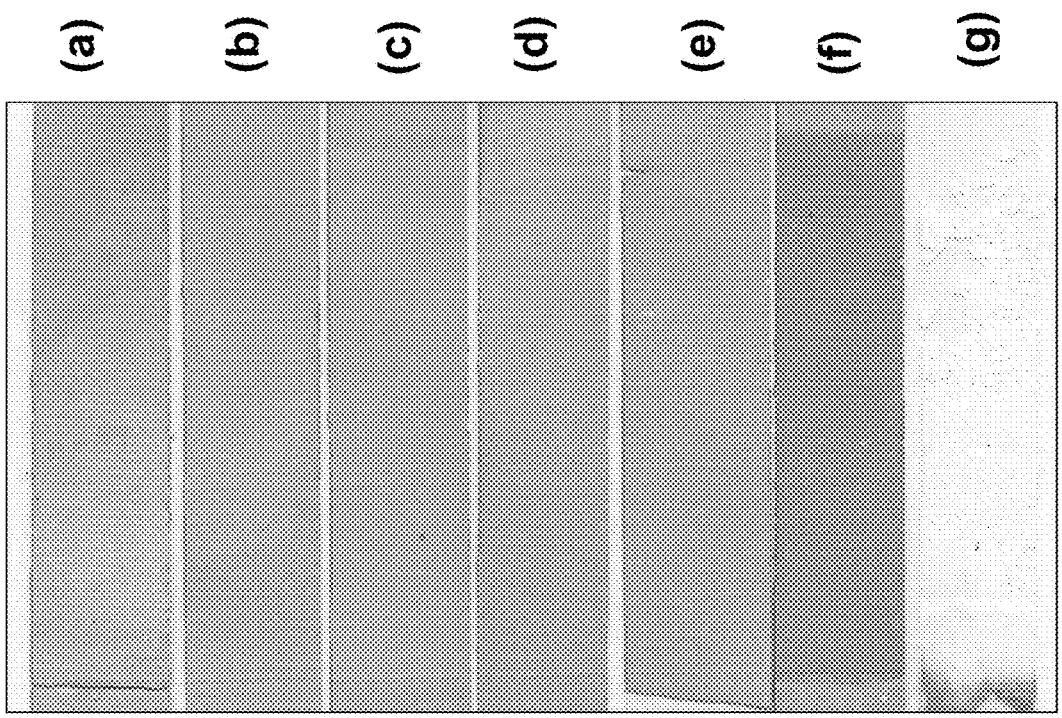
FIG. 43 shows an example of a ethylene oxide sterilization indicating device made from a aluminum powder and a precursor treated with different sterilization conditions.

FIG. 43 shows samples of an ethylene oxide sterilization indicating device made from aluminum ink and sodium thiocyanate treated under different conditions (see Example 29 for detail for this indicating device). Activators, such as sodium thiocyanate produce most likely produce sodium hydroxide when reacted with ethylene oxide. Sodium hydroxide etches the metal particles and the device becomes transparent.

Figure 44:
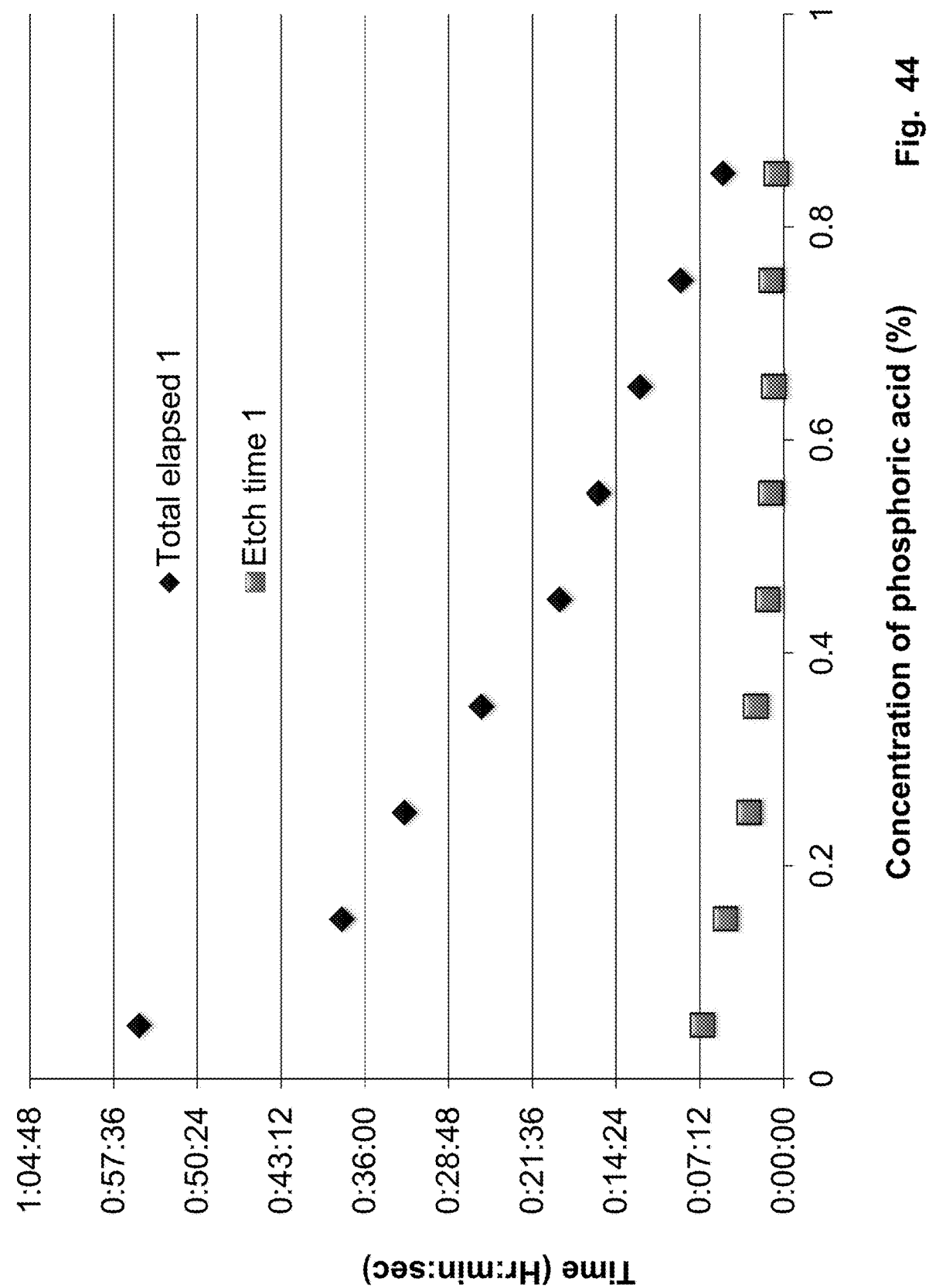
FIG. 44 shows plots of time required for phosphoric acid to make an aluminum layer to start to become almost transparent and that for completely transparent versus its concentration.

FIG. 44 shows plots of time required for phosphoric acid to make an aluminum layer of about 125 Angstroms to become almost transparent and that for completely transparent versus its concentration (see Example 33 for detail for this indicating device).

It is also possible to create more than one indicating devices on one indicator/metal layer, substrate or object. For example, one can apply activator tapes of (1) temperature and time-temperature, (2) temperature, time-temperature and radiation, (3) freeze and time-temperature and (4) thaw and time-temperature indicating devices. They can be designed to operate at the same or different time or under different conditions.

Some of the concepts disclosed herein were demonstrated using examples of an indicator substrate having a metal layer only on one side and similarly using an activator substrate having an activator layer only on one side. However, in many instances, e.g., making of EAS device, one can use an indicator substrate having metal coating on both sides and the metal coating could be of the same or different thicknesses and the same or different metals or metal alloys. Similarly, one can also use an activator substrate having activator coating on both sides and laminated/activated with metal indicator on each side. The activator coating could be of the same or different thicknesses and the same or different activators. One can also prepare the devices where an activator layer is sandwiched between two metal layers and an indicator/metal layer sandwiched between two activator layers.

One can make a multi-layer devices, e.g., metal-layer1/permeable-substrate1/message-layer1/metal-layer2/permeable-substrate2/message-layer2 . . . and so on.

One or more layers, especially the top layer of the said devices could be permeable or porous so an activator, agent or their vapors can pass through. The porous or permeable layer (not shown in the FIGS) could be selective to particular activator, so it will let only that or similar classes of activators pass through. Cellulosic paper, cloth, synthetic paper and selective membranes can be used. This porous/selective layer could be transparent or opaque.

As the device has a very thin aluminum layer, lots of information can be written similar to that on a CD (compact disc) and read like a CD. Thus, each device can have its own ID and information.

Though may not be required but for additional security and information, one can also print e.g., how to use, interpret, warnings, notices, ID, color reference charts etc either on the device or on the side of the device.

The devices disclosed herein can be used upside down with appropriate changes.

All these devices of the present invention could also be made tamper indicating according to materials and methods disclosed in our provisional patent application No. 61/127,565 filed on May 14, 2008. For example, the indicating device could have one or more tamper indicator layers or made from tamper indicating materials. If the device is tampered or the integrity of the device is destroyed, a message, such as "VOID" or "TAMPERED" will appear.

As many of the indicating devices disclosed herein have two pressure sensitive adhesive layers, one containing activator and the other to apply to a substrate, one can also use tamper or void indicator for each.

All devices disclosed here has one or more layers. Though not stated so, each layer has two surface and they could be continuous or discontinuous, uniform or non-uniform or smooth or uneven. Printed images, messages and alike are also considers as layers or indicia.

The visually noticeable indication can include latent indicia which initially are not visible and become visible or noticeable and indicia which are initially noticeable and become invisible, obscure or can be seen, noticed or machine read under different conditions, such as under UV light.

The activator, indicator and the devices could be essentially in any common shape and size, including inks, paints, crayons and gels. They also could be in form pen, aerosol can and stick. The indicator layer could be in form of a very thin layer, e.g., prepared by vacuum evaporation or by a coating of inks/paints having fine particles of a metal.

Some of the indicating devices can be made by applying an activator coating from a molten mixture of an activator and a binder on an indicator surface and rapidly cooling the mixture so there is a little effect on the indicator layer. Similarly, the indicating devices can be made by applying a mixture of molten binder containing an activator and fine particles of a metal, preferably supplied separately, rapidly mixed, coating the mixture on a substrate and cooled rapidly or binder cured by a cross-linker or radiation.

Light sources and mirrors which reflect light usually draw our attention much faster than any other object. Due to the highly reflective (mirror like) nature of the aluminum coating, indicating device using a metallized plastic film as an indicator will draw our attention and be easily noticed. However, metallized plastic films are usually flat. They will reflect light depending upon shape of the indicating device and the angle of incidence of the light. The indicating device having flat metallized surface can be noticed only from certain angles depending upon the location of the light source, indicating device and the viewer. If the surface of the indicator is uniformly uneven which would reflect light in all directions, then it can be easily noticed from any angle. For example, an embossed, e.g., having a cone, wavy or pyramidal shaped metallized plastic film will reflect light in all directions and the indicating device can be easily noticed. If a plastic surface having a mat finish is metallized, it will be more reflective in all directions. Such films are more desirable for the indicating device. Similarly, metallized plastic films having holograms also can be used and will be easily noticed and can be used for security. As the device has a reflective surface it can be read even in low light of night.

It is also possible to create different classes of sterilization indicating devices. Moving boundary devices can be used as multi-class indicating devices.

We have demonstrated with a number of materials, devices and processes that in essence, the current inventions can be used to improve performance of a large number of the prior art indicating devices (mentioned herein or not) by many different ways, for examples, 1) replacing their coloring/developing materials such as dyes, pigments or other reactants (so called indicators in the prior art) which are affected by the types of activators/precursors disclosed herein with a thin layer of metal or fine particles of a metal, 2) where an activator disclosed herein can be used for etching of a thin layer of metal or fine particles of metal, and 3) by applying a destructible barrier or permeable layer. Inventions disclosed herein can be combined with prior art compositions, processes and devices to make best of the both technologies.

The above and those disclosed herein are some common examples of possible variations, alterations, modifications and options of the materials, devices and processes. By permutation—combination, it is possible to have a very large number of variations, modifications and options for the devices and processes, e.g., by changing properties of components, position of a layer, multiplicity of a layer, adding an extra layer, changing color, opacity and a reflectivity of a layer, adding image/message, by varying the size and shape of a layer or the device, varying nature of the materials, applying the concepts to prior art devices and many other parameters including those mentioned in this application.

Comparison of the Prior Art and Current Inventions

The current indicating devices on the first glance may appear to be somewhat similar to that of the prior art two-tape and other similar devices and processes. However, the current devices are not only significantly different but very innovative, novel, unique and differ in many ways from the devices of the prior art and hence offer most of the desired properties and many advantages over the prior art devices. Some of the unique and novel features of the current devices are not possible with the prior art devices.

There are only a few common similar features between devices of the prior art and current invention. For example, the devices of prior art and current invention have an activator tape composed of a substrate having a matrix containing an activator. Both the devices have an indicator substrate and an option of using a permeable layer for introduction an induction period, if desired. The following processes are also the same: (1) making the activator tape, i.e., by coating a matrix containing an activator on an activator substrate and (2) activation of the devices, i.e., by applying the activator tape on to the indicator tape. This is where significant similarities between the prior art and the current devices and processes end.

A number of dyes and pigments, depending upon the activator, can be used for the prior art devices. The pigments and dyes change colors but don't get destroyed. A very thin coating of a metal, e.g., aluminum is used as an indicator for the current devices. The metal layer is completely and irreversibly destroyed at the end of the reaction. The metal layer can't be recreated. In the prior art devices, the color change can be reversed, e.g., by changing the pH.

A typical thickness of color/indicator layer in the prior art ranges from 2.5-50 microns. For example, the thinnest coating of an indicator layer in a time indicating device disclosed by Hass et al in U.S. Pat. No. 5,930,206 is ~2.5 microns thick ink dots and an opaque layer of ~12 microns. The thickness range of the indicator layer in a foldable two-tape device disclosed by Ko et al in U.S. Pat. No. 7,294,379 is 2-20 gsm (gram per square meter), i.e., 2.5-50 microns thick.

The typical thickness of the aluminum layer of the current devices is only 0.0001-0.0005 mil (15-150 Angstroms), about a thousand times thinner than the thinnest coating of the prior art devices and still provides higher opacity as metals are the most opaque substances. At optical density of 2 (average thickness of ~100 Angstroms), the metallized polyester blocks ~99% of the ambient light (Scharr Industries, FIG. 2.3a of Mount III, Eldridge M., editor, AIMCAL Metallizing Committee Metallizing Technical Reference, 3rd ed., the Association of Industrial Metallizers, Coaters and Laminators, March 2001). When the coating of the indicator layer is about a thousand times thinner, the quantity of activator required will also be significantly lower.

Typically the reaction products, e.g., aluminum phosphate are opaque. However, because of the thinness (~100 Angstroms), the layer is essentially transparent.

The concentration of the indicator/metal layer in the current invention is 100%. The concentration range of the indicator/dye/pigment in the prior art devices is usually less than 5%. For example, the concentration of an indicating dye in a two-tape device of Ko et al in U.S. Pat. No. 7,294,379 was about 0.4% to about 2% by weight.

Most of the metals and their alloys form a protective layer, typically an oxide layer to protect their exposed surfaces from further oxidation. This naturally formed oxide layer acts as a barrier or permeable layer for the activator and hence there is a delayed effect. In the prior art, one needs to apply a barrier/permeable layer. The protective coat can be naturally formed including other than oxides, e.g., carbonate, sulfate and halide or applied for protecting the metals or their alloys.

The indicator tape in the prior art is made by coating a matrix, usually polymeric, containing an indicator, usually a dye or a pigment on an indicator substrate. One major and unique difference is that the indicator tape of the current invention does not have a matrix and does not need one. The indicator tape of the current invention is made by applying a layer of an indicator directly on a substrate, i.e., by depositing a metal layer on a plastic film.

In order to introduce an induction period for the time required for the color change, the prior art devices require a neutralizer in the indicator layer. The current devices neither need nor can a neutralizer be added in to the indicator layer for introduction of the induction period. The indicator layer itself provides an induction period as the reaction occurs only at the surface of the indicator.

The indicator layer of the current invention is nearly 100% opaque. Anything behind it can't be seen. When the metal layer is destroyed, the indicator layer becomes essentially transparent. Any color, design, image and message printed under the metal layer become visible. This will indicate expiration of the device. The prior art devices don't disclose materials, layers and methods of getting essentially unlimited colors, designs, images and messages. One can obtain essentially any color, design, image and message including a barcode, number and photo, symbols by simple means, e.g., by printing them under the metal layer of the current invention.

The color changes in the prior art devices are gradual and non-linear (rapid in the beginning and slow at the end). The indicator layer of current invention undergoes a change in transparency and the change is very abrupt as shown schematically in FIGS. 2 and 9 and demonstrated in FIGS. 33 and 39 which is essentially completely opposite.

The prior art devices require a color reference chart to indicate the expiration because they don't have true end point. The devices of this invention have a true end point. The prior art devices also require a note on the devices to explain how to read or interpret the color change. The reason is that the color changes in the commercially available devices and those report in the prior art are not dramatic and almost impossible to get a change from colorless/clear→opaque or vice versa. The current devices do not require any color reference chart. They are self-reading, self explanatory and self instructing. Thus, the devices of the current invention are significantly superior and unique in providing clear required messages with little no further instructions. They also provide the most desired messages of go/no-go type as shown schematically in FIGS. 5-7 and demonstrated in FIGS. 33-36.

Patel et al in U.S. Pat. No. 3,999,946 has reported a TTI device based on the solid state polymerization of a diacetylene (2,4-hexadiyne-1,6-diol-bis-p-toluene sulfonate which happens to be toxic) having an induction period of polymerization. Other prior art devices require a permeable layer or a neutralizer for the activator in the indicator matrix for the induction period. The current invention has an induction period of its own without the use of a permeable layer or a neutralizer. The message behind the metal layer does not become visible until the metal layer is destroyed, thereby the current devices provide an induction period. This makes the current devices more suitable for monitoring usable period.

As the reaction in the prior art devices is asymptotic, a typical uncertainty in expiration time of prior art devices is about ±20%. Because of the induction period, the typical uncertainty in expiration time of the devices current invention is better 5% and can be better than a fraction of percent (For example, see Example 33 and FIG. 44) if thicker coating of metal is used. At the time of determination of the end point or expiration of the devices, the reaction is the typically slowest, for example see of plot (a) of FIG. 2 in the area marked as "end point determination zone" for the prior art devices. While the noticeable rate is the maximum and the maximum change occurs at the time of expiration for the current invention, see plot (b) of FIG. 2 in the area marked as "end point determination zone".

As the conductivity is expected to change from $10^6$ to $10^{-6}$ S/cm, these devices will be highly sensitive.

Asymptotic reactions of the prior devices keep on going for a very long time (in principle for ever), even after so called expiration of the devices. The reaction ends completely (100%) in the case of devices of the current invention.

Aluminum, with its protective oxide layer is environmentally highly stable metal. Metallized plastic films, especially those having a layer of aluminum are widely used and stable for a number of years under normal ambient conditions. Thus, the indicator tape made from metallized plastic film is environmentally stable and can be stored for years. This makes the current devices tamper resistant and least likely to provide false signals. The container labels or time tickets with indicator sticker (i.e., metallized plastic film) can be pre-made, stored for long time, even after applying on the container. The indicator is then activated by applying the activator tape when the container is filled with the perishable. Similarly, time indicating devices can also be made and activated when issued to a visitor.

Aluminum is approved by the US FDA for direct contact with food as we use aluminum foils and aluminum pans to cook the food.

The prior art devices are based on diffusion of an activator or dye through a matrix, usually that of the indicator matrix. The devices of current invention do not have the indicator matrix and the reaction is not based on diffusion. The color change of the current devices is due to the etching reaction and hence destruction of the metallic indicator by an activator. The indicator layer being impermeable, the reaction occurs only on the surface, i.e., heterogeneous reaction.

The reaction between the activator and the indicator in the prior art devices is homogeneous and inside a matrix while in the current devices it is heterogeneous, i.e., the liquid activator reacts with a solid indicator (aluminum) on the surface. The reaction between the metal layer and acids produce a tiny quantity of hydrogen gas, especially if acids are used as activators. Production of hydrogen gas is a uniqueness of the current devices. However, hydrogen gas produced is very little because the metal layer is only ~100 Angstroms thick and hence it is not a concern about production of an explosive mixture with oxygen. Hydrogen being the smallest molecule diffuses through the plastic films of the devices.

All indicating devices, including time and time-temperature, reported in the literature and used in the field have a binder to hold the coloring materials in the layer and to bond it with other surfaces including the substrate. No layer is destroyed in the prior art devices. The color changing reaction in the prior art devices occurs between the activator and indicator in a matrix/binder which maintains integrity of the devices at all times.

Aluminum layer in the current devices is bonded to a plastic film without any binder. The metal layer does not have any binder. Metal atoms have the property to bond strongly to themselves. In the current case, the metal layer which bonds with an adhesive of activator tape or with a permeable layer is destroyed and the bonding between the activator tape and indicator tape/substrate is lost unless special bonding materials are used to prevent de-lamination.

Because aluminum layer has no binder/matrix and because it is non-porous and non-permeable layer, the activator can't diffuse through. It is very difficult even for hydrogen gas (the smallest molecule) to diffuse through the aluminum layer. The reaction between the activator and the metal occurs only on the surface of the metal layer.

Though the above description points out some of the novelties of the current inventions and major differences between the current invention and the prior art for indicating devices (e.g., time and time-temperature indicators, especially sticker type indicating devices), there are many other novelties of the current inventions and differences between the current invention and the prior art for all other devices, e.g., sterilization indicating devices (e.g., steam, dry heat, plasma and ethylene oxide), humidity indicating devices, microwave doneness indicating devices, defrost/thaw indicating devices, temperature indicating devices, self-heating food indicating devices, electronic circuitry, EAS systems, patterning, RFID and similar devices, and processes associated with them. Many of these novelties and differences are disclosed and/or will become apparent from the other disclosures herein.

Preferred Embodiment

A material which is metallic in nature and has properties as defined earlier can be used can be used as an indicator for one or more of the devices of the present inventions/system.

The terms metal, metal like, metallic and having properties of metal are used interchangeably herein for the indicators of the devices of the system.

Indicators could have a co-indicator. Co-indicator could be a moderator/modulator. It could increase or decrease the effect of an indicator as desired. Sometimes two indicators can have synergistic effect while the other could reduce the effectiveness. Addition of a co-metal, such as indium in aluminum can increase the sensitivity of aluminum to water while addition of aluminum and/or tin in copper and zinc could reduce reactivity of copper and zinc. A non-metallic impurity, such as carbon and sulfur can be used as a co-indicator or additive. Crystallinity and amorphousness of the metal layer can also affect their reactivity with an activator. Addition of impurity which makes the metal layer more susceptible to activator can be used as a co-indicator. The terms, alloys, co-indicator, moderator and modulators are used interchangeably herein.

Materials which can be easily noticeable from distance, capable of being produced by vacuum evaporation or sublimation, environmentally stable, requiring no binder or matrix, substantially non-porous, substantially impermeable, self colored, being capable of irreversibly destroyed by an activator, thinner than 25 microns, non-migrating, self binding, capable of binding to a substrate without a binder, polymeric, capable of reacting on the surface only and being capable of producing a message or image can also be used as indicators and are preferred indicators.

The most preferred material for the indicator is a metal or an alloy, especially a thin layer, in form of a thin foil or coated on a substrate, such as a metallized plastic film. Most preferred metals or alloys are those which are attacked by non-toxic or non-hazardous materials such as food additives and nutrients. Low melting metals, bronzes and alloys are also preferred. Alkali, alkaline earth, transition metals, post transition metal, lanthanoid and actinoid metals and their alloys can be used as indicators. Aluminum, tin, zinc, copper, manganese, magnesium, nickel, cobalt, iron, sodium, potassium, lithium, calcium, gallium, cesium, germanium, indium and their alloys are preferred metals. Aluminum and its alloys are the most preferred materials for the indicating devices, especially coated on a plastic film, such as polyethylene, polypropylene, polyester, nylon, polyvinyl chloride, polystyrene, cellulose acetate and their copolymers.

Alloys of many metals can be used as indicators for the present invention. Alloys of aluminum with magnesium, lithium, gallium etc are more sensitive to water and also to acids, bases, oxidizing agent and salts. Alloys of aluminum may accelerate or retard the reaction. Depending upon the application, the present invention needs a metal layer which is more and as well as less sensitive than pure aluminum layer. An alloy of more than one metal, such as that of aluminum-magnesium-copper can also be used. Alloys of aluminum are described in many books, e.g., "Aluminum and aluminum alloys", Joseph R. Davis, J. R. Davis & Associates, ASM International, Materials Park, Ohio, 1993 and many of them could be used to make the indicator.

Though metals which produce colored compounds can be used, the most preferred metals are those which produce colorless or white salts when reacted with activators. They include metals like aluminum, zinc, magnesium and tin. Aluminum is preferred over other metals for several reasons, such as aluminum and most of its compounds are nontoxic. Most of the compounds of aluminum are white or transparent. It is also relatively very reactive/susceptible metal and still stable under normal ambient conditions because of formation of a protective oxide layer. It is a very light metal of density 2.7 g/cc compared to lead (who salts are used as steam sterilization indicating devices) which has density of 11.3 g/cc. Hence, per pound, aluminum provides higher coverage and settlement in the ink is less. Inks containing aluminum particles and plastic films coated with aluminum are readily available.

A variety of aluminum bronzes of differing compositions have found industrial uses, with most ranging from 5% to 11% aluminum by weight, the remaining mass being copper or other alloying agents, such as iron, nickel and silicon. Aluminum and other bronzes, such as copper-zinc can be used as indicators.

Aluminum is well known for its large negative free energy for the formation of its oxide. Hence, aluminum has the thermodynamic ability to split water. Metals with large negative free energy are preferred as indicators.

Aluminum is coated on plastic films from its vapor under vacuum. A very thin, e.g., 10 Angstroms to several microns thick coating of aluminum can be obtained by this vacuum deposition method. A preferred method of producing an indicator layer and also a destructible barrier layer is a vacuum deposition, vacuum evaporation and sputtering.

When a metal object, such as a metal container is used as an indicator, the activator can be sprayed, coated, printed or applied in form of a tape on the metal object.

Use of a metal layer as an indicator offers another advantage of creating security features and devices if needed. Holograms created on an aluminum layer are widely used for security and as tamper indicating device. Aluminum layer with holograms can be used to make high security and/or temper indicating devices of the current invention. A metal layer can be applied on anon-metallic holograms for a high security feature.

One can use more than one layer of different metals, e.g., of different colors or reactivities, e.g., aluminum (white and more reactive), copper (red) and gold (yellow and significantly less reactive) or alloys (e.g., brass and bronzes). These layers may be separated by a layer of different nature. In this case a metal layer can act as a destructible barrier layer.

Certain indicating devices, such as a time-temperature indicating device based on polymerization of diacetylenes available from Temptime, Morris plain, NJ require a red color filter to protect the device from ambient light. In contrast, metallized plastic films are so stable to almost all kind of normal environment that they are used to protect a wide variety of materials including perishables from ambient environment. Thus indicating devices made from metallized plastic film will be highly environmentally stable.

It is also important that the indicating devices be easily noted by the users. Reflecting surface is easy to notice than any other surface or color. Hence, possibility of a consumer or store keeper not noticing the device is less. Similarly, a visitor's pass can be easily noted from a distance.

Similarly, fine (e.g., 1-100 microns) particles flat or round, of metals, such as that of aluminum, copper, zinc and their alloys dispersed in a binder can also be used as an indicator layer. The reaction will still be heterogeneous and the induction period will be even longer. This indicating layer will maintain the integrity of the device even upon the expiration.

Indicator can also be microencapsulated. Most of the metals have a naturally formed oxide layer but metal particles can be coated with inorganic and organic, especially polymeric materials.

Materials whose thin layers provide a very intense color or opacity and undergo a substantial change in color or transparency with an activator can also be used as indicators. They include materials, such as polymeric dyes, poly-diacetylenes and sublimed dyes. This type indicator may have a destructible barrier layer so one can have a longer and sharper induction period.

A colorless resist can be printed in form of a message. The resist printed area of the indicator will remain unreacted thereby creating a message. The area of aluminum exposed to activator will disappear first and may be followed by a very slow disappearance of the whole layer due to under etching.

Metal bonds are different from covalent and ionic bonds. Metal atoms possess strong bonds. In metals electrons can move freely in all directions which make them good conductor of heat and electricity. Metal bonds can be considered as positive ions in a sea of electrons. Most metals and their alloys are solid. Metals could be crystalline as well as amorphous.

Copper and its alloys are also preferred indicator because copper and brass objects disinfect themselves of many bacteria within a period of eight hours including MRS, *Escherichia coli* and other pathogens. Antimicrobial metals are preferred indicators.

Metals (especially transition metal and their alloys), their salts and complexes are widely used as catalysts for a variety of reactions. Metallized plastic films (including naturally formed metal oxide or complexes specifically synthesized on the surface) can be used as an indicator for monitoring those reactions.

Semimetals and semiconductors are elements, alloys and compounds having conductivity between that of a conductor (e.g., $63 \times 10^6$ S/cm for silver) and an insulator (e.g., below $10^{-6}$ for plastics). A semimetal is material with a small overlap in the energy of the conduction band and valence bands. In a metallic conductor, current is carried by the flow of electrons. In semiconductors, current can be carried either by the flow of electrons or by the flow of positively-charged "holes" in the electron structure of the material. The conductivity of a semiconductor material can be varied under an external electrical field. Semiconductor devices include the transistor, many kinds of diodes including the light-emitting diode, the silicon controlled rectifier, and digital and analog integrated circuits. Solar photovoltaic panels are large semiconductor devices that directly convert light energy into electrical energy. Examples of semi-conducting materials are silicone, germanium, gallium arsenide and silicon carbide. A semiconductor can be "intrinsic" or made p-type and n-type by doping. If the activator is a dopant, one can create a semiconducting device.

Some representative examples of inorganic semiconductors are aluminum antimonide, boron nitride, gallium phosphide, indium gallium phosphide, aluminum gallium indium phosphide, cadmium selenide, zinc sulfide, cadmium zinc telluride, lead sulfide and copper(I) oxide.

Opaque semimetal and semi-conductors are preferred for the indicating devices of the system.

A thin layer of vacuum deposited metals, such as sodium, lithium, potassium, magnesium and their alloys can be used for monitoring humidity or moisture as these metals and their alloys are sensitive to moisture and many chemicals. Sensitivity of the metal layer to an activator can be adjusted by selecting proper co-metal. For example, sensitivity of aluminum to water can be adjusted by adding many co-metals, such as sodium, lithium and indium.

Like copper many other metals produce color compounds. By selecting a proper activator, one can produce additional colors. Plastic films coated with copper and its alloys and inks with fine particles of copper and its alloys also preferred for monitoring sterilization processes.

A powder of a metal or an alloy, preferably micron and nano sized, dispersed in a binder like an ink or paint, is one of a preferred coating formulation, especially for sterilization indicating devices. Metals, such as copper and its alloy which readily react with activators are further preferred metals. Smaller the metal particles (higher surface area), more readily they will react with activator to provide the change. A mixture of a metal powder and activator in an ink or paint formulation is a preferred ink or coating formulation for monitoring sterilization. Sterilization processes include steam, oxidants, (such as hydrogen peroxide and peracetic acid) and toxic/hazardous gases, such as ethylene oxide.

A continuous layer of a metal (e.g., that prepared by vacuum evaporation of a metal on a plastic film) having thickness of less than one micron (10,000 Angstroms), preferably less than 0.1 micron (1,000 Angstroms) and discontinuous/dispersed layer of a metal, e.g., that composed of metal particles, having thickness of less than one hundred microns, preferably less than 20 microns are preferred sizes and are more useful for practical purposes of the devices and processes proposed herein.

It is preferred to use fine metal particles of relatively uniform size for the devices disclosed herein. Small spherical particles are preferred but any other shapes, including irregularly shaped flat particles of indicators can also be used.

Mixture of two pigments, one heavier than the others are of special interest. During coating the lighter will mainly float/come on the surface and hence dominate the color of the coating. For example, when aluminum ink and copper or copper based alloy inks are mixed in 1:1 proportion, the aluminum pigments being lighter come on the surface the surface mainly appear silvery. When etched with some selective etchant, aluminum gets etched first or faster and a copper color, a color of silvery white to red appears. In case of lighter color pigments, especially organic, they float on the surface and hence their color dominates. Hence, a mixture of two or more indicating pigments or one indicating and one non-indicating pigments can be used.

Leafing and non-leafing type metallic pigments can be used for the indicating devices. However, for proper etching of the metal pigments, non-leafing pigments are preferred.

Ultra thin metal pigment/flakes, e.g., created from vacuum coated metals can also be used.

Nobel metals such silver and gold can also be used as indicators with strong activators for monitoring vigorous or severe conditions and usually long time.

The preferred substrate for the metals is a plastic film. However, it could be any other substrate including other metals, fabric, paper, wood, an adhesive film and glass. For example, a transfer adhesive tape, reinforced paper and fabric having thin layer of metal can be used as substrate for the current devices.

The shape of the coated indicator could be any, e.g., flat, circular, fiber, cylindrical, or any irregular shape.

When an alloy is used as an indicator layer, it is also possible that one metal may get etched faster than the other and for certain alloys, such as bronzes (e.g., that of zinc and copper) one can get gradual color change.

Because of the metallic indicator layer, one can create indicating device for very high temperatures (e.g., 500° C. or higher) as long as, activator, substrate, and other organic materials can withstand such high temperatures. The devices can also be used at very low temperatures, e.g., minus 100° C.

Copper and many of its alloys are red or yellow and salts of copper are usually blue or green. We have observed that when copper and its alloys/bronzes (e.g., copper-zinc alloys, which appear yellow, like gold) are treated with certain activators they produce green salts of copper, e.g., upon sterilization with steam, dry heat, plasma and ethylene oxide, which can be used for red-to-green color changes or gold to green color changes. Salts of aluminum and zinc are usually colorless (white or transparent). If the resultant salts of copper and its alloys are substantially transparent, a message, e.g., "STERILIZED" printed under the coating will appear along with the color change when the devices are sterilized. Indicators for copper ion can also be added for enhancement of the color changes.

Other systems which can be used instead of dissolution/etching of a metal for many of the devices and processes of the current system disclosed herein are formation of a metal. For example, one can use silver diamine/di-ammonia complex formed by adding ammonia in silver nitrate as an indicator and glucose as an activator. This system/process is known as Tollen reagent or test. Glucose will reduce the silver complex to silver and a metallic/opaque surface/coating can appear. A message printed under the coating will become invisible. Many other metal salts and complexes and reducing agents, such as aldehydes can be used.

Similarly, commonly known as electroless plating process can also be used for making many devices proposed herein. In the process of electroless plating (also known as chemical or auto-catalytic plating) process, sensitizing agents, such as $SnCl_2$, $PdCl_2$ are used. The reduction of the complex to metal (typically copper or nickel) is accomplished by a reducing agent, normally sodium hypophosphite or an aldehyde. Thus, this system can also be used for monitoring formaldehyde and other reducing agents and sterilization with them. A message printed under the coating will become invisible when metal gets deposited. A message printed with the palladium catalyst can be selectively plated. A message (e.g., "STERILIZED") can be made visible by many different ways, including those disclosed herein, for example, by printing the message with a catalyst or reducing agent and by selective masking.

Likewise, other systems that can be used instead of etching of a metal or deposition of a metal for the devices and processes disclosed herein are formation of an opaque material. For example, Fehling or Benedict solution which contains copper(II) ion complexed with tartrate ion in a basic media can be used as an indicator. Copper(II) ion complexed with tartrate ion prevents its precipitation as copper(II) hydroxide. A reducing agent, such as an aldehyde can be used as an activator. Aldehyde will reduce the copper complex to copper(I) oxide, which is black/opaque. Again a message printed under the coating will become invisible. Thus, this system can also be used for monitoring formaldehyde and other reducing agents.

Immersion plating is a process for the deposition of a metallic coating on another metal immersed in a solution of metal compound without using external electric current. Still another way of making the indicating devices disclosed herein is to have a metal salt, such as copper chloride or copper sulfate in an activator tape and iron foil, thin layer of iron particles as an indicator. Iron will get plated with copper and will change from white to red.

In order to monitor radiation, one can use the so called photo-reduction of metal salts and complexing agents to produce a metal for monitoring radiation. The most common examples of such reactions are photo-reduction of silver halide to silver and so called blue print where a coating of a mixture of ferric ammonium citrate and potassium ferrocyanide, produces a blue color complex (Prussian blue) when exposed to light. These types of photo-reduction and photo-oxidation reactions can be used to make the radiation sensitive devices, such as radiation dosage indicating devices for monitoring sterilization.

In the processes and devices disclosed above which are not based on etching of a metal, the indicator is in form of precursor for an indicator. These non-etching devices could also have many of the features, such as creating a self reading message.

Instead of dissolution of a metal by an activator, one can also create a variety of indicating devices disclosed herein by dissolving an opaque or dark material (colored or white) which can be dissolved or swollen with an activator and becoming transparent. The opaque material could be monomeric or polymeric. A non-permeable, destructible layer of these opaque materials can also be used as indicators for the system.

The final products from metallized inks can be transparent or opaque. Depending upon the need, an opaque material can be converted to clear and vice versa by selecting proper reactant/activator. For example, when sodium hydroxide reacts with aluminum, it can provide opaque aluminum oxide, which can be converted to transparent by adding chemicals, such as sodium phosphate to make it transparent and vice versa. The opaque coating can be made transparent by secondary reaction/reactant, i.e., by adding another reactant/additive which reacts with, dissolves or swells the opaque products.

For certain indicating devices, such as temperature indicating devices one can coat an activator on an indicator or vice versa. This way the activator and indicator are in closest proximity and hence the reaction will be faster. The coating of an activator on the indicator and vice versa can be done first and then dispersed in a binder. For example, a metal particle can be coated with an activator by a number of methods for example, an encapsulation method.

One can also use conductive polymers (also known as synthetic metals), both soluble and insoluble and both un-doped and doped as indicator. Synthetic metals have narrow bad gap. Examples of conductive polymers are doped polyaniline, polyacetylene and polypyrrole. Electronic devices can also be created by using a dopant as activator or by neutralizing effect of the dopant for conducting polymers and inorganic semi-conductors.

Any chemical which can react with the said indicators can be used as an activator. Metals may also undergo a displacement reaction with activators. Metals and their alloys/bronzes are attacked by a large number of chemicals. Water, oxygen, acids, bases, salts and oxidizing agents readily attack metals and are preferred activators.

The content of an activator will depend on many factors including the nature and thickness of the indicator but preferably be ~5% by weight or higher, more preferably—10-40% by weight.

Activators could have a co-activator. Co-activator could be a moderator/modulator. It could increase or decrease the effect of an activator as desired. Sometimes two activators can have synergistic effect. For example, a mixture phosphoric acid and substituted or un-substituted aliphatic and aromatic sulfonic acids are more effective, especially in presence of water, than individual acids. A solvent, wetter, surfactant or plasticizer can also be used as co-activator. Certain solvents can retard the effectiveness while other could increase the effect. The terms, co-activator, moderator and modulators are used interchangeably herein.

High boiling and solid solvents which can dissolve an activator can be used to facilitate migration of activator, especially through a binder for the activator and/or the permeable layer. When solvents are used, one can use solid activators. High boiling solvents, such as cinnamoyl alcohol, xylenol, phenolethanol, diphenylether and a large number of other organic and inorganic compounds can be used as solvents for activators.

We have observed that often solvents, expedite the diffusion of the activator and reaction with the indicators i.e., dissolution of the metal layer. For example, p-toluene sulfonic acid in an adhesive (S8510 of Avery Dennison) as an activator with little or no water (dried at 100° C. for 30 minutes) is extremely slow (takes almost a week at 25° C.) in dissolving 100 Angstroms aluminum layer while that containing about 20% water makes it to react hundreds of times faster (e.g., 5 minutes at 25° C.). In this and similar cases, most probably water is an activator and the acid is a catalyst.

A material comprising one or more capabilities of: reacting with a metal, changing chemical nature of the indicators, reducing reflectivity, destroying conductivity, tarnishing, coloring, reducing noticeability of the said indicators, reducing opacity of said indicators, reducing environmentally stability of said indicators, not migrating through the indicator layer, irreversibly reacting with said indicators, reacting with the said indicators at its surface and substantially destroying said indicators can be used as an activator.

The rate of reaction will depend on the sensitivity of the metal to the activators. Weak activators will require harsher conditions, e.g., higher concentration, temperature and/or take longer time for the change and vice versa.

When water is required as etchant, co-etchant, catalyst or a solvent, inorganic compounds having water of hydration can be used. Likewise hygroscopic materials can also be used as a co-activator.

As water can act as a reactant and/or catalyst and is often required for etching or dissolution of metals, one can use organic and inorganic compounds having water as water of crystallization (often referred as water of hydration) as activators or precursor for activators. Many materials have water chemically combined with a substance in such a way that it can be removed and made available, e.g., by heating. For example, anhydrous copper sulfate is a white solid with the formula $CuSO_4$. When crystallized from water, a blue crystalline solid $CuSO_4.5H_2O$. Alums $AlK(SO_4)_2.12H_2O$ has 12 water molecules. The water is released at certain temperature or temperature range, e.g., hydrated ammonium oxalate and barium chloride release water at about 115° C. and calcium sulfate at about 200° C.

Examples of other salts with higher number of water molecules as water of crystallization that can be used as activators are hexahydrated aluminum chloride, ferric chloride and magnesium chloride, octahydrated calcium sulfate and barium hydroxide, decahydrated sodium sulfate, borax, sodium borate, sodium carbonate and tetrasodium diphosphate, dodecahydrated sodium phosphate diabasic, aluminum potassium sulfate, ammonium ferric sulfate, trisodium phosphate, ammonium iron sulfate, potassium aluminum sulfate, sodium ferrocyanide and tetrakis(4-sulfophenyl) methane and higher hydrated compounds, such as 1,4,8,11-Tetra(2-carboxy)ethyl-1,4,8,11-tetraazacyclotetradecane (H2TETP)2, hexadeca hydrate and aluminum sulfate octadecahydrate.

Activators could be monomeric, oligomeric, polymeric, mono-functional or multi-functional., e.g., sulfuric acid, di and higher functional aromatic sulfonic acids, polystyrene sulfonic acid and polyethyleneimine.

Acids include Bronsted-Lowry and Lewis acids, mineral acids, inorganic and organic acids can be used as activators or catalysts for etching, especially with a protonic solvent such as water. Acids are electrolytes and etchants. Specific examples of acids are perchloric, perchloroacetic, hydrochloric, sulfuric, nitric, phosphorous acid, phosphoric acid, hypophosphorous acid sulfonics, methanesulfonic, ethanesulfonic, benzenesulfonic, toluenesulfonic, naphthanol sulfonic, camphor-10-sulfonic, 3-hydroxypropane-1-sulfonic, carboxylics, formic, acetic and citric acids. Alkyl or aromatic acids and bases are preferred. Partially esterified acids can also be used. The most preferred is phosphoric acid, phosphorous acid, hypophosphorous acid, their derivatives and mixtures. Halo-acids and halo-alcohols, such as trichloroethanol and trichloroacetic acid can also be used.

Acids and their esters, including partial esters are often used as tackifiers. Thus, acids, such as phosphoric acid can make a non-tacky resin a PSA or increase the tackiness of a PSA. Hence, it is likely that phosphoric acid will form a solid solution with the matrix/PSA.

Bases also attack metals and hence can be used as activators or catalysts for activators, especially with a protonic solvent such as water. Some examples of bases are hydroxides of sodium, potassium, calcium, lithium and tetrabutyl ammonium, aryloxide and alkoxides (e.g., ethoxides and methoxides of sodium, lithium and potassium). Amines, such as aliphatic, cyclic and aromatic, substituted or un-substituted amines, including primary, secondary and tertiary amines, e.g., ethylamine, diethylamine, triethylamine, aziridine, piperidine, pyridine and aniline can also be used as activators.

A variety of amines are available. Amines, such as primary, secondary, tertiary and quaternary amines of mono or multi-substituted or un-substituted aliphatic, acyclic and aromatic compounds can be used as activators for some of the devices. Examples of amines and their salts include: adamantanamine, adenine, amino cyclohexanol, amino diethylaminopentane, amino dodecanoic acid, amino ethyl dihydrogen phosphate, amino ethyl hydrogen sulphate, amino pentenoic acid, amino propyl imidazole, amino propyl pipecoline, amino sorbitol, amino undecanoic acid, amino-butanol, aminodeoxy-d-sorbitol, aminoethyl dihydrogen phosphate, aminopropyl imidazole, ammonium acetate, ammonium bromide, ammonium carbaminate, ammonium carbonate, ammonium chloride, ammonium dihydrogen phosphate, ammonium ferrocyanide hydrate, ammonium formate, ammonium hydrogen carbonate, ammonium hydroxide, ammonium iron(11) sulfate, ammonium iron(III) citrate, ammonium iron(III) oxalate trihydrate, ammonium nitrate, ammonium per sulfate, ammonium phosphate dibasic, ammonium sulfamate, ammonium sulfate, benzyl-n-methylethanolamine, benzyltrimethylammonium chloride, bis(dimethylamino) benzophenone, chloroethylamine monohydrochloride, chlorohydroxypropyl trimethyl hydrochloride, chloronitroaniline, choline, choline chloride, choline hydroxide, choline iodide, cy clohexy amine, decylamine, diallyl dimethyl ammonium chloride, diaminodiphenylamine, diaminododecane, diaminoheptane, diaminohydroxypropane, diaminononane, diaminooxapentane, diaminopropane, dibutylamino propylamine, dibutyl amino benzaldehyde, diethanolamine, diethyl amine, diethyl aminopropylamine, diisopropyl ethylamine, dimethyl amine, dimethyl amino ethylmethylamino ethanol, dimethyl amino benzaldehyde, dimethyl aminopropoxy benzaldehyde, dimethyl aminopropylamine, dimethyl ammopyridine, dimethyl glycine, dimethyl glyoxine, dimethyl imidizole, dimethyl imidizolidinone, dimethyl prop ane-di amine, diphenylamine, diphenylamine, diphenylbenzidine, dodecylamine, dodecyltrimethylammoniumbromide, ethanolamine, ethanolamine hydrochloride, ethyl amine, ethyl aminobenzoate hydrochloride, glycidil trimethyl ammonium chloride, histidine, hydroxylamine hydrochloride, hydroxylamine sulphate, imidazole, imidazolidone, iminodiacetic acid, methyl amine, methyl imidizole, nitro aniline, nitro diphenylamine, octa decylamine, phenylenediamine, polyethylenimine, tetrabutyl ammonium hydroxide, tetrabutyl ammonium iodide, tetraethylammonium bromide, tetraethylammonium hydroxide, tetrafluorophenylimidizole, tetrahexylammonium bromide, tetramethyl ammonium acetate, tetramethyl ammonium chloride, tetramethyl ammonium hydroxide, tetramethyl ethylenediamine, tetramethyl ethylethylenediamine, tetramethyl hexanediamine, tetramethyl propanediamine, tetramethyl guanidine, triallylamine, triethanolamine, triethylamine, triethylenetetramine, triethylenetetramine hydrochloride, triethylethylenediamine, tridecylamine, trimethyl ammonium chloride, trimethylpropanediamine, trimethylamine hydrochloride, trioctylamine, trioxa-tridecanediamine, triphenylamine, tris (hydroxymethyl) aminomethane and tris(methoxyethoxy) ethylamine.

Even though acids, bases, salts and similar compounds often act as catalysts for etching of metals/indicators and water as activator, they are referred herein as activatrs.

There are a large number of salts, e.g., salts of a weak acid and a strong base, a strong acid and a weak base, a strong acid and a strong base or a weak acid and a weak base can be used as activators for the devices. Many organic and inorganic corrosive chemicals, salts, such as aluminum chloride, ammonium phosphates, ammonium sulfate, calcium chloride, iron chloride, lithium carbonate, lithium carbonate, phosphonates, phosphites, salts of amines and acids, such as amine:hydrochlorides (e.g., triethanolamine: HCO, potassium benzoate, potassium, sodium and lithium salts of 2,4-dihydroxybenzoic acid and 2,4,6-trihydroxybenzoic acid, sodium acetate, sodium bicarbonate, sodium carbonate, tetrabutylammonium acetate, zinc chloride, can also be used as activators.

One of the preferred class of compounds as activators are those of phosphorus. They include phosphoric acid, phosphorous acid, hypophosphorous acid, organic and inorganic phosphines ($PR_3$), phosphine oxide ($OPR_3$), phosphinite ($P(OR)R_2$), phosphate ($P(OR)_3$), phopshinate ($OP(OR)R_2$), phosphonate ($OP(OR)_2R$) and phosphate ($OP(OR)_3$).

It is also possible to use buffers to catalyze dissolution of metals. In order to maintain a steady reactivity/rate one may add a proper buffer to maintain the pH. A large number of buffers are reported in the literature which potentially can be used. Examples of common buffer compounds include: 3-{[tris (hydroxymethyl) methyl]amino}propane sulfonic acid, N,N-bis (2-hydroxyethyl) glycine, tris (hydroxymethyl) methylamine, N-tris (hydroxymethyl) methyl glycine, 4-2-hydroxyethyl-1-piperazine ethane sulfonic acid, 2-{[tris (hydroxymethyl) methyl] amino} ethanesulfonic acid, 3-(N-morpholino) propane sulfonic acid, piperazine-N,N'-bis (2-ethane sulfonic acid), dimethylarsinic acid, 2-(N-morpholino) ethanesulfonic acid, mono potassium phosphate and diammonium phosphate.

Instead of using inorganic halide salts, one can use organic halide salts as activators or precursor for activators. Some representative examples of organic bromide are: alkyltrimethylammonium bromide, benzyltributylammonium bromide, benzyldodecyldimethylammonium bromide, dimethyldioctadecylammonium bromide, dodecylethyldimethylammonium bromide, dodecyltrimethylammonium bromide, ethyltriphenylphosphonium bromide, ethylhexadecyldimethylammonium bromide, hexadecyltrimethylammonium bromide, myristyltrimethylammonium bromide, polybrene, poly(benzophenonetetracarboxylic dianhydride-ethidium bromide), tetraheptylammonium bromide, tetrakis(decyl)ammonium bromide, thonzonium bromide. One can also use other halides salts, such as fluoride, chloride and iodide. Polymeric halide salts, such as polybrene can also be used. These halides can also be used as precursors for many chemicals and processes.

Mild and strong, organic and inorganic oxidizing agents can also react with metals and their alloys. An oxidizing agent can also be used as an activator. Representative common oxidants (oxidizing agents) include: ammonium persulfate, ammonium nitrate, potassium permanganate, potassium dichromate, potassium chlorate, potassium bromate, potassium iodate, sodium hypochlorite, nitric acid, chlorine, bromine, iodine, cerium(IV) sulfate, iron(III) chloride, peroxides, such as hydrogen peroxide, manganese dioxide, sodium bismuthate, sodium peroxide, sodium nitrate, oxygen, sulfoxides, persulfuric acid, ozone, osmium tetroxide, N-bromosaccharin, tert-butyl hydroperoxide, dimethyl sulfoxide, ferric chloride, ferric nitrate, formic acid, hydrogen peroxide urea adduct, sodium perborate and halogens such as chlorine and bromine.

Metal surfaces have an oxide layer and hence commonly known as metal surface cleaners can be used as an activator or co-activators. Metal surface cleaning formulations disclosed in U.S. Pat. Nos. 7,384,901; 6,982,241; 6,669,786; 5,688,755; 5,669,980; 5,571,336; 5,545,347; 5,532,447 and variations of them can be used. Some of the polishing compositions may act as activator.

The co-activator may comprise a chelating or complexing agents. The complexing agent is any suitable chemical additive that reacts or weakens the naturally formed barrier/permeable layer or reacting the products of metals with activators. The choice of chelating or complexing agents will depend on the type of naturally or intentionally applied barrier or permeable layer. Examples of chelating or complexing agents include, carbonyl compounds (e.g., acetylacetonates), simple carboxylates (e.g., acetates, aryl carboxylates), carboxylates containing one or more hydroxyl groups (e.g., glycolates, lactates, gluconates, gallic acid and salts thereof), di-, tri-, and poly-carboxylates (e.g., oxalates, phthalates, citrates, succinates, tartarates, malates, edetates (e.g., dipotassium EDTA), mixtures thereof), carboxylates containing one or more sulfonic and/or phosphonic groups, and the like. Suitable chelating or complexing agents also can include, for example, di-, tri-, or polyalcohols (e.g., ethylene glycol, pyrocatechol, pyrogallol, tannic acid) and amine-containing compounds (e.g., ammonia, amino acids, amino alcohols, di-, tri-, and polyamines).

Other examples of chelating agents include trisodium pyrophosphate, tetrasodium diphosphate, sodium hexametaphosphate, sodium trimetaphosphate, sodium tripolyphosphate, potassium tripolyphosphate, phosphonic acid, di-phosphonic acid compound, tri-phosphonic acid compound, a salt of a phosphonic acid compound, ethylene diaminetetra-acetic acid, gluconate, or another ligand-forming compound. The chelating agents also include phosphonic acid-based chelating agents, such as aminotri (methylenephosphonic acid), 1-hydroxyethylidene-1,1-diphosphonic acid and ethylenediaminetetramethylenephosphonic acid; aminocarboxylate-based chelating agents, such as ethylenediaminetetraacetates and nitrilotriacetates; hydroxyaminocarboxylate-based chelating agents, such as dihydroxyethylglycine; or mixtures thereof.

Still further examples of chelating agents include amino acids, such as glycine, serine, proline, leucine, alanine, asparagine, aspartic acid, glutamine, valine, lysine, etc.; polyamine complexes and their salts, including ethylenediaminetetraacetic acid, N-hydroxyethylethylenediaminetriacetic acid, nitrilotriacetic acid, iminodiacetic acid, diethylenetriaminepentaacetic acid, and ethanoldiglycinate; polycarboxylic acids, including phthalic acid, oxalic acid, malic acid, succinic acid, mandelic acid, mellitic acid; alkali metal or ammonium salts of acetic acid, citric acid, tartaric acid, gluconic acid, lactic acid, propionic acid, or mixtures thereof.

The content of a chelating agent will depend on many factors including the nature and thickness of the indicator but preferably be ~1% by weight or higher, more preferably~5% by weight or more.

One can also use metal complexes such that of transition metal, e.g., copper chloride ammonia/amine complexes and nickel chloride ammonia/amine complexes as activators.

A very thin layer or microencapsulated fine particles of pyrophoric materials can be used as activators for monitoring oxygen and/or humidity. The pyrophoric materials include: alkylated metals, metal alkoxide, non-metal halides, such as dichloro(methyl)silane, Grignard reagents (RMgX), metal hydrides or nonmetal hydrides (diborane hydride), iron sulfide, partially or fully alkylated derivatives of metals and nonmetals (diethylaluminum hydride, butyllithium, triethylboron), metal carbonyl, methanetellurol and phosphorus (white, or yellow).

The pyrophoric metals for monitoring oxygen and moisture include alkali metals, finely divided metals, such as iron, magnesium and calcium and hydrogenation catalyst, such as Raney nickel.

Often water and air react/etch many metals. However, these reactions are often very slow for certain metals. These reactions can be accelerated with a catalyst. Many of the compounds listed herein as activators or precursor for activators may also be catalysts. For example, many metal salts of carboxylic acids, such as sodium acetate and calcium citrate may be catalysts, for example, for steam sterilization indicating device of Example 26. When a mixture of aluminum pigments and sodium acetate in a binder is treated with steam at 120° C. for 30 minutes, the aluminum particles get dissolved and the coating becomes light white and essentially transparent and a color, e.g., green and a message, e.g., STERILIZED printed underneath become visible. However, when aluminum pigments in a binder without any catalysts is treated with steam at 120° C. for 30 minutes, the aluminum particles essentially remain unaffected. When a solution of these salts, such as sodium acetate is steamed at 120° C., its pH remains unchanged.

Preferred catalysts for etching of metals are acids, bases and their salts. Further preferred catalysts are salts of a weak acid and a strong base, such as tetrabutylammonium acetate and that of a strong acid and a weak base, such as ammonium fluoride. Preferred catalysts are food additives, such as sodium acetate and sodium diacetate. Other preferred catalysts are carboxylic acid salts, acetylacetonates, cyanates, tetrafluoroborates and phosphates of alkali metals, such as lithium, sodium and potassium and group II metals, such as magnesium and calcium and other metals, such as copper, nickel, iron, zinc and aluminum. The following salts are effective in dissolving fine particles of aluminum when treated with steam at 120° C. in a binder: potassium acetate, lithium formate, calcium acetate, copper(II) acetate, magnesium acetate, lithium acetylacetonate, sodium acetylacetonate potassium acetylacetonate, sodium cyanate, sodium tetrafluoroborate and sodium phosphates. The coatings don't change color with dry heat (140° C. for 30 minutes) which indicates that water is an activator and these salts are catalysts.

It is also possible that some activators may initiate an auto-catalytic dissolution of metals. Especially acids, such as hydrochloric acid produced during radiation of halo compounds, such as carbon tetrachloride, chlorinated polyolefins and polyvinylidene chloride in presence of water can dissolve metals, such as aluminum.

It is also possible to substantially and selectively etch one metal of an alloy, one metal from a mixture of fine particles of two or more metals and their alloys or a top coating of a metal over the other. These types of processes can also provide color changes. For example, it is possible to substantially selectively etch zinc and aluminum from their alloy with copper. For example, when a gold (zinc-copper bronze) ink coating containing potassium bromide is treated with a dry heat at 160° C. for 30 minutes (a dry heat sterilization indicating device), it is possible to substantially selectively etch aluminum and zinc leaving copper behind which is indicated by a color change from yellow to red. In these cases of alloys or a thin coating of a one metal over the other metal of different colors, the surface etching could be good enough for the color changes and hence the reaction could be much more effective and sensitive. Similarly, it is possible to selectively etch aluminum particles from a mixture of fine particles of aluminum and that of an alloy of zinc/aluminum and copper. For example, when a mixture of 4:3 mixture of a silver ink (aluminum particles) and a gold ink (a bronze of copper and zinc) containing sodium diethyldithiocarbamate is treated with steam at 120° C. for 30 minutes, the aluminum particles get dissolved leaving red color copper particles behind, a color change of silvery white to red.

For certain applications, such as dissolution of an antenna of an RFID or making one may need a stronger or a higher concentration of an etchant. One can use strong acids and bases, such as potassium hydroxide or nitric acid or very reactive salts, such as aqueous ferric chloride as an etchant. One can also create these strong etchants from precursors, for example, by reaction of sodium nitrite and sodium nitrate with a weak acid, such as phosphoric acid.

Nobel and many other metals are difficult to etch. Silver and gold are widely used in electronic industry. Silver based paint, inks and pastes/plastisols are used to make a variety of electronic products including printed electronics such as antenna for RFID. These metals are attacked only by limited number of etchants such as nitric acid, and sulfide such as hydrogen sulfide.

One can also create electronic devices, such as RFID and printed circuit boards by applying a layer of a photoresist followed by a layer of an activator or precursor layer on a metallized plastic substrate. The circuit can be created by exposing a photoresist by a conventional method. The activator will diffuse through the more permeable portions, e.g., degraded by radiation and etch the metal underneath, thereby create the device.

The indicating devices could also be created by applying a layer of a precursor (e.g., that of a halo, halonium, sulfonium, nitronium and phosphonium compound) on a metal layer which produces an etchant upon irradiation. Metal under the irradiated portions will be etched. Thus, one can create electronic devices without having a photoresist.

Some of the reactions of metal produce hydrogen gas while others don't (normally known as displacement reactions). Preferred reactions/activators are that which does not produce hydrogen but activators which produce hydrogen, such as phosphoric acid can be used.

Water is an activator for metals. In order for metal particles to form a color compound, a wide variety of reactants/activators can be used including salts, chelating/complexing agents and dyes. For example, if one want to form metal sulfide from metal powder, one uses a sulfur source selected from the group consisting of elemental sulfur, metal sulfide, metal thiosulfate, thiourea, thiocyanates and thiosemicarbazide. Specific examples are potassium thiosulfate, sodium thiosulfate, ammonium thiosulfate, barium thiosulfate, potassium disulfite, sodium metabisulfite, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-.rho.-tolyl-2-thiourea, 4,6-dihydroxy-2-mercaptopyrimidine and 2-thiohydantoin. Many other compounds/indicators which can form color compounds with metal ions, especially with copper, such as 8-hydroxyquinoline, benzoin or oximes, rubeanic acid (dithioxamide), cupferon (nitroso phenylhydroxyamine), dithiazone, rhodamine and diethylthiocarbamate can also be used as activators.

Certain chemicals can be used to accelerate or retard the reaction. Iron compounds and complexes, such as iron chlorides and potassium ferrocyanide and potassium ferrocyanide can accelerate or catalyze the reaction.

1,3-diketones having the general formula R—CO—CH—CO—R' wherein R and R' are each individually monovalent organic radicals selected from the group consisting of alkyl, aryl, aralkyl, alkaryl, cycloalkyl, alkoxy, haloalkyl, and haloaryl radicals having from 1 to 12 carbon atoms can also be used as activators for the steam indicating devices.

Activators, their mixtures and solutions which melt at certain temperatures or freeze at lower temperatures can be used to activate the devices at a desired temperature or temperature range. These types of formulations are desired for thaw indicating devices and high temperature indicating devices including humidity, microwave doneness and sterilization indicating devices. These types of activators will be essentially inactive till the device reaches certain temperature.

The inventions disclosed herein can use a heat-fusible activator, which melts and flows above a pre-determined temperature. When the heat-fusible activator is exposed to a temperature above the pre-determined temperature, the heat fusible activator will melt, diffuse through the matrix and react with the metal indicator. Heat fusible activator could have melting point below room temperature. This type of systems can be used for monitoring class 3 type sterilization indicators.

Precursors for activators are the materials which don't react or react very slowly with a metal/indicator but produce activator for the indicator when subjected to a process or an agent. Precursors for activators are often referred to as simply as precursors, irrespective of a process, an agent or a device. Creation, coating, printing, layer and alike of a precursor will be essentially similar to that of the activator. Like an activator, a precursor can be printed on the metal/indicator layer or a metal layer can be created on the metal/indicator layer and can have a substrate, mask and a protective layer.

Sometimes there is no sharp line of demarcation between a precursor and an activator. Many of the acids, bases and salts listed herein can also be precursor under certain circumstances. It is also possible that (1) a reactant may produce a precursor for an activator which may need another reactant or precursor to produce an activator, (2) two precursors may react to produce an activator, (3) a precursor may undergo more than one reaction to produce an activator and/or may need (4) a catalyst and alike to produce an activator. Phosphorus, white and yellow phosphorus in particular is an example. White phosphorus reacts with oxygen to produce phosphorus oxide which reacts with water to produce phosphoric acid which is an activator. Thus, phosphorus is not a direct precursor but reacts with oxygen and water, to produce an activator. Thus white phosphorus can be used as precursor for monitoring oxygen, phosphorous pentoxide for monitoring humidity and phosphoric acid for monitoring time and time-temperature. A precursor or activator and a device made from it can be used for multipurpose, i.e., for monitoring more than one processes and/or agents as well.

Precursors or activators which are difficult to add in the ink or coating formulation for one reason or the other, e.g., because they crosslink or degrade the binder, can also be produced in situ. These types of compounds can be considered precursors for the precursors but are included in the definition of an activator and its precursor. For example, some of the polyvalent metal ion compounds, such as their salts (e.g., sulfates, phosphates and halides) of copper, iron, zinc, magnesium, crosslink, aluminum, nickel, cobalt, indium, tin and their alloys may be good activators but can't be added directly as they will crosslink or precipitate many common binders, such as polyacrylics. Such activators or precursor for the activators may be produced by adding fine powder of an element (e.g., a metal, such as copper) or compounds which decompose and produce an activator and another reactant. For example, copper bromide is a good activator but it can't be added directly in some inks because it crosslinks many binders. However, it can be produced in situ by adding fine particles of copper or its alloy, e.g., in an aluminum ink containing sodium bromide as a precursor. Upon a process treatment, e.g., sterilization, e.g., with steam, sodium bromide will react with copper particles and produce copper bromide which can act as a catalyst/activator for dissolution of aluminum particles.

It is also possible to etch/dissolve metals by a precursor which decomposes to produce activators/etchants upon a treatment, such as steam and dry heat.

A precursor can also be an organic or inorganic polymeric substance which degrades to a low molecular activator when contacted with an agent, such as radiation, water, humidity, oxygen, toxic chemical, an agent, including chemical or biological agent. An example is polyphosphoric acid and sodium metasilicate (which exist in polymeric state) which when contacted with water or water vapor produce activator such as phosphoric acid and monomeric hydrated sodium metasilicate respectively. Another example is halogenated polymers which produce halo-acids when radiated with ionizing radiation or heated.

Any chemical which produces reactive species, such as acids, bases and salts upon reaction with ETO can be used as a precursor for the activator for ETO. The acids, bases and salts thus produced can react with an indicator/metal and produce the change or dissolution of the metal or surface of metal particles. A metal cation, such as that of (1) monovalent metals, such as sodium and potassium, (2) the other halides, such as bromides or iodides, of di or higher valent metals, (3) organic halides, such as tetrabutylammoniun bromides and (4) other salts, both organic and inorganic, such as sodium thiocyanate can be used as precursor for activator for the ETO indicating device. These compounds react with ETO and probably produce a base, such as sodium hydroxide which can react with metals, such as aluminum and copper and their alloys.

Any chemical which produces reactive species, such as acids, bases and salts with oxidants such as hydrogen peroxide and peracetic acid or their plasmas can be used as a precursor for the activator for plasmas and strong oxidants. The acids, bases and salts thus produced can react with an indicator/metal and produce color change or dissolution of the metal or surface of metal particles. A variety of classes of organic and inorganic compounds can be used as activators for monitoring hydrogen peroxide and its plasma. They include alcohols, amides, amines, bisulfites, bisulfates, carbonates, carbamates, chelates, metal complexes, cyanates, esters, halides, halocarbons, ketones, nitrites, nitrates, nitriles, nitro, nitroso, oximes, phenols, phosphates, sulfates, sulfides, sulfites, thiocyanates, ureas, urethanes, salts, oxidants and reducing agents. Organic and inorganic salts, especially halides can be very effective activators or precursors for activators. These halides include, acetyl choline chloride, ammonium bromide, choline chloride, choline iodide, dodecyltrimethylammonium bromide, glycidil trimethyl ammonium chloride, potassium bromide, potassium iodide, sodium iodide, tetrabutyl ammonium iodide, tetraethyl ammonium bromide, tetrahexyl ammonium bromide, tetramethyl ammonium chloride and tetrabutyl phosphonium bromide.

Certain compounds are unstable under certain conditions can also be used as precursors. For examples, ammonium carbonate decomposes to ammonia and carbon dioxide. Ammonia can react with many metals and hence can be use as a precursor for time, time, and time-temperature indicating devices.

It is also possible to use complexes of acids and bases, e.g., aminoacid:phosphoric acid, urea:phopshoric acid and ferric phosphate complexes.

A mixture of a radiochromic dyes and a halo compounds are widely used as high dose (dose higher than about 10 Gy or 1,000 rads) indicating devices/dosimeters for monitoring ionizing radiations, such as X-ray and electrons. Organic halocompounds, especially polymeric, such as polyvinylidene chloride and a pH sensitive dye are used to make the dosimeters, including monitoring UV light exposure. Upon radiation with ionizing radiation, such as UV (e.g., 10 eV) to 100 MeV energy photons and electrons, organic halo compounds produce hydrochloric acid which changes color of the pH dye. Such halo compounds and a metal can be used for monitoring radiations, especially for monitoring high dose used for sterilization.

Certain iodinium salts, such as, diphenyliodinium hexafluoroarsenate, and diphenyliodinium chloride produce protonic acids, such as, HCl, HF, $HBF_4$ and $HASF_6$ upon irradiation with high energy radiation (J. Crivello, Chemtech, October 1980, page 624; and "The Chemistry of Halides, Pseudohalides, and Azides", S. Patai (Ed.), John Wiley, New York, 1983). The sulfonium, iodinium and alike compounds, in which the primary photochemical reaction produces a super acid and this super acid is employed catalytically to generate other acids. Thus, the color development is amplified. Such systems, which been described in U.S. Pat. No. 6,242,154 and references cited in there. These types of halonium, sulfonium and alike compounds which produce acids and super acids and a metal can be used for monitoring radiation, especially for monitoring high dose used for sterilization and radiation of perishables.

There is no report on use of halo, halonium or sulfonium type compounds as activators (i.e., precursor activators) and a metal as indicator for monitoring radiation. Radiation dosimeters for monitor ionizing radiation, such as UV light to 100 MeV energy photons, electrons and protons can be developed using these systems. Halo, halonium or sulfonium type compounds can be used as activators (i.e., precursor activators) and a metal as indicator.

A large number of halo compounds can be used as precursor for activators to make a radiation dosimeter using a metal layer or fine particles of a metal as an indicator. The halo compounds include, 1-chloro-1-nitropropane, chloroform, carbon tetrachloride, chloroacetic acid, chloropropionic acid, ethyl trichloroacetate, heptachloropropane, hexachlorocyclohexane, methyltrichloroacetimidate, pentachloroethane, tetrachloroethane, trichloro ethanol, trichloro methyl benzyl acetate, trichloro methyl propanol hydrate, trichloro propane, trichloroacetamide, trichloroacetic acid, tri chl oro ethanei s o cy ante, trichloromethylbenzylacetate, trichloromethylpropanol, trichloropropane, commercially available chlorinated paraffins, such as Paroil 150A, Paroil 152, Paroil 170, Paroil 1061 and Paroil 1650 of Dover chemical, Dover, Ohio, halo polymers, such as polyvinyl chloride, polyvinylidene chloride, polyepichlorhydrin and halogenated polymers, such as chlorinated polyisoprene and chlorinated polyvinylchloride.

Other halo compounds include, 1,1-bis [p-chlorophenyl]-2,2,2-trichloroethane (DDT); 1,1-bis [p-methoxyphenyl]-2,2,2-trichloroethane; 1,2,5,6,9,10-hexabromo cyclododecane; 1,10-dibromodecane; 1,1-bis [p-chlorophenyl]-2,2-dichloroethane: 4,4'-dichloro-2-(trichloromethyl) benzhydrol; hexachlorodimethyl sulfone; 2-chloro-6 (trichloromethyl) pyridine; 0,0-diethyl-0-(3,5,6-trichloro-2-pyridyl) phosphorothionate; 1,2,3,4,5,6-hexachloro cyclohexane; N(1,1-bis [p-chlorophenyl]-2,2,2-trichloroethyl) acetamide; tris [2,3-dibromopropyl] isocyanurate; 2,2-bis [p-chlorophenyl]-1,1-dichloroethylene; tris [trichloromethyl] s-triazine; and their isomers, analogs, homologs, Though bromo and iodo compounds can be used as the precursors, generally, chloro compounds provide better stability than bromo and iodo compounds and hence chloro compounds are preferred precursors.

Inorganic halo compounds, such as bromide and iodide are light sensitive compounds, such as ammonium iron(III) citrate may also be used as the precursors.

Some nitro-compounds which can produce nitric acid upon radiation, such as nitroalkanes and cellulose nitrate may also be used as the precursors.

UV absorbers can be added in or above the precursor layer to protect from UV/sunlight when higher energy radiations are monitored. The best protection from UV light is the indicator, metal layer itself, when the metal layer is on the top layer.

A coating of these halo compounds, preferably in a polymeric binder, in a suitable solvent, can be coated on metallized polymer film.

If required, bases, such as amines can be used to neutralize acid produced for monitoring higher dose.

In order for faster migration of acid to the metal layer, it is preferred that binder used is permeable to acid produced and/or use solvents such as water. Water or similar solvents/liquids are desired as they are activators and an acid can catalyze the reaction.

In order to prevent the acid escaping into the atmosphere and/or being affected from ambient conditions, an acid impermeable and protective layer, such as that of polyethylene can be applied on the open side of the precursor layer.

One can use a mixture of an activator and a precursor for the activator.

There are many pairs of indicators and activators that can be used for certain devices such as time-temperature indicating devices. However, the most preferred pair is aluminum and phosphoric acid. Aluminum is highly stable and non-toxic metal and phosphoric acid is non-toxic food additive used in soft drinks. The by-product, aluminum phosphate is water insoluble and also non-toxic and used as a deodorant.

Acids, bases and salts are used as activators and hence if desired their reaction can be monitored with pH, cation and anion sensitive dyes. For example, bromophenol blue when exposed to a base, such as sodium hydroxide turns blue. When blue-colored bromophenol blue is exposed to acids, such as acetic acid it will undergo a series of color changes, such as blue to green to green-yellow to yellow. Aluminum ion reacts with alizarins to give a red precipitate; copper ions react with cuproine to give a pink purple color, ferrous ion gives a red color with 2,2'-dipyridyl, ferric ion reacts with potassium ferrocyanide to give a blue color, magnesium ion gives a blue color with magneson and nickel ion reacts with dimethylglyoxime to give a red color. Test methods are also well known for the detection of inorganic compounds, their cations and anions, which are associated with a color change. These reactions and corresponding compounds can also be used in the device, especially if a color change is also desired. Inorganic compounds and indicators for their detection are described in references: J. Bassett, R. C. Denney, G. H. Jeffery and J. Mendham, Vogel's Textbook of Quantitative Inorganic Analysis, Longman Scientific and Technical, p. 294, 1986.; Fritz Feigl, Vinzenz Anger and Ralph E. Oesper, Spot Test in Inorganic Analysis, Elsevier Publishing Company, 1972, p. 526-616.; Products for Analysis, Catalog of Hach Company, 1986-87 (are cited as references herein).

These are dyes or compounds which react almost instantly with activators to introduce a color change can be used as indicators to indicate activation of the device. These are typically pH dyes. These dyes are coated on the aluminum layer or a permeable layer on it. The preferred material is a colored dye which becomes colorless when contacted with the activator. A thin layer of the activation indicator can be applied on the metal layer by many coating methods including by subliming a dye. The reaction between the activation indicator and the activator should occur almost instantly as the label applicator will apply hundreds of labels a minutes and hence in order to monitor activation, the color change should be as fast as possible. The reaction of phosphoric acid with many pH dyes is almost instant. It is highly desirable to have this feature. Just an application of an activator tape on the indicator tape does not mean the device is activated. The activation indicators will confirm that the device is activated and also visually noticed The current devices have some internal indicators for monitoring tampering.

Uniformity, destruction of aluminum layer, the way it is destroyed, formation of final products, such as aluminum phosphate etc can be used as internal indicators for monitoring tampering. One can also add some internal indicators. Tamper indicator could be for physical as well as for undesirable effects, e.g., effect of humidity, oxygen, light etc.

A large number of reactions are associated with a change in fluorescence rather than a color change in the visible region. Such compounds can be used as indicator and for security in the device. All colors herein could also be fluorescence colors as well.

We tested the concepts with a number of organic and inorganic compounds. On a metallized (~125 Angstroms aluminum) polyester film were added a pinch of a number of inorganic compounds and a few drops of water and covered with a plastic film to prevent evaporation of water. The time required for dissolution of the metal layer was noted at room temperature and then at 60° C. for one day.

The following compounds dissolved the aluminum layer very fast (within hours at room temperature): ammonium iron[III] sulfate, barium acetylacetonate, barium hydroxide, bismuth[III] nitrate, calcium acetylacetonate, calcium chloride, calcium hydroxide, calcium sulfide, cobalt bromide, cobalt chloride, copper chloride, ferric salicylaldehyde, iron [III] sulfate, lithium acetylacetonate, lithium hydroxide, lithium tantalate, mercuric acetate, mercury iodide, nickel chloride, palladium[III] chloride, palladium[III] nitrate, phosphoric acid, phosphorous pentoxide, potassium acetylacetonate, potassium carbonate, potassium hydroxide, potassium iodide, potassium phosphate, potassium bromide, silver sulfate, sodium carbonate, sodium diethyldithiocarbamate, sodium fluorocarbonate, sodium fluoride, sodium hydroxide and sodium tetrafluoroborate.

The following compounds dissolved the aluminum layer slowly (within a day at 60° C.): aluminum acetylacetonate, aluminum chloride, aluminum nitrite, aluminum phosphate, aluminum sulfate, ammonium dihydrogen phosphate, ammonium ferrocyanide, ammonium iron[II] sulfate, ammonium iron[III] oxalate, ammonium iron[III] oxalate, ammonium phosphate, cadmium sulfide, calcium bromide, calcium chloride, calcium oxalate, calcium pyrophosphate, cerium carbonate, cobalt acetylacetonate, cobalt hydroxide, cobalt oxalate, cobalt sulfide, copper acetate, copper acetylacetonate, copper thiocynate, cupric benzoate, dimethyamine borane, ferric acetylacetamide, gluconic acid iron[III]salt, iron[III] sulphate, iron[III] chloride, iron[II] bromide, iron[III] bromide, lithium chloride, lithium formate, lithium nitrate, magnesium[II] acetylacetonate, magnesium acetate, magnesium sulfate, magnesium oxide, nickel bromide, potassium ferricyanide, potassium ferrocyanide, silver acetate, silver nitrate, sodium acetylacetonate, sodium bisulfate, sodium bisulfate, sodium bisulphate, sodium bisulphate, sodium cyanate, sodium dithionitrite, sodium ethoxide, sodium hexametaphosphate, sodium hydrogen carbonate, sodium hydrogen phosphate, sodium hydrosulfide, sodium nitrite, sodium oxalate, sodium phosphate, sodium sulfide, sodium sulfite, sodium thiocyanate, sodium thiosulfate, titanium isopropoxide zinc acetate, zinc oxide, and zinc sulfate.

The following showed very little or no dissolution of aluminum layer under the conditions we tried: aluminum hydroxide, aluminum sulfate, ammonium thiosulfate, ammonium acetate, ammonium bromide, ammonium carbonate, ammonium chloride, ammonium sulfate, barium acetate, barium bromide, benzene boronic acid, borane t-butylamine, boric acid-tin-butyl ether, cobalt orthophosphate, dibutyl tin maleate, gadolinium oxide, magnesium sulfate, silver cyanate and sodium sulfate. These compounds may dissolve aluminum under vigorous conditions, such as higher temperature, higher concentration, or may dissolve other more reactive metals and alloys.

In another experiment about 0.5 g of the above compounds/activators were dissolved in about 4 g of Joncryl 77 (a polyacrylic binder from S.C. Johnson and Sons, Racing, Wis.). Some of them did not dissolved and other caused precipitation of Joncryl 77. Excess ammonium hydroxide was added to re-disperse Joncryl 77. The mixtures were coated on 100 microns metallized (about 125 Angstroms aluminum) polyester film with #20 and #40 wire wound rods and dried at 70° C. Pieces were exposed to 100% humidity for 1 day at 60° C., steam at 100° C. for 30 minutes, steam at 120° C. for 30 minutes, 100% ethylene oxide saturated with humidity at 50° C. for six hours, hydrogen peroxide vapor at 50° C. for six hours, dry heat at 160° C. for 30 minutes. Many of them dissolved the metal layer, some with only one, some with more than one activator and some activators dissolved the metal layer under almost all treatments. For example, (1) ammonium thiocyanate, potassium ferrocyanide, sodium iodide and zinc chloride dissolve the metal layer with hydrogen peroxide, (2) lithium acetylacetonate, lithium chloride, lithium formate, potassium acetate, potassium benzoate, potassium bromide, potassium chloride, potassium formate, potassium ferrocyanide, sodium acetate, sodium bromide, sodium diethyldithiocarbamate, sodium thiosulfate, sodium thiocyanate and sodium sulfite dissolve the metal layer with ethylene oxide, (3) calcium chloride, potassium acetate, and sodium carbonate dissolved the metal with dry heat at 160° C. and (4) calcium chloride, lithium acetylacetonate, lithium formate, potassium acetate, potassium ferrocyanide, potassium formate, sodium acetate, sodium sulfite and sodium tetraborate dissolve the metal layer with steam at 120° C. Thus by selecting proper activator and its concentration, binder and other additives, one can make self reading sterilization indicator selective for only one or more than one treatment/chemical.

In another experiment, about 0.5 g of the above listed inorganic compounds were added in about 3 g of aluminum ink (Product #9W2967J of Braden Sutphin, Milwaukee Wis.) and in about 3 g of bronze ink (zinc-copper bronze, Product #9W3021N of Braden Sutphin), mixed, heated if required.

Some compounds reacted in minutes, some crosslinked the binder, while the remaining remained fluidy. The fluidy mixtures were coated with #20 wire wound rod on 100 microns polyester films. The coated films were dried at 60° C. for about 15 minutes. The pieces of films were cut and exposed to dry heat at 140° C. for 30 minutes, 160° C. for 30 minutes, 100% humidity at 60° C. for 16 hrs, steam at 100° C. for 30 minutes, steam at 120° C. for 30 minutes, ethylene oxide gas having about 50% humidity and vapor of hydrogen peroxide for six hours at 40° C. Many of the above activators dissolved aluminum particles and tarnished bronze particles.

An ink made from selected metal particles can be coated on words such as "sterilized" (e.g., preferably on green color) or on a block printed with green color/symbol. When the metal particles of the ink get dissolved upon a sterilization treatment, the message, e.g., "sterilized" will appear.

Solvents or liquids as aids, facilitator, promotors to migration of activator useful in the invention devices includes the following: water, C1-C15 aliphatic, aromatic and substituted aliphatic and aromatic amides preferably acetamide, dimethylformamide and chloroacetamide; alcohols, preferably amyl alcohol, hexyl alcohol, and dichloropropanol; esters, preferably methylpropionate, amylformate, diethyl maleate, ethylene glycol diacetate, ethylsalicylate, and triacetin; nitroalkanes preferably nitropropane; aldehydes, preferably butyraldehyde; carbonates, preferably diethylcarbonate and propylene carbonate; aromatic alcohols/phenols, preferably dihydroxy benzene, benzyl alcohol and phenol; amines, preferably diethanolamine, dimethylpyridine and cyclohexane diamine; ether-esters preferably ethoxyethylacetate, trioxane, tetraethylene glycol dimethylether, benzyl ether, phenylether, propylene glycol ethylether acetate and propylene glycol butylether; alcohol-esters, preferably ethylene glycol monoacetate; acids, preferably glutaric acid, isobutyric acid, mandelic acid, and toluene sulfonic acid; ketones, preferably methylethylketone and hydroxyacetophenone; ketone-esters, preferably methylacetoacetate; lactones, preferably propiolactone and butyrolactone, methylpyrrolidone and mixture thereof. One can use more than one activator solvent in varying proportions. One may use additives, such as co-solvents (especially highly polar organic solvents, such as alcohols, acids and amines, and ethers) surfactants and nucleating agents. Many of these solvents can also be used as a wetter in the activator tape to wet the metal surface.

Specific examples of solvents include butoxy-2-ethyl-stearate, butyrolactone, diethyl fumarate, dimethyl maleate, dimethylcarbonate, dioctyl phthalate, ethylene glycol dimethyl ether, ethyl salicylate, polyethylene glycol dimethylether, propylene carbonate, triacetin, benzyl ether, dodecyl-1,2-methyl pyrrolidone, ethoxyethylacetate, ethylene glycol diacetate, ethyltrichloroacetate, methylpyrrolidone, methyl sulfoxide, polyethylene glycols of different molecular weight, dimethylformamide, cyclohexane, p-dioxane, tetrahydrofuran, p-xylene, acetone, 2-butanone, ethyl acetate, propyl acetate, toluene, xylene and hexane. Many of these solvents can also be used as a wetter in the activator tape to wet the metal surface.

Solvents are used in making paint, inks and plastisols described herein.

As the reaction between the activator (acids which are usually liquids) and the indicator (aluminum) is heterogeneous, a phase transfer catalyst can be used and wetting agents, such as a surfactant can also be used to promote the reaction and uniformity of the reaction. Wetting agent to wet metals with phosphoric acid can be used. High boiling wetting agents stable to acids and bases, typically used in acidic and basic plating solutions can also be used.

Activator may contain a solvent and/or surfactant for uniform wetting of the indicator and uniform reaction. A large number of surfactants are available commercially including: polyoxyethylene alkyl phenols, polyoxyethylene esters, polyoxypropylene esters, salts of fatty long chain acids and sulfonates, polyethylene oxides, and polypropylene oxides.

The activator tape for certain applications such as time-temperature indicating device, can be prepared by mixing an activator or a precursor and a binder/an adhesive, such as a PSA and applying on a substrate, such as a plastic film. Most of the widely used coating techniques can be used for coating activator/matrix on a substrate. A release tape can be applied to wind the activator tape for storage.

Certain devices such as time-temperature can be activated by applying activator tape on the indicator tape or vice versa. The device can be activated and stored cold till applied on an object. The devices disclosed herein can be sealed at its peripheral edges to prevent migration of activator or reaction with the environment. Sealing can be done by heat sealing or by applying a non-permeable coating.

When the indicator is sensitive to gases and vapors, the device gets activated when exposed to such gases and vapors. For example, a metal coating which is sensitive to oxygen and water vapor, can be activated by exposing the coating to oxygen and humidity/steam or can be used for monitoring them.

Depending upon the application and from which side the device is viewed, the expiration indicating layer could be above or below the indicator substrate. If the indicator substrate is colored, the substrate itself can be an expiration indicating layer. The message can be printed above or below the substrate but preferably below the indicator layer. Dyed plastic films are readily available and hence there is no need to coat if only a color is required as an expiration indicating.

A top or protective coat can be applied over an indicating material if the chemical to be monitored is permeable to the coating material. For example, a protective coat or film which is permeable to steam can be applied on steam indicating device and permeable to ethylene oxide for ethylene oxide indicating device. A protective coat can minimize the undesirable effects of ambient or environmental conditions.

Though the current inventions do not require color reference chart, it can be used. This is particularly useful when use of color reference chart is mandatory, has become a tradition/practice or is preferred. The color reference charts for the current invention could be similar to those described in the prior art devices or those used in the market. The color reference chart could be any shape, e.g., circular, rectangular, square and alike, and could have one or more color reference bars for estimation of different stages of the shelf life or advancement of the processes. Color reference bars could be on any layer or by having an additional layer as long as they are visible or become visible when required.

Indicator tape having a thinner metal layer (e.g., about 50 Angstroms) will provide shorter and gradual induction period and hence can provide gradual color change. Thus indicator tape having thinner indicator layer can be used to make indicating devices similar to those available in the market with or without a color reference chart.

The indicating device can be both self reading and with or without color reference charts.

Though the messages and color of the expiration indicating could be any, it is preferred to be a gray colored because the aluminum layer becomes gray colored as it gets thinner.

The message layer could also be under the aluminum layer, preprinted on its substrate before the metallization.

The size of the indicating devices can be as small as a few square millimeters to several centimeters or larger (e.g., square meters if needed). The thickness of the device typically can be from a thousandth of a centimeter to a millimeter, or thicker, if desired.

The device can also be in form of a very long tape which can be wrapped on any object including boxes containing food packages or cut into small pieces and applied on individual object. The long tape indicating device can also be applied on closer of a perishable container so it can be easily noticed and shelf life can be monitored.

The device can also be in form of large labels, stickers and alike.

As the indicator layer of the current device is environmentally highly stable, the indicator tape can be pre-applied on any object including perishable containers and activated when desired, e.g., when container is filled with a perishable.

The thickness of the indicator, activator and other layers can be varied as needed. The thickness of the indicator layer can be varied thin e.g., 10 Angstroms to 0.01 mm. However, the other layers can have thickness in the range of about 0.001 mm to 1 mm, preferably in the range of 0.05 mm to 0.5 mm. Generally, varying the thickness of the permeable layer will vary the time required for the color change.

The concentration of activator in the activator matrix can be in the range of 0.01 to 0.9 g/cc of the matrix and preferably 0.05 to 0.5 g/cc. of the matrix. The concentration of an additive (any chemical other than activator and indicator) in any layer can range from 0.01 to 0.2 g/cc. The concentration of the indicator will be very high, nearly 100% (e.g., aluminum only) and can be higher than 30% if a dye is used as an indicator. Thinner layer of the indicator is preferred. Similarly, if an opaque layer is used in the device, it is preferred that the opaque layer be the thinnest possible and concentration of the colorant be higher.

Instead of using a color coating in the back of the metal layer and at other places, one can use the PSA activator layer having a dye or pigment, or a message can be printed with an adhesive containing a dye or a pigment.

An ink which fades and becomes colored to colorless with steam and sterilants and/or with other processes and materials disclosed herein including time, time-temperature can be used to write messages, e.g., "NOT" of "NOT STERILIZED". For example, many dyes fade with hydrogen peroxide and steam. Some dye formulations containing materials, such as sodium thiocyanate change to colorless when exposed to ethylene oxide. Upon the treatment, e.g., sterilization, the message of "NOT" becomes invisible.

When an ink is made of metal particles and is used as an indicator, the activator has to diffuse through the binder to reach the indicator. This type of devices may have some properties of diffusion based devices and properties of heterogeneous reaction.

The permeable layer, wedge or flat can have a neutralizer. There could be an extra layer of neutralizer as well. The permeable layer could be a polymeric neutralizer, e.g., polyacrylic acid or polyethyleneimine.

Preferred method of making the tape and certain devices, such as time and time-temperature indicators is to make and store the activator and indicator tapes in form of big rolls till needed to make the indicating devices. The rolls can subsequently be loaded onto a suitable processing machine/equipment. In order to activate the devices, the release layer is removed and applied to an object depending upon the indicating device and its application. Commercially available equipment for application of labels can be used. The devices can be pre-activated (that activator tape applied on to the indicator tape) and frozen at a lower temperature, e.g., deep freezer or dry ice. The activated indicating device should be kept cold till applied on the objects.

Any solid substrate can be used as a substrate for the indicating device. Preferred substrate is a flexible plastic film and natural (cellulose) and synthetic (e.g., spun bonded polyolefins, e.g., Tyvek®) papers. Fiber reinforced substrate can be used for sealing tape indicating device. Plastic substrate could be self colored (pigmented) or coated with a color layer. It could be transparent, semi-transparent, translucent or colored with various intensities. The polymer films include polyolefins (linear or branched), polyamides, polystyrenes, nylons, polyesters, polyurethanes, polysulfones, styrene-maleic anhydride, styrene-acrylonitrile, ionomers based on sodium or zinc salts of ethylene methacrylic acid, polymethyl methacrylates, cellulosics, acrylic polymers (acrylates, such as ethylene methacrylic acid, ethylene methyl acrylate, ethylene acrylic acid and ethylene ethyl acrylate), polycarbonates, cellophane, polyacrylonitriles, ethylene-vinyl acetate and their copolymers can be used as substrate for the devices. The preferred substrates are polyethylene, polypropylene, polyester, cellulose acetate, polyvinyl chloride and their copolymers. Substrate could be porous as well, such as natural and synthetic paper and fabric for certain applications. These substrates can be metallized.

The substrate can have any thickness that is suitable for the intended use. The thicknesses of the substrate can be in the range from about 8 to about 500 microns. Preferred thickness is 25 to about 100 microns.

Adhesives or viscoelastic materials, for example, include the use of synthetic elastomers, acrylates, silicone, synthetic latex and vinyl acetate, as representative examples of pressure sensitive adhesives (PSA) are one of the preferred material for the PSA layer. Included are pressure sensitive adhesives having an elastomer or rubbery polymer as the elastic component and a low molecular weight tackifying viscous component. Common rubber based pressure sensitive adhesives include natural elastomers, synthetic elastomers, such as polychloroprene, polyurethane, and random and block copolymers of styrene-butadiene, styrene-isoprene, polyisobutylene, butyl rubber, and amorphous polypropylene. An illustrative, but by no means exclusive, list of viscoelastic materials which may be suitable for use with the indicator of the present invention includes natural rubber, butyl rubber, polybutadiene and its copolymers with acrylonitrile and styrene, poly alpha olefins, such as polyhexene, polyoctene, and copolymers of these and others, polyacrylates, polychloroprene, silicone pressure sensitive adhesives, and block copolymers, such as styrene-isoprene block copolymers, and mixtures of any of the above. The pressure sensitive adhesive can comprise, for example, a polyisoprene, atactic polypropylene, polybutadiene, polyisobutylene, silicone, ethylene vinyl acetate, or acrylate based pressure sensitive adhesive, and can typically include a tackifying agent and/or a plasticizing agent. The adhesives also include isooctyl acrylate (IOA) or isooctyl acrylate/acrylic acid (IOA/AA) based pressure sensitive adhesive.

Common acrylic adhesives, such as polymers of 2-ethylhexylacrylate, butyl acrylate, ethylacrylate, and acrylic acid can be used. These acrylic adhesives are inherently pressure sensitive. Polymers and copolymers of vinyl ethers, such as vinylmethylether, vinylethylether and vinylisopropylethers are used as pressure sensitive adhesives. Two types of silicone gums; 1) all methyl based and 2) the phenyl modified can also be used as pressure sensitive adhesives. The silicone resin is used as a tackifier and by adjusting the resin to gum ratio, they can be made with a wide range of adhesion properties. High silicone gum content adhesives are extremely tacky. Silicone adhesives are also crosslinked (cured) by catalysts, such as benzoyl peroxide and amino silane.

Hot melt pressure sensitive adhesives typically comprise a block copolymer, a tackifying resin and a plasticizing oil can also be used. The block copolymer provides flexibility, integrity and smooth peel adhesion properties. It also further provides a medium for dissolution or suspension of the tackifying resin and the plasticizing oil. The tackifying resin enhances tack properties and adhesion and reduces viscosity and the plasticizing oil reduces peel values, viscosities, glass transition temperatures and storage modulus and increases flexibility.

UV and peroxide curable adhesive can also be used. Activator can be added in the precursor and cured with peroxide or with radiation.

A PSA which easily supplies, as fast as needed and least affected by activator or does not affect activator is preferred. Some of the acrylates can be used but may not be very suitable for certain activator, such as strong acid and bases.

PSA is preferred but any other adhesive can be used.

For certain devices, such as time indicating devices or visitor badges, it is preferred that the bonding of the PSA layer is much stronger with the indicator layer so it can't be easily tampered.

Many water soluble/swellable polymeric systems, such as those based on plasticized and unplasticized polymethyl methacrylate, polyethylene glycol, cellulose ethers, polyvinylpyrrolidone, polyvinyl methyl ether, polyaminomethylmethacrylate, polyacrylates, copolymer of methyl and/or ethylesters of acrylic acid and methacrylic acid, vinyl pyrrolidone/vinyl acetate, vinyl pyrrolidone, methacrylic acid, methyl methacrylate and natural products, such as dextrin, gelatin, casein and starch can also be used a binder/PSA for activator for monitoring humidity/moisture. The system described in U.S. Pat. Nos. 4,215,025; 4,331,576; 4,490,322; 4,775,374; 5,133,970; 5,296,512; 5,296,512; 5,395,907; 5,565,268; 6,326,524; 6,444,761 and 7,465,493; EP 1458366; U.S. Patent Applications 20090018514; 20090030361 and 20090062713 and WO/1995/005416; WO0230402; WO0021582 and WO 0154674 and references, formulations and processes cited therein can also be used as a binder for activator and indicator. These patents and patent applications are hereby incorporated by reference into the specification of the present invention.

The release layer could be composed of a nonstick material which does not bond or bonds very weakly with a PSA. The release materials include silicone, fluoropolymers such polytetrafluoroethylene, highly crosslinked resins, and oils. The preferred release material is a silicone and a fluoro-polymer.

Materials which form a gel can also be used as a binder. Polymers which are crosslinked or can be crosslinked can also be used. They include natural and synthetic polymers, such as gelatin, agar, agarose, "Super Slurper", which is a sodium salt of 60% graft copolymer of starch, polyacrylamide and acrylic acid. The advantage of using Super Slurper (commercially available from the Aldrich Chemical, Milwaukee, Wis.) is that a gel can be formed at room temperature without the necessity of heating followed by cooling to room temperature. One can use a variety of polymers, copolymers and their mixtures as binders to get desired properties, such as high gel strength and high gelling temperature. Polymers which can retain solvent or activator are preferred. Water insoluble polymers which form a gel in a combination of solvent and nonsolvent can also be used for this device. Reversible gel forming polymers listed in the following books and reviews can also be used: (1) "Reversible Polymeric Gels and Related Systems", Paul S. Russo, ACS Symposium Series #350, Washington, D.C., 1987; (2) L. L. Hench and J. K. West, Chem. Rev., 90, 33 (1990); (3) "Hydrogels" reported by Nagasaki and K. Kataoka, in Chemtech, p23 March 1997; E&E News, Jun. 9, 1997 p26, Encyclopedia of Polymer Science Technology, 7, 783 (1986); (4) "Reversible Crosslinking", Encyclopedia of Polymer Science Technology, 4, 395, (1986), L. Z. Rogogovina and G. L. Slonimiski, and Russian Chemical Review, 43, 503 (1974) and (5) "Polymer Handbook" by A. Hiltner, Third Edison (J. Brandrup and E. H. Immergut Eds), John Wiley and Sons, New York, N.Y. 1989.

The activator resist, referred herein also as "mask", "resist" "barrier" or "etch resist", is typically applied on the indicator layer, most often to cover only a desired portion of the indicator layer. The activator resist and etch resist are used interchangeably herein. The activator resist bonds with an indicator layer and being impermeable prevents the covered portion of the indicator from being affected by it, at least during certain pre-determined period. It is usually a least permeable layer of the activator and prevents or minimizes its diffusion.

Selection of activator resist will depend upon the nature of activator and the device. Preferred activator resist materials are polymers. Many of those polymers listed herein, including metals and some organic and inorganic compounds which are resistant to activator can be used as resist or barrier as long as they prevent permeation of the activator. As activators are polar, nonpolar or less polar polymers, such as polyethylene, polypropylene, polybutylene and polystyrene will be better resists.

The barrier/protective layer/coating could be organic, inorganic or organometallic. It could be substantially crystalline or amorphous. The coating could be a ceramic, such as inorganic oxides, such as aluminum oxide, tin oxide, salts, such as halides and phosphates. When a metal is used as a barrier layer, it can act as an indicator and barrier layer. Many metals naturally form an oxide layer. The passive layer could be other than oxide, e.g., phosphate and chromate. It also can be another metal layer or applied on the surface. The barrier layer can be continuous or grainy and porous. Barrier materials can also be resist materials.

The barrier/protective coating can be deposited by methods, such as sputter, physical vapor deposition, chemical vapor deposition, thermal evaporation, electron beam evaporation, pulsed laser ablation, cathodic arc vaporization, ion beam deposition, anodizing, conversion, powder, sol-gel, electroless plating and electroplating.

The thickness of the barrier will depend upon the nature of the barrier. It could be from a few Angstroms to a millimeter.

The barrier/protective layer should be able to disintegrate by a physical and/or chemical reaction with an activator or precursor for an activator. Disintegratable or destroyable layer is a material which physically or chemically changes its nature for migration of activator which includes disintegration, degradation, falling apart, dissolving, melting, crumbling, breaking up, collapsing, rupturing, fracturing, cracking, failing, changing in glass transition temperature and phase changing.

A barrier/protective layer can also react or form complex with an activator, precursor of activator and/or an additive. Chelates can be added in the activator layer to disintegrate the barrier layer. Solvents which dissolve the barrier layer can also be used in the activator layer. The most preferred is an activator which reacts and destroys the barrier layer, i.e., becomes permeable layer.

The devices may have both the barrier and permeable layers (or a layer which is barrier but becomes permeable under certain conditions) over the indicator layer. In certain cases, such as a metal like aluminum, the barrier layer could be naturally formed, e.g., by oxidation. Indicator layer could have one naturally formed and another layer applied on to the naturally formed layer. These layers could be one organic and another inorganic.

The induction period observed when metallized polyester film is used an indicator can also be due the oxide layer on aluminum layer. When 85% phosphoric acid is poured on a metallized polyester film, there is essentially no visible reaction for almost five minutes, then there is formation of bubbles (due to formation of hydrogen) on the metal layer and after six minutes the layer becomes clear. No formation of hydrogen gas for five minutes probably indicates that phosphoric acid may be reacting with top aluminum oxide layer. Formation of hydrogen gas after the destruction of the aluminum oxide indicates that phosphoric acid reacts with the metal. Weak acid, such as phosphoric acid may be taking longer time to dissolve. This indicates that the low activation energy (below 10 Kcal/mole) may be due to destruction of the aluminum oxide layer. When an aqueous solution of ferric chloride is poured on a metallized polyester film, the metal starts dissolving at the edges of the solution and gradually the boundary moves at center. This may be due to protection of aluminum layer by its oxide.

Often there is very little line of demarcation between resist and barrier materials/lay ers.

Permeable layer as defined herein is a layer which is permeable to activator. Any material which lets activator diffuse or migrate through under controlled conditions can be used to make a permeable layer. Preferred permeable layer is a polymer. The nature of the permeable layer will depends on the activator. It is mainly used to vary/increase the time required for the transparency change and vary the activation energy of the reaction/device. Permeable layer materials include glassy polymers, semi-crystalline polymers, physically and chemically crosslinked elastomers, segmented polyesters, polyamides, radiation crosslinked polybutadiene, and pressure sensitive adhesives. Examples of suitable glassy polymers include polystyrene, polyvinyls, and halopolymers, such as polyvinylchloride, polyepichlorohydrin and acrylates, such as polymethyl methacrylate. Examples of suitable semi-crystalline polymers include polyethylene, polypropylene and polyesters. Examples of suitable physically crosslinked elastomers include triblock copolymers, such as styrene-isoprene-styrene block copolymers, and segmented polyurethane elastomers. An example of a suitable chemically cross-linked elastomer is sulfur crosslinked natural rubber. In the one embodiment, the permeable layer material is a pressure sensitive adhesive including acrylic pressure sensitive adhesives, silicone pressure sensitive adhesives, rubber resin blend pressure sensitive adhesives, triblock copolymer pressure sensitive adhesives, and vinyl ether polymer pressure sensitive adhesives. Rubber resin blend pressure sensitive adhesives include natural rubber, polybutadiene, polyisobutelene, styrene butadiene random copolymers, synthetic polyisoprene, and butyl rubber. Useful triblock copolymer pressure sensitive adhesives include styrene-isoprene-styrene copolymers, styrene-butadiene-styrene copolymers, styrene-ethylene butylene-styrene copolymers, and styrene-ethylene propylene-styrene copolymers. Commercially available latexes, and the raw (without any color) materials for making inks, paints, lacquers, varnishes and adhesives can be used as a permeable layer materials. Thickness of the permeable layer can be in the range of 0.001 mm to 0.1 mm. Permeable layer could have a neutralizer of activator.

Polyvinyl alcohol, polyvinyl acetate, partially hydrolyzed polyvinyl acetate, polyvinyl ether, cellulose derivatives, such as nitrocellulose, cellulose acetate, cellulose acetate butyrate, methyl cellulose, ethyl cellulose, gums, such as guar gums, starch, proteins, such as gelatin can be used as permeable layer, Water soluble polymers can also be used as a binder for activator, adhesive and permeable layer. The examples of water soluble polymers include: agar, agarose, alginic acidamylase, beta-glucan, carboxymethylcellulose, carrageenan, cellulose etherschicle gum, chitin, dammar gum, ethylcellulose, gelatin, gellan gum, guar gum, gum arabic, gum ghatti, gum tragacanth, gum xanthan, hydroxy ethyl cellulose, hydroxy ethyl starch, karaya gum, locust bean gum, mastic gum, partially hydrolyzed polyacrylamide, poly acrylamide, poly acrylic acid, poly crotonic acid, poly hydroxy-2-ethylmethaacrylate, poly hydroxy-3-butyric acid, poly lysine, poly methacrylic acid, poly methyl vinyl ether, poly propylene glycol, poly vinyl acetate—partially hydrolized, poly vinyl alcohol, poly vinyl methyl ether, poly vinyl phenol, poly vinyl pyrrolidone, polyacrylates, polyacrylic acids, polyallylamine, polyaminoacids, polyethylene/acrylic acid, polycarboxylates, polyethylene glycol, polyethyleneimine, polystyrene sulfonic acid, polyvinylamine, polyvinylpyrrolidone, sodium alginate, spruce gum, tara gum, xanthan gum, their copolymers, block copolymers, derivatives, including copolymers with water insoluble polymers. Water soluble polymers are preferred binders for activator for thaw indicating device because when water is used as a solvent for activator, it can freeze the whole layer and may either prevent or minimize the migration of activator and provide controlled release of the activator.

Sealing tape indicating device is a longer version of a time, time-temperature and sterilization indicating devices. It can have all the basic features described herein including activators, indicators, binders, substrates, adhesives, different layers and other properties and processes.

Sealing tape indicating devices could have zebra type pattern of the indicator, that discontinuous indicator.

The indicating sealing tape device could be applied all over the object or sealed only where required.

Velcro type fastener can also developed by using one part metallized while the other coated with an activator.

All indicating devices including sealing tape indicating devices can have a tamper indicating feature, e.g., that created by printing with a silicone coating under the indicator/metal layer.

The indicating sealing tape device is preferably applied at the point where boxes are typically sealed.

Boxes can be pre-applied with one tape e.g., metal/activator tape on one flap and activated later on by applying the activator tape. Other enclosures such as envelops can be made this way.

Activated indicating device can be applied under the existing sealing tape so one does not need to re-formulate or change currently used tape for a particular application.

In addition to making sealing tape of the current inventions (e.g., those shown in Example 10 and FIG. 35), we also made some sealing tapes for (1) steam sterilization using a commercially available formulations, such as that of lead and bismuth, (2) sterilization with ethylene oxide, (3) hydrogen peroxide and its plasma (all obtained from NAMSA, Northwood, Ohio), (4) time-temperature, temperature and radiation indicating tapes made from a diacetylene 4BCMU [R—C≡C—C≡C—R, where R=$(CH_2)_4OCONH(CH_2)COO(CH_2)_4H$] and its partially polymerized form and (5) time and time-temperature indicating tape made from a tape from a commercially available direct thermal film (Product #TF200 C Clear D.T., IIMAK, Amherst, N.Y.) and our phosphoric acid activator tape. Small boxes were sealed with the above tapes and were subjected to the appropriate conditions. However, all these tapes displayed gradual color changes.

As the current devices have a thin and highly opaque indicator layer, which becomes transparent at the end of the reaction, one can print (1) a message on the indicator layer (e.g., aluminum layer) or on a surface of any layer above the indicator layer and (2) another message below the indicator on a surface of any layer below the indicator layer. Both the messages could be the same or different shapes, patterns, numbers, photos, images or barcode, aligned properly if required. Both the messages could form a new or different message or that of different colors. If one message is yellow color and the other could be any other color, e.g., blue, the message will appear green when the indicator layer becomes transparent. By properly aligning the two images, one can create an optical effect of two or three dimensional effect and hence if tampered can be known and authenticity of the indicator confirmed. If the images are barcodes, one can make them non-readable or vice versa or properly readable when the indicator layer becomes transparent. This is a different and a better method to make a barcode readable or non readable or read both of them than disclosed in U.S. Pat. No. 7,157,048. In the current invention, the barcodes are printed on different layers.

These chemical indicating devices can also have almost all features of time and time-temperature indicating devices described herein and vice versa.

As the device has a thin conductive metal layer, a change in a device can be detected/monitored with a small and sensitive metal detector. As the device is reflective, it can be read from a distance using a CCD type camera and other scanners.

As the device has two-tapes, the device can be assembled with a substantially impermeable release layer, e.g., a release plastic film between the tapes. This device is activated by pulling the impermeable layer film out and pressing the tapes to activate the device.

One also can create a moving boundary as described in FIGS. 10 and 34 by using a non-uniform, wedge shaped permeable layer between the activator and the indicator layers.

Moving boundary version of a time, time-temperature and sterilization indicating devices can additionally have all the basic features described herein including activators, precursor for activators, indicators, binders, substrates, adhesives, different layers and other properties and processes.

The moving boundary devices could have a scale and/or numbers to indicate degree of the reaction. It also could have most of the messages and images of those having no permeable layer or that of uniform thickness.

The moving boundary devices can generate a series of messages for example for reminding when to take a drug/medicine. Take $1^{st}$, $2^{nd}$, $3^{rd}$ . . . dose etc. This will remind patients and others when to take a prescribed drug or other instruction do this, do that, don't do this etc. Pharmacists can apply the indicators when a prescription is filled.

The moving boundary devices could have a top layer with windows to see selected portions of the boundary. The scale and messages can also be on the top of the device or on any other layer of the device.

The moving boundary devices can be created for other indicating device disclosed herein, for example, steam, ethylene oxide, plasma of oxidants, such as hydrogen peroxide, formaldehyde, dry heat, temperature and radiation.

As shown in FIG. 10 and demonstrated in a prototype device made manually in FIG. 34, the movement of the boundary is sharper and linear with time. The linear movement of the boundary with time differentiate this indicating device from similar other devices and make this indicating device much more useful. Very few reactions and none of the indicating device reported in the literature has zero order reaction, i.e., linear with time. This is the uniqueness of this device.

We have discovered that a diffusion based sterilization, TTI and other types of moving boundary indicating devices can also be created by replacing the liquid material with an activator/precursor and the porous substrate with a layer of a metal. For certain devices, such as sterilization indicators, one needs to select a proper activator/precursor, which reacts with a material to be detected, e.g., vapor of a chemical including humidity, steam, ethylene oxide and hydrogen peroxide produces a liquid product or dissolve the activator/precursor and reacts with a metal layer. The solution of the activator can then flow and depending upon the design can create a moving boundary device by etching the metal layer. In case of other devices, such as TTI, one can use an activator which is a solution or a molten liquid. The indicator strip could be a metallized porous substrate, metallized PET film having a wettable coating or any porous substrate, such as a strip of paper. A coloring/indicating material can be added in the activator or substrate so the movement of the boundary can be seen.

The band and other indicating device can have an outer surface, an inner surface and first and second ends. The band could also have some additional layers including an adhesive layer so it can be applied on an object. An indicating layer is on the outer surface of the band proximate the first end. The activator layer can be in proximate to the second end. The activator is applied on the inner surface of the band proximate the second end. When the band is wrapped around an object, e.g., a user's wrist, with the outer surface exposed, the outer surface of the first end and the inner surface of the second end overlay and are in contact, preferably in adhesive contact, with each other. The activator and indicator react to cause a visually perceptible change. Such visually perceptible change is viewable from the outer surface.

The band and other indicating devices can have a device, such as an extended layer of an adhesive tape, Velcro or snap-in button etc for further securing the integrity of the band.

Length of the band will depend upon the object it is intended for and could vary from a cm long to several meters or longer.

It can be used as a bracelet incorporating a patient name, a patient number or other identifying information.

The band could have a tamper indicating mechanism.

Substrate for the band could be a paper, cloth, woven or non-woven film.

The band disclosed herein could be an identification band, time indicating band, time-temperature indicating band or sterilization band.

In certain cases the devices can be inactivated, e.g., when acids are used as activator, bases, such as ammonia can be used to inactivate the devices. Sometimes gases, such as ethylene oxide can be used for inactivation as well.

Any design, pattern, messages, images and alike can be created by printing with a mask and etching the unmasked metal layer with hot water, steam or an activator tape. This procedure is much simpler and safer to create any type of design, pattern, messages, images, greeting cards, photo, electronic circuits and alike than by etching by other etchants, such as that with a liquid acid or a base. Games, toys, gimmicks, entertainment, secret messages etc can be created by this process.

The activation energy for the TI and TTI devices reported in the literature is usually higher than 15 kcal/mole, usually around 25 Kcal/mole. The activation energy of the etching reaction of the current device is only about 7 kcal/mole. This makes the current indicating device very suitable as time indicating device. Higher activation energy, e.g., higher than 20 Kcal/mole can be obtained by using a proper permeable or barrier layer. The permeable layer lets the activator diffuse through and hence time required for the change can be varied by varying the nature and thickness of the permeable layer.

In addition to those mentioned herein, by selecting proper indicator, such as a metal, metal alloy of varying metal ratio and alike (e.g., aluminum, copper, copper-aluminum alloys) and activators, precursors and mixtures of them, one can achieve from very low (a few Kcal/mole) to a very high (e.g., 100 Kcal/mole or higher) activation energy (Ea). The activation energy can also be varied by varying nature of binder and additives.

An indicating device having a metal layer on each side of a substrate, e.g., both having the same or different thicknesses can also be used. This device would need two activator tapes, one on each side. The activator tapes could also be of different nature and one or both the layers can be activated. Thus, the device essentially becomes a double indicating device. This double indicating device could also have all other features described herein.

An indicating device having an activator layer on each side of a substrate can also be used. Either single sided or two sided metallized plastic films can be applied on each side of the double activator tape. The activator and indicator layers could also be of different nature and one or both the activator layers can be activated. Thus, this device essentially becomes a double indicating device. This double indicating device could also have all other features described herein.

Devices can also be created by having an activator layer on each side of the metal layer. For the sealing tape indicating device, the activator layer could be narrower than the activator layer and vice versa. Activated tape can be applied on current sealing tape.

The RFID-indicating device can be used on an individual object or on a box/package containing many objects, such as perishables. It can be used as TI, TTI and SI. RFID-indicating device is ideal for visitor's badges, managing entrance and exit of people and inventory control of perishables. The current indicating device can also be applied on a RFID device as well. One can also use a commercially available RFID or similar devices, e.g., electronic time or time-temperature indicating devices and indicating device on the same object. The current device can be applied on electronic time-temperature loggers as well.

The RFID-indicating device can also be applied inside or outside an object, such as a box.

The dispensing system for the RFID-indicating device could be in form of two rolls, one that of RFID inlay and the other that of an activator tape.

RFID-indicating device inlays or its portion which we don't need to etch could have a protective film, coat of protective layer, e.g., etch mask.

There could be one chip and many different antennas of different nature, thickness etc connected to the same chip and activated with a tape of different thicknesses including wedge shaped activator. RFID-indicating device could also have one antenna and two chips as well one of them can get etched away.

RFID-indicating device can be written and read essentially the same way as normal RFID. The same software and equipment can be used. All commonly used compositions, devices and processes of writing, reading and reporting the information related to RFID are incorporated herein as references.

There could be more than one RFID and RFID-indicating devices on an object.

The inventions reported herein for etching antenna of a RFID device can be used to create or destroy circuits of many electronic devices.

The circuit in the printed circuit boards, RFID, EAS and similar devices disclosed herein could have more than one electronic chips or components for monitoring different parameters, such as time, time-temperature and other effects disclosed herein simultaneously.

All other devices disclosed herein can also have an RFID device.

Other display devices can be connected to RFID, to display change in conductivity.

Inexpensive RFID tags can be created by techniques proposed herein and by creating electronic chip from organic semi-conducting materials.

Like RFID one can make magnetic tape inactive by dissolving iron oxide of the magnetic tape with an activator.

The present invention is also directed towards a very thin metal conductive layer which is formed by vapor deposition or sputtering of the conductive metal on a polymeric film substrate or metal film which is then coated or printed with an activator which has capability of etching the metal. The printed activator will be in form of pattern of an electronic circuitry. The polymeric film substrate can be made of any plastic, preferably an epoxy-based polymer.

Preferably, the polymer film comprises a flexible, dimensionally stable material with good tear and chemical resistances. The polymer film should be able to tolerate above-ambient temperatures. Preferably, the polymer film is made of a material having low absorbed moisture and residual solvent.

The polymer film suitable for the practice of the present invention include polyesters, such as polyethylene terephthalate, polybutylene terephthalate and polyethylene naphthalate, polypropylene, polyvinyl fluoride, polyimides, nylons and their copolymers. The other polymeric material suitable for the present invention also include (but not limited to) epoxy resins cured by phenolic or dicyandiamide hardeners, cyanate esters, bismaleimides, and polyimide systems.

The metals suitable for the present invention include zinc, indium, tin, cobalt, aluminum, chrome, nickel, nickel-chrome, brass, bronze or their alloys. Other suitable metals include magnesium, titanium, manganese, bismuth, molybdenum, silver, gold, tungsten, zirconium, antimony and their alloys.

Polymeric layers for the metal and the protection include at least one suitable thermoplastic polymer. These layers can also be formed of the same material, or they can be formed of different materials. Specific examples of suitable thermoplastic polymers include, polyethylene, polystyrene, polycarbonate, polyethylene terephthalate, glycol-modified polyethylene terephthalate, polyvinylchloride, thermoplastic polyurethane, acrylonitrile butadiene styrene, polymethylmethacrylate, polypropylene, polyvinyl fluoride, polyethylene naphthalate, polymethylpentene, polyimide, polyetherimide, polyether ether ketone, polysulfone, polyether sulfone, ethylene chlorotrifluoroethylene, cellulose acetate, cellulose acetate butyrate, plasticized polyvinyl chloride, polyester polycarbonate blends, ionomers, and co-extruded films or sheets of these thermoplastics, etc. The thermoplastic polymers can be elastomeric thermoplastics, and are commonly referred to as thermoplastic elastomer.

The circuitry including antennae for EAS systems can be created using the same or similar devices, formulations and processes disclosed herein for creation of RFID and other electronic devices, which would include creation of proper circuitry on both the sides of a proper substrate.

The EAS or security systems disclosed here can be used for detecting and preventing theft or unauthorized removal of articles or goods from retail establishments and/or other facilities, such as libraries. The EAS device or EAS tag can be affixed to, associated with, or otherwise secured to an article or item to be protected or its packaging. The EAS may take on many different sizes, shapes, and forms, depending on the particular type of security system in use, the type and size of the article, etc.

The security tags that are the subject of this invention can be designed to work with electronic security systems that sense disturbances in radio frequency (RF) electromagnetic fields. Such electronic security systems generally establish an electromagnetic field in a controlled area defined by portals through which articles must pass in leaving the controlled premises. The resonant tag circuit is attached to each article, and the presence of the tag circuit in the controlled area is sensed by a receiving system to denote the unauthorized removal of an article. The tag circuit is deactivated, detuned or removed by authorized personnel from any article authorized to leave the premises to permit passage of the article through the controlled area with alarm activation.

As microwave burn and disintegrate a thin layer of metal, a design for RFID, circuits, pattern, designs, printing plates etc can also be created by selective irradiation with microwave.

Instead of circuits and other patterns, it is also possible to prepare printing plates for presses by printing the desired image on a metallized substrate with a mask type ink (e.g., using an inkjet printer) or tonner followed by etching with an activator tape and then removing the activator tape when fully etched. It is also possible to create hydrophobic and hydrophilic areas by the selective etching.

The activator tape or a coating of activator can be used for etching names and other information on metal items e.g., wire, films, blocks, pots, containers and tools. One can write the information with a marker/mask, apply activator tape and remove when etched. The nature and concentration of etchant will depend upon the metal and alloy. Similar tapes can be made for etching ceramics/glass and plastics, e.g., by reaction of sodium fluoride and an acid, i.e., by applying one tape/coating of one-precursor first followed by applying the second tape/coating of the second precursor which will produce an etchant. This will minimize the hazard and makes the process simple. Apply a tape containing phosphoric acid, followed by that of sodium nitrite/sodium nitrate to produce nitrous/nitric acid for etching metals.

This process can also be used to create small and large signs and boards by selective etching of environmentally resistant metals and alloys.

The steam sterilization device disclosed here is a primary or direct device where the reactant is an activator.

The steam sterilization indicating device will be identical to that shown herein for TI and TTI. However, the steam sterilization devices do not need an activator or activator tape all the time because water acts as an activator. Hence, a metallized plastic film can be used as a steam sterilization indicating device.

The steam sterilization indicating device can also have all the basic features described herein including activators, indicators, binders, substrates, adhesives, different layers and other properties.

A multi-cycle sterilization indicating device can also be developed by several means, such as using a thicker aluminum layer which will dissolve only after certain number of cycles. Moving boundary is one example where it can be used for multi-cycle indicating device.

The steam sterilization indicating device could have printed thereon, under or on the side other indicating devices, such as that for ethylene oxide.

In addition to process indicating devices which indicate that an object has gone through a process of sterilization, higher classes of indicating devices, integrators and emulators can also be created by using proper activators, indicators, devices and processes disclosed herein.

Class 2: Indicators used for specific test procedures. Air-removal tests for vacuum steam sterilizers fall into this category. These indicators assess only the efficiency of the vacuum pump and the presence of air leaks or gases in the steam. They indicate the efficiency of the air removal system but not sterilization efficacy. As etching of metals also depends on presence or absence of air for oxidation and condensation of steam, one can also develop class 2 indicating devices.

Class 3: Single-parameter indicating devices. These indicating devices are designed to respond to one critical sterilization parameter, such as temperature. A common type of class 3 indicating device is a glass temperature tube containing a chemical that melts and changes color when a minimum temperature is reached. These indicating devices do not indicate the total time at one temperature or whether the temperature was exceeded. They are used to determine whether the appropriate temperature was achieved at the center of large packs. By selecting a proper activator which melts at a desired temperature, one can create class 3 indicating devices.

Class 4: Multi-parameter indicating devices. These indicating devices are designed to indicate exposure to a sterilization cycle at stated values of the chosen parameters while also reacting to two critical parameters of sterilization.

An example of this type of indicating device would be one containing ink that changes color when exposed to the correct combination of sterilization parameters. As etching of metals also depends on time and temperature or temperature and steam (or other sterilants), one can also develop class 4 indicating devices by selecting a proper pair of activator and indicator.

Class 5: An indicating device/integrator sensitive to two or more parameters, and reacting within 15% of expected targets. In this category, the change of color must be abrupt, happens within 15% of expected targets and must not happen if the targeted temperature is not achieved within 1° C. For example, an indicating device that accepts (OK or pass) at 132° C. for 4 min must reject (fail) a 131° C. for 3 minutes and 22 seconds. As etching of metals also depends on time, temperature, steam (and other sterilant) and have sharp induction period including the moving boundary devices, one can also create class 5 indicators by selecting a proper pair of activator and indicator.

Class 6: An indicating device/integrator sensitive to two or more parameters, and reacting within 6% of expected targets. In this category, the change of color must be abrupt, happens within 6% of expected targets and must not happen if the targeted temperature is not achieved within 1° For example, an indicating device that accepts (OK or pass) at 132° C. for 4 min must reject (fail) a 131° C. for 3 minutes and 45 seconds. As etching of metals also depends on time, temperature and steam (and other sterilant) and have sharp induction period including the moving boundary devices, one can also develop class 6 indicating devices by selecting a proper pair of activator and indicator.

Similarly high classes of indicating devices/integrators for other sterilization processes, such as ethylene oxide, plasma, formaldehyde, dry heat and radiation can be made by using the activators, indicators, devices and processes disclosed herein for those indicating devices.

We have observed that dissolution of a thin aluminum layer of aluminum under steam get delayed if there is condensation of water on the metal layer. Thus one can make devices, such as Bowie-Dick by using metallized plastic film or those having a special coating which can be wetted, dissolved, swollen with water but not by dry steam. Patterned coating of a permeable material on the metal layer can be used as Bowie-Dick devices. If there is condensation during the steam sterilization process, that portion of the metal will not get etched.

Instead of using continuous plated plastic film one can use designed, ruled, fine lined metallized plastic films.

Water based inks may have a coating to prevent tarnish and reaction with activator but at high temperature it could melt of dissolve and hence can be used for steam sterilization indicating device. For water based metal powder, the activator could be water insoluble and vice versa.

The reaction does not require complete dissolution of metal powder as long as it can be tarnished by an activator.

The metal particles could be nano sized to large flakes.

Dry heat indicating devices including dry heat sterilization indicating devices can be created by selecting a proper etchant which melts at or below the dry heat temperature used for sterilization or similar processes. The matrix could be essentially any, e.g., a PSA, hot melt adhesive or just a coating of the activator in a non-adhesive resin. Non-adhesive matrix is preferred for the dry heat indicating device. The molten activator can etch the metal/indicator. These devices can also be used for microwave doneness indicating device, especially when the metal layer is very thin.

Polyvinyl chloride (PVC), polyvinylidene chloride (PVDC), halogenated polyolefins and other halogenated polymers and their copolymers are suitable as activators for dry heat indicating devices as well. For examples, when coatings of a PVDC containing fine particles of aluminum, zinc, copper and their alloys are heated at 160° C., they undergo a transparency change, most likely by reaction of hydrochloric acid (produced due to thermal decomposition of the halides) with the metals. Other additives, activators, precursors for activators and catalysts can be used to alter the reaction rate.

Salts, especially that of strong acids, such as sulfonic acids and amines, e.g., primary amines, especially that of long chain which melt at desired temperature can also be used for making a dry heat or temperature indicating device.

The activator could also be microencapsuled. The microcapsule should rupture at or below 160° C. for monitoring sterilization with dry heat.

An ink or paint formulation composed of fine particles of a metal, such as aluminum and its alloys, a binder, a vehicle and a reactant, such as an acid, base, salt or oxidizing agent (including their precursors) having capability of reacting with the said metal or a dried coating of it on a substrate can be used as indicating devices disclosed herein, e.g., steam sterilization indicating device. The reactant will react with the metal and either tarnish or completely dissolve (react with) it. One can also add a dye or pigment in the said ink or paint. The added dye or pigment may or may not necessarily have to undergo a color change with steam. For example, when auramine-O is added in silvery ink of aluminum, it appears gold color. Upon steam treatment, auramine-O becomes colorless and gold color coating changes to silvery white. There are a number of dyes and pigment which undergo color changes, e.g., Janus green B, Basic blue 66 and basic blue 41 change to red and then essentially become colorless when steam treated and hence they and similar other dyes and pigments can be used to get other color changes with steam. Thus, dyes and pigments, whether they change color or not can be added in the steam sterilization indicating device.

The activator for steam and other indicating devices could also be water insoluble for water based inks and solvent insoluble for solvent based inks.

By adding proper activators and/or precursors in a metallic ink (ink having fine particles of a metal or alloy) one can also make a variety of other indicating inks. For an example, by adding temperature activators/precursor in a metallic ink one can create a thermochromic inks for different temperature. Similarly, one can create inks for a number of other processes such as time, time-temperature, pressure, radiation and materials such as humidity, chemicals, chemical and biological agents.

The binder system for indicating compositions according to the present invention may comprise a film-forming carrier which is permeable to steam and other sterilants in order to obtain a satisfactory change under steam sterilization conditions. Preferably, binder systems provide steam sterilization and other indicating devices with film-forming properties, good adhesion to objects, and heat and moisture resistance. The ink of the invention preferably also comprises a binder. The binder may comprise any water resistant, heat resistant polymer. Suitable polymers include soluble polymers such as ethyl and nitro cellulose, cellulose acetate and its derivatives, hydroxypropyl cellulose, polystyrene, polymethacrylates, polyvinyl chloride, polyvinyl acetate; emulsion latexes, such as polyvinylidene chloride, acrylics and polyvinyl acetate; cross-linking resins, such as phenol-formaldehyde, urea-formaldehyde and melamine-formaldehyde; polyethylene, polypropylene, polyurethanes, polyesters, polycarbonates, polybutylene, polyvinylbutyral, polybutadiene, and their copolymers, UV curing systems; and drying oils.

One aspect of the invention is an ink that includes an aqueous dispersion of a metallic pigment and a film-forming resin. The metallic pigment can be a leafing (typically flaked) or non-leafing type. A metallic pigment preferably is a metal pigment selected from the group consisting of aluminum, copper, bronze, oxides thereof, anodizes thereof (e.g., to provide an iridescent finish), and combinations of any of the foregoing. The metallic pigment is also defined to include other lustrous substances that can provide a metallic or iridescent appearance, such as pearlescent agents (e.g., bismuth oxychloride (BiOCl)), which can be used in addition to, or instead of, a metal pigment.

Though larger metal particles can be used for applications disclosed herein, preferred size is less than about 15 microns or in a range of about 2 to 15 microns. The metal pigment preferably is included in an ink in a range of about 2 wt. % to about 30 wt. %, preferably about 5 wt. % to about 10.

Suitable film-forming resins also include water-soluble resins, such as hydantoin-formaldehyde co-polymers, e.g., dimethylhydantoin-formaldehyde (DMHF) and 5,5-dimethylhydantoin formaldehyde polymer (also called 5,5-dimethyl-2,4-imidazolidinedione). A preferred is dimethyl hydantoin-formaldehyde film-forming resin. Other resins for use in an ink of the invention include polyvinyl alcohol and water-borne urethane polymers. The film-forming resin preferably is included in an ink in a range of about 10 wt. % to about 70 wt. % and preferably about 30 wt. % to wt. 50%.

An anti-settling agent can be added in very small quantities. It can aid in the stability of the ink. Preferably, an anti-settling agent is present in the ink in a range of about 0.001 wt. % to about 0.11 wt. %. A preferred anti-settling agent for use in an ink is gums, such as xanthan gum.

It is also preferred to add a preservative (e.g., a fungicide and/or bactericide) to the ink formulation. An example of preservative is 1,2-benzisothiazolin-3-one in a range of about 0.05 wt. % to about 0.15 wt. %.

The devices disclosed herein, can also be made by applying a coating of an activator or a precursor for an activator in a UV curable binder followed by curing with radiation, such as UV light. There may be an additional protective layer to protect the activator coat from the ambient conditions. Selection of the activator, precursor, binder, curing agent and any additive will depend upon the application the device it is intended for. For example, to make a humidity indicator, one can coat phosphorous pentoxide in a UV curable binder which is permeable to water vapor on a metallized plastic film. When exposed to water, phosphorous pentoxide, being very hygroscopic will react with water to form phosphoric acid and etch the metal layer.

This type of UV curing method is a preferred method of making the devices disclosed herein as the method is fast.

The binder should be permeable to the material used for processing, e.g., steam, ethylene oxide, hydrogen peroxide, formaldehyde etc.

The activator layer can have fine nano to micro particles of materials, such as zinc oxide, titanium dioxide, microcrystalline cellulose. This may help for uniform reaction on the surface.

Antioxidant, such as butylated hydroxyanisole and butylated hydroxytoluene (BHT) can be added to minimize oxidation.

Humectants, such as propylene glycol, super absorbing polymers, sorbitol and lactic acid can be added in the activator layer to prevent drying out of the devices herein.

For many applications, such as steam indicating devices or where water is used as a component or affects the performance of the indicator, it is preferred to use water insoluble resins, self crosslinking emulsions, latexes, solutions of resins upon drying or heating.

Microwave doneness indicating device may have many of the general features of all other indicating device disclosed herein.

Though many of the designs, formulations and processes disclosed herein can be used as microwave doneness indicating device with proper modifications by using a very thin layer of aluminum metal (normally referred as susceptor in prior art) having optical density in the range of 0.05 to 0.5, most preferred are those having optical density of about 0.2.

The microwave doneness indicating device could be anywhere in or on, inner or outer surface of the container. These indicating devices can also be incorporated as part of the container or as a part of a heating pad. The design can also be identical to that of microwave susceptor reported in the prior art.

The activators for microwave doneness indicating device will be higher melting compounds which melts at a desired temperature and etches the metal. The activator could also be microencapsulated.

The time temperature indicating (TTI) devices disclosed herein can also be used for self-heating packages that function without application of external energy. Heat is generated by contact of a heat-producing composition, such as calcium oxide and an activating solution which is typically water. TTI for self-heating packages would require higher temperature activator or weaker activator and/or strong/resistant or thicker indicator. Many of those activators and indicators listed herein can be used. Activators which melt at elevated temperatures would be preferred for self-heating packages. This indicating device could be anywhere in or on, inner or outer surface of the container The thaw (freeze to thaw) indicating device for monitoring frozen state and shelf life of the frozen items/perishables, such as frozen foods will be essentially identical to that of time-temperature indicating device, e.g., composed of an activator tape and an indicator tape, and made essentially by the same methods as described herein. The major difference will be the state of the activator or activator layer. The activator for the thaw indicating device will become essentially solid and/or non-migratable/nondiffusable in case of the thaw indicating devices when the item it is applied on is frozen. The indicator tape will be essentially the same as that of the time-temperature, e.g., a thin layer of an adhesive containing activator on a substrate. One can make a thaw indicating device, e.g., by applying an indicator tape over and activator tape.

The temperature and time-temperature required for the transparency change can be varied by adding a co-activator, salts or a solvent.

A thaw indicating device can also be created by making (1) an indicator tape by coating a layer which becomes clear when contacted with water or water vapor over a metal layer or any printed message and (2) an activator tape by coating a water based adhesive and partial drying. A thaw device is created by applying the activator tape over the indicator and freezing. If the device is brought to temperature above freezing, the ice in glue will melt and slowly diffuse through the opaque layer and make it clear, thereby making the metal layer or message printed underneath visible. The indicator tape may have an activator which can get dissolved with water and etches the metal layer.

A thaw indicating device can also be developed from a mixture of fine metal particles and an activator which melts at 0° C. and slowly dissolves the metal particles. A UV curing binder would be better for this type of systems. A low temperature (below 0° C., e.g., −40° C.) indicating device can be developed by selecting proper activator having such low melting point.

A freeze indicating device can be prepared, for example, by coating microcapsules on a metallized plastic film, whereby the microcapsules rupture when frozen and release an etchant/activator. Proper core materials, such as activator and solvent and membrane/wall material need to be selected for making the microcapsules for the freeze indicating device. By selecting proper materials and methods of microencapsulation one can make microcapsules which would rupture upon freezing and release the activator in them.

A number of activators listed herein can be used for the freeze indicating device. Both water soluble and water immiscible activators can be used. Liquid activators which are not miscible with water and can be encapsulated with water. Preferred solvent for the activators is water. A co-solvent or a chemical which changes the freezing point of water can be used for changing the temperature required for freezing. It is preferred that the co-solvent is water miscible.

The freeze indicating device will provide the time delay required for the color change and will have many other properties of time-temperature as disclosed herein.

A mixture of two different types of microcapsules, e.g., one containing an activator or a solvent which does not freeze solid while the other containing an activator or a solvent which does freeze solid when cooled to a predetermined low temperature can also be used.

The activator does not need to be frozen solid when cooled. If the activator does not freeze solid but has some vapor pressure or volatility, it can still react with the metal and can introduce the changes.

Once the activator is released, the device could become a time-temperature indicating device. The transparency change will be faster above the freezing temperature. The etching could also change color during thawing and can be used as a thaw indicating device. Thus by selecting proper activator, solvent, co-solvent or mixture thereof, one can develop either freeze or thaw indicating device.

The microencapsulated activator could be dispersed in a binder, including a pressure sensitive adhesive and applied on a metallized plastic film. The adhesive could be prepared by coating UV curable monomers and/or oligomers so it can be easily coated without rupturing them.

Instead of microcapsules one can use any similar device or mechanism which provides controlled release of activator.

Activators or solvents which can phase separate (e.g., as described in U.S. Pat. No. 6,472,214) and etch metal layer can also be used.

These freeze devices will essentially be a solid state and thin freeze indicating devices.

These temperature indicating devices can also have almost all features of time and time-temperature indicating devices described herein and vice versa.

Many liquids either expand or contract significantly upon freezing. Water is an example. It expands by ten percent upon freezing. Many materials, such as metals and plastics have vast difference in their expansion and contraction during heating and cooling, i.e., significant difference in thermal expansion coefficient. A thin coating of a brittle material on another material having sufficient difference in thermal expansion coefficient can result into cracking of the brittle material. For example, unplasticized polyvinyl chloride is a brittle plastic has thermal expansion coefficient of $52 \times 10^{-6}$ per K compared to $23 \times 10^{-6}$ per K for aluminum. The dye solution can pass through the crack and indicate the cracking thereby change in temperature or freezing. The thermal expansion coefficient of water at 5° C. is $0.16 \times 10^{-4}$ per K compared to $-0.68`10^{-4}$ per K at 0° C.

Similarly, an adhesive, e.g., pressure sensitive adhesive containing some water (e.g., partially dried an aqueous pressure sensitive adhesive formulation) containing a coloring material can be applied on a thin layer of a brittle material, especially an opaque brittle material. Upon freezing (e.g., below 0° C.) water will expand and being a part of an adhesive which is bonded to the brittle layer, it can crack the thin brittle layer. Upon thawing the colored water can diffuse through and can indicate the freezing. If the partially dried adhesive also has a colored liquid which does not freeze, it can diffuse through the cracks and indicate the freezing while in the frozen state.

One can also use microencapsulated color water containing an activator to make the freeze device. One can also use the phase separation technique disclosed in U.S. Pat. No. 6,472,214 to release an activator.

One can print a message or image on the substrate of the device and under the dispersion of formulations disclosed in U.S. Pat. No. 7,343,872 and similar formulations which become clear from opaque. When the dispersion formulations described in that patent become substantially clear or transparent upon freezing. One can also make emulsion of two liquids, such as water, toluene. The latex or emulsion could be just a single component and no additive of any kind or simply having nano particles for nucleation or dye having light green color and the background red, so when it melts light green will become much lighter and bright red with message "frozen" will appear. The message could be any.

The freeze indicator tape may also contain devices, formulations and processes disclosed in U.S. Pat. Nos. 6,472, 214 and 7,343,872 or any commercially available devices, such as those based on rupturing of microcapsules including those available commercially from American Thermal Instruments, Dayton, Ohio.

If the wall material of the microcapsules is made from materials, such as fatty chain, wax and other compounds as disclosed in U.S. Pat. Nos. 6,602,594, 4,729,671 and 4,643, 588 one can create a temperature indicating devices.

High temperature (above 25° C.) indicating devices can be developed by using the materials and processes disclosed herein for freeze-thaw indicating devices for higher temperatures, e.g., by using an activator which melts at the desired temperature.

By selecting a proper alloy for the indicator can be made highly sensitive moisture/humidity and can be used as a humidity indicating device. Similarly, one can make oxygen indicating device. Metals useful for humidity and oxygen indicating device are sodium, lithium, potassium, cesium and alike and their alloys. In the cases of humidity, steam and oxygen indicating devices, oxygen and water are activators. Fine powder of metals, such as aluminum and indium can be used as desiccant.

Several metals and metal oxide, such as sodium and calcium and their oxides can be used as precursor for activator for moisture indicating devices. Non-metal hygroscopic and desiccant materials, such as anhydrides, phosphorus and its oxides can also be used. $P_2O_5$, phosphorous pentoxide (and its homologs) is a desired precursor because it is extremely hygroscopic and produces an acid (phosphoric acid) reacts with water and etches metals. A coating of dissolved or finely dispersed phosphorous pentoxide on a metal layer can be used as a humidity indicating device.

Phosphorous oxychloride ($POCl_3$) reacts with water to produce HCl. Phosphorous pentachloride and trichloride ($PCl_5$ and $PCl_3$), which produce an acid can be used as precursors for activators for monitoring moisture/humidity. These materials can be microencapsulated. Similarly, halides which decompose at higher temperatures to produce acids can be used for other indicators including sterilization, especially for steam.

The humidity indicators can be used in diapers as wetness indicators.

An activator for a humidity indicating device was created by coating a solution of polyethylene oxide in methanol containing p-toluene sulfonic acid on Teflon coated polyester release film followed by drying in an oven at 80° C. A humidity indicating device was created by applying the dried coating on a metallized polyester film and removing the release liner. The device was exposed to ambient humidity (about 80%). The metal layer got dissolved in about 2 hours.

An oxygen scavenger, absorber, or reactants which can produce an activator can be used for monitoring time and time-temperature after opening a container.

Metal alloys, such as bronze alloy which gets etched (tin or zinc getting etched and leaving copper behind which turns black when exposed to ambient conditions) can be used for monitoring ambient conditions after opening a container. Microporous metals and or fine particles of metals which oxidize/react with air/oxygen and/or water can be used for monitoring air time after opening a container.

White and yellow phosphorus reacts with oxygen but not with water and produces phosphorus oxide which when reacts with water/humidity produces phosphoric acid which is an activator. Thus white or yellow phosphorus, e.g., thin coating or encapsulated, can be used for monitoring time after opening a container. Oxygen reactive compounds which produce an activator can be used for these applications.

When a thin layer of a metal is used as an indicator for monitoring sterilization, the device can also have almost all features of time and time-temperature indicating devices described herein and vice versa. The sterilization indicating devices can have essentially identical designs, shapes, sizes, colors, patterns, numbers, photos, images or barcodes and made to undergo essentially identical changes as time and time-temperature indicating devices described herein and vice versa. There will be some changes required depending upon the application.

The dosimeters, monitors and indicating devices disclosed herein are mainly presented in form of two dimensional indicating devices. Using the activators, indicators and binders disclosed/described herein, one can also make three dimensional indicating devices by making them thicker. A three dimensional dosimeter for ionizing radiation can be made by materials and processes disclosed herein. A polymeric material having ultra fine particles of a metal and an activator/precursor can be made for the 3D dosimetry. The device can also be made by alternating multi layers of an indicator and an activator/precursor.

Wear indicating devices are known in the art, e.g., U.S. Pat. No. 7,267,880. It is also possible to create a wear indicating devices by using the materials and processes disclosed herein. Wear indicating device includes rub, scuff, grind, erode and use/discard indicating device. Many devices, e.g., razor should be not be used or not recommended to be used after certain uses or wear. A message or color can be printed under a metal or an opaque coating. After certain uses the indicating opaque/metal layer will wear out and be indicated by the message/color printed underneath.

Wherever a metal, in form of thin coating, strip, fiber, film, hologram and alike is used in a security system, the current invention can be used for detecting a forgery, tampering and/or identifying whether the system is genuine or not, including monitoring age and effect of ambient conditions. Many paper currencies have a metal fiber or strip. The metal surface can be coated with an activator system. The nature of an activator will depend on the metal and intended use. Metal and/or activator surface may have printing. The activator layer could be on or under the printing. The inventions disclosed herein can also be used for coins.

Controlled release systems, such as microencapsulation known in the prior art can be used for controlled release of activator. A pressure sensitive adhesive (PSA) with an activator is a controlled release system and hence any other control release system can be used as activator layer or activator tape.

Activators can be microencapsulated. The devices can be activated by rupturing the microcapsules either by applying pressure or by melting.

Controlled released technology is used in many fields for controlled release of a variety of substances. Because an activator such as water and oxygen has ability to dissolve certain metals, the technology disclosed herein can be used for control release of a variety of substances including pharmaceuticals, foods and agricultural applications, pesticides, cosmetics and household products coated thin with a metal. Selection of a metal or an alloy will depend upon the material and the application. By selecting proper metal and thickness one can create sustained-release, extended-release, time-release or timed-release, controlled-release or continuous-release of pharmaceuticals, foods and agricultural applications, pesticides, cosmetics and household products. The activator either can be added or environment, e.g., body fluid, water, can be an activator. Provided are control release devices wherein a thin layer of metal is used to encapsulate, cover, protect a substance to be released by dissolution of the said metal.

As water and salts dissolve very thin metal layer and hence can be used for control release of pharmaceuticals, foods and agricultural applications, pesticides, cosmetics and household products.

The control release devices could be small particles having a very thin layer of metal or other shapes, such as flat devices having at least one thin layer of metal.

Many of the indicating devices disclosed herein can also be made from coating microcapsules having proper activator, indicator, and materials and processes for making the microcapsules. For steam sterilization indicating devices, one can select microcapsules which release activator or a colored material at desired temperature and humidity/steam. By controlling the release of the activator and other materials of microcapsules one can make indicating devices by controlled release of activator and other materials.

There are many different ways directly thermally printable, ruptureable or activatable materials can be used for making many of the devices and processes disclosed herein using a metal as an indicator and an activator. The devices can be made using microcapsules containing an activator, such as phosphoric acid and/or by coating the metal layer or metal particles. In these devices, (1) both activator and indicator could be on the same side of a substrate, i.e., by coating a layer of microcapsules of activator on the metal layer, (2) the metal layer on one side and the microcapsule layer on the other side of a substrate and (3) the metal layer on one substrate and the microcapsules on other substrate and brought together to make the devices.

There can be additional layer(s) of traditionally available color developing microcapsules so desired messages can be printed.

A metallized plastic film having thermally printable coating on one side can be used to print messages using a thermal printer. Similarly, a metallized plastic film having directly thermally printable coating on one side to print a message and other information and a coating of microcapsules containing an activator, such as phosphoric acid can be made and used to print and activate the devices using a thermal printer.

With the direct thermal printing technique, it can be easier to create the double message of "NOT STERLIZED" to "STERLIZED". This can be done by coating a block on the indicating device with directly thermally printable formulation. A part of the message (e.g., "NOT") can be printed with a thermal printer on the block. The block, including the word "NOT" will become black when heated or steamed above 70° C. or higher (depending upon the nature of the direct thermal coating). By controlling and selecting proper materials, one can make the block go black when the product is sterilized. Thus, only word sterilized will be visible upon sterilization. Alternatively, the word NOT can be printed on the top and a mask on the metal under NOT. Such direct thermal coating, microencapsulated or not can be used for monitoring sterilization.

Instead of printing with directly thermally printable technique/formulations, one can use other similar printing techniques/formulations.

One can write "NOT STERILIZED" in one color and on the backside of the metallized film coat with the same color in form of a block in the same color so the word "NOT" cannot be seen when the device/product is sterilized. The word sterilized could be written as a mask.

The messages can be printed in any languages or in any shapes.

The message also can be created to identify the device and or process used, for example, "EO", "STEAM", "PLASMA" appearing before processing and "EO PROCESSESD", "EO STERILIZED", "STEAM PROCESSED", "STEAM STERILIZED", "PLASMA PROCESSED", or "PLASMA STERILIZED" after being processed/sterilized. This type of messages can identify which process was used.

A message can also be printed with metallized ink and an activator. When sterilized, the message will disappear due to etching of the metal.

Direct thermal printing layer can be at any location in the device. However, the preferred location is on the surface or a layer near the surface of a device.

Thermochromic materials which change color upon heating, including those changing color upon melting, are used to make thermal paper. Thermochromic and photochromic films and papers which can be printed or activated with heat and light can be used for direct printing.

Examples of leuco dyes that can be used herein include: (a) leuco bases of triphenylmethane dyes, such as 3,3-bis (p-dimethylaminophenyl)-phthalide, 3,3-bis(p-dimethylaminophenyl)-6-dimethylaminophthalide (Crystal Violet Lactone), 3,3-bis(p-dimethylaminophenyl)-6-diethylaminophthalide, 3,3-bis(p-dimethylaminophenyl)-6-chlorophthalide, and 3,3-bis(p-dibutylaminophenyl)-phthalide; (b) leuco bases of fluoran dyes, such as 3-cyclohexylamino-6-chlorofluoran, 3-(N-N-diethylamino)-5-methyl-7-(N,N-Dibenzylamino)fluoran, 3-dimethylamino-5,7-dimethylfluoran and 3-diethylamino-7-methylfluoran; (c) miscellaneous fluoran dyes, such as 3-diethylamino-6-methyl-7-chlorofluoran, 3-pyrrolidino-6-methyl-7-anilinofluoran, and 2-[3,6-bis(diethylamino)-9-(0-chloroanilino)xanthybenzoic acid lactam]; and (d) lactone compounds, such as 3-(2'-hydroxy-4'-dimethylaminophenyl)-3-(2'[-methoxy-5'-chlorophenyl)phthalide, 3-(2'-hydroxy-4'-dimethylaminophenyl)-3-(2'methoxy-5'-nitrophenyl-phthalide, 3-(2'-hydroxy-4'-diethylaminophenyl)-3-(2'methoxy-5-methylphenyl)phthalide, and 3-(2'-methoxy-4'-dietnethylaminophenyl)-3-(2'-hydroxy-4'-chloro-5'-methylphenyl)-phthalide.

Examples of suitable developers are phenol compounds, organic acids or metal salts thereof and hydroxybenzoic acid esters Examples of phenol compounds include 4,4'-isopropylene-diphenol (bisphenol A), p-tert-butylphenol, 2-4-dinitrophenol, 3,4-dichlorophenol, p-phenylphenol, 4,4-cyclohexylidenediphenol. Useful examples of organic acid and metal salts thereof include 3-tert-butylsalicylic acid, 3,5-tert-butysalicylic acid, 5-a-methylbenzylsalicylic acid and salts thereof of zinc, lead, aluminum, magnesium or nickel.

Sensitizers or thermo-sensitive promoter agents are used in the recording materials of the present invention to give a good color density to the images obtained. Some of the common sensitizers which are suitable are fatty acid amide compounds, such as acetamide, stearic acid amide, linolenic acid amide, lauric acid amide, myristic acid amide, methylol compounds or the above mentioned fatty acid amides, such as methylenebis (stearamide), and ethylenebis (stearamide), and compounds of p-hydroxybenzoic acid esters, such as methyl p-hydroxybenzoate, n-propyl p-hydroxybenzoate, isopropyl p-hydroxybenzoate, benzyl p-hydroxybenzoate.

The encapsulated material may contain color former, color developer, sensitizer and a color or white pigment as normally found in direct thermal papers and films.

Microencapsulated solid and solution of activators, such as phosphoric and phosphorous acids can be used as activators which can be released upon demand. Phosphoric acid (melting point 73° C.) and phosphorous acid (melting point 43° C.) having low melting can help in encapsulation. Preferred wall materials are those used for encapsulation of materials for direct thermal paper.

The wall material for thermally printable microcapsules containing an activator, such as phosphoric acid, can be made using wall materials, such as fatty chain amines (primary, secondary and tertiary, e.g., dodecyl amine), fatty chain ammonium hydroxides (such as dodecyl tetrabutylammonium hydroxide), fatty chain acids, waxes like candelilla wax, paraffin wax and bee wax, unsaturated and crosslink polymers which can be crosslinked to desired degree.

In order to protect activator and/or indicator from undesirable effects and/or from any undesirable pre-mature reaction, they can be protected by coating with a protective material. The protective material would be less permeable or high barrier material, usually polymeric or oligomeric. In order to control the reactivity of activator with indicator, they can be encapsulated. The encapsulation material often referred to as wall material.

Similar to direct thermally printable coating, a coating can be made from encapsulated activator, indicator, their precursors, permeable material, barrier material, catalyst and/or additives. There can be more than one type of microcapsules containing different types of materials. It is not necessary to encapsulate all of these materials. The coating may have all or one reactant encapsulated. Selection of materials will depend upon the application. The indicating devices made from these materials can be activated by thermal, pressure, solvent etc before the application. With time, time-temperature, sterilization and other treatment conditions, the indicating layer or portion thereof will undergo the change.

A direct thermal imaging apparatus as used herein refers to any apparatus which is suitable for the application of thermal energy to the recording material to activate indicator compounds in the recording material. Direct thermal printing is generally described in the Handbook of imaging Materials, 1991, ed. by Arthur S. Diamond (Marcel Dekker, New York).

Direct thermal printing offers on-demand, on-line and customized printing and activation of the devices. Any message in any language and shape can be printed. Name of institution, user, date, logo and any other information required/desired etc can be printed when desired.

The devices can be activated by a physical or a chemical method. The device can be activated with time (controlled released), temperature, pressure, laser, water/steam/moisture, a solvent, a chemical (e.g., sterilants, such as hydrogen peroxide), ultrasonication etc depending upon the nature and design of the device and intended use. The devices can also be activated by an inkjet method e.g., an activator/solvent/chemical is jetted on activator or vice versa.

In addition to applying the activator tape on to the indicator tape and other methods disclosed herein, there are many different ways the devices proposed herein can be activated. They include the followings:

A barrier layer which is a good barrier for activator but melts or ruptures by mechanical, heating or similar processes and opens the way for passage of activator can be used for activation of the devices.

Activation of microcapsules could be partial or complete. Coating of encapsulated materials may be also partial or complete.

There can be more than one layer of microcapsules, each having the same or different nature, function and properties.

Encapsulated material could also be released under controlled conditions, e.g., controlled release of activator.

There are many different ways the devices containing microcapsules can be made and activated. The following are some of the examples:

Method 1 (FIG. 28): Take a metallized plastic film having a PSA layer [FIG. 28(a)] and a release liner (not shown) on the plastic side. Apply a coat of thermally and/or mechanically ruptureable microcapsules containing an activator, such as phosphoric acid and a binder on the metal layer [FIG. 28(b)]. Optionally, apply a protective coat on the microcapsule layer [FIG. 28(c)]. Using a thermal printer, IR laser or mechanically, one can write or print a message or image [FIG. 28(d)]. The devices can also be activated by passing through a heating system, such as heated roller or IR laser. The microcapsules will rupture and release the activator/phosphoric acid. An image will appear, e.g., white/translucent to clear/metallic [FIG. 28(e)]. Remove the release liner from the back and apply the activated device on to an object, such as a perishable, medical supply or visitor. The released activator/phosphoric acid will etch the metal layer. When the metal is completely etched, a message and/or color printed underneath will appear [FIG. 28(f)].

Method 2 (FIG. 30): Take a metallized plastic film having a printable surface. Apply pressure sensitive adhesive containing an activator (e.g., phosphoric acid) and optionally a color dye or pigment (e.g., red color) on e.g., one half of the metal layer [FIG. 30(a)]. Apply a release liner on the PSA layer [FIG. 30(b)]. Activator will dissolve the metal layer underneath and make activator portion of the metallized plastic film clear [FIG. 30(b)]. Print the information (e.g., expired or a photo of a visitor depending upon the application) on the back of the printable film, e.g., under the other half of the metal layer [FIG. 30(c)]. Remove the release liner from the activator layer, fold the device in the middle and apply pressure to make uniform contact between the PSA and the metal layers [FIG. 30(d)]. Photo and information will be on the top of the activated device. When the device expires (metal layer gets dissolved), a color and/or a printed message, e.g., red color, "X", "Not Valid" etc can appear under the photo [FIG. 30(e)]. There are many other ways these devices can be made. E.g., one can join a polyester film tape having a PSA (plus a red dye/pigment) containing an activator with a metallized plastic tape. The two-tapes can be glued, heat sealed, ultrasonically welded etc. Yet another way is to apply a PSA (plus a red dye/pigment) containing an activator on back of printable thermally printable plastic film and then splice with a metallized plastic film. Many other devices disclosed herein, can be made by these and other methods disclosed herein.

Method 3: Take a metallized plastic film and coat thermally printable coating (normally coated on a paper for thermal printing) on the plastic side. The film can be thermally, inkjet, laser, etc printed. An image will appear in black and white, in color, or in clear depending upon the nature of the microcapsule and material contained therein. Apply an activator tape on the metal side to activate the device. When the metal layer is etched, it will change the appearance of the image.

A visitor's badge was made (1) by printing a photo on a thermally printable film obtained from IIMAK (Product #TF200C Clear D.T., Amherst, N.Y.) having a PSA layer of activator formulation of Example 3 on back of using a thermal printer and (2) laminating the activator on a metallized polyester film. When metal layer was etched the photo became clear.

The reverse is also possible that the indicator is protected or particles of indicator are protected by microencapsulation.

Activator and indicators tapes can be separate or connected (e.g., glued/spliced) and could be of the same or different size and shape. The devices can be activated by applying one tape on to the other or by folding the connected tapes.

The coating on a substrate may contain only encapsulated indicator (e.g., encapsulated metal powder), only activator (e.g., encapsulated phosphoric acid), one encapsulated and the other not (e.g., encapsulated phosphoric acid and uncoated metal powder) or a mixture of encapsulated indicator and activator. The coating may have other additives. Depending upon the application, the substrate could be clear, opaque and colored and could be fully or partially coated. The substrate may have additional coating as required. The coating may have one or more protective coatings. The thickness of the coating will also depend upon the application can vary from a micron to 1,000 microns.

The coatings can have a dye or indicator for the development of color.

The coating may be composed of two or more encapsulated materials, such as a leuco dye or pH sensitive dye (color former/changer) as an indicator and an acid, such as phosphoric acid as an activator and selectively releasing activator only. The coating can be on metallized or un-metallized substrate. The coating can also be composed of metal particles (encapsulated/coated or not) and encapsulated activator. A variety of combinations are possible.

Physical and chemical methods, such as spray drying, spray chilling, rotary disk atomization, fluid bed coating, stationary nozzle co-extrusion, centrifugal head co-extrusion, submerged nozzle co-extrusion, pan coating, phase separation, solvent evaporation, solvent extraction, interfacial polymerization, simple and complex co-acervation, insitu polymerization, liposome technology and nanoencapsulation can be used for encapsulations of indicators and activators disclosed herein. Wall or shell materials, such as proteins, polysaccharides, starches, waxes, fats and lipids, natural and synthetic polymers and resins can be used for encapsulations of indicators and activators disclosed herein.

Many encapsulated chemicals, such as sodium bicarbonate, sodium bromide, sodium chloride and sodium diacetate are available commercially. They can be used as activators for the devices disclosed herein, especially for the sterilization indicating devices. Others can be similarly microencapsulated and used.

U.S. Pat. No. 4,675,161 discloses use of epoxy coated microcapsules and azo dyes for sterilization including heat and ethylene oxide. However, use of other dyes and other wall materials are not known.

We have found that the direct thermal coatings made from certain dyes are too sensitive to EO gas. The reaction can be slowed down by coating on a metallized PET and coating thinly with a metal (e.g., 10A) or laminating with thinly metallized plastic film, film having selective/spaced lines metallized. By using wedge metallized film one can create moving boundary EO device.

We discovered that commercially available directly thermally printable labels (e.g., those available Brady, IIMAK and used by Federal Express and UPS) when exposed to ethylene oxide (EO) gas, humid or dry, gradually turned black within minutes at room temperature. The same labels coated with Joncryl 77 (Johnson and Sons, Racing, Wis.) turned black much slower. Thus, time required for the coatings to turn black by EO gas sterilization can be varied either by selecting proper wall material, barrier coat and/or dye.

The labels can be used for monitoring EO gas as these labels are generally environmentally stable.

The labels were also exposed to hydrogen peroxide vapor overnight at 50° C. They also tuned slightly darker overnight. However, when old dot matrix fax paper which we bought in late 1980s from Quill Corporation, turned black within a few hours at 50° C. It seems that the wall material and/or protective coat are more permeable to hydrogen peroxide. As dyes used in thermal or dot matrix paper are reduced dyes, they should also turn black/colored with other oxidizing agents, such as peracetic acid and ozone.

The indicating devices described herein can be read visually or can also be read with higher accuracy by a machine. The devices and processes described in our US Patent Application #20080023647 entitled General purpose, high accuracy dosimeter reader can also be used in the present inventions. The devices and processes of patent application #20080023647 and references cited therein are herein incorporated as references.

Some of current inventions including formulations, devices and processes, e.g., packaging tape, double messages, such as "VALID" to "NOT VALID", "FRESH" to "NOT FRESH" and "NOT STERILIZED" to "STERILIZED" can be applied to the prior art formulations, devices and processes. In order to demonstrate wide applicability of some of the inventions, we made several prior devices, such as time, time-temperature, radiation, freeze, thaw, microwave doneness, hot water dish washing indicator and sterilization indicating devices having present inventions. Some representative examples summarized below:

We made a packing tape by applying an activator tape and labels containing phosphoric acid on a commercially available thermally printable tape. On a closed box a word "FRESH" was written. The box was sealed with a clear/translucent thermally printable film/tape (iimak, Amherst, N.Y., Product #TF200C Clear D.T.) having a pressure sensitive adhesive. Over the thermally printable coating, a pressure sensitive adhesive activator tape containing phosphoric acid (that of example 5) was applied. The box was placed at 60° C. The colorless coating gradually changed to light grayish green→gray green→gray→black color within one hour. A similar box took almost a week for the color change at room temperature.

On the top part of a thermally printable clear film labels (supplied by IIMAK) "FRESH" was printed with a thermal printer. On the bottom portion of the film was written "NOT FRESH" with a latex, Joncryl 74 and allowed to dry. "NOT FRESH" was barely visible. An activator tape of example 5 was applied. The device was placed in an oven at 60° C. The area surrounding the word "FRESH" gradually became darker and the word "FRESH" became essentially unnoticeable. At the same time, the area word "NOT FRESH" became darker and made easily noticeable. By applying a proper permeable layer over the thermally printable coating one can match the appearance of "NOT FRESH" with the disappearance of "FRESH". These types of devices can be used as TTI for monitoring shelf life of perishables. Similarly other devices with the words such as "VALID" and "NOT VALID" were made for visitor badges.

We also created a moving boundary device by coating a wedge shaped permeable layer of a polyvinylacetate latex on the thermally printable coating and using an activator tape containing phosphoric acid. Similarly, many other devices disclosed herein, e.g., bar code devices, bandage indicators, sterilization indicators, hot water indicators, microwave doneness indicators, freeze indicators by phase separation technique, humidity indicators, thaw indicators, tamper indicators, radiation indicators and gimmicks can be made using the prior art formulations, devices and processes and inventions disclosed herein. Though we used phosphoric acid as activator and thermally printable film for demonstration of some concepts but other indicators and activators can also be used. Some appropriate changes may be required.

The prior art devices, especially color changing/developing can be made self reading. UV expose (e.g., with a UV laser) the sensor if the sensing material is a diacetylene, pre-thermal treat if the sensing material is thermal sensitive, or just print with a suitable printer. One can create the numbers, barcodes, messages etc. Diacetylenes are sensitive to UV light and thermal annealing (i.e., time and temperature of storage) and hence are self activating. Activate the device if required. After certain time and/or time-temperature, the color development of the sensor will match color of the printed messages indicating expiration.

The color changes in all these prior art devices were gradual.

The devices disclosed herein can also be used as employee ID or high security self expiring ID both with and without RFID. One can also make a variety of self expiring products from the concepts and formulations proposed herein.

The devices can also be created on line. For example, (1) printing an indicator tape (e.g., metallized plastic film) with an activator or vice versa, (2) by activator followed by indicator or vice versa or (3) by spraying or ink jetting activator and indicator simultaneously.

Softwares for monitoring and cataloging the devices disclosed herein can be developed and used.

Different indicators and activators will produce different by-products due to reaction of an activator with a metal. If required, the process, degree of processing and the devices can be further analyzed by analyzing the by-products and their concentrations.

Many of the inventions (compositions, devices and processes) disclosed herein, can be easily applied to other devices irrespective of their origin.

The designs proposed herein are interchangeable. A design of one indicating device can be used for the others with required or appropriate changes. For example, "Expired" message and red color of time-temperature indicating device can be replaced with "Sterilized" and green color for sterilization indicating device.

A variety of processes/equipment have been developed for coating adhesives, inks, lacquers, and other polymeric materials. Common coating methods are: air knife, brush, calendar, cast coating, curtain, dip, extrusion, blade, floating knife, gravure, kiss roll, off-set, reverse roll, rod, spray, and squeeze roll. Most of the above methods can be used for coating the matrix on a wide range of base materials.

Many of the indicating devices can be made by proper printing of activator and indicator, using a variety of printing processes. Ink may contain an activator or metal type indicator. An indicator, e.g., in form of a message can be printed on a layer of activator or vice versa. Essentially any ink or printing process, including inkjet, laser tonner, dye sublimation and conventional inks and processes can be used.

Water and solvent based inkjet inks are commercially available. A mask in form of a message can be easily printed with an inkjet ink without any pigment or that containing said indicators, preferably activators. The ink could also be UV curable.

Screen printing is also used to make sterilization indicating devices. It is also possible to make plastisol, both water and solvent based, for making the indicating devices by screen printing. The indicators, activators and the precursors can be dispersed or dissolved in a plastisol or very viscous vehicles, such as plastisol of polyvinyl chloride and similar polymers.

Many chemicals are detected with color developing reagents which when reacted with the chemicals introduce a color change. Transparent glass and plastic tubes filled with an inert substrate coated with these color developing (detecting/indicating) reagents are widely used for monitoring a variety of hazardous chemicals. A known volume of contaminated air is passed through the tube filled with these agents and color change is monitored.

Metals and their alloys also react with a large number of chemicals many of them are referred herein as activators and precursors for activators. Inert materials, porous or otherwise, thinly coated with metals and their alloys can also be used for monitoring a number of chemicals. The inert materials could be opaque as well as transparent, for example, glass or plastic beads, flakes, fiber, film and pieces. An empty glass tube thinly coated inside or solid fiber thinly coated with a proper metal or its alloy can also be used for monitoring certain chemicals.

There are many different shapes of metallized substrate that can be used for monitoring chemicals. They include metallized optical fiber, tube, film, strips and beads.

In addition to monitoring activators and precursors for activators listed herein, the above described metallized substrates can also be used for detecting/monitoring carboxylic acids and acid chlorides, such as formic acid, acetic acid and acetyl chloride, ammonia and amines e.g., methyl amine, ethylamine, diethylamine, pyridine and aniline, halogens and halo compounds, such as chlorine and chlorine dioxide, mineral acids, such as hydrochloric acid, hydrofluoric acid and nitric acid, mercaptans and sulfides, such as methyl mercaptan, hydrogen sulfide and carbon disulfide, oxides, such as sulfur dioxide, nitrogen dioxide, phosphines and phosgene, phenols, such as cresols, oxidants, such as peroxides including hydrogen peroxide and ozone, hydrogen cyanides, aldehydes, such as formaldehyde and furfural, epoxides, such as ethylene oxide, propylene oxide and epichlorohydrin, metal vapors, such as mercury, oxygen, carbon dioxide, carbon monoxide, water/humidity and chemicals whose reaction can be catalyzed by metals and metal alloys. By selecting proper metals and their alloys, one can also achieve selectivity to certain chemicals.

The reaction can be followed visually or by monitoring change in conductivity, including ionic conductivity. As metal gets etched, its conductivity will decrease.

Biological materials and organisms, live or dead, bacteria, virus, strand, enzymes, proteins and alike, which can generate an activator for a metal layer can be used for monitoring biomaterials. Biomaterials may need a so called substrate, i.e., a reactant from which a biomaterial produces a product, in this case an activator or a catalyst. Such bio-materials can be used for analysis body material including urine and blood. Body parts and fluids have a number of inorganic and organic chemicals (bio-chemicals) such as acids, salts, glucose, nitrites, amino acids and enzymes. By selecting proper substrate, enzyme, media, precursor, catalyst and alike one can control the nature of the reaction to produce an activator which will etch/react with a very thin layer of a metal. Products such as glucose-6-phosphate may etch certain metals and/or alloy.

As metals and their oxides and complexes react with a number of chemicals, they (especially thinly coated) can be used for determination of their concentrations. For example, aluminum reacts with a number of acids, bases and salts. The time required for dissolution of a thin layer of a metal of known thickness, such as 100 Angstroms pure aluminum depends on concentration of a given acid, base or salt. Once calibrated, a substrate coated a thin layer of metal, with or without a permeable coating, can be used for determination of concentration of a variety of chemicals, including toxic agents.

We have found that it is also possible to monitor a large number of chemicals/agents using a thin layer of metal such as metallized plastic film with or without a layer of precursor. Many toxic chemicals such as bromine react with metals such as aluminum.

War chemicals that can be monitored using the materials, devices and processes disclosed herein include lethal, blister, blood, nerve, pulmonary, incapacitating and riot control agents. The examples include cyanogen chloride and hydrogen cyanide, ethyldichloroarsine, methyldichloroarsine, phenyldichloroarsine, Lewisite, 1,5-dichloro-3-thiapentane, 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether, bis(2-chloroethyl) ethylamine, bis(2-chloroethyl) methylamine, tris(2-chloroethyl)amine, tabun, cerin sarin, soman, cyclosarin, GV, VE, VG, VM, VR, VX chlorine, chloropicrin, phosgene, diphosphene, agent 15 (BZ), EA 3167, kolokol-1, pepper spray, CS gas, CN gas and CR gas.

Toxic industrial chemicals that can be monitored using the materials, devices and processes disclosed herein include acetone cyanohydrin, acrolein, acrylonitrile, allyl alcohol, allyl amine, allyl chlorocarbonate, allyl isothiocyanate, ammonia, arsenic trichloride, arsine, boron tribromide, boron trichloride, boron trifluoride, bromine, bromine chloride, bromine pentafluoride, bromine trifluoride, carbon disulfide, carbon monoxide, carbonyl fluoride, carbonyl sulfide, chlorine, chlorine pentafluoride, chlorine trifluoride, chloroacetaldehyde, chloroacetone, chloroacetonitrile, chloroacetyl chloride, chlorosulfonic acid, crotonaldehyde, cyanogen, 1,2-dimethyl hydrazine, diborane, diketene, dimethyl sulfate, diphenylmethane-4'-diisocyanate, ethyl chloroformate, ethyl chlorothioformate, ethyl phosphonothioicdichloride, ethyl phosphonous dichloride, ethylene dibromide, ethylene imine, ethylene oxide, fluorine, formaldehyde, hexachlorocyclopentadiene, hydrogen bromide, hydrogen chloride, hydrogen cyanide, hydrogen fluoride, hydrogen iodide, hydrogen selenide, hydrogen sulfide, iron pentacarbonyl, isobutyl chloroformate, isopropyl chloroformate, isopropyl isocyanate, methanesulfonyl chloride, methyl bromide, methyl chloroformate, methyl chlorosilane, methyl hydrazine, methyl isocyanate, methyl mercaptan, n-butyl chloroformate, n-butyl isocyanate, nitric acid, fuming, nitric oxide, nitrogen dioxide, n-propyl chloroformate, parathion, perchloromethyl mercaptan, phosgene, phosphine, phosphorus oxychloride, phosphorus pentafluoride, phosphorus trichloride, sec-butyl chloroformate, selenium hexafluoride, silicon tetrafluoride, stibine, sulfur dioxide, sulfur trioxide, sulfuric acid, sulfuryl chloride, sulfuryl fluoride, tellurium hexafluoride, tert-butyl isocyanate, tert-octyl mercaptan, tetraethyl lead, tetraethyl pyrophosphate, tetramethyl lead, titanium tetrachloride, toluene 2,4-diisocyanate, toluene 2,6-diisocyanate, trichloroacetyl chloride, trifluoroacetyl chloride and tungsten hexafluoride.

The devices of this invention use a layer of metal or metal particles as an indicator and a layer of activator or chemicals which react with metal to destroy the metal. As a result, one can measure the progress of the reactions/phenomenon by measuring the electrical conductivity, specific conductivity, conductance, resistance and resistivity of the devices disclosed herein. The conductivity can change from about $37 \times 10^6$ Siemens per meter ($S.m^{-1}$) to essentially of that of salt water, i.e., about 5 $S.m^{-1}$ or lower if aluminum is used as an indicator. That is over a million times change in conductivity. Thus, many of the phenomena of the current invention can be monitored with very high accuracy. Using this method of measuring conductivity one can measure concentration of chemicals in ppm (parts per million) and ppb (parts per billion) concentration. Measurement of conductivity is simpler than many other properties.

A metallized film or a fiber coated with a metal layer can be coated with one or activator, precursor, catalyst, biological substrate for selective monitoring more than one chemical, or an agent including chemical or biological agent. Accuracy can further be increased by increasing the length of the conductive paths.

For some devices, it can be done by folding or using metallized fiber. Several methods can be used for making the devices having folded or spiral conductive paths. For example, methods used for making printed circuit boards, burning a metallized surface with a laser or a modified method of making CD (compact disc).

Super high accuracy is not required for certain devices, such as time-temperature, de-frost, freeze, microwave doneness and sterilization indicating devices. Higher accuracy of one percent may be preferred for certain devices, such as time indicating device for a month or years. However, very high accuracy is desired for certain indicating devices/dosimeters, such as radiation dosimeters and monitoring of chemicals. If one can measure radiation and chemicals with accuracy of better than a tiny fraction of a percent, one can monitor a very low dose with high accuracy. With the expected linear change in conductivity, one can measure dose with higher accuracy over a very wide dose range.

A conductive paint composed of conductive particles, an activator and a binder can be used for making many of the devices disclosed herein and monitoring the phenomenon with change in conductivity.

The optical waveguide device of instant invention will be essentially identical to those of prior art, except that the indicating/cladding layer will be a metal or an alloy, with and without a layer of an activator or its precursor. The optical fiber can be metallized by the methods reported in the literature, for example, those disclosed in U.S. Pat. Nos. 6,798,963 and 7,158,708.

A detecting device can be developed for detecting changes in chemical or physical parameters, comprising a sensing optical fiber having a core surrounded by a thin layer of metal or an alloy, with or without a layer of an activator or its precursor.

The device may contain a reference fiber without a coating of the metal and/or the activator or without being treated or exposed.

The core material of the sensing optical fiber will be substantially the same as the core of an optical fiber.

The device can also be made up of two optical fibers, one extending from each end of the sensing optical fiber to be connected at their remote ends to a light source and detector respectively. Alternatively, a single optical fiber may extend from one end of the sensing optical fiber, the other end of which is made reflective, the single transmitting fiber being connected to both sources and detector using a beam splitter.

Because of the uneven expansion and contraction of the cladding materials (metals) and the core material (glass or plastic optical fiber), one can monitor many physical phenomena, such as temperature, pressure and stresses as well using the devices of this invention.

For monitoring physical phenomenon, such as time, temperature, freezing, defrost, time-temperature, radiation and alike, an activator layer is usually required and the activator layer could be over the metal layer or vice versa. However, for devices like sterilization and detection of chemicals, the activator coating should be over the metal coating.

The conductive layer could be semi-conductive layer as well.

Instead of coating the activator on a metallized optical fiber, one can make similar devices by inserting it in a solution or liquid activator or precursor for the activator. This type of devices will be faster and more sensitive.

The substrate in these devices will be an optical fiber made from glass or polymers.

The optical waveguide (fiber) of this invention is conductive and hence one can also monitor all these phenomena by monitoring change in conductivity.

Activators and precursors for activators listed herein can be used for the optical waveguide devices. The activators and their precursors can be dissolved or dispersed in a polymeric binder and coated on a metallized optical fiber or metallized after the coating. They also can be applied by some conventional coating techniques, such as dipping and vacuum evaporation/sublimation.

These waveguide indicating devices can also have many of the features of time and time-temperature indicating devices described herein and vice versa.

Like the conductivity devices, the optical waveguide device will be significantly more accurate.

The quantitative progress of a reaction of a phenomenon of the devices disclosed herein can also be measured by other parameters, such as change in magnetic properties and change in reflectivity, transmission and spectral shift.

All indicating devices and their components could also be made in form rolls. The indicating device rolls may then be die cut or peeled and applied on an object. The shape of the indicating device may be, for example, circles, ovals, other curvilinear shapes, preferably symmetrical, triangles, squares, rectangles, hexagons, and other polygons, including right polygons and equilateral polygons.

All indicating devices disclosed herein could have other types of indicating devices, e.g., a temperature indicating device on TTI, ammonia gas indicating device on TTI, sterilization indicating device with time-temperature or temperature indicating device, or radiation indicating device on TTI.

There could be more than one indicating device on an object or substrate for monitoring two different conditions, so that one device sends one set of messages while the other one sends the other type of messages or one after the other.

The devices disclosed herein can be combined to make multi-process and multi-material indicators. For example, a TTI on radiation indicating device or vice versa can be used for monitoring radiation of perishable, such as food and blood and shelf life. Indicating device can also have other indicating devices, such as temperature indicating device.

For different processes one can use one or more activators for different processes, e.g., an activator for steam and ethylene oxide or a mixture of one activator for steam and the other for ethylene oxide. The devices can also be for more than two processes as steam, ethylene oxide and plasma. This can be done by selecting a mixture of more than one activator, especially a mixture of individual activator for each process it is intended for.

The time required for the transparency change and the activation energy of the current indicating devices can be varied by one or more of the following major parameters: 1) Thickness of an activator matrix, 2) Thickness of an indicator and co-indicator, 3) Thickness of a permeable layer, including an oxide layer, 4) Concentration of an activator and co-activator, 5) Concentration of a precursor, 6) Concentration of an additive, 7) Nature of a solvent, surfactant and catalyst, 8) Nature of an activator matrix, 9) Nature of an indicator and co-indicator, 10) Nature of a permeable layer, including an oxide layer, 11) Nature of an activator and co-activator and 12) Nature of an additive. All parameters will vary the time required for the transparency change. The parameters 1-6 will vary only the time required for the transparency change while the activation energy and time required for the transparency change can be varied with parameters 7-14.

The devices and associated processes which use metal as an indicator and an etchant as an activator offer some of the following major uniqueness which are rarely found in other indicating devices:

Indicators:
The thickness of the indicator layer is incredibly ultra thin, only ~100 Angstroms.

The indicator is a metal, usually aluminum which is non-toxic and its salts are also non-toxic.

Metallized plastic films having different thicknesses of aluminum layer (~25 Å-700 Å) and different colors are readily available. Hence, no need to make the indicator tape.

Even 100 Å thick layer of aluminum provides 99% opacity. About ~20 Å is semi transparent but reflective and transparent below 10 Å.

Average accuracy is about 80% but as much as 99% is possible.

The change is from opaque and reflective/shiny to transparent. Shiny/reflective surface is easily noticeable.

Metallized inks are readily available. Commercially available aluminum (called silver) and a bronze (an alloy of copper and zinc called gold) inks can be used instead of metallized plastic films.

A number of metals and a large number of their alloys having different sensitivities to different activators can be used to make a variety of indicators and processes using materials having different properties.

Indicator does not migrate or stain.

Activators:

Reactions can be carried out with common nontoxic materials, such as water, oxygen, acids, bases and salts.

A large number of activators and precursors for activators can be used to develop a variety of indicating devices.

Activator tapes can be made by coating a pressure sensitive adhesive (PSA) containing an activator. PSA tape technology is a well developed technology.

Reaction:

The reaction is 100% irreversible.

The reaction is heterogeneous. It occurs only on the surface of the metal and hence gives zero order kinetics, i.e., linear with time, which is one of the most desired properties. This also makes the devices highly accurate. The reaction for almost all indicating devices is usually the first order/asymptotic, i.e., fast in the beginning and slows down with time.

Reaction products are usually colorless, white salts (when metals, such as aluminum and zinc are used).

Indicator layer being super ultra thin, even opaque reaction products, e.g., aluminum oxide are essentially nearly transparent.

Even though the reaction occurs at a steady rate, opaque layer becomes transparent only when about 10-20 Å layer is left unreacted. Thus, it provides a very long induction period which is most desired for go/no-go type indicating devices.

Colors and Messages:

Typically, an indicating device undergoes a color change. These devices are based on change in transparencies.

Change in transparency makes it possible to print any message or color under the metal layer, i.e., provide unlimited final colors/messages.

By printing a part of a message (e.g., "GOOD") over the metal layer and another under the metal layer (e.g., "NOT"), it is possible to create two messages (GOOD→NOT GOOD, FRESH→NOT FRESH, NOT STERILIZED→STERILIZED).

It is also possible to create moving boundary devices for continuous monitoring of a process or material possible.

That makes the devices self reading, accurate and idiot proof.

Machine readable and remotely readable.

Applications:

Using proper pairs of activators and indicators, it is possible to monitor a variety of materials and processes including:
  Time (e.g., self expiring visitor's badges, employee IDs).
  Temperature (e.g., microwave doneness).
  Time-temperature (e.g., monitoring shelf life of perishables).
  Freeze (e.g., for fresh blood, produce, some vaccines).
  Thaw/defrost (e.g., for frozen foods).
  Humidity (e.g., pharmaceuticals and foods).
  Sterilization (e.g., monitoring sterilization of medical supplies and perishables):
    Steam.
    Ethylene oxide.
    Plasma/hydrogen peroxide.
    Radiation.
  Toxic chemicals and biochemicals (e.g., chemical and biological agents).
  Electronic devices.
    RFIDs.
    Electronic article surveillance.
    Circuit boards.

There was a need and no indicating device/monitor technology was available which:
  Is self reading and idiot proof
  Provides unlimited colors and messages.
  Provides long induction period with two messages of go and no-go.
  Provides the same colors for a number of materials and processes, i.e., universalizing the technology.
  Is highly accurate, machine readable and remotely readable.
  Is very economical.
  Is suitable for individual unit as well as for a container of units.

The devices disclosed herein have these and many other desired properties and fills that technological gap. The combination of all these and many other desired properties makes the devices unique among unique. They are literally dream indicating devices.

A large number of devices, such as time, temperature, time-temperature, freeze, thaw, sterilization and radiation indicating devices are commercially available from a number of manufacturers. Even for a given indicating device, e.g., steam sterilization indicating device, each manufacturer has its own colors, color changes, size, shape and design which are different from all others. Hence, it requires training the users how to use and interpret. The self reading devices disclosed herein requires no training of the users and all indicating devices will be essentially identical. Thus this technology offers an opportunity to universalize the indicator technology.

EXAMPLES

The following examples are illustrative of carrying out the claimed inventions but should not be construed as being limitations on the scope or spirit of the instant inventions.

Example 1

Prior Art

A two-tape TTI device obtained from Avery Dennison, Pasadena, Calif. was activated by applying the activator tape (containing an acid in a PSA on a clear plastic film) on to the indicator tape (containing a pH dye in a resin on a white plastic film). The activated device gradually changed from yellow→light purple→purple→dark purple within a day at room temperature and within about one hour at 50° C. The color development/change was rapid in the beginning and slower at the end. As the device is diffusion based there was no abrupt color change.

Example 2

Effect of Phosphoric Acid and Its Concentration

A 100 microns metallized polyester film (having about 125 Angstroms thick layer of aluminum) was used for demonstrating the feasibilities of the concepts. Alphabet "A" was written on the metal layer of the metallized film and "1" was written on the back. The film was placed on a red paper and 1 ml of 85% phosphoric acid was poured on "A". Tiny bubbles (of hydrogen) appeared on the aluminum layer after about four minutes. The red color paper and "1" were not visible for five minutes. The aluminum layer got completely dissolved and "1" and the red color paper became fully visible after six minutes. Thus, the device has a very long induction period (about 80% for this system) for the color change (silver to red), i.e., no red color for five minutes and red color appears in about one minute. The time required for complete dissolution of the metal layer increased from 6 minutes for 85% phosphoric acid to 38 minutes for 15% phosphoric acid as shown in Example 33 and FIG. 44.

Example 3

Making of An Activator Adhesive Formulation for an Activator Tape

In a 500 ml beaker were added 150 g a PSA (Product #S8510, Avery Dennison, Pasadena, Calif.) with 150 g of isopropanol and 25 g of 85% phosphoric acid and mixed. The concentration of phosphoric acid was varied as per need of a device.

Example 4

Effect of PSA Formulation, Concentration and Solvent of the Activator on Etching of a Metallized Polyester Film A 100 microns polyester film having about 125 Angstroms thick coating of aluminum (referred herein as a 100 microns metallized polyester film or metallized polyester film) was placed on a red paper and 1 ml of PSA formulation of Example 3 was poured on the metal side of the film at RT. The red color paper was not visible for almost 25 minutes. The aluminum layer got dissolved and a red color paper became fully visible after 35 minutes. The time required for the dissolution of the metal layer depends on several factors, such as concentration, solvent, temperature, dryness and thickness of dry activator layer.

Example 5

Making of An Activator Tape

The activator formulation of Example 3 was coated on a 100 microns clear (un-metallized) polyester film using #50 and #30 wire wound rods. The coatings were dried at 70° C. for 10-50 minutes. Some activator films were used to create the devices while the other covered with 50 microns polyester release film having a silicone coating on both the sides. Pieces from this film were used to make the devices in some of the following examples after removing the release film.

Example 6

Making of Simple Devices

A metallized polyester film having a red coating on one side was laminated with a piece of the activator tape of Example 5 with the PSA layer facing the metal layer. The activator dissolved the metal layer of the device and the red color became visible after 5 hrs at room temperature and in about 30 minutes at 60° C. The devices annealed at 60° C. had some impressions of bubbles or cracking of the metal layer.

Pieces of the activator tape of Example 5 were applied on seven 50 microns metallized polyester films having different color coatings (obtained from CP Film, Canoga Park, Calif.) with the PSA layer facing the metal layer. The CP films were composed of three layers, 50 microns polyester film having a thin color ink coating on which had ~125 Angstroms thick coating of aluminum. The laminated films were placed in an oven at 55° C. The metal layer got dissolved in about one hour and the colors of inks became visible.

Similarly, devices were also created by using a polyester film metallized on both the sides and a polyester films having coating of the activator on both the sides.

Examples of control experiments: The activator tape was applied on a 15 micron thick aluminum foil and annealed at 50° C. for a few weeks. The tape did not dissolve the foil. However, when a few drops of phosphoric acid were placed on the same 15 micron thick aluminum foil, the foil got dissolved within one hour at 50° C.

Example 7

Making of Self Reading Devices Similar to FIG. 7

7.1 Activator tape with a part of the message: Word "FRESH" was printed on a 100 microns clear polyester film using a laser printer. The back side of this film was coated with the activator formulation of Example 3 using a #30 wire wound rod and dried at 70° C. for ten minutes.

7.2 Indicator tape with the other part of the message: Words "ness not gaurunteed" in reversed/mirror image and a bar code were printed on the non-metal side of a 100 microns metallized polyester film using a laser printer.

7.3 Activation of the device: The activator tape was applied on the indicator tape with the adhesive (activator) layer facing the metal (indicator) layer. Care was taken for the proper alignment of the films. Devices were cut from the laminated/activated film [see FIG. 33(a)] and stored in a freezer.

7.4 Testing of the device: Some the activated devices were annealed at different temperatures (25° C., 45° C. and 55° C.). The devices were removed from the ovens and scanned at different time intervals. The word "FRESH" was visible on the top of the device. FIG. 33 shows a device annealed for 27, 34 and 38 hrs at 25° C. The message "ness not gaurunteed" and the bar code were not visible for 25 hrs at 25° C. They started appearing at about 27 hours as shown in FIG. 33(b), became almost visible at about 34 hours and completely readable at about 38 hours as shown in FIGS. 33(c) and 33(d) respectively. The device has an induction period of about 70-80%. It can be extended by using a permeable layer. The device is self reading.

The activation energy of the reaction was determined by plotting the logarithm of induction period versus 1/T (T=absolute temperature). The activation energy of the device was about 7 kcal/mole. The low activation energy makes the device more useful for monitoring time, e.g., as a visitor's badge.

Devices with many different types of messages (including different symbols and languages) were also made including a few with double bar codes.

Example 8

Making of Moving Boundary Devices with a Wedge Shaped Permeable Layer 8.1 Activator tape. A 100 microns clear polyester film was coated with the activator formulation of Example 3 using a #30 wire wound rod and dried at 70° C. for ten minutes.

8.2 Indicator tape with a wedge shaped coating: The metal surface of a 100 microns metallized polyester film was coated with 10% solution of polyepichlorohydrin in toluene using a 0-250 microns wedge shaped 10 cm long bar and dried at 70° C. for 5 minutes. A wedge shaped coating of polyepichlorohydrin was obtained with 0 to about 25 microns dried thickness of wedge shaped coating.

Some films were coated with 0-250 microns 5 cm long wedge shaped bar.

Some metallized polyester films were printed with red color and numbers and a scale in the black and gray color on the uncoated side.

8.3 Activation of the device: The activator tape was applied on the indicator tape with the adhesive (activator) layer facing the metal (indicator) layer. Many devices of about 1-2 centimeter wide were cut.

8.4 Testing of the device: Some devices were annealed at different temperatures (25° C., 45° C. and 55° C.). The devices were removed from the oven at different periods of time and scanned. FIG. 34 shows a device annealed for different periods of time at 55° C. As can be seen from FIG. 34, a boundary was created by dissolution of the metal layer and the boundary moved from the thin to the thick end of the wedge shaped coating of polyepichlorohydrin with the annealing time. The movement of the boundary was almost linear with time.

In the moving boundary devices, the thinning of the aluminum layer can be seen (as evident by gradual increase in transparency of the metal layer) which indicates the reaction occurs on the surface.

The movement of the boundary is essentially linear with time, i.e., zero order reaction which is a unique and highly desirable property for most indicators. The linearity of the movement of the boundary may be due to combination of many parameters but mainly due to two reactions, (1) diffusion of the activator through the permeable layer and (2) etching of aluminum layer. The color change/development of all known time and time-temperature indicating devices is asymptotic (i.e., the first order reaction). They develop color rapidly in the beginning and slowly with time.

The current device has one of the most desired properties for an indicating device, which is a long induction period followed by linear color change with time.

It is evident from FIG. 34 that by increasing the thickness of the permeable layer one can increase the induction period, higher the thickness of the permeable layer longer the induction period.

8.5 Kinetics of the Diffusion/Reaction.

The distance travel by the boundary was determined for the devices annealed at different temperatures (25° C., 45° C. and 55° C.). The activation energy was determined from the plots of logarithm of time required to travel, e.g., 1 and 2 cm versus 1/T. The activation energy was 21 Kcal/mole. The higher activation energy may be due to the diffusion based reaction, i.e., diffusion of phosphoric acid through the permeable layer of polyepichlorohydrin.

Example 9

Permeable Layer of Different Thicknesses 9.1 Activator tape. A 100 microns clear polyester film was coated with the activator formulation of Example 3 using a #30 wire wound rod and dried at 70° C. for ten minutes.

9.2 Indicator tape with different thicknesses of a permeable layer: The metal surface of a 100 microns metallized polyester film was coated with 10% solution of polyepichlorohydrin using a 27, 75, 125 and 300 microns bars and dried at 70° C. for 10 minutes.

9.3 Activation of the device: The activator tape was applied on the indicator tape with the adhesive (activator) layer facing the metal (indicator) layer. Many devices were cut and annealed at 45° C. The time required for the aluminum layer to get dissolved was noted. Table 1 shows approximate thickness of the permeable and time required for the dissolution of the aluminum layer.

TABLE 1

Approximate thickness of polyepichlorohydrin and time required for the dissolution of the aluminum layer at 45° C.

| Thickness (mil) | Time (hrs) for the dissolution |
|---|---|
| 0 | 3 |
| 0.015 | 5.5 |
| 0.03 | 13 |
| 0.05 | 23 |
| 0.06 | 28 |

Thus, the time required for the dissolution of the metal layer can be varied by varying the thickness of the permeable layer.

Example 10

Packaging Tape

One side of a 50 microns clear polyester film was printed with "Expired, Do Not Sell, Return to Manufacturer" with red background and the other side was coated with the activator formulation of Example 3 to make an activator tape. The activator tape and the indicator tape (the metallized PET film) were laminated (activator/adhesive layer facing the metal/indicator layer) to activate the device. Strips of about 5 cm wide were cut. These strips were placed on a commercially available 5 cm wide sealing tape. A small box (5"×5"×3") was closed and sealed with the activated tape as shown in FIG. 35(a) and stored at room temperature. The message started appearing at about 18 hrs and was completely visible as shown in FIG. 35(b) after about 25 hrs at room temperature.

One can use a PSA on the back of the activated device to apply on an object.

Several other types of indicating sealing tapes devices were also made, e.g., (1) wedge shaped moving boundary sealing tape devices was created by using a wedge shaped permeable layer and also by activating with an activator tape having a wedge shaped PSA layer, (2) using a narrow metallized polyester strip under the activator tape and (3) with word "Fresh" on the top and "Not" in the back.

Example 11

Visitor's Badge with Moving Boundary

A photo was printed on the non-metal side of a 100 microns polyester metallized film using a laser printer. The back metal side of the photo was coated with 10% polyepichlorohydrin solution in toluene using a 0-250 microns wedge shaped bar and dried. A 100 microns black opaque polyester film was coated with the activator formulation of Example 3 and dried to make an activator tape. The device (visitor badge) was activated by applying the activator tape over the wedge coating. The resultant badge, as shown in FIG. 36(a), was placed in an oven at 55° C. A black boundary was created at the bottom of the photo after about 2 hrs and the boundary move upwards with time as shown in FIGS. 36(b)-36(f). It took almost a month for the boundary to move from one end to the other at room temperature.

Example 12

Visitor's Badge with Red Background and X

A photo was printed on the non-metal side of a 100 microns polyester metallized film using a laser printer. A red polyester film was printed with black X and was coated with the activator formulation of Example 3 and dried to make an activator tape. The device (visitor badge) was activated by applying the activator tape over the metal layer (back of the photo). The resultant badge was stored at room temperature. There was no color change for ten hours. A red background and the X started appearing after about 11 hours and appeared completely after about 16 hrs.

Similarly, visitor's badges were created with red background only, only X, "Expired" and "Valid" on the top and "Not" on the back.

As the photo is not destroyed in this device, it can be archived.

Example 13

Toy, Gimmicks and Greeting Cards

Devices similar to Example 7 but with words, such as "Happy Birthday", figures, such as hearts, clover leaves, photos, many hand drawn designs and other type of messages and figures were printed instead of bar code and red background. The images, figures and messages appeared instead of a bar code. Activated devices were also cut in several shapes, such as hearts and flowers with red background. They all changed color from metallic to red.

Example 14

Wrist Band

The ½ of the un-metallized side of a 100 microns, 25 cm×20 cm metallized polyester film was coated with an activator mixture of Example 3 using #30 wire wound rod and dried. A strip of 25 cm×1 cm was cut and folded so that the activator coating laminated with the metallized side to make band on a wrist. The laminated surface changed color within ten hours at RT while the un-laminated portion remained the same.

Similarly, wrist bands as shown schematically in FIGS. 13 and 14 were also created.

Example 15

Making a RFID Inlay Non-Readable (Deactivation)

Over a RFID inlay/transponder [obtained from Mu-Gahat, Sunnyvale, Calif. and shown in FIG. 37(a)] was applied an activator tape having a thicker layer and higher concentration of the activator. The antenna of the RFID inlay was made from a thin layer of aluminum. The antenna of the device slowly started getting dissolved at room temperature. The different stages of dissolution of the antenna with time are shown in FIGS. 37(b)-37(d). Complete RFID inlay is shown on top of each photo. The antenna near the chip got dissolved in about 2 days. The etching of antenna made the chip non-readable.

Example 16

Etching Mask

16-A: A 100 microns metallized polyester film was screen printed using a mask on the metallized side with an image using a resist (Joncryl 77, S.C. Johnson Polymers, Racine, Wis.). The image was essentially transparent and can't be seen. The device was activated with an activator tape of Example 5 and placed in an oven at 55° C. The screen printed image appeared within 30 minutes.

16-B: An antenna circuit for a RFID inlay was created and printed with a printer on the metal of a metallized polyester film. The film was laminated with the activator tape of Example 5 with the metal coating facing the activator coating. Two such samples (one upside down) are shown in FIG. 38(a). After two days all unmasked aluminum was dissolved and an antenna was created as shown in FIG. 38(b).

Similar antenna circuits were created by placing the antenna masked metallized polyester film in steam and boiling water.

Example 17

Change in Transparency with Time

A metallized polyester film was laminated with the activator tape of Example 5. The transparency of the device was measured with Thwing-Albert Digital Opacity Meter, Model 628 at different period at 25° C. The plot of transparency versus time is shown in FIG. 39. As can be seen from the plot for almost 20 hours there was a very little change in transparency. The laminated device became more transparent with time and became almost visually transparent at about 27 hours. The results show that the device has an induction period of about 70%.

Example 18

Etching of Metallized Polyester Film with Hot Water and Steam

A 100 microns metallized polyester film having about 125 Angstroms thick layer of aluminum was placed in a clean 500 ml conical flask containing 200 g of distilled water at 100° C. The metal layer started getting unevenly dissolved first where water was boiling/bubbling (also likely to some extent due to aerial oxidation) within ten minutes and it got completely dissolved in 15 minutes.

A 100 microns metallized polyester film having about 125 Angstroms thick layer of aluminum was placed over a beaker with boiling water with metal layer facing the seam. The metal layer started getting unevenly dissolved (slow dissolution where condensation of steam was occurring) and got completely dissolved in ten minutes.

Though slower but the metal layer also got dissolved with steam under vacuum.

As thin layer of aluminum layer on polyester film gets dissolved in hot or boiling water, it can be used for monitoring washing and drying of items, such as dishes and laundry.

Example 19

Etching of Aluminum Foil/Control Experiment

A 15 micron thick aluminum foil was treated with steam over boiling water six hours and in a pressure cooker at 125° C. (20 PSI) for two hours. The metal foil got slightly tarnished but did not get dissolved.

Example 20

Effect of Dry Heat (Control Test)

A 100 microns metallized polyester film was heated at 180° C. for 2 hours. Except slight loss of shine, there was little change.

Example 21

Effect of Permeable Layer on Steam Sterilization Indicating Device

A 100 microns metallized polyester film was coated with 10% solutions of the following polymers and dried to make 8 microns dry coatings on the metal side. Pieces of the films were cut and steamed at 120° C. for 2-30 minutes. The time required for dissolution of the metal is shown in the following table (Table 2).

TABLE 2

| Time for complete dissolution of the aluminum layer under 8 microns coating of some permeable polymers. ||
| --- | --- |
| Polymer | Time (minutes) |
| None | 5 |
| PECH | 10 |
| CAB | 15 |
| PolyiBM | 15 |
| CAA | 30 |

PECH: Polyepichlorohydrin
CAB: Cellulose acetate butyrate
PolyiBM: Polyisobutylmethacrylate
CAA: Polyvinylchloride-polyvinylacetate-polyvinylalcohol copolymer

Example 22

Effect of Nature Permeable Layer on Permeability of an Activator

A 100 microns metallized polyester film was coated with 10% solutions of the following polymers and dried to make 8 microns dry coatings on the metal side. Pieces of the films were cut and laminated with an activator tape of Example 5. The activated samples were placed in an oven at 55° C. and time required for the activator (phosphoric acid) was determined. The time required for dissolution of the metal is shown in the following table (Table 3).

TABLE 3

Time for complete dissolution of the aluminum layer at 55° C. having 8 microns of permeable layer of different polymer.

| Polymer | Time (minutes) |
| --- | --- |
| None | 20 |
| CAB | 65 |
| PVAc | 75 |
| PECH | 120 |

CA2 and polyiBM about 10 days
Polystyrene and PVC: No sign even after six months month
PVAc: Polyvinylacetate
PECH: Polyepichlorohydrin
CAB: Cellulose acetate butyrate Example 23

Effect of Additives on Tarnishing of a Solvent Based Gold Ink

A solvent based gold (copper-zinc alloy) ink (PMS 871 Gold) of Braden Sutphin, Cleveland, Ohio was diluted to 50% with dioxolane. In 2 ml of diluted gold paint were added about 0.25 g of 30 different organic additives, heated to dissolve the additives and coated on 100 microns polyester film with #10 wire wound rod. Small strips were cut and treated with steam at 120° C. for 5, 10, 20, 30 and 50 minutes. The following additives were effective in tarnishing the gold coat with time and made gold coating into almost dark brown/black.

Gallic Acid
Glyoxal trimeric dihydrate
Methyltrihydroxybenzoate
3,3',4,4' benzophenone tetracaboxylic acid
Propyl galliate
Ferric salicylate
Zinc sulfide With water based gold paint the following additives were effective in tarnishing the gold coating:

Potassium ferrocyanide
Potassium ferricyanide

A number of other activators having different chemical functionalities and properties were tried. Strong acids, bases and oxidants, such as hydrochloric acid and sodium hydroxide, were over effective, i.e., started reacting at room temperature in mixture/pot (started frothing, most likely by production of hydrogen gas). Some milder acids and base, such as phosphoric acid and sodium carbonate reacted slowly at room temperature but within minutes of mixing, they also started frothing. However, relatively milder acids, bases and oxidants, such as sodium hydrogen carbonate, sodium nitrite, sodium phosphate and sodium acetate have almost right reactivities. Lower concentrations of the additives were less effective and vice versa.

Most desired activators are those which are relatively mild or weak, which melt or dissolve near the desired processing/sterilization temperature. By this way one can prevent premature reaction under ambient conditions.

Example 24

Effect of Additives in Permeable Layers on Steam Sterilization Indicating Device A 100 microns metallized polyester film was coated with 10% solutions of cellulose acetate butyrate in tetrahydrofuran containing about 40% (on solid basis) of a number of additives having different chemical functionalities and properties. Strong and mild acids, basis and oxidant were over effectives. However, weak acids (carboxylic, phenols and poly-ols), bases (amines) and oxidants had desired properties. The following additives were effective in dissolving the metal layer when treated with steam at 120° C. For example, propyl galliate, benzoic acid, benzilic acid, ammonium iron oxalate and iron acetylacetonate had desired properties, i.e., they dissolved the aluminum layer when treated with steam at 120° C. for 30 minutes.

A 100 microns metallized polyester film was printed with "sterilized" on the non-metal side coated using a laser copying machine. The metal side was coated with 10% solutions of cellulose acetate butyrate containing about 40% of propylgalliate and dried. The strips were exposed to steam at 120° C. for 30 minutes. The metal layer got dissolved and the word "Sterilized" appeared.

Example 25

Etching with Hydrogen Peroxide

A solvent based gold ink, (copper-zinc alloy, PMS 871 Gold) of Braden Sutphin, Cleveland, Ohio was diluted to 50% with dioxolane. In ~2 ml of the diluted paint were added about 0.25 g of different additives, heated to dissolve and coated on 100 microns polyester film with #10 wire wound rod. Small strips were cut and treated with saturated vapor of hydrogen peroxide at 70° C. for 4 hours. Sodium dihydrogen phosphate and tetrabutylammonium bromide first tarnished the gold paint and then developed a greenish tint.

0.5 g and 1 g of tetrabutylammonium bromide were dissolved in 5 g of Joncryl 77 and coated on the metal side of a metallized polyester film and dried in an oven at 70° C. for five minutes. A piece of the coating was exposed to saturated vapor of hydrogen peroxide at 70° C. for 4 hours. The metal coating got dissolved and the film became clear.

Example 26

Metal Particles as Indicator for Steam Sterilization

In a one liter plastic container 250 g of a binder (Braden Sutphin metallic ink extender, product #9w3021N) and 400 g of sodium acetate solution (40 g in 360 g water) were mixed under moderate stirring. In a 2 liter plastic container was taken 500 g of metallic ink indicator [Braden Sutphin aluminum ink (called silver ink), product #9W2967J] and was mixed with the above mixture of sodium acetate under vigorous stirring. The resultant metal ink was coated on a 50 microns polyester film with #10 wire wound rod. The coating was dried in an oven at 70° C. for 10 minutes.

Pieces of the coated film [FIG. 40(a)] were subjected to different treatment conditions, such as dry heat at 160° C. for 30 minutes [FIG. 40(b)], steam at 100° C. for 30 minutes, saturated humidity at 50° C. for one week [FIG. 40(c)], hydrogen peroxide vapor at 60° C. for one hour and 100% ethylene oxide gas at room temperature for two hours. The coating did not become transparent under these conditions. The coating became transparent and message and color printed underneath became visible when treated with steam at 120° C. for 30 minutes as shown in FIG. 40(*d*).

Example 27

Moving Boundary Steam Sterilization Indicating Device

The metal surface of a 100 microns metallized polyester film was coated with a commercially available polyurethane latex (#8294, Clear Gloss, Waterborne polyurethane, General Coating, Ridgewood, N.J.) using a 0-10 mil wedge shaped 10 cm long bar and dried at 70° C. for 15 minutes. A wedge shaped coating of polyurethane was obtained.

In a one liter plastic container 40 g of sodium acetate was dissolved in 250 g of Joncryl 77. This mixture was coated on the wedge shaped coating of polyurethane and dried at 70° C. for 15 minutes.

Small strips were cut, mounted on a green paper and treated with steam at 120° C. for different periods of time. One such piece [FIG. 41(*a*)], treated with steam for 15 minutes [FIG. 41(*b*)], 21 minutes [FIG. 41(*c*)], 30 minutes [FIG. 41(*d*)], and 45 minutes [FIG. 41(*e*)] at 120° C. are shown in FIG. 41. The sample was removed from the sterilizer, scanned and re-treated for the said total time.

This type of devices offer an opportunity to create all-in-one or many-in-one, classes 1-6 or classes 1, 3-6 (may be even higher classes) type indicators for steam and other sterilants by using proper metal, metal thickness, material and thickness for the wedge layer and activator or per-cursor for activator.

Example 28

Metal Particles as Indicator and Tetrabutyl Ammonium Bromide as Precursor for Activator for Hydrogen Peroxide and its Plasma In a plastic container were taken 50 g of the metallic ink indicator (Braden Sutphin silver/aluminum ink, product #9W2967J) and 20 g of 50% solution of tetrabutylammonium bromide in water and mixed. The resultant metal ink was coated on a 50 microns polyester film with #10 wire wound rod. The coating was dried in an oven at 70° C. for 15 minutes.

Pieces of the coated film [FIG. 42(*a*)] were subjected to different treatment conditions, such as dry heat at 160° C. for 30 minutes [FIG. 42(*b*)], saturated humidity at 60° C. for one day [FIG. 42(*c*)], steam at 100° C. for 30 minutes [FIG. 42(*d*)] and steam at 120° C. for 30 minutes [FIG. 42(*e*)], The coating did not become transparent under these conditions. The coating started becoming transparent when exposed to hydrogen peroxide vapor for more than 6 hours at 60° C. as shown in FIG. 42(*f*).

Example 29

Metal Particles as Indicator and Sodium Thiocyanate as Pre-Cursor for Activator for Sterilization with Ethylene Oxide In a plastic container were taken 50 g of the metallic ink indicator (Braden Sutphin silver/aluminum ink, product #9W2967J) and 20 g of 50% solution of sodium thiocyanate in water and mixed. The resultant metal ink was coated on a 50 microns polyester film with #10 wire wound rod. The coating was dried in an oven at 70° C. for 15 minutes.

Pieces of the coated film [FIG. 43(*a*)] were subjected to different treatment conditions, such as dry heated to 160° C. for 30 minutes [FIG. 43(*b*)], saturated humidity at 60° C. for one day [FIG. 43(*c*)], steam at 100° C. for 30 minutes [FIG. 43(*d*)], steam at 120° C. for 30 minutes [FIG. 43(*e*)] and hydrogen peroxide vapor at 60° C. for 6 hours [FIG. 43(*f*)]. The coating did not become transparent under these conditions. The coating became transparent when exposed to humid ethylene oxide at 60° C. for 6 hours FIG. 43(*g*).

Examples 28 and 29 also indicate that thin layers of metals and their particles can be used for monitoring chemicals.

The results of Examples 26-29 show that selective and self reading sterilization indicators can be developed using the current inventions.

Example 30

A Halo Compound as Precursor and a Binder

In a 500 ml jar fitted with a magnetic stirrer was added 200 g of tetrahydrofuran and 50 g of Chlorez-700 (Dover Chemical, Dover, Ohio) followed by 50 g of a copolymer of polyvinylidene chloride-acrylonitrile under moderate stirring. The solution was stirred for one hour for dissolution of the binders. The solution was coated with a 5 mil bar on a metallized polyester film having about 50 Angstroms aluminum layer and dried at 50° C. for 5 minutes. The coating was laminated with 1 mil polyethylene film. The laminated sample was exposed to sunlight with coating facing the sun. The metal layer got dissolved in about two hours and a red color paper printed with "RADIATED", placed under the metal film appeared.

Similar devices having polyvinylacetate as a binder and trichloroethane, trichloroacetamide and ethyltrichloroacetate as precursors (partially dried) were also prepared.

Example 31

Very Viscous Oligomeric Halo Compounds without a Binder

About 50 microns layers of several Chlorez (e.g., Clorez 700), Paroil (e.g., Paroil 121) and Dovergaurd (e.g., Dovergaurd 991) supplied by Dover Chemical, Dover, Ohio) were prepared by coating them on a polyester film having a 50 Angstroms layer of aluminum printed with "RADIATED" on polyester. The devices were laminated with a 25 micron polyethylene film to prevent escape of hydrogen chloride produced during radiation and exposed to about 500,000 rads of 100 KeV X-ray. The metal layer got dissolved and the message "RADIATED" became visible.

Example 32

Radiation Indicating Device

When a mixture of fine particles of bronze (e.g., a bronze of copper and zinc) and halogenated paraffins (e.g., Chlorez 700 of Dover Chemical) is radiated with ionizing radiation, such as UV/sunlight light, the gold color particles changes to red. Similarly fine particles of aluminum get dissolved upon the radiation. Thus, a mixture of a halo-compound and a metal can be used as a radiation dosage indicator.

Example 33

A Method for Determination of Concentration of an Activator

On a metallized polyester film having 125 Angstroms aluminum layer and a red paper behind it, a few drops of phosphoric acid solutions of different concentrations (5-85%) were poured at different locations on the metal layer and the time when the red paper just started appearing (i.e., when a very thin layer, e.g., ~10-20 Angstroms left un-etched) and completely visible (i.e., when the metal layer is essentially completely dissolved) were noted. The data are plotted in FIG. 44.

It should be noted that difference between the first sign of being transparent and completely transparent increase with decrease in concentration. This means the induction period and the end point determination zone can be varied by varying the concentration of an activator (or its precursor).

The same time intervals were also determined for phosphoric acid solution of 50% in increment of 0.05%. This method of determining concentration of a chemical/activator is so sensitive that one can determine concentration with ±0.05%.

The similar experiments were also conducted on a metallized plastic film coated with a permeable polymer.

The method can also be used for determination of concentration of activators or their precursor in a gas or vapor phase.

One can determine concentration of activators by dipping strips of metallized plastic film with or without a permeable coating in the solution or exposing to vapor or gases.

Example 34

A Device for Monitoring Radon and Alpha Particles

A do/measure-it-yourself device for monitoring alpha particles and alpha emitting radioactive elements, such as radon was created by applying a thin (~15 microns) layer of cellulose nitrate on a metallized PET and etching with potassium hydroxide. These devices were similar to those disclosed in U.S. Pat. No. 4,788,432 (cited herein as a reference), except that the dye/indicator layer was replaced with a thin metal layer.

Twenty five grams of cellulose nitrate (12% nitrogen) powder containing ~30% alcohol was added in the mixture of 125 g of ethyl acetate, 5 g of butyl alcohol, 8 g of ethylene glycol monoethyl ether and 4 g of dioctylphthalate under stirring. A 4% solution of cellulose nitrate was made by diluting 40 g of the stock solution of cellulose nitrate with 100 ml of ethyl acetate.

A 100 microns metallized polyester film having about 100 Angstroms layer of aluminum was coated with above described dilute solution of cellulose nitrate using a 0.003 inch film applicator. The coating was dried in an oven at 70° C.

The film was then irradiated with alpha particles from a polonium-210 source and placed on a red paper. A six molar potassium hydroxide solution was poured on the radiated film for selective etching of the latent tracks.

Tiny spots (red in color because of the red paper) started appearing after about three hours. The spots grew in size with time. The spots are due to selective, faster etching of the latent tracks produced by alpha particles with potassium hydroxide. Potassium hydroxide also etched the thin metal layer under the etched tracks and appeared as red spots.

The materials (other than dyes) and processes disclosed in U.S. Pat. No. 4,788,432 can also be used for the device disclosed herein and are cited herein by reference.

The sensitivity of this radon monitoring device can be increased by placing a layer of activated carbon over the device (metallized plastic film having a thin coating of latent track producing material such as cellulose nitrate), where radioactive materials such as radon and its daughters (including those produced by neutron-alpha reaction) can get absorbed on the activated carbon and when they emit alpha particles, they will produce latent tracks in the cellulose nitrate layer.

The invention claimed is:

1. An indicating system comprising:
a substrate having thereon:
a) a metallic material, said metallic material comprising a metal layer, a nonporous metal oxide layer on a surface of the metal layer, and optionally one or more polymeric binders or adhesives; and
b) an activator or its precursor;
wherein
the metal layer is a metal or its alloy;
the metallic material is a continuous material or particles in the one or more polymeric binders or adhesives;
the metallic material and the activator each having its own layer or both in one layer;
the nonporous metal oxide layer is between the metal layer and the activator or its precursor; and
wherein
the activator or the activator produced from its precursor is capable of destroying the metal layer and nonporous metal oxide layer causing an irreversible change in opacity, reflectivity or electrical conductivity of the metallic material;
the indicating system provides an induction period caused by a delay in the destruction of the metal layer and nonporous metal oxide layer; and
the destruction or the induction period is measured by a delay in a visual indication or a change in opacity, reflectivity or conductivity.

2. The indicating system of claim 1 wherein the metal is selected from group consisting of alkali metals, alkaline earth metals, transition metals, post transition metals, lanthanides and actinides metals and their alloys.

3. The indicating system of claim 2 wherein the metal is selected from the group consisting of aluminum, tin, zinc, copper, manganese, magnesium, nickel, cobalt, iron, sodium, potassium, lithium, calcium, gallium, cesium, germanium, indium, silver and their alloys.

4. The indicating system of claim 1 wherein the activator is selected from group consisting of water, water vapor, a base, acid, salt, chelate, organometallic, halide, oxide, nitrate, nitrite, phosphate, phosphite, phosphonate, silicate, sulfate, bisulfate, sulfite, sulfide, bisulfide, sulfonate, cyanate, cyanide, thiocyanate, acetylacetonate, carboxylate, percarboxylate, carbonate or bicarbonate, a mono, di and trivalent cation of a metal, cation of nitrogen, sulfur, alcohol, amide, amine, carbamate, ester, halocarbon, ketone, nitro, nitroso, oxime, phenol, urea, urethane and a mixture thereof.

5. The indicating system of claim 4 wherein the activator is selected from the group consisting of ammonium bromide, ammonium thiocyanate, calcium chloride, copper chloride, copper ammonia complexes, lithium acetylacetonate, lithium chloride, lithium formate, potassium acetate, potassium benzoate, potassium bromide, potassium chloride, potassium ferrocyanide, potassium ferrocyanide, potassium formate, sodium acetate, sodium bicarbonate, sodium bromide, sodium carbonate, sodium cyanate, sodium diethyldithiocarbamate, sodium iodide, sodium metasilicate, sodium nitrate, sodium sulfite, sodium tetrafluoroborate, sodium tetraborate, sodium thiocyanate, sodium thiosulfate, tetraethylammonium bromide, tetrabutylammonium bromide, zinc chloride and a mixture thereof.

6. The indicating system of claim 1 wherein the precursor is selected from the group consisting of a monomeric or polymeric acid, base, salt or organometallic compound.

7. The indicating system of claim 6 wherein the precursor of the activator is a cyanate, thiocyanate, halo, halide, halonium, sulfonium or phosphonium compound.

8. The indicating system of claim 7 wherein the precursor of the activator is tetraalkylammonium bromide, benzyltributylammonium bromide, benzyldodecyldimethylammonium bromide, dimethyldioctadecylammonium bromide, dodecylethyldimethylammonium bromide, dodecyltrimethylammonium bromide, ethyltriphenylphosphonium bromide, ethylhexadecyldimethylammonium bromide, hexadecyltrimethylammonium bromide, myristyltrimethylammonium bromide, polybrene, poly(benzophenonetetracarboxylic dianhydride-ethidium bromide), tetraheptylammonium bromide, tetrakis(decyl)ammonium bromide, thonzonium bromide, acetyl choline chloride, ammonium bromide, choline chloride, choline iodide, glycidil trimethyl ammonium chloride, potassium bromide, potassium iodide, sodium iodide, tetrabutyl ammonium iodide, tetraethyl ammonium bromide, tetrahexyl ammonium bromide, tetramethyl ammonium chloride, tetrabutyl phosphonium bromide, sodium thiocyanate and potassium thiocyanate.

9. The indicating system of claim 1 wherein the one or more binders are selected from the group consisting of ethyl cellulose, nitro cellulose, cellulose acetate, hydroxypropyl cellulose, polystyrene, polymethacrylates, polyvinyl chloride, polyvinyl acetate; polyvinylidene chloride, polyacrylics, polyethylene, polypropylene, polyurethanes, polyesters, polycarbonates, polybutylene, polyvinylbutyral, polybutadiene and their copolymers.

10. The indicating system of claim 1 which further comprises an additional one or more layers which are selected from the group consisting of a protective layer, a permeable to activator layer, a wedge shaped permeable to activator layer, a barrier to activator layer, a reactive, destroyable or degradable barrier layer, an expiration indicating layer, a tamper indicating layer, an activation indicating layer, a message or image creating layer, a separating layer, a removable layer, a disappearing layer, an activatable layer, a microencapsulated layer and a printed layer.

11. The indicating system of claim 1 which further comprises: a) an indicator tape affixed to a first substrate wherein said indicator tape comprises said indicator layer; and b) an activator tape affixed to a second substrate wherein said second substrate having thereon said activator layer composed of a matrix layer containing said activator or the precursor of the activator wherein said indicator tape and said activator tape are bonded together with at least one adhesive.

12. The indicating system of claim 1 which has at least one message which appears as a color, word or symbol on at least one or both sides of a layer of the device.

13. The indicating system of claim 12 which contains at least two messages wherein a first message of said two messages does not start to appear at a same time as a second message of said two messages.

14. The indicating system of claim 13 wherein a first appearing message indicates a status or quality of an item when the indicating system is applied on or before a treatment of the item and a second appearing message alone or in combination with the first indicates status or quality of the item after the treatment.

15. The indicating system of claim 14 wherein the first appearing message indicates un-doneness, freshness, usability, acceptability, untreated, unexposed, or non-sterile, non-usability, not-acceptability and the second appearing message alone or in combination with the first indicates doneness, expiration, spoilage, not usability unacceptability, treated, exposed, sterile, usability and acceptability.

16. The indicating system of claim 12 wherein the symbol is at least one barcode.

17. The indicating system of claim 16 wherein the barcode is read before and after the treatment and the results are recorded.

18. The indicating system of claim 1 further comprising at least one electronic chip or component connected to a conductive path composed of the metallic material.

19. The indicating system of claim 18 wherein said activator or the precursor of the activator, with or without a substrate is applied on at least a portion of at least one conductive path of an electronic device composed of at least one electronic chip or component wherein the activator or the activator produced from the precursor has capability of destroying the conductive path.

20. The indicating system of claim 19 wherein the electronic device is a radio frequency identification device or an electronic article surveillance device.

21. The indicating system of claim 20 wherein the electronic device is read before and after the treatment and the results are read with a reader and recorded.

22. The indicating system of claim 1 which is in the form of a label, sticker, band, moving boundary, or a packaging tape.

23. The indicating system of claim 1 which is a monitor for a material or a process.

24. The indicating system of claim 23 wherein the material is a toxic chemical, a chemical agent or a biological agent.

25. The indicating system of claim 24 wherein the chemical agent is a lethal agent, a blister causing agent, a blood affecting agent, a nerve agent, a pulmonary agent, an incapacitating agent or a riot control agent.

26. The indicating system of claim 25 wherein the chemical agent is selected from the group consisting of cyanogen chloride, hydrogen cyanide, ethyldichloroarsine, methyldichloroarsine, phenyldichloroarsine, Lewisite, 1,5-dichloro-3-thiapentane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl)sulfide, bis(2-chloroethylthio)methane, bis(2-chloroethylthiomethyl)ether, bis(2-chloroethylthioethyl)ether, bis(2-chloroethyl)ethylamine, bis(2-chloroethyl)methylamine, tris(2-chloroethyl)amine, tabun, cerin sarin, soman, cyclosarin, GV, VB, VG, VM, VR, VX chlorine, chloropicrin, phosgene, diphosphene, agent 15 (BZ), EA 3167, kolokol-1, pepper spray, CS gas, CN gas and CR gas.

27. The indicating system of claim 24 wherein the toxic chemical is selected from the group consisting of acetone cyanohydrin, acrolein, acrylonitrile, allyl alcohol, allyl amine, allyl chlorocarbonate, allyl isothiocyanate, ammonia, arsenic trichloride, arsine, boron tribromide, boron trichloride, boron trifluoride, bromine, bromine chloride, bromine pentafluoride, bromine trifluoride, carbon disulfide, carbon monoxide, carbonyl fluoride, carbonyl sulfide, chlorine, chlorine pentafluoride, chlorine trifluoride, chloroacetaldehyde, chloroacetone, chloroacetonitrile, chloroacetyl chloride, chlorosulfonic acid, crotonaldehyde, cyanogen, 1,2-dimethyl hydrazine, diborane, diketene, dimethyl sulfate, diphenylmethane-4'-diisocyanate, ethyl chloroformate, ethyl chlorothioformate, ethyl phosphonothioicdichloride, ethyl phosphonous dichloride, ethylene dibromide, ethylene imine, ethylene oxide, fluorine, formaldehyde, hexachlorocyclopentadiene, hydrogen bromide, hydrogen chloride, hydrogen cyanide, hydrogen fluoride, hydrogen iodide, hydrogen selenide, hydrogen sulfide, iron pentacarbonyl, isobutyl chloroformate, isopropyl chloroformate, isopropyl isocyanate, methanesulfonyl chloride, methyl bromide, methyl chloroformate, methyl chlorosilane, methyl hydrazine, methyl isocyanate, methyl mercaptan, n-butyl chloroformate, n-butyl isocyanate, nitric acid, fuming, nitric oxide, nitrogen dioxide, n-propyl chloroformate, parathion, perchloromethyl mercaptan, phosgene, phosphine, phosphorus oxychloride, phosphorus pentafluoride, phosphorus trichloride, sec-butyl chloroformate, selenium hexafluoride, silicon tetrafluoride, stibine, sulfur dioxide, sulfur trioxide, sulfuric acid, sulfuryl chloride, sulfuryl fluoride, tellurium hexafluoride, tert-butyl isocyanate, tert-octyl mercaptan, tetraethyl lead, tetraethyl pyrophosphate, tetramethyl lead, titanium tetrachloride, toluene 2,4-diisocyanate, toluene 2,6-diisocyanate, trichloroacetyl chloride, trifluoroacetyl chloride and tungsten hexafluoride.

28. The indicating system of claim 1 which is an indicator for monitoring time, temperature, time-temperature, freeze, thaw, humidity, doneness of food, pressure, radiation and sterilization.

29. The indicating system of claim 28 wherein the time-temperature indicator is used for monitoring shelf life, usability and freshness of perishables comprising one or more of fresh, refrigerated, or frozen, vegetables, fruits, meats, fish, poultry, dairy products, bakery products, juices, pre-cooked foods, soft and alcoholic beverages, sera, blood, and blood products, and the non-food item comprising a pharmaceutical, vaccine, biological sample, cosmetic, reactive chemical compound, biochemical product, battery, x-ray film and photographic film.

30. The indicating system of claim 28 wherein time indicator is a reminding sticker, self-timing retail sticker, self-expiring sticker to prevent re-use, security ID label, visitors badge, self-expiring parking tag, package and shipping label, wrist band, time indicating ticket for trains, buses, spot events, theaters, self-expiring pass for tours, emergency rooms, hospitals, museums, and other locations, race track pass, security label for screened luggage, purse, bag at airports to indicate that such items have been inspected, or a self-expiring visitor label issued at unmanned but video controlled entrances for visitors.

31. The indicating system of claim 28 wherein the sterilization indicator is used for monitoring sterilization with one or more sterilants selected from the group consisting of humidity, water, steam, ethylene oxide, aldehydes, oxidizing agents, plasmas of vapors or gases, dry heat and ionizing radiation.

32. The sterilization indicating device of claim 31 wherein the sterilant is microwave, UV, X-ray, gamma ray, electrons, ozone, or a vapor, liquid or solution of formaldehyde, glutaraldehyde, hydrogen peroxide, or peracetic acid with or without water.

33. The indicating system of claim 28 wherein the radiation is microwave, UV light, X-ray, gamma ray, electrons, beta ray, neutrons, radon and alpha particles.

34. The indicating system of claim 1 which is a toy, gimmick, message, pattern, design, gift card, or greeting card.

35. A process of monitoring a material or a process which comprises monitoring with the indicating system of claim 1.

36. The process of claim 35 which comprises monitoring process of time, temperature, time-temperature, freeze, thaw, humidity, doneness of food, pressure, radiation, and sterilization.

37. The process of claim 35 for monitoring material which comprises a toxic chemical, a chemical agent and a biological agent.

38. A process of monitoring a sterilization process comprising:
   1) placing the indicating system of claim 1 in the same environment as an item to be sterilized;
   2) adding a sterilant to the environment; and
   3) monitoring an irreversible change in opacity, reflectivity or electrical conductivity of the indicating system.

39. A process to monitor the status of a medical product, food, or biological waste which comprises placing indicating system of claim 1 on or near a packaging of said medical products, food, or biological waste and monitoring the indicating system for a change in opacity, reflectivity or electrical conductivity of the indicating system.

40. A process to monitor a toxic chemical, a chemical agent or a biological agent which comprises: placing the indicating system of claim 1 in the environment of the toxic chemical, the chemical agent or the biological agent and monitoring the indicating system for a change in opacity, reflectivity or electrical conductivity of the indicating system.

41. A process to make the indicating system of claim 1 comprising laminating an indicator tape comprised of a layer of metallic material, with or without a binder on a substrate and an activator tape comprised of a layer of an activator or a precursor of said activator in a binder on a substrate to make the indicating system.

42. A process to make the indicating system of claim 1 comprising placing a metallic material layer with or without a binder on a substrate and applying a layer of an activator or a precursor of said activator in a binder on the metallic material layer and optionally applying a protective layer or a polymeric film to make the indicating system.

43. The process of making the indicating system of claim 42 comprising at least one additional layer selected from the group consisting of a permeable layer, a wedge shaped permeable layer, a barrier layer, a reactive, a destroyable or degradable barrier layer, an expiration indicating layer, a tamper indicating layer, an activation indicating layer, a message or image creating layer, a separating layer, a removable layer, a disappearing layer, an activatable layer, a microencapsulated layer and a printed layer.

44. A process to monitor a change in a material or a process comprising measuring a change in the material or the process with an indicating system of claim 1.

45. The process of claim 44 wherein the material is a perishable, an item to be sterilized, a medical product, a toxic chemical, a chemical agent or a biological agent.

46. The indicating system of claim 1, wherein the non-porous metal oxide layer is naturally formed on the surface of the metal layer.

* * * * *